(12) United States Patent
Gryko et al.

(10) Patent No.: US 9,595,680 B2
(45) Date of Patent: Mar. 14, 2017

(54) HETEROCYCLIC FLUORESCENT DYES AND METHOD OF PRODUCTION THEREOF

(71) Applicant: BASF SE, Ludwigshafen (DE)

(72) Inventors: Daniel T. Gryko, Warsaw (PL); Marek Grzybowski, Szczecin (PL)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/770,867

(22) PCT Filed: Mar. 3, 2014

(86) PCT No.: PCT/EP2014/054060
§ 371 (c)(1),
(2) Date: Aug. 27, 2015

(87) PCT Pub. No.: WO2014/135491
PCT Pub. Date: Sep. 12, 2014

(65) Prior Publication Data
US 2015/0380660 A1    Dec. 31, 2015

Related U.S. Application Data

(60) Provisional application No. 61/773,166, filed on Mar. 6, 2013.

(30) Foreign Application Priority Data

| Mar. 6, 2013 | (EP) | 13157961 |
| Jun. 25, 2013 | (EP) | 13173518 |
| Nov. 6, 2013 | (EP) | 13191722 |
| Dec. 4, 2013 | (EP) | 13195706 |

(51) Int. Cl.

| C07D 471/22 | (2006.01) |
| H01L 51/00 | (2006.01) |
| C07D 491/22 | (2006.01) |
| C07D 495/22 | (2006.01) |
| C09B 57/00 | (2006.01) |
| C09B 69/00 | (2006.01) |
| C09B 69/10 | (2006.01) |
| C07D 487/04 | (2006.01) |
| C07D 487/22 | (2006.01) |
| C07D 517/22 | (2006.01) |
| C07D 519/00 | (2006.01) |
| C08G 69/00 | (2006.01) |
| C08G 69/42 | (2006.01) |
| G01N 33/52 | (2006.01) |
| H01L 51/05 | (2006.01) |
| H01L 51/42 | (2006.01) |

(52) U.S. Cl.
CPC ........ *H01L 51/0062* (2013.01); *C07D 471/22* (2013.01); *C07D 487/04* (2013.01); *C07D 487/22* (2013.01); *C07D 491/22* (2013.01); *C07D 495/22* (2013.01); *C07D 517/22* (2013.01); *C07D 519/00* (2013.01); *C08G 69/00* (2013.01); *C08G 69/42* (2013.01); *C09B 57/004* (2013.01); *C09B 69/008* (2013.01); *C09B 69/109* (2013.01); *G01N 33/52* (2013.01); *H01L 51/0003* (2013.01); *H01L 51/0053* (2013.01); *H01L 51/0071* (2013.01); *H01L 51/0073* (2013.01); *H01L 51/0074* (2013.01); *H01L 51/0558* (2013.01); *H01L 51/42* (2013.01); *Y02E 10/549* (2013.01)

(58) Field of Classification Search
CPC ...... C07D 471/22; H01L 51/00; C09B 57/004
USPC ........................ 546/41, 31, 26; 313/499, 504
See application file for complete search history.

(56) References Cited

U.S. PATENT DOCUMENTS

| 8,940,895 B2 * | 1/2015 | Grzybowski ......... C09B 57/004 |
| | | 313/499 |
| 2011/0004004 A1 | 1/2011 | Hao et al. |

(Continued)

FOREIGN PATENT DOCUMENTS

| WO | WO-2006/061343 A1 | 6/2006 |
| WO | WO-2010/108873 A1 | 9/2010 |
| WO | 2013092474 | 6/2013 |

OTHER PUBLICATIONS

Ling Deng, "Synthesis and Application of Sulfydryl fluorescent probes based on diketopyrrolopyrrole (DPP)", Masteral Thesis of Dalian University of Technology, Engineering Technology I, pp. 23 and 24 (Jun. 2012).

(Continued)

*Primary Examiner* — Charanjit Aulakh
(74) *Attorney, Agent, or Firm* — Marshall, Gerstein & Borun LLP

(57) ABSTRACT

The invention relates to novel compounds of formula (III) that can be used as heterocyclic dyes of unique structure and properties. These compounds can be obtained in a three-step synthesis from simple substrates. The compounds according to the invention have excellent solubility in organic solvents and excellent film-forming properties. In addition, high efficiency of energy conversion, excellent field-effect mobility, good on/off current ratios and/or excellent stability can be observed, when the compounds according to the invention are used in organic field effect transistors, organic photovoltaics (solar cells) and photodiodes.

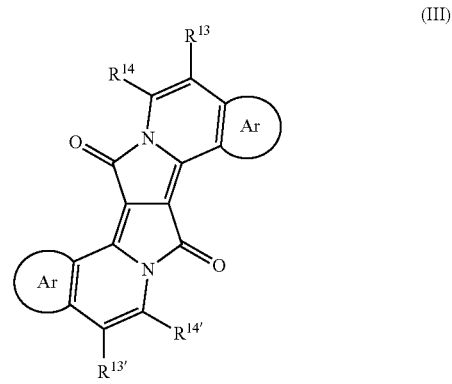

(III)

19 Claims, No Drawings

(56) References Cited

U.S. PATENT DOCUMENTS

2011/0028644 A1    2/2011   Brown et al.
2014/0357869 A1   12/2014   Grzybowski et al.
2016/0181534 A1    6/2016   Hayoz et al.

OTHER PUBLICATIONS

Nowak-Krol, A. et al., "Strong two-photon absorption enhancement in a unique bis-porphyrin bearing a diketopyrrolopyrrole unit", Chem. Commun., 2013, vol. 49, pp. 8368-8370.

Grzybowski, M. et al., "Bright, Color-Tunable Fluorescent Dyes Based on π-Expanded Diketopyrrolopyrroles", Organic Letters, 2012, vol. 14, No. 11, pp. 2670-2673.

* cited by examiner

HETEROCYCLIC FLUORESCENT DYES AND METHOD OF PRODUCTION THEREOF

CROSS-REFERENCE TO RELATED APPLICATIONS

This application is a National Stage Entry of International Application PCT/EP2014/054060 filed Mar. 3, 2014, which claims the benefit of U.S. Provisional Application No. 61/773,166, filed Mar. 6, 2013 and claims priority to EP 13157961.7 filed Mar. 6, 2013, EP 13173518.5 filed Jun. 25, 2013, EP 13191722.1 filed Nov. 6, 2013, and EP 13195706.0 filed Dec. 4, 2013, wherein the contents of all foregoing applications are herein incorporated by reference.

FIELD OF THE INVENTION

The invention relates to novel compounds that can be used as heterocyclic dyes of unique structure and properties. These compounds can be obtained in a three-step synthesis from simple substrates. The compounds according to the invention have excellent solubility in organic solvents and excellent film-forming properties. In addition, high efficiency of energy conversion, excellent field-effect mobility, good on/off current ratios and/or excellent stability can be observed, when the compounds according to the invention are used in organic field effect transistors, organic photovoltaics (solar cells) and photodiodes.

BACKGROUND OF THE INVENTION

Organic dyes are known, which are diketopyrrolopyrroles (DPPs) of formula (I), which are employed as pigments, used in the production of durable paints and varnishes.

Daniel T. Gryko et al. Organic Letters 14 (2012) 2670 disclose a synthetic approach to π-expanded diketopyrrolopyrroles. A three-step strategy appears to be very general and starts with the preparation of diketopyrrolopyrroles followed by N-alkylation with bromoacetaldehyde diethyl acetal and electrophilic aromatic substitution. The final reaction regioselectively furnishes fluorescent dyes.

WO2013/092474 relates to compounds of formula (III):

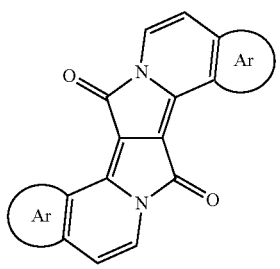

where Ar denotes a homo- or heteroaromatic system.

Daniel T. Gryko et al. Chemical Communications 49 (2013) 8368 (DOI: 10.1039/c3cc44728f) report the synthesis of π-expanded diketopyrrolopyrroles. The new functional dyes possess enhanced properties when compared with expanded DPPs in terms of fluorescence quantum yield. By placing two amine groups at peripheral positions of the resulting dyes, values of 2PA (two-photon absorption) cross-section on the level of 2000 GM were achieved, which in combination with high $\phi_{fl}$, generated a two-photon brightness of ~1000 units at 840-970 nm.

There is still a need for stable water-insoluble organic pigments, which might find application in the dyeing industry. In addition, the development of fluorometric techniques and the extensive use thereof in modern biomedical techniques and diagnostics (e.g. optical imaging) means there is steady growth in demand for new compounds with improved fluorescence properties in the visible range. Provision of compounds with high fluorescence quantum yield is required.

SUMMARY OF THE INVENTION

It is another object of the present invention to provide compounds, which show high efficiency of energy conversion, excellent field-effect mobility, good on/off current ratios, good film-forming properties and/or excellent stability, when used in organic field effect transistors, organic photovoltaics (solar cells) and photodiodes.

Said objects have been solved by compounds of formula (III):

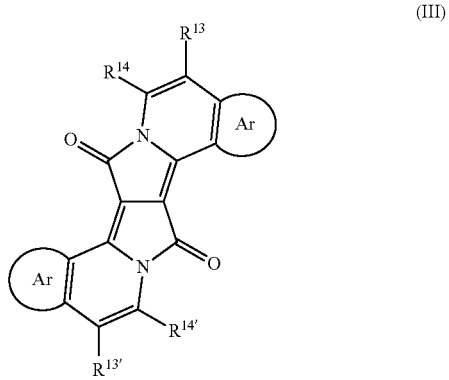

where Ar denotes a homo- or heteroaromatic system, which may be substituted, or unsubstituted. The homo- or heteroaromatic systems (Ar) may be different, but are preferably the same.

The new compounds of the present invention show high fluorescence quantum yield and solubility. Advantageously, the compounds of the present invention, or an organic semiconductor material, layer or component, comprising the compounds of the present invention, can be used in organic photovoltaics (solar cells) and photodiodes, or in organic field effect transistors (OFET).

The homo- or heteroaromatic system (Ar) is selected from the group consisting of benzene, furan, thiopene, pyrrole, selenophene, benzofuran, benzothiophene, indole, benzoselenophene, thieno[2,3-b]thiophene and thieno[3,2-b]thiophene.

The homo- or heteroaromatic system may be unsubstituted, or substituted. Examples of substituents are halogen, especially F; cyano, $C_1$-$C_{25}$alkoxy, $C_1$-$C_{25}$alkyl, $C_1$-$C_{25}$alkyl substituted with one or more halogen atoms, especially F;

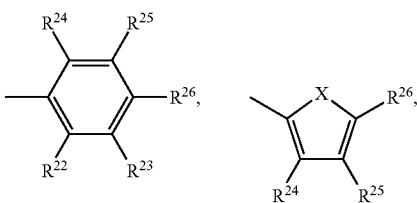

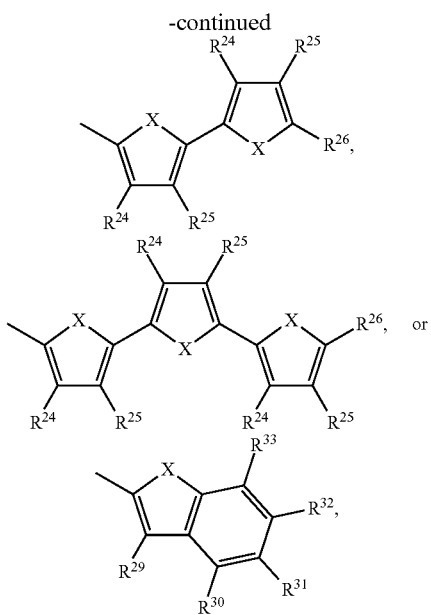

wherein X, $R^{22}$ to $R^{26}$ and $R^{29}$ to $R^{33}$ are as defined below. $R^{13}$, $R^{13'}$, $R^{14}$ and $R^{14'}$ are independently of each other hydrogen, $C_1$-$C_{25}$alkyl, $C_2$-$C_{25}$alkenyl, $C_2$-$C_{25}$alkenyl, which may optionally be interrupted a group $D^{Si}$, or by one or more oxygen or sulphur atoms and/or is optionally substituted by a group $E^{Si}$ or one or more halogen atoms, especially F; $C_2$-$C_{25}$alkinyl, $C_3$-$C_{12}$cycloalkyl, $C_3$-$C_{12}$cycloalkyl-alkyl, which may optionally be interrupted by a group $D^{Si}$, or one or more oxygen or sulphur atoms and/or is optionally substituted by a group $E^{Si}$ or one or more halogen atoms, especially F; $C_7$-$C_{25}$arylalkyl, $C_7$-$C_{25}$arylalkyl which may optionally be interrupted by a group $D^{Si}$, or one or more oxygen or sulphur atoms and/or is optionally substituted by a group $E^{Si}$ or one or more halogen atoms, especially F; $C_6$-$C_{18}$aryl; $C_6$-$C_{18}$aryl which is substituted by halogen, $C_1$-$C_{18}$alkyl, or $C_1$-$C_{18}$alkoxy, or $C_1$-$C_{25}$alkyl, which may optionally be interrupted by one or more oxygen or sulphur atoms and/or is optionally substituted by one or more halogen atoms, especially F; $C_3$-$C_{10}$heteroaryl; $C_3$-$C_{10}$heteroaryl, which is substituted by halogen, $C_1$-$C_{18}$alkyl, or $C_1$-$C_{18}$alkoxy; or $C_1$-$C_{25}$alkyl, which may optionally be interrupted by a group $D^{Si}$, or one or more oxygen or sulphur atoms and/or is optionally substituted by one or more halogen atoms, especially F;

$E^{Si}$ is —$SiR^{161}R^{162}R^{163}$ or —O—$SiR^{161}R^{162}R^{163}$;

$D^{Si}$ is —$SiR^{161}R^{162}$—, —$SiR^{161}R^{162}$—(O—$SiR^{161}R^{162}$)$_d$— or —O—$SiR^{161}R^{162}$—;

$R^{161}$, $R^{162}$ and $R^{163}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—$SiR^{164}R^{165}R^{166}$, —(O—$SiR^{164}R^{165}$)$_d$—$R^{166}$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl, which is substituted 1 to 3 times by $C_1$-$C_{25}$alkyl, halogen, cyano or $C_1$-$C_{25}$alkoxy;

$R^{164}$, $R^{165}$ and $R^{166}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—$SiR^{169}R^{170}R^{171}$, —(O—$SiR^{169}R^{170}$)$_d$—$R^{171}$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl which is substituted 1 to 3 times by $C_1$-$C_{25}$alkyl, halogen, cyano or $C_1$-$C_{25}$alkoxy;

$R^{169}$, $R^{170}$ and $R^{171}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—$Si(CH_3)_3$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl, which is substituted 1 to 3 times by $C_1$-$C_{25}$alkyl, halogen, cyano or $C_1$-$C_{25}$alkoxy;

$R^{167}$ and $R^{168}$ are independently of each other hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms; or $C_7$-$C_{25}$arylalkyl;

d is an integer from 1 to 50; with the proviso that at least one of $R^{13}$, $R^{13'}$, $R^{14}$ and $R^{14'}$ is different from hydrogen.

$R^{13}$ and $R^{13'}$ may be different, but are preferably the same. $R^{14}$ and $R^{14'}$ may be different, but are preferably the same.

Preferably, two of the substituents $R^{13}$, $R^{13'}$, $R^{14}$ and $R^{14'}$ are different from hydrogen, more preferred $R^{13}$ and $R^{13'}$ are different from hydrogen and most preferred $R^{14}$ and $R^{14'}$ are hydrogen and $R^{13}$ and $R^{13'}$ are different from hydrogen.

Preferably, $R^{13}$ is $C_1$-$C_{25}$alkyl, $C_2$-$C_{25}$alkenyl, $C_2$-$C_{25}$alkenyl, which may optionally be interrupted by one or more oxygen atoms and/or is optionally substituted by a group $D^{Si}$ or one or more halogen atoms, especially F; $C_3$-$C_{10}$heteroaryl; $C_3$-$C_{10}$heteroaryl, which is substituted by halogen, $C_1$-$C_{18}$alkyl, or $C_1$-$C_{18}$alkoxy; or $C_1$-$C_{25}$alkyl, which may optionally be interrupted by one or more oxygen atoms and/or is optionally substituted by a group $E^{Si}$ or one or more halogen atoms, especially F. More preferred, $R^{13}$ is $C_1$-$C_{25}$alkyl, or $C_1$-$C_{25}$alkyl, which may optionally be interrupted by one or more oxygen atoms and/or is optionally substituted by a group $E^{Si}$ or one or more fluorine atoms. Most preferred $R^{13}$ is $C_1$-$C_{25}$alkyl.

Preferably, $R^{14}$ is H, $C_1$-$C_{25}$alkyl, $C_2$-$C_{25}$alkenyl, $C_2$-$C_{25}$alkenyl, which may optionally be interrupted by one or more oxygen atoms and/or is optionally substituted by a group $D^{Si}$ or one or more halogen atoms, especially F; $C_3$-$C_{10}$heteroaryl; $C_3$-$C_{10}$heteroaryl, which is substituted by halogen, $C_1$-$C_{18}$alkyl, or $C_1$-$C_{18}$alkoxy; or $C_1$-$C_{25}$alkyl, which may optionally be interrupted by one or more oxygen atoms and/or is optionally substituted by a group $E^{Si}$ or one or more halogen atoms, especially F. More preferred, $R^{14}$ is H, $C_1$-$C_{25}$alkyl, or $C_1$-$C_{25}$alkyl, which may optionally be interrupted by one or more oxygen atoms and/or is optionally substituted by a group $E^{Si}$ or one or more fluorine atoms. Most preferred $R^{14}$ is H.

In another preferred embodiment is phenyl, which may optionally be substituted by one or more halogen atoms, especially F, $C_1$-$C_{25}$alkyl groups, or $C_1$-$C_{25}$alkoxy groups. $R^{14}$ is preferably H.

Among the compounds of formula III compounds are preferred, wherein $R^{14}$ and $R^{14'}$ are hydrogen. More preferred are compounds of formula III, wherein $R^{14}$ and $R^{14'}$ are hydrogen and $R^{13}$ and $R^{13'}$ are different from hydrogen and are the same.

$E^{Si}$ is —$SiR^{161}R^{162}R^{163}$, or —O—$SiR^{161}R^{162}R^{163}$, preferably —$SiR^{161}R^{162}R^{163}$.

$D^{Si}$ is —$SiR^{161}R^{162}$—, —$SiR^{161}R^{162}$—(O—$SiR^{161}R^{162}$)$_d$—, or —O—$SiR^{161}R^{162}$—, preferably —$SiR^{161}R^{162}$—, or —$SiR^{161}R^{162}$—(O—$SiR^{161}R^{162}$)$_d$—.

$R^{161}$, $R^{162}$ and $R^{163}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—$SiR^{164}R^{165}R^{166}$, —(O—$SiR^{164}R^{165}$)$_d$—$R^{166}$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl, which is substituted 1 to 3 times by $C_1$-$C_{25}$alkyl, halogen, cyano or $C_1$-$C_{25}$alkoxy; preferably hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—$SiR^{164}R^{165}R^{166}$, —O—($SiR^{164}R^{165}$)$_d$—$R^{166}$ or phenyl; more preferably $C_1$-$C_8$alkyl, $C_5$-$C_6$cycloalkyl, which might optionally be substituted with $C_1$-$C_4$alkyl; $C_1$-$C_8$haloalkyl, $C_2$-$C_8$alkenyl, —O—$SiR^{164}R^{165}R^{166}$, —(O—$SiR^{164}R^{165}$)$_d$—$R^{166}$ or phenyl; most preferably $C_1$-$C_8$alkyl, $C_1$-$C_8$haloalkyl, especially $C_1$-$C_8$alkyl which is substituted one, or more times with fluorine atoms; —O—$SiR^{164}R^{165}R^{166}$ or —(O—$SiR^{164}R^{165}$)$_d$—$R^{166}$.

$R^{164}$, $R^{165}$ and $R^{166}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—$SiR^{169}R^{170}R^{171}$, —(O—$SiR^{169}R^{170}$)$_d$—$R^{171}$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl, which is substituted 1 to 3 times by $C_1$-$C_{25}$alkyl, halogen, cyano or $C_1$-$C_{25}$alkoxy; preferably hydrogen, $C_1$-$C_{25}$alkyl, $C_1$-$C_{25}$haloalkyl, $C_2$-$C_{25}$alkenyl, —O—$SiR^{169}R^{170}R^{171}$, —(O—$SiR^{169}R^{170}$)$_d$—$R^{1771}$, or phenyl; more preferably $C_1$-$C_8$alkyl, $C_1$-$C_8$haloalkyl, $C_2$-$C_8$alkenyl, —O—$SiR^{169}R^{170}R^{171}$, —(O—$SiR^{169}R^{170}$)$_d$—$R^{171}$, or phenyl; most preferably $C_1$-$C_8$alkyl, $C_1$-$C_8$haloalkyl, especially $C_1$-$C_8$alkyl which is substituted one or more times with fluorine atoms; —O—$SiR^{169}R^{170}R^{171}$ or —(O—$SiR^{169}R^{170}$)$_d$—$R^{171}$.

$R^{169}$, $R^{170}$ and $R^{171}$ are independently of each other hydrogen, $C_1$-$C_{25}$alkyl, $C_3$-$C_{12}$cycloalkyl, which might optionally be substituted with $C_1$-$C_4$alkyl, $C_1$-$C_{25}$haloalkyl, $C_2$-$C_{25}$alkenyl, —O—$Si(CH_3)_3$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl, which is substituted 1 to 3 times by $C_1$-$C_{25}$alkyl, halogen, cyano, or $C_1$-$C_{25}$alkoxy; preferably hydrogen, $C_1$-$C_{25}$alkyl, $C_1$-$C_{25}$haloalkyl, $C_2$-$C_{25}$alkenyl, —O—$Si(CH_3)_3$, or phenyl; more preferably $C_1$-$C_8$alkyl, $C_1$-$C_8$haloalkyl, $C_2$-$C_8$alkenyl, —O—$Si(CH_3)_3$, or phenyl; most preferably $C_1$-$C_8$alkyl, $C_1$-$C_8$haloalkyl, especially $C_1$-$C_8$alkyl which is substituted one or more times with fluorine atoms; or —O—$Si(CH_3)_3$.

d is an integer from 1 to 50, preferably 1 to 40, even more preferably 1 to 30, still more preferably 1 to 20, more preferably 1 to 15, still more preferably 1 to 10 and even more preferably 1 to 5 and most preferably 1 to 3.

$R^{167}$ and $R^{168}$ are independently of each other hydrogen, $C_1$-$C_{25}$alkyl, $C_1$-$C_{25}$haloalkyl, $C_3$-$C_{25}$alkenyl, or phenyl; preferably $C_1$-$C_{25}$alkyl, $C_1$-$C_{25}$haloalkyl, or phenyl; most preferably $C_1$-$C_{25}$alkyl.

In a particularly preferred embodiment $E^{Si}$ is —$SiR^{161}R^{162}R^{163}$. $R^{161}$, $R^{162}$ and $R^{163}$ are independently of each other $C_1$-$C_{25}$alkyl, especially $C_1$-$C_8$alkyl; $C_1$-$C_{25}$haloalkyl, especially $C_1$-$C_8$haloalkyl, such as, for example, —$CF_3$, —$(CH_2)_2CF_3$, —$(CH_2)_2(CF_2)_5CF_3$ and —$(CH_2)_2(CF_2)_6CF_3$; $C_2$-$C_{25}$alkenyl, especially $C_2$-$C_8$alkenyl; $C_3$-$C_{12}$cycloalkyl, especially $C_5$-$C_6$cycloalkyl, which might optionally be substituted with $C_1$-$C_4$alkyl; phenyl, —O—$SiR^{164}R^{165}R^{166}$, Or —(O—$SiR^{164}R^{165}$)$_d$—$R^{166}$. In case of a group —O—$SiR^{164}R^{165}R^{166}$ $R^{164}$, $R^{165}$ and $R^{166}$ are independently of each other $C_1$-$C_8$alkyl, $C_1$-$C_8$haloalkyl, $C_2$-$C_8$alkenyl, or phenyl. In case of a group —(O—$SiR^{164}R^{165}$)$_d$—$R^{166}$ $R^{164}$ and $R^{165}$ are independently of each other $C_1$-$C_8$alkyl, $R^{166}$ is $C_1$-$C_8$alkyl, or phenyl and d is an integer of 2 to 5.

Examples of preferred groups $E^{Si}$ are shown below:

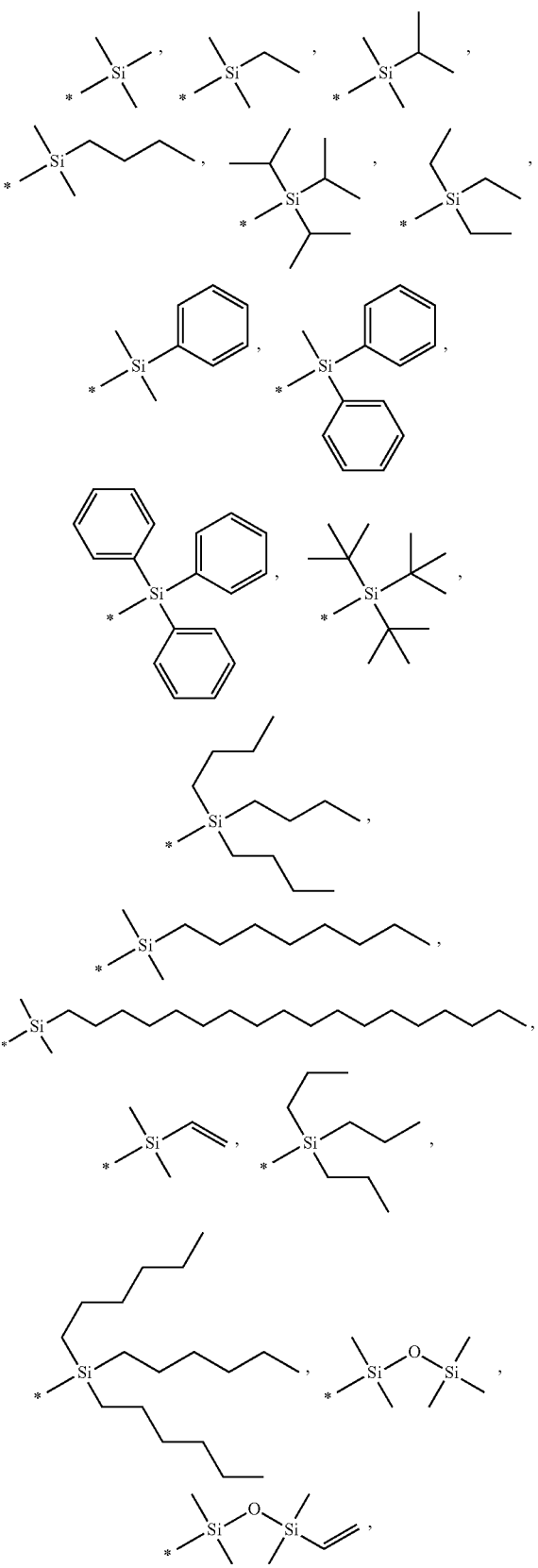

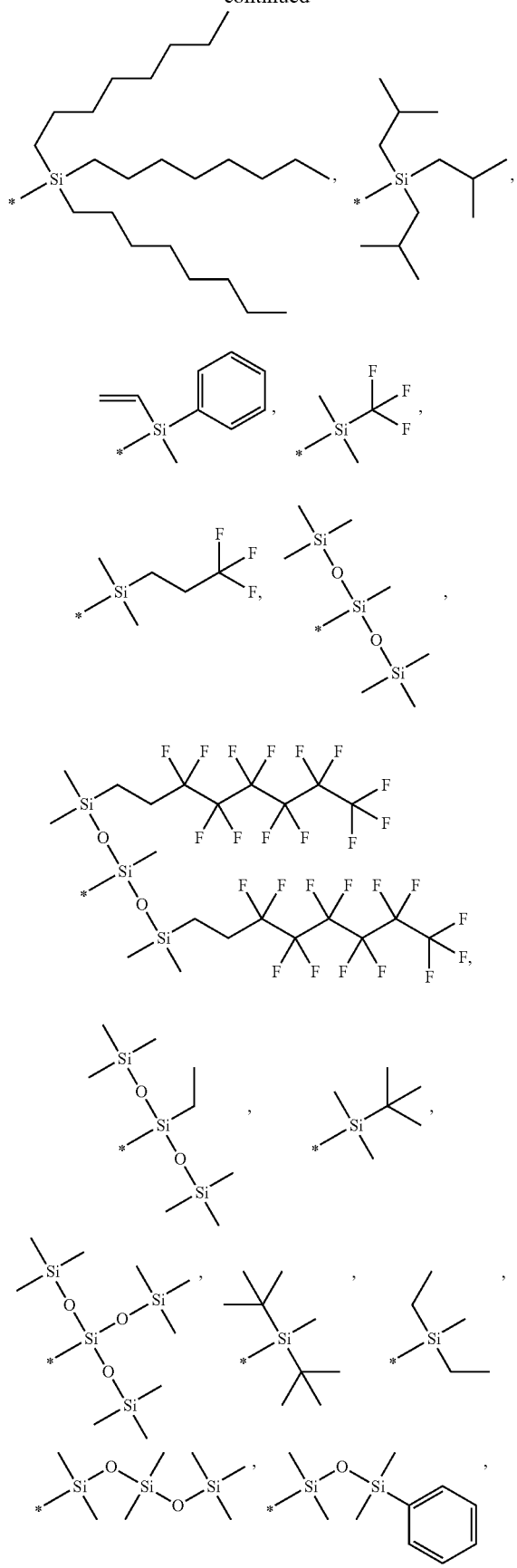

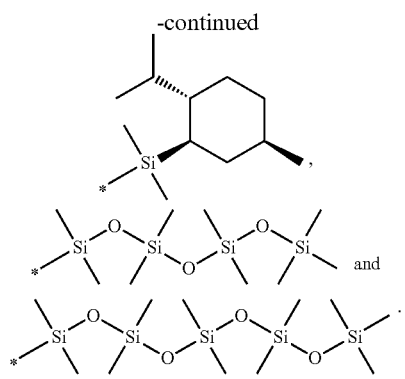

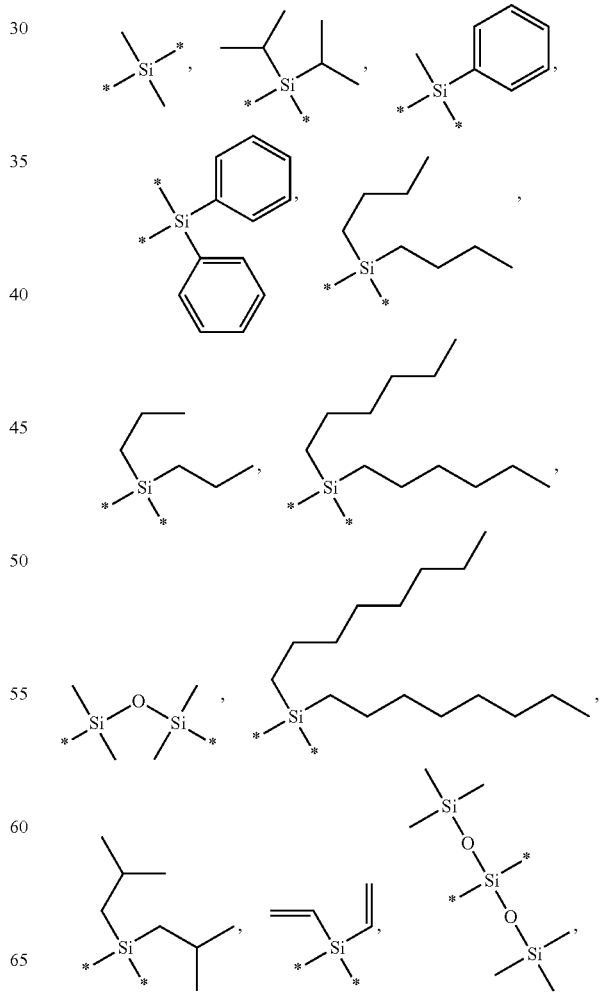

In a particularly preferred embodiment $D^{Si}$ is —$SiR^{161}R^{162}$—, wherein $R^{161}$ and $R^{162}$ are independently of each other $C_1$-$C_{25}$alkyl, especially $C_1$-$C_8$alkyl; $C_1$-$C_{25}$haloalkyl, especially $C_1$-$C_8$haloalkyl, such as, for example, —$CF_3$, —$(CH_2)_2CF_3$, —$(CH_2)_2(CF_2)_5CF_3$ and —$(CH_2)_2(CF_2)_6CF_3$; $C_2$-$C_{25}$alkenyl, especially $C_2$-$C_8$alkenyl; or phenyl.

In another particularly preferred embodiment $D^{Si}$ is —$SiR^{161}R^{162}$—(O—$SiR^{161}R^{162}$)$_d$—, wherein d is 2 to 5 and $R^{161}$ and $R^{162}$ are $C_1$-$C_{25}$alkyl, especially $C_1$-$C_8$alkyl.

Examples of preferred groups $D^{Si}$ are shown below:

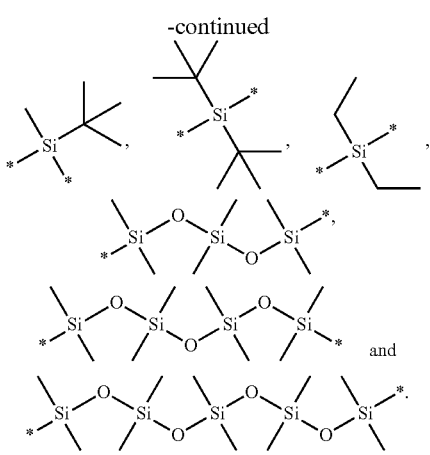

Specific examples of homo- or heteroaromatic system (Ar) are shown below:

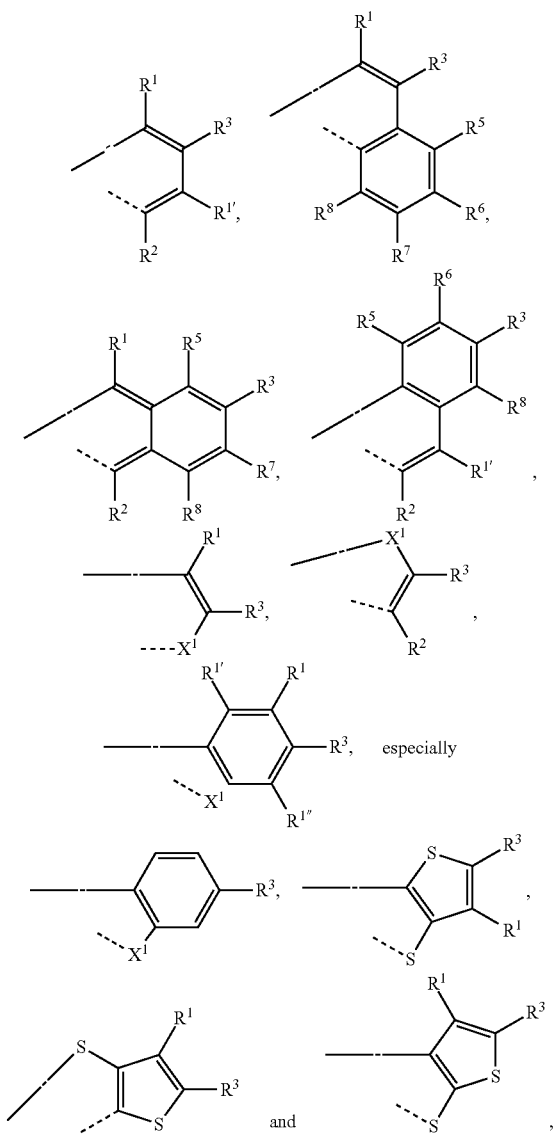

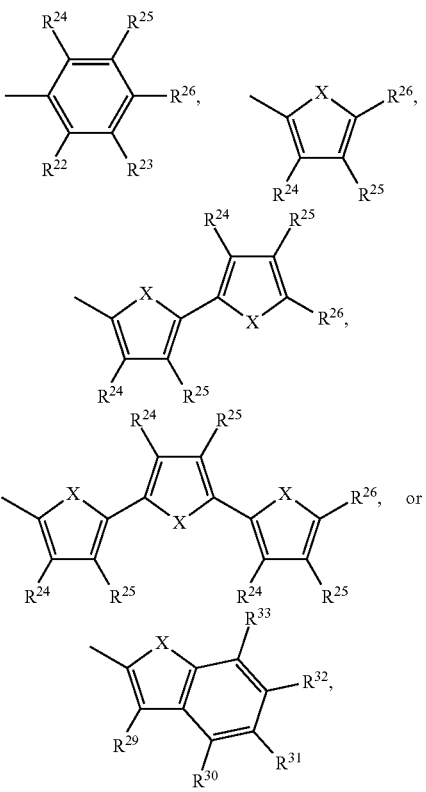

wherein the dotted lines denotes the bonds to the 6-membered ring (the dotted line -- indicates the bond to the carbon atom in para-position to the nitrogen atom, the dotted line ----- indicates the bond to the carbon atom in meta-position to the nitrogen atom), $R^1$, $R^{1'}$ and $R^{1'''}$ are independently of each other H, halogen, especially F; cyano, $C_1$-$C_{25}$alkoxy, $C_1$-$C_{25}$alkyl substituted with one or more halogen atoms, especially F; or $C_1$-$C_{25}$alkyl, $R^2$ is H, halogen, especially F; cyano, $C_1$-$C_{25}$alkoxy, or $C_1$-$C_{25}$alkyl, $R^3$ is hydrogen, halogen, especially F; cyano, $C_1$-$C_{25}$alkoxy, $C_1$-$C_{25}$alkyl substituted with one or more halogen atoms, especially F; $C_1$-$C_{25}$alkyl, wherein $R^{22}$ to $R^{25}$ and $R^{29}$ to $R^{33}$ represent independently of each other H, F, cyano, $C_1$-$C_{25}$alkoxy, $C_1$-$C_{25}$alkyl substituted with one or more halogen atoms, especially F; or $C_1$-$C_{25}$alkyl, and $R^{26}$ is H, F, cyano, phenyl, $C_1$-$C_{25}$alkoxy, $C_1$-$C_{25}$alkyl substituted with one or more halogen atoms, or $C_1$-$C_{25}$alkyl;

$R^5$, $R^6$, $R^7$ and $R^8$ are independently of each other hydrogen, halogen, especially F; cyano, $C_1$-$C_{25}$alkyl, $C_1$-$C_{25}$alkoxy, or $C_1$-$C_{25}$alkyl substituted with one or more halogen atoms, especially F;

X and $X^1$ are independently of each other O, S, Se, or $NR^4$, $R^4$ is hydrogen, $C_6$-$C_{18}$aryl; $C_6$-$C_{18}$aryl which is substituted by $C_1$-$C_{18}$alkyl, halogen, especially F; or $C_1$-$C_{18}$alkoxy; $C_1$-$C_{25}$alkyl, which may optionally be interrupted by one or more oxygen or sulphur atoms and/or is optionally substituted by one or more halogen atoms, especially F; or $C_7$-$C_{25}$arylalkyl.

In another preferred embodiment $R^3$ is a group of formula —$NA^1A^{1'}$, or a group

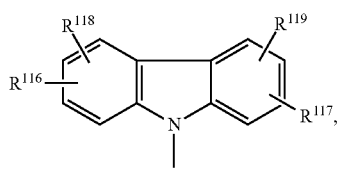

wherein $A^1$ and $A^{1'}$ are independently of each other $C_1$-$C_{18}$alkyl,

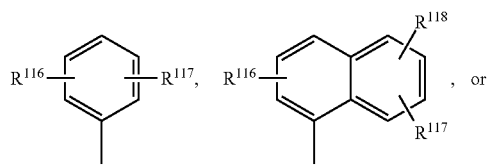

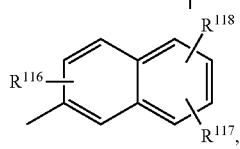

$R^{116}$, $R^{117}$, $R^{118}$ and $R^{119}$ are independently of each other hydrogen, $C_1$-$C_{18}$alkyl, which may optionally be interrupted by —O—, or $C_1$-$C_{18}$alkoxy.

Preferably, X is O, S, or Se, more preferably X is O, or S, most preferred, X is S.

Preferably, $X^1$ is O, S, or Se, more preferably X is O, or S, most preferred, X is S.

Preferably, $R^4$ is hydrogen, or $C_1$-$C_{25}$alkyl, which may optionally be interrupted by one or more oxygen or sulphur atoms. More preferably, $R^4$ is $C_1$-$C_{25}$alkyl.

$R^5$, $R^6$, $R^7$, and $R^8$ are preferably hydrogen, halogen, especially F; $C_1$-$C_{25}$alkyl, or $C_1$-$C_{25}$alkyl substituted with one or more halogen atoms, especially F; more preferred hydrogen or $C_1$-$C_{25}$alkyl, most preferred H.

DETAILED DESCRIPTION OF THE INVENTION

Preferably the compound according to the invention is selected from the group consisting of the following compounds of formulae:

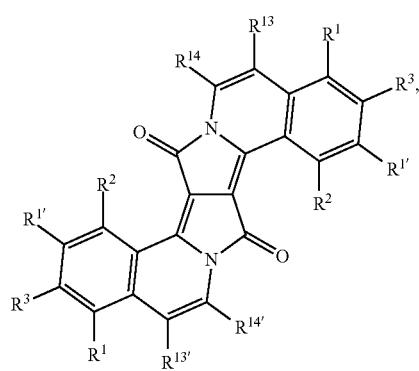

(IIIa)

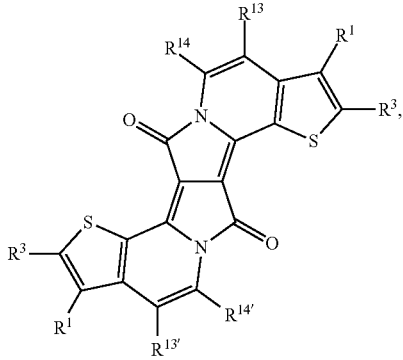

(IIIb)

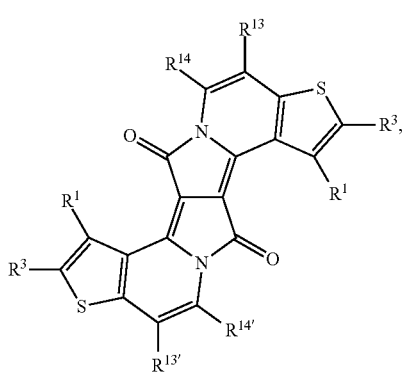

(IIIc)

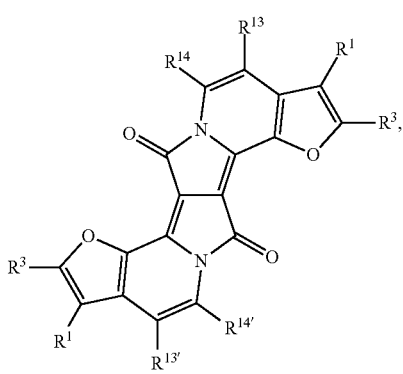

(IIId)

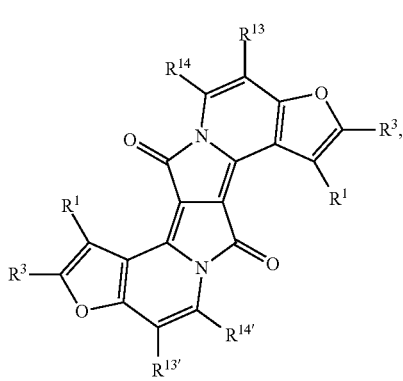

(IIIe)

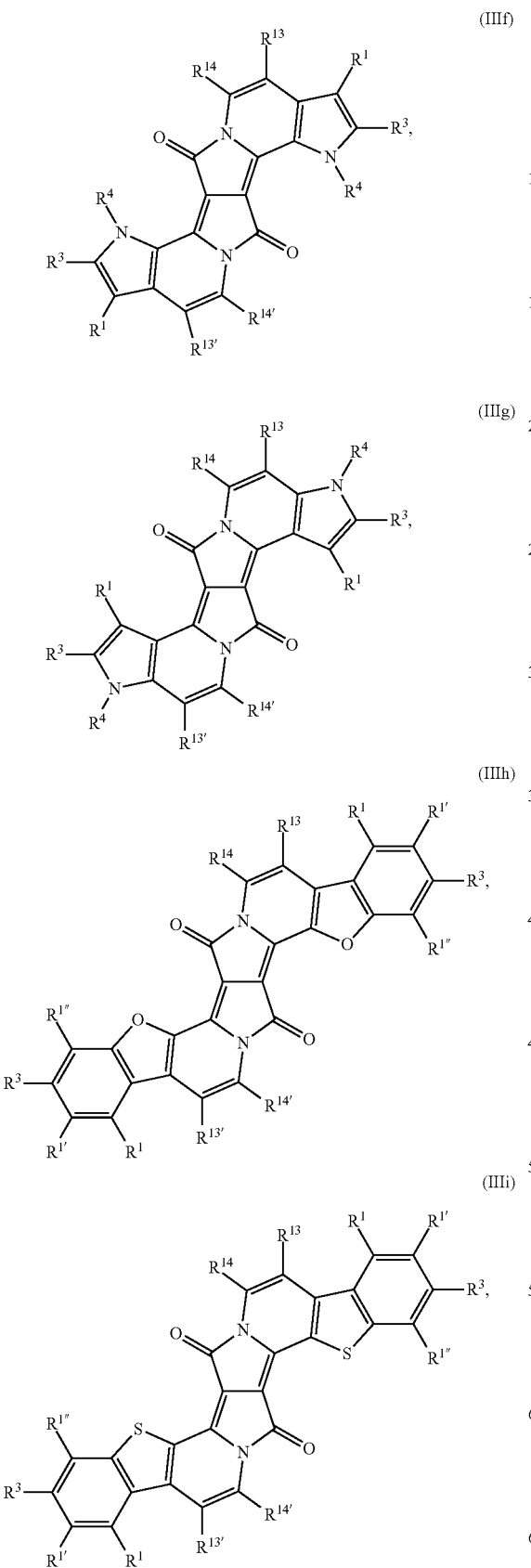
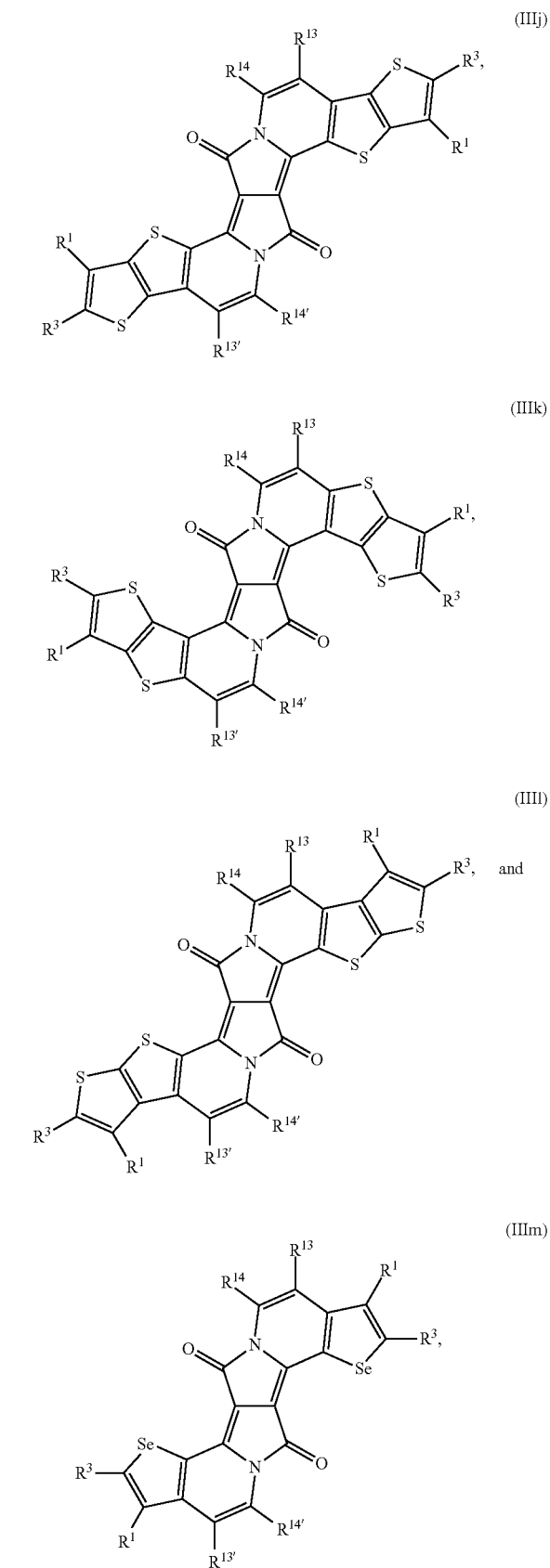

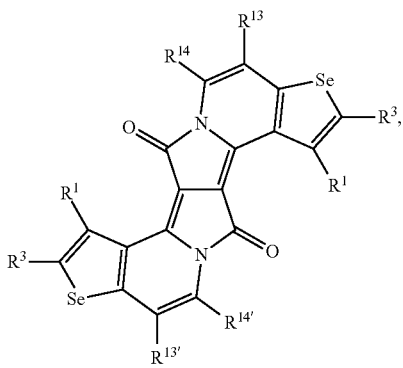

(IIIn)

wherein $R^1$, $R^{1'}$, $R^{1''}$, $R^2$, $R^3$, $R^4$, $R^{13}$, $R^{13'}$, $R^{14}$ and $R^{14'}$ are as defined above. Compounds of formula (IIIa), (IIIb), (IIIc), (IIId), (IIIe), (IIIf), (IIIg), (IIIh), (IIIi), (IIIj), (IIIk), (IIIl), (IIIm), and (IIIn) are preferred. Compounds of formula (IIIa), (IIIb), (IIId), (IIIf), (IIIh), (IIIi), (IIIj) and (IIIm) are more preferred. Compounds of formula (IIIb), (IIId) and (IIIj) are most preferred.

$R^1$ is preferably H, $C_1$-$C_{25}$alkoxy, or $C_1$-$C_{25}$alkyl; more preferred hydrogen, or $C_1$-$C_{25}$alkyl, most preferred hydrogen.

$R^{1'}$ is preferably H, $C_1$-$C_{25}$alkoxy, or $C_1$-$C_{25}$alkyl; more preferred hydrogen, or $C_1$-$C_{25}$alkyl, most preferred hydrogen.

$R^{1''}$ is preferably H, $C_1$-$C_{25}$alkoxy, or $C_1$-$C_{25}$alkyl; more preferred hydrogen, or $C_1$-$C_{25}$alkyl, most preferred hydrogen.

$R^2$ is preferably H, $C_1$-$C_{25}$alkoxy, or $C_1$-$C_{25}$alkyl; more preferred hydrogen, or $C_1$-$C_{25}$alkyl, most preferred hydrogen.

Among compounds of formula (IIIa) to (IIIn) compounds are more preferred, wherein $R^{14}$ and $R^{14'}$ are hydrogen. $R^{13}$ and $R^{13'}$ may be different, but are preferably the same and are selected from $C_1$-$C_{25}$alkyl, $C_2$-$C_{25}$alkenyl, $C_2$-$C_{25}$alkenyl, which may optionally be interrupted by one or more oxygen atoms and/or is optionally substituted by a group $E^{Si}$ or one or more halogen atoms, especially F; $C_6$-$C_{18}$aryl; $C_6$-$C_{18}$aryl which is substituted by halogen, $C_1$-$C_{18}$alkyl, or $C_1$-$C_{18}$alkoxy, or $C_1$-$C_{25}$alkyl, which may optionally be interrupted by one or more oxygen or sulphur atoms and/or is optionally substituted by one or more halogen atoms, especially F; $C_3$-$C_{10}$heteroaryl; $C_3$-$C_{10}$heteroaryl, which is substituted by halogen, $C_1$-$C_{18}$alkyl, or $C_1$-$C_{18}$alkoxy; or $C_1$-$C_{25}$alkyl, which may optionally be interrupted by one or more oxygen atoms and/or is optionally substituted by a group $E^{Si}$ or one or more halogen atoms, especially F. More preferred, $R^{13}$ is $C_1$-$C_{25}$alkyl, or $C_1$-$C_{25}$alkyl, which may optionally be interrupted by one or more oxygen atoms and/or is optionally substituted by a group $E^{Si}$ or one or more fluorine atoms; or phenyl, which may optionally be substituted by one or more $C_1$-$C_{25}$alkyl. Most preferred $R^{13}$ is $C_1$-$C_{25}$alkyl, or phenyl.

$D^{Si}$ is preferably —$SiR^{161}R^{162}$—, wherein $R^{161}$ and $R^{162}$ are independently of each other $C_1$-$C_{25}$alkyl, especially $C_1$-$C_8$alkyl; $C_1$-$C_{25}$haloalkyl, especially $C_1$-$C_8$haloalkyl, such as, for example, —$CF_3$, —$(CH_2)_2CF_3$, —$(CH_2)_2(CF_2)_5$$CF_3$ and —$(CH_2)_2(CF_2)_6CF_3$; $C_2$-$C_{25}$alkenyl, especially $C_2$-$C_8$alkenyl; or phenyl; or —$SiR^{161}R^{162}$—(O—$SiR^{161}R^{162})_d$—, wherein d is 2 to 5 and $R^{161}$ and $R^{162}$ are $C_1$-$C_{25}$alkyl, especially $C_1$-$C_8$alkyl.

$E^{Si}$ is preferably —$SiR^{161}R^{162}R^{163}$. $R^{161}$, $R^{162}$ and $R^{163}$ are independently of each other $C_1$-$C_{25}$alkyl, especially $C_1$-$C_8$alkyl; $C_1$-$C_{25}$haloalkyl, especially $C_1$-$C_8$haloalkyl, such as, for example, —$CF_3$, —$(CH_2)_2CF_3$, —$(CH_2)_2(CF_2)_5$$CF_3$ and —$(CH_2)_2(CF_2)_6CF_3$; $C_2$-$C_{25}$alkenyl, especially $C_2$-$C_8$alkenyl; $C_3$-$C_{12}$cycloalkyl, especially $C_5$-$C_6$cycloalkyl, which might optionally be substituted with $C_1$-$C_4$alkyl; phenyl, —O—$SiR^{164}R^{165}R^{166}$, or —(O—$SiR^{164}R^{165})_d$—$R^{166}$. In case of a group —O—$SiR^{164}R^{165}R^{166}$$R^{164}$, $R^{165}$ and $R^{166}$ are independently of each other $C_1$-$C_8$alkyl, $C_1$-$C_8$haloalkyl, $C_2$-$C_8$alkenyl, or phenyl. In case of a group —(O—$SiR^{164}R^{165})_d$—$R^{166}$$R^{164}$ and $R^{165}$ are independently of each other $C_1$-$C_8$alkyl, $R^{166}$ is $C_1$-$C_8$alkyl, or phenyl and d is an integer of 2 to 5.

More preferably the compound according to the invention is selected from the group consisting of the following compounds of formulae:

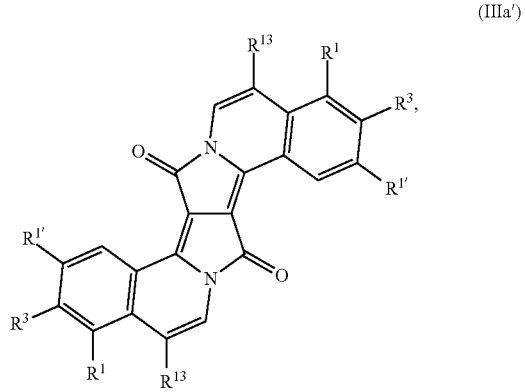

(IIIa')

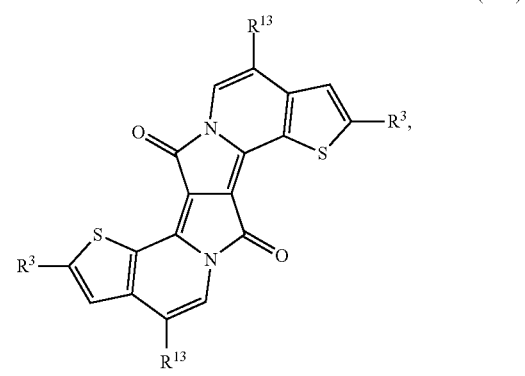

(IIIb')

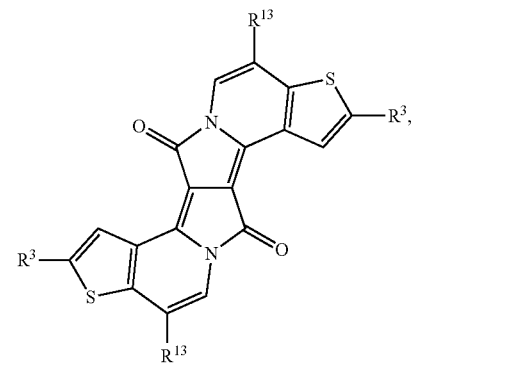

(IIIc')

-continued
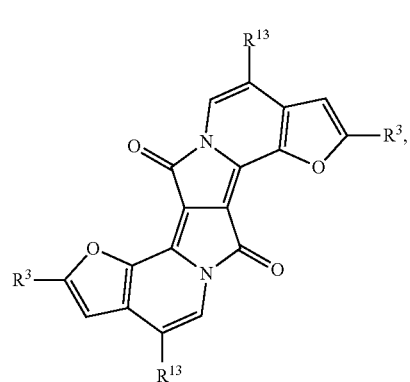
(IIId')
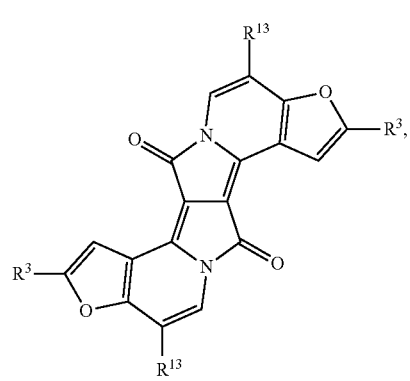
(IIIe')
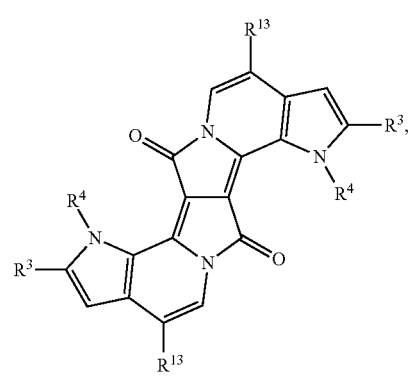
(IIIf')
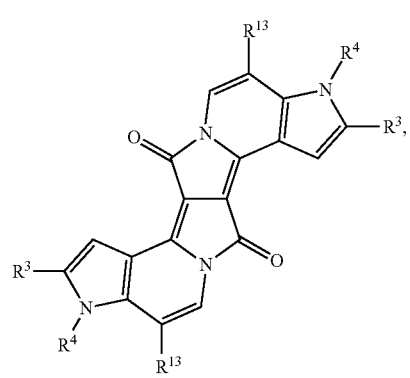
(IIIg')
-continued
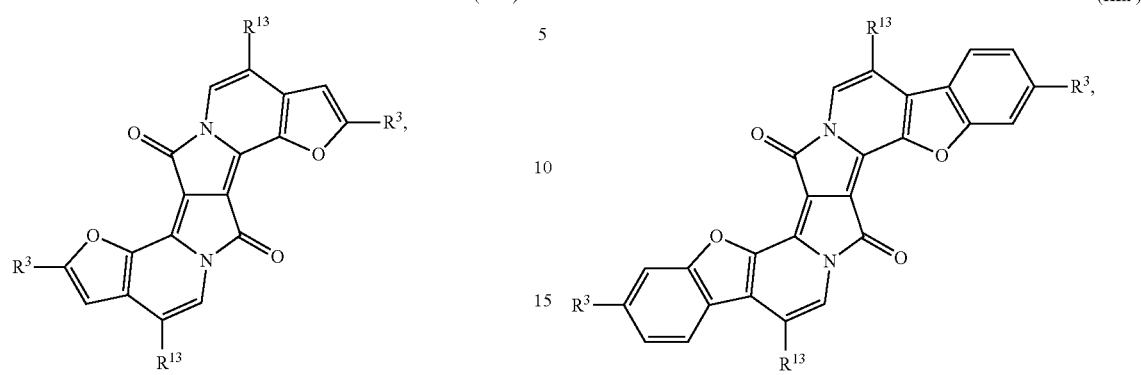
(IIIh')
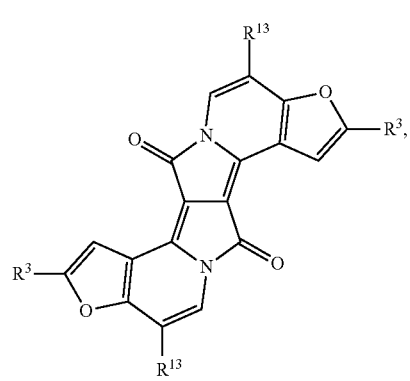
(IIIi')
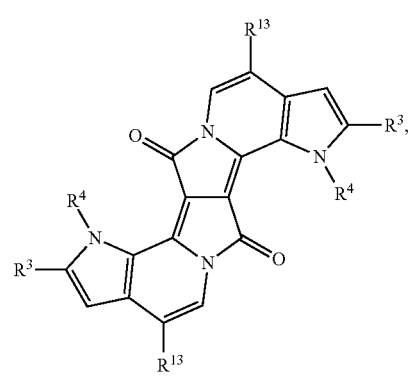
(IIIj')
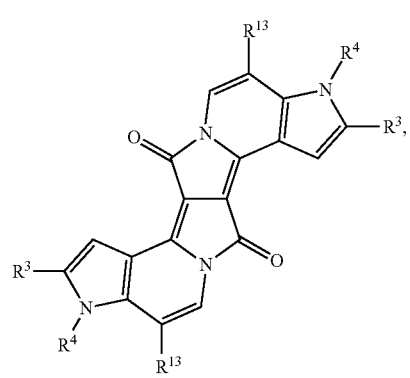
(IIIk')

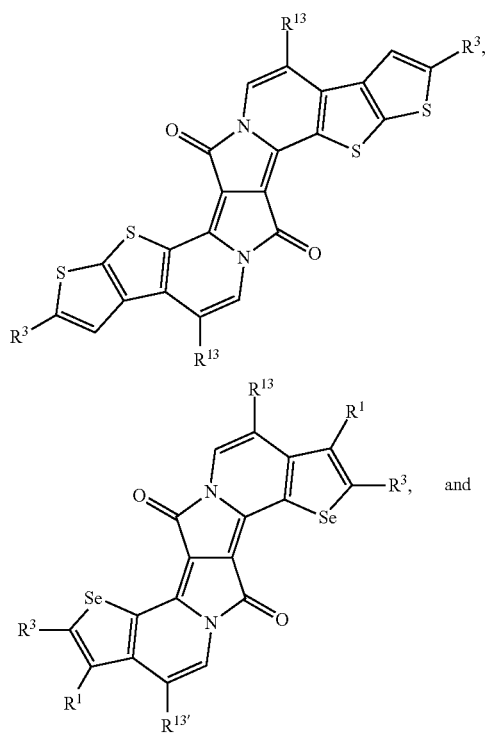
(IIIl')

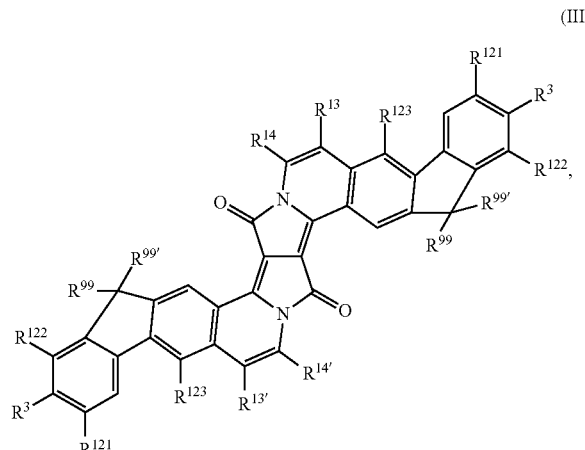
(IIIm') and

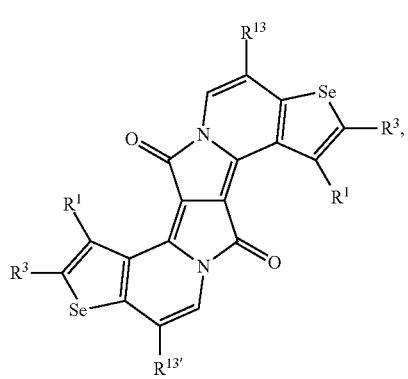
(IIIn')

wherein $R^1$, $R^{1'}$, $R^3$ and $R^4$ are as defined above. Compounds of formula (IIIa'), (IIIb'), (IIIc'), (IIId'), (IIIe'), (IIIf'), (IIIg'), (IIIh'), (IIIi'), (IIIj'), (IIIk'), (IIIl'), (IIIm') and (IIIn') are preferred. Compounds of formula (IIIa'), (IIIb'), (IIId'), (IIIf'), (IIIh'), (IIIi'), (IIIj') and (IIIm') are more preferred. Compounds of formula (IIIb'), (IIId') and (IIIj') are most preferred.

In another preferred embodiment the compound according to the invention is selected from the group consisting of the following compounds of formulae:

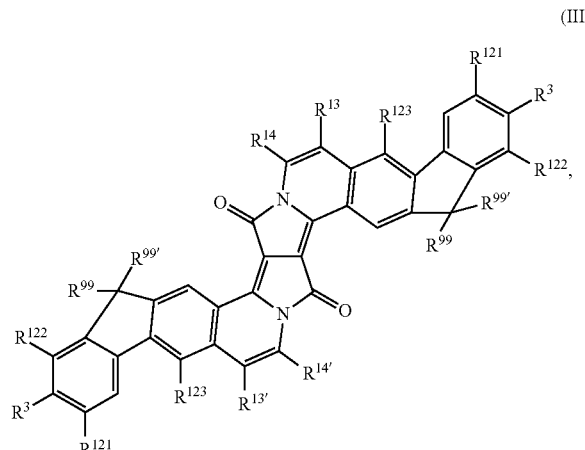
(IIIo)

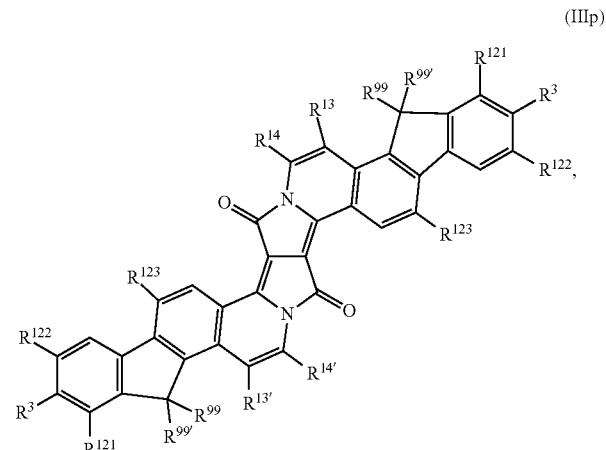
(IIIp)

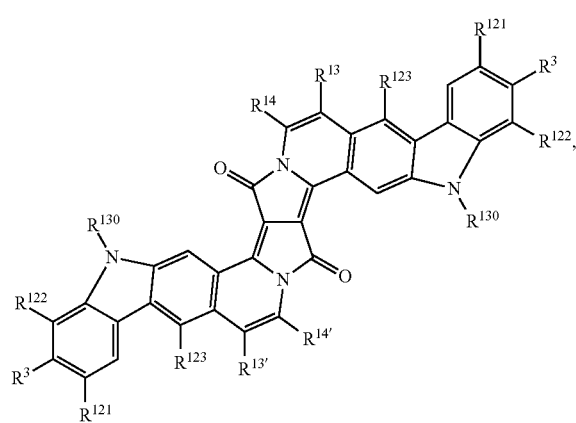
(IIIq)

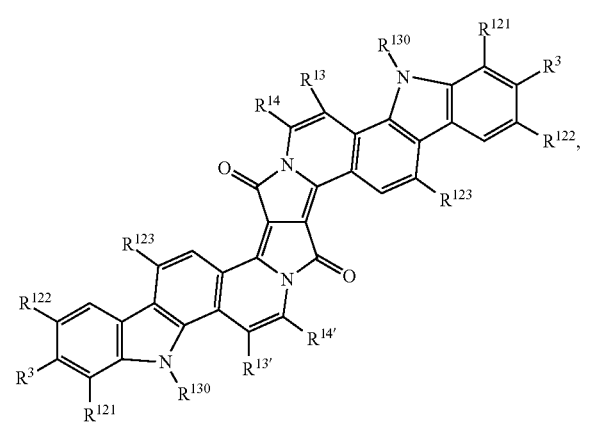
(IIIr)

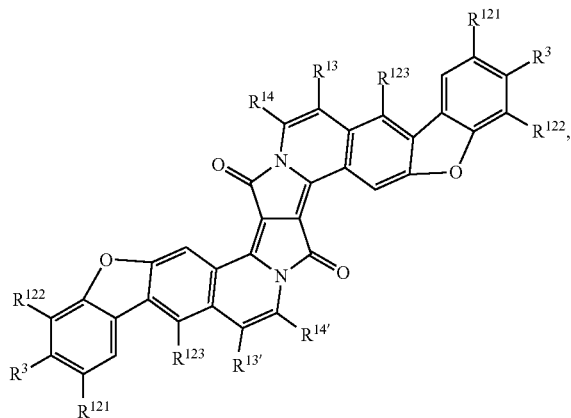
(IIIs)
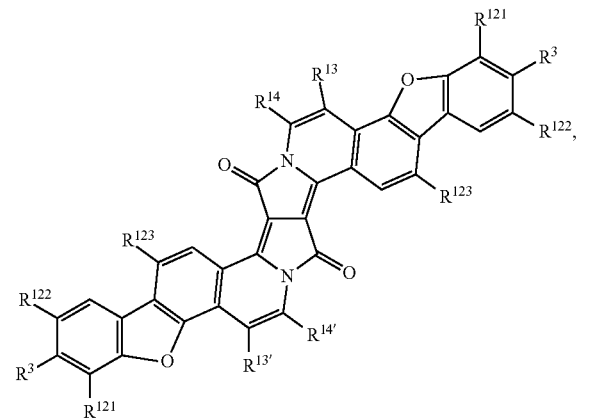
(IIIt)
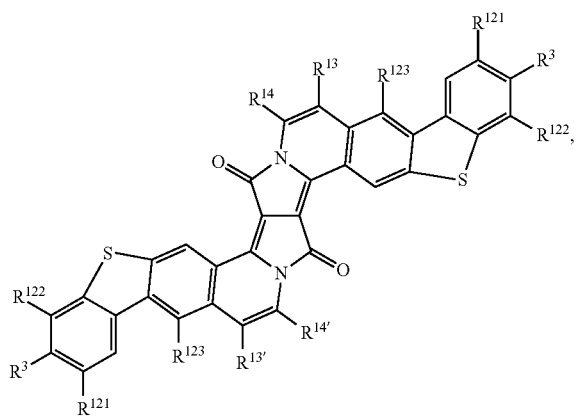
(IIIu)
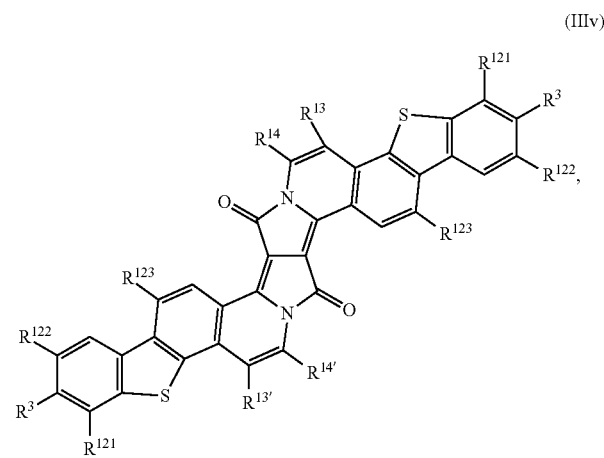
(IIIv)
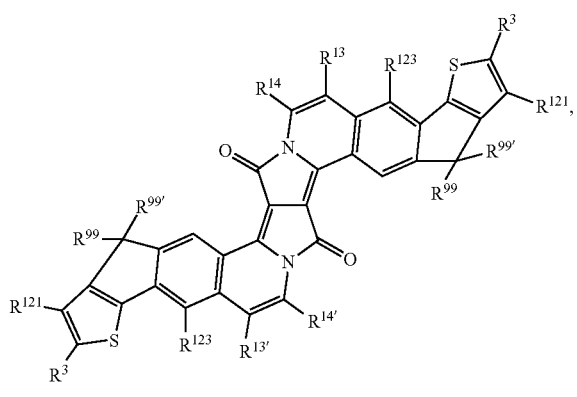
(IIIw)
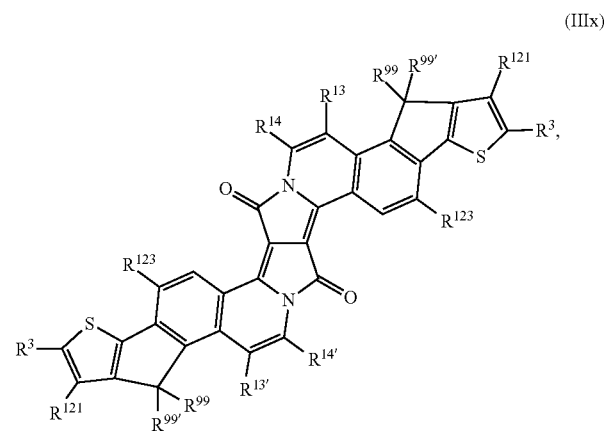
(IIIx)

-continued
(IIIy)
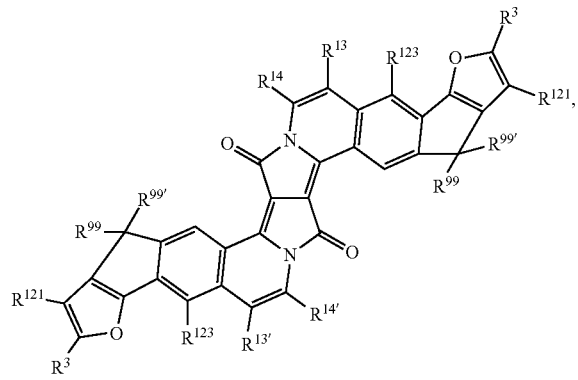
(IIIz)
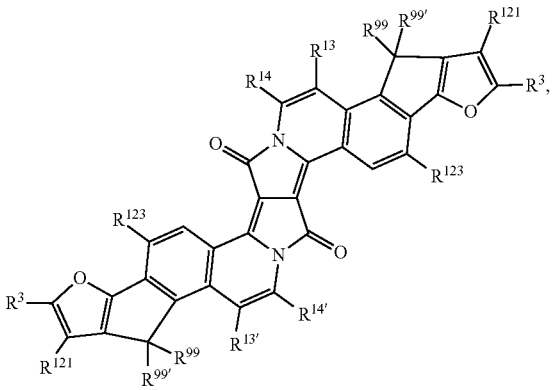
(IIIaa)
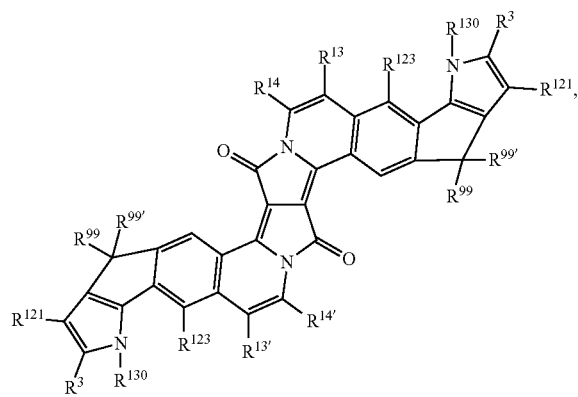
(IIIab)
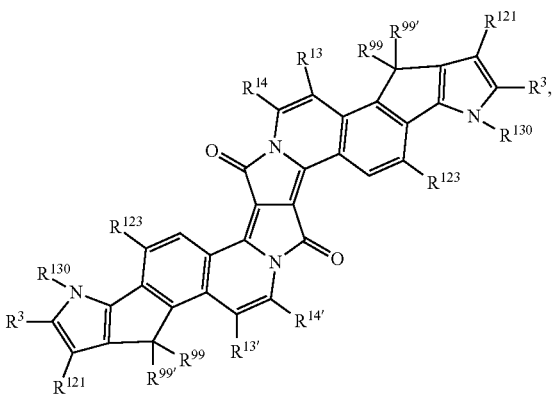
(IIIac)
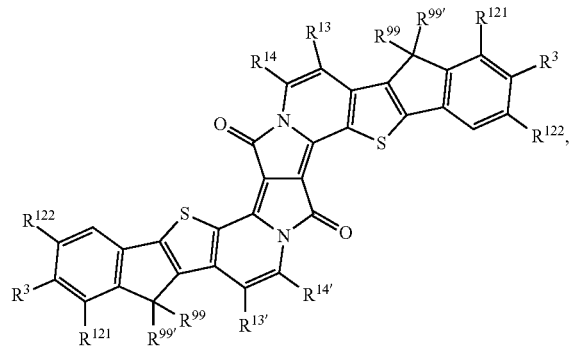
(IIIad)
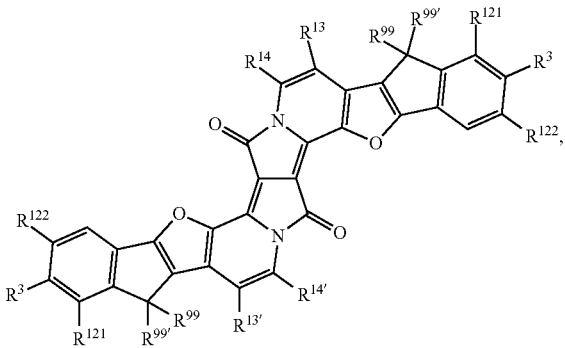
(IIIae)
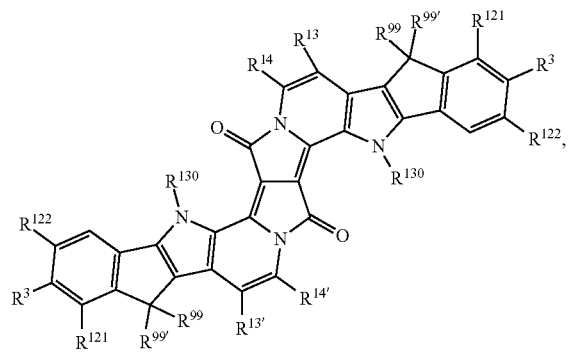
(IIIaf)
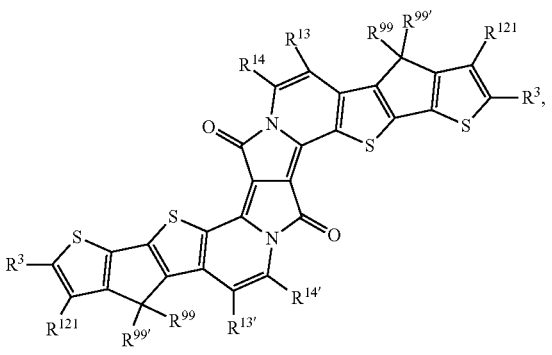

-continued
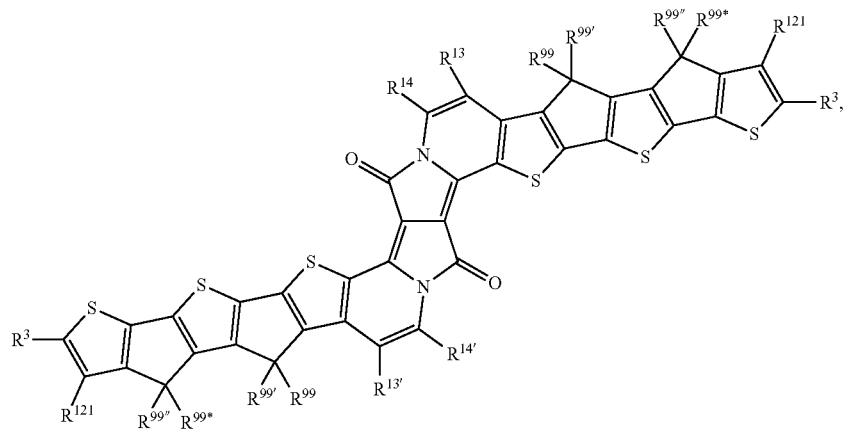
(IIIag)
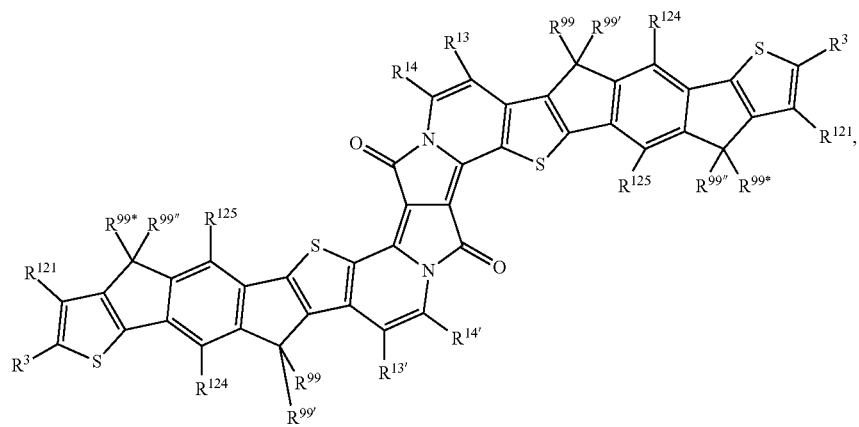
(IIIah)
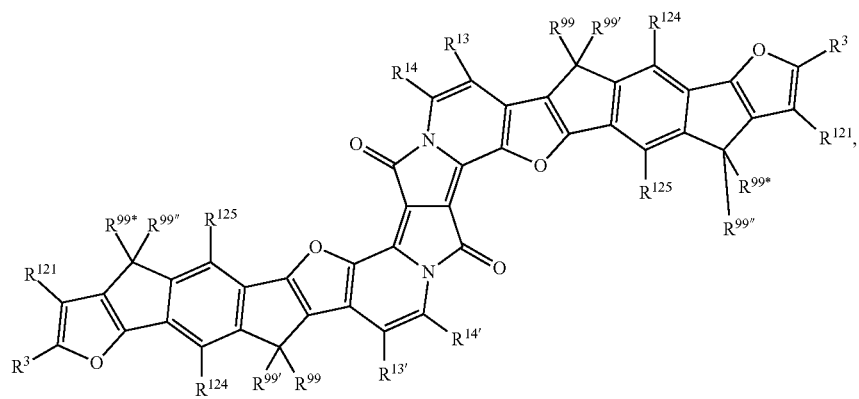
(IIIai)

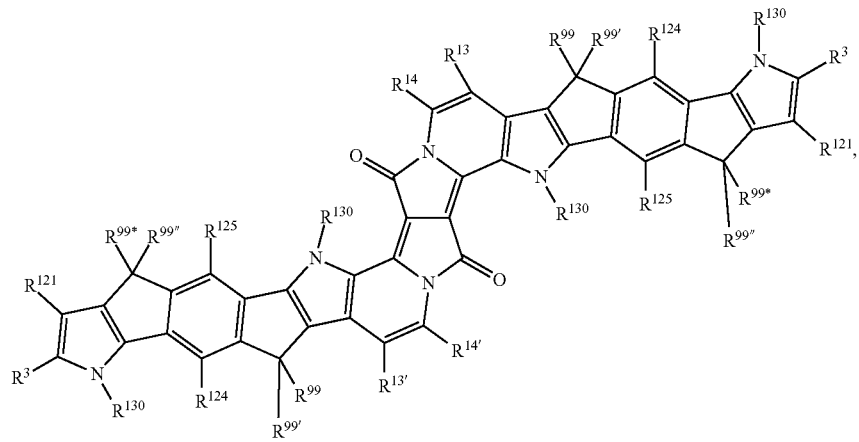
(IIIaj)
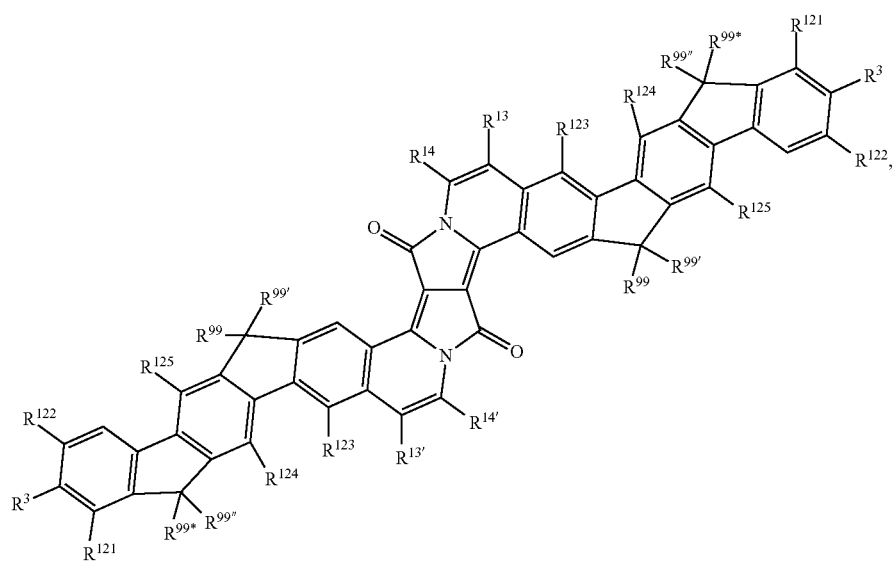
(IIIak)
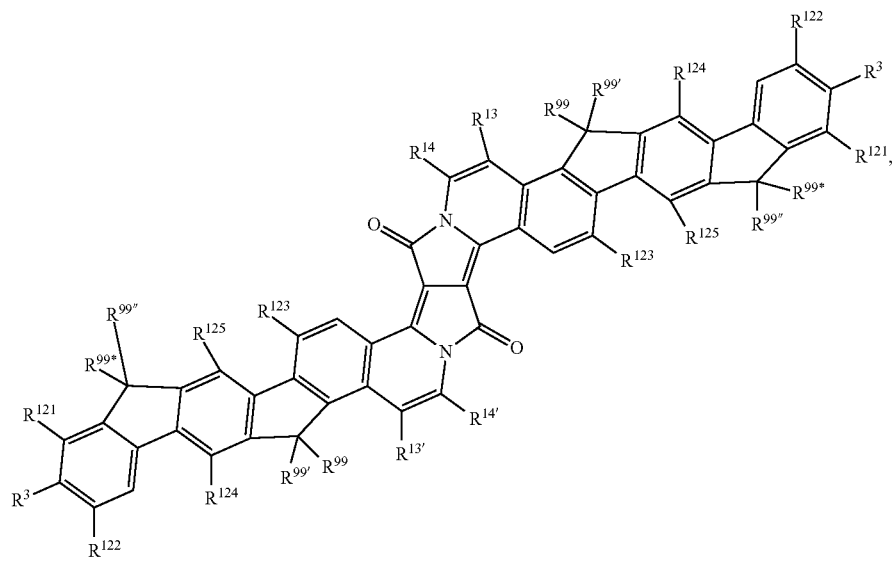
(IIIal)

-continued

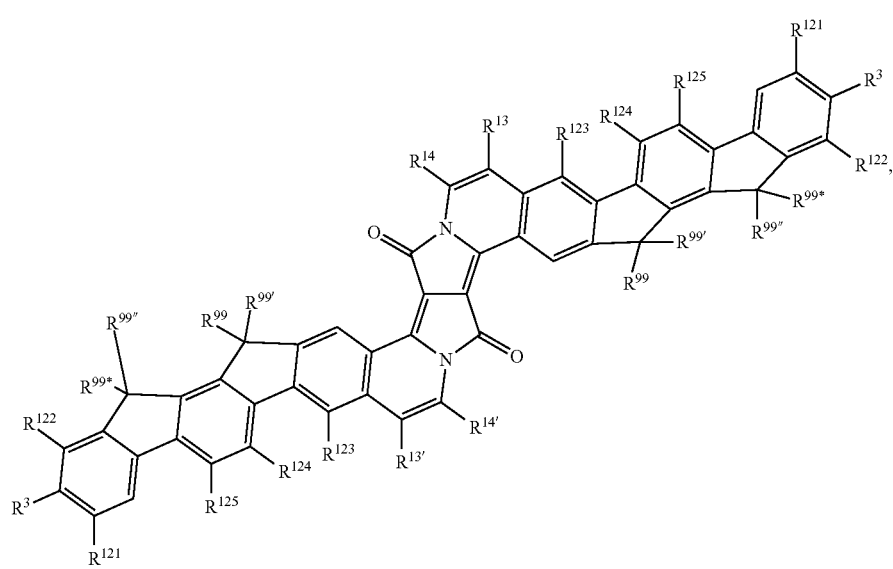
(IIIam)

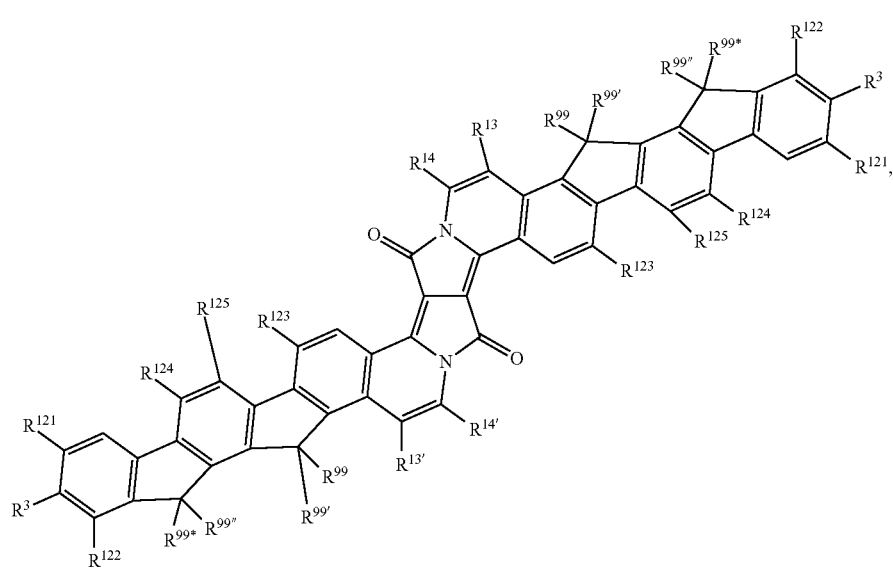
(IIIan)

wherein
$R^{13}$, $R^{13'}$, $R^{14}$ and $R^{14'}$ may be the same or different and are selected from hydrogen or a $C_1$-$C_{38}$alkyl group;
$R^{99}$, $R^{99'}$, $R^{99''}$ and $R^{99*}$ are independently of each other hydrogen, $C_1$-$C_{25}$alkyl, or $C_1$-$C_{25}$alkyl interrupted by one or more oxygen atoms; preferably $C_3$-$C_{25}$alkyl, or $C_3$-$C_{25}$alkyl which is interrupted by one or more oxygen atoms;
$R^{121}$, $R^{122}$, $R^{123}$, $R^{124}$ and $R^{125}$ are independently of each other hydrogen, halogen, $C_1$-$C_{18}$alkoxy or $C_1$-$C_{25}$alkyl; preferably hydrogen;
$R^{130}$ is hydrogen, $C_6$-$C_{18}$aryl; $C_6$-$C_{18}$aryl which is substituted by $C_1$-$C_{18}$alkyl, halogen, especially F; or $C_1$-$C_{18}$alkoxy; $C_1$-$C_{25}$alkyl, which may optionally be interrupted by one or more oxygen or sulphur atoms and/or is optionally substituted by one or more halogen atoms, especially F; or $C_7$-$C_{25}$arylalkyl; and $R^3$ is as defined above.
$R^{99}$, $R^{99'}$, $R^{99''}$ and $R^{99*}$ are independently of each other hydrogen, $C_1$-$C_{25}$alkyl, or $C_1$-$C_{25}$alkyl substituted with one or more halogen atoms and/or interrupted by one or more oxygen atoms, or two moieties $R^{99}$ and $R^{99'}$ or $R^{99''}$ and $R^{99*}$ can form a 5 or 6 membered alkyl ring, which optionally can be substituted with one or more halogen atoms and/or interrupted by one or more oxygen atoms. Preferably $R^{99}$, $R^{99'}$, $R^{99''}$ and $R^{99*}$ are independently of each other hydrogen, $C_1$-$C_{25}$alkyl, or $C_1$-$C_{25}$alkyl substituted with one or more halogen atoms and/or interrupted by one or more oxygen atoms. More preferably $R^{99}$, $R^{99'}$, $R^{99''}$ and $R^{99*}$ are independently of each other hydrogen, $C_1$-$C_{25}$alkyl, or $C_1$-$C_{25}$alkyl interrupted by one or more oxygen atoms. Most preferably $R^{99}$, $R^{99'}$, $R^{99''}$ and $R^{99*}$ are independently of each other $C_3$-$C_{25}$alkyl, or $C_3$-$C_{25}$alkyl interrupted by one or more oxygen atoms.
$R^{121}$, $R^{122}$, $R^{123}$, $R^{124}$ and $R^{125}$ are independently of each other hydrogen, halogen, $C_6$-$C_{18}$aryl; $C_6$-$C_{18}$aryl which is substituted by $C_1$-$C_{18}$alkyl, halogen; or $C_1$-$C_{18}$alkoxy; $C_1$-$C_{25}$alkyl, which may optionally be interrupted by one or more oxygen or sulphur atoms and/or is optionally substituted by one or more halogen atoms, especially F; or $C_7$-$C_{25}$arylalkyl; preferably hydrogen, halogen, $C_1$-$C_{18}$alkoxy or $C_1$-$C_{25}$alkyl; most preferably hydrogen.

Among compounds of formula (IIIo) to (IIIan) compounds are more preferred, wherein $R^{14}$ and $R^{14'}$ are hydrogen. $R^{13}$ and $R^{13'}$ may be different, but are preferably the same and are selected from H, $C_1$-$C_{25}$alkyl, $C_2$-$C_{25}$alkenyl, $C_2$-$C_{25}$alkenyl, which may optionally be interrupted by one or more oxygen atoms and/or is optionally substituted by a group $E^{Si}$ or one or more halogen atoms, especially F; $C_6$-$C_{18}$aryl; $C_6$-$C_{18}$aryl which is substituted by halogen, $C_1$-$C_{18}$alkyl, or $C_1$-$C_{18}$alkoxy, or $C_1$-$C_{25}$alkyl, which may optionally be interrupted by one or more oxygen or sulphur atoms and/or is optionally substituted by one or more halogen atoms, especially F; $C_3$-$C_{10}$heteroaryl; $C_3$-$C_{10}$heteroaryl, which is substituted by halogen, $C_1$-$C_{18}$alkyl, or $C_1$-$C_{18}$alkoxy; or $C_1$-$C_{25}$alkyl, which may optionally be interrupted by one or more oxygen atoms and/or is optionally substituted by a group $E^{Si}$ or one or more halogen atoms, especially F. More preferred, $R^{13}$ is H, $C_1$-$C_{25}$alkyl, or $C_1$-$C_{25}$alkyl, which may optionally be interrupted by one or more oxygen atoms and/or is optionally substituted by a group $E^{Si}$ or one or more fluorine atoms or phenyl, which may optionally be substituted by one or more $C_1$-$C_{25}$alkyl. Most preferred $R^{13}$ is $C_1$-$C_{25}$alkyl or phenyl. In another preferred embodiment $R^{13}$, $R^{13'}$, $R^{14}$ and $R^{14'}$ in the compounds of formula (IIIo) to (IIIan) are hydrogen.

Preferably, $R^1$, $R^{1'}$ and $R^{1''}$ are independently of each other H, $C_1$-$C_{25}$alkoxy, or $C_1$-$C_{25}$alkyl. More preferred, $R^1$, $R^{1'}$ and $R^{1''}$ are independently of each other hydrogen, or $C_1$-$C_{25}$alkyl, most preferred hydrogen.

Preferably, $R^2$ is H, $C_1$-$C_{25}$alkoxy, or $C_1$-$C_{25}$alkyl. More preferred, $R^2$ is hydrogen, or $C_1$-$C_{25}$alkyl. Most preferred $R^2$ is hydrogen.

Preferably, $R^3$ is H, F, trifluoromethyl, cyano, $C_1$-$C_{25}$alkyl, a group of formula

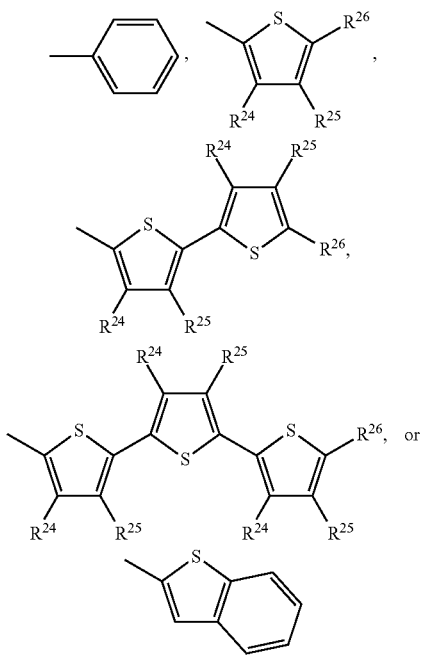

wherein $R^{24}$ to $R^{26}$ are as defined above and are preferably H, or $C_1$-$C_{25}$alkyl, more preferably H. More preferred, $R^3$ is H, F, cyano, $C_1$-$C_{25}$alkyl,

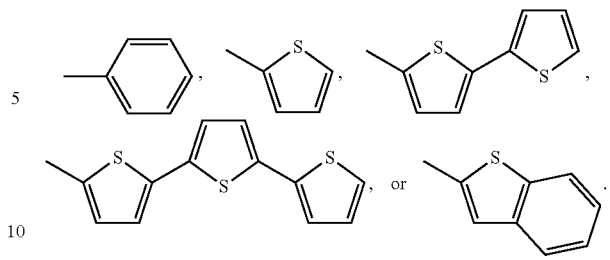

Most preferred, $R^3$ is H,

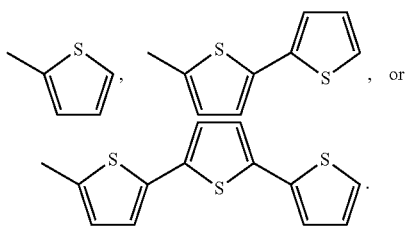

In a preferred embodiment the present invention is directed to compounds of formula (IIIa), (IIIb), (IIIc), (IIId), (IIIe), (IIIf), (IIIg), (IIIh), (IIIi), (IIIj), (IIIk), (IIIl), (IIIm) and (IIIn), especially (IIIa), (IIIb), (IIId), (IIIf), (IIIh), (IIIi), (IIIj) and (IIIm), very especially (IIIb), (IIId) and (IIIj); wherein $R^1$, $R^{1'}$ and $R^{1''}$ are independently of each other H, $C_1$-$C_{25}$alkoxy, or $C_1$-$C_{25}$alkyl, $R^2$ is H, $C_1$-$C_{25}$alkoxy, or $C_1$-$C_{25}$alkyl, $R^3$ is H, F, trifluoromethyl, cyano, $C_1$-$C_{25}$alkyl, a group of formula

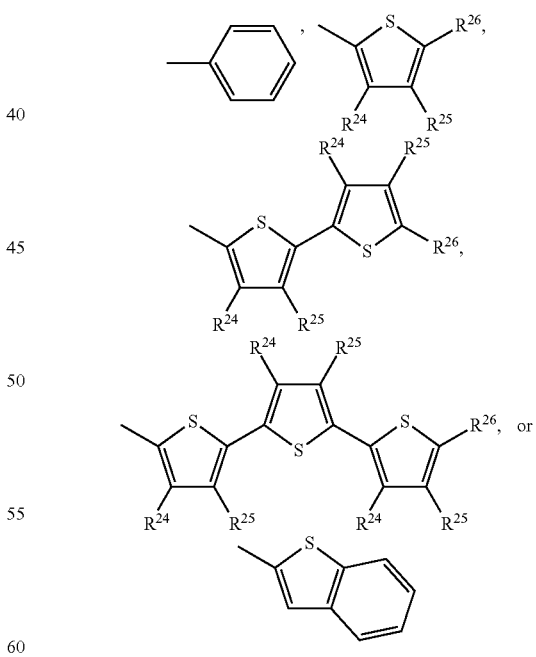

wherein $R^{24}$ to $R^{26}$ are as defined above, $R^4$ is hydrogen, or $C_1$-$C_{25}$alkyl, which may optionally be interrupted by one or more oxygen or sulphur atoms, and X is O, S, or Se. $R^{24}$ to $R^{26}$ are preferably H, or $C_1$-$C_{25}$alkyl. $R^{14}$ and $R^{14'}$ are H. $R^{13}$ is $C_1$-$C_{25}$alkyl, $C_2$-$C_{25}$alkenyl, $C_2$-$C_{25}$alkenyl, which may optionally be interrupted by one or more oxygen atoms and/or is optionally substituted by a group $E^{Si}$ or one or more halogen atoms, especially F; $C_3$-$C_{10}$heteroaryl; $C_3$-$C_{10}$heteroaryl, which is substituted by halogen, $C_1$-$C_{18}$alkyl, or $C_1$-$C_{18}$alkoxy; or $C_1$-$C_{25}$alkyl, which may optionally be interrupted by one or more oxygen atoms and/or is optionally substituted by a group $E^{Si}$ or one or more halogen atoms, especially F. More preferred, $R^{13}$ is $C_1$-$C_{25}$alkyl, or $C_1$-$C_{25}$alkyl, which may optionally be interrupted by one or more oxygen atoms and/or is optionally substituted by a group $E^{Si}$ or one or more fluorine atoms. Most preferred $R^{13}$ is $C_1$-$C_{25}$alkyl.

$D^{Si}$ is preferably —Si$R^{161}R^{162}$—, wherein $R^{161}$ and $R^{162}$ are independently of each other $C_1$-$C_{25}$alkyl, especially $C_1$-$C_8$alkyl; $C_1$-$C_{25}$haloalkyl, especially $C_1$-$C_8$haloalkyl, such as, for example, —$CF_3$, —$(CH_2)_2CF_3$, —$(CH_2)_2(CF_2)_5CF_3$ and —$(CH_2)_2(CF_2)_6CF_3$; $C_2$-$C_{25}$alkenyl, especially $C_2$-$C_8$alkenyl; or phenyl; or —Si$R^{161}R^{162}$—(O—Si$R^{161}R^{162})_d$—, wherein d is 2 to 5 and $R^{161}$ and $R^{162}$ are $C_1$-$C_{25}$alkyl, especially $C_1$-$C_8$alkyl.

$E^{Si}$ is preferably —Si$R^{161}R^{162}R^{163}$. $R^{161}$, $R^{162}$ and $R^{163}$ are independently of each other $C_1$-$C_{25}$alkyl, especially $C_1$-$C_8$alkyl; $C_1$-$C_{25}$haloalkyl, especially $C_1$-$C_8$haloalkyl, such as, for example, —$CF_3$, —$(CH_2)_2CF_3$, —$(CH_2)_2(CF_2)_5CF_3$ and —$(CH_2)_2(CF_2)_6CF_3$; $C_2$-$C_{25}$alkenyl, especially $C_2$-$C_8$alkenyl; $C_3$-$C_{12}$cycloalkyl, especially $C_5$-$C_6$cycloalkyl, which might optionally be substituted with $C_1$-$C_4$alkyl; phenyl, —O—Si$R^{164}R^{165}R^{166}$, or —(O—Si$R^{164}R^{165})_d$—$R^{166}$. In case of a group —O—Si$R^{164}R^{165}R^{166}R^{164}$, $R^{165}$ and $R^{166}$ are independently of each other $C_1$-$C_8$alkyl, $C_1$-$C_8$haloalkyl, $C_2$-$C_8$alkenyl, or phenyl. In case of a group —(O—Si$R^{164}R^{165})_d$—$R^{166}R^{164}$ and $R^{165}$ are independently of each other $C_1$-$C_8$alkyl, $R^{166}$ is $C_1$-$C_{58}$alkyl, or phenyl and d is an integer of 2 to 5.

In a more preferred embodiment the present invention is directed to compounds of formula (IIIa), (IIIb), (IIIc), (IIId), (IIIe), (IIIf), (IIIg), (IIIh), (IIIi), (IIIj), (IIIk), (IIIl), (IIIm) and (IIIn), especially (IIIa), (IIIb), (IIId), (IIIf), (IIIh), (IIIi), (IIIj) and (IIIm), very especially (IIIb), (IIId) and (IIIj); $R^1$, $R^{1'}$ and $R^{1''}$ are independently of each other hydrogen, or $C_1$-$C_{25}$alkyl, especially hydrogen; $R^2$ is hydrogen, or $C_1$-$C_{25}$alkyl, especially hydrogen, $R^3$ is H, F, cyano, $C_1$-$C_{25}$alkyl,

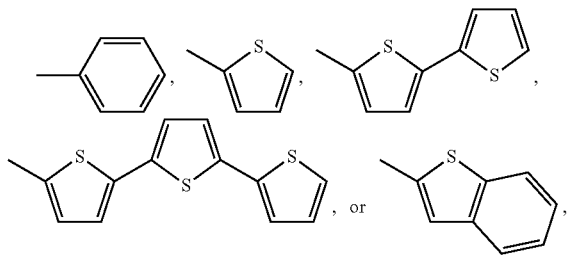

especially cyano,

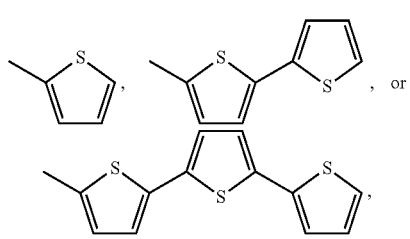

$R^4$ is $C_1$-$C_{25}$alkyl; and X is O, or S, especially S. $R^{14}$ and $R^{14'}$ are H. $R^{13}$ is $C_1$-$C_{25}$alkyl, or $C_1$-$C_{25}$alkyl, which may optionally be interrupted by one or more oxygen atoms and/or is optionally substituted by a group $E^{Si}$ or one or more fluorine atoms. More preferred $R^{13}$ is $C_1$-$C_{25}$alkyl.

$D^{Si}$ is preferably —Si$R^{161}R^{162}$—, wherein $R^{161}$ and $R^{162}$ are independently of each other $C_1$-$C_{25}$alkyl, especially $C_1$-$C_8$alkyl; $C_1$-$C_{25}$haloalkyl, especially $C_1$-$C_8$haloalkyl, such as, for example, —$CF_3$, —$(CH_2)_2CF_3$, —$(CH_2)_2(CF_2)_5CF_3$ and —$(CH_2)_2(CF_2)_6CF_3$; $C_2$-$C_{25}$alkenyl, especially $C_2$-$C_8$alkenyl; or phenyl; or —Si$R^{161}R^{162}$—(O—Si$R^{161}R^{162})_d$—, wherein d is 2 to 5 and $R^{161}$ and $R^{162}$ are $C_1$-$C_{25}$alkyl, especially $C_1$-$C_8$alkyl.

In a preferred embodiment the present invention is directed to compounds of formula (IIIo), (IIIp), (IIIq), (IIIr), (IIIs), (IIIt), (IIIu), (IIIv), (IIIw), (IIIx), (IIIy), (IIIz), (IIIaa), (IIIab), (IIIac), (IIIad), (IIIae), (IIIaf), (IIIag), (IIIah), (IIIai), (IIIaj), (IIIak), (IIIal), (IIIam), or (IIIan), especially (IIIo), (IIIw), (IIIx), (IIIy), (IIIz), (IIIac), (IIIad), (IIIaf), (IIIag), (IIIah), (IIIai), (IIIak), (IIIal), (IIIam), or (IIIan), very especially (IIIo), (IIIw), (IIIac), (IIIaf), (IIIag), (IIIah), (IIIak), or (IIIam), wherein $R^3$ is H, F, trifluoromethyl, cyano, $C_1$-$C_{25}$alkyl, a group of formula

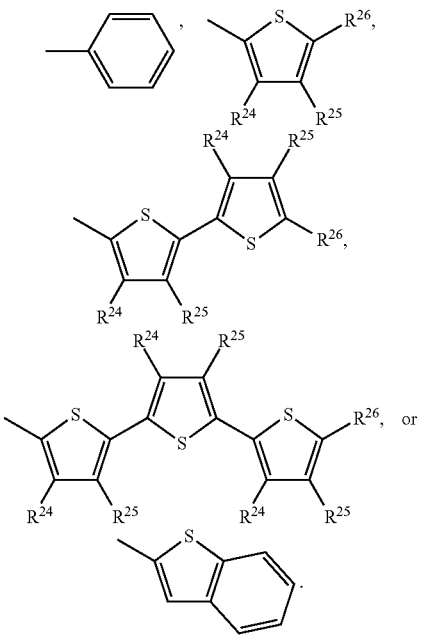

$R^{24}$ to $R^{26}$ are as defined above, $R^4$ is hydrogen, or $C_1$-$C_{25}$alkyl, which may optionally be interrupted by one or more oxygen or sulphur atoms, and X is O, S, or Se. $R^{24}$ to $R^{26}$ are preferably H, or $C_1$-$C_{25}$alkyl. $R^{99}$, $R^{99'}$, $R^{99''}$ and $R^{99*}$ are independently of each other $C_3$-$C_{25}$alkyl, or $C_3$-$C_{25}$alkyl interrupted by one or more oxygen atoms. $R^{121}$, $R^{122}$, $R^{123}$, $R^{124}$ and $R^{125}$ are independently of each other hydrogen, halogen, $C_1$-$C_{18}$alkoxy or $C_1$-$C_{25}$alkyl; most preferably hydrogen.

$R^{130}$ is $C_1$-$C_{25}$alkyl.

In a more preferred embodiment the present invention is directed to compounds of formula (IIIo), (IIIw), (IIIx), (IIIy), (IIIz), (IIIac), (IIIad), (IIIaf), (IIIag), (IIIah), (IIIai), (IIIak), (IIIal), (IIIam), or (IIIan), especially (IIIo), (IIIw), (IIIac), (IIIaf), (IIIag), (IIIah), (IIIak), or (IIIam), very especially (IIIo), (IIIaf), or (IIIah), wherein $R^3$ is H, F, cyano, $C_1$-$C_{25}$alkyl,

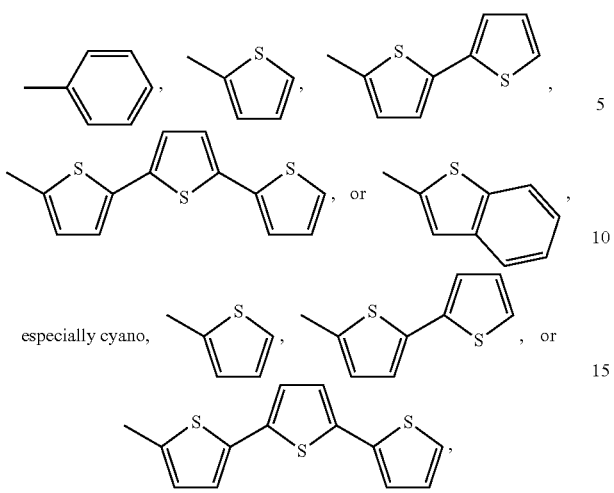

especially cyano, $R^{99}$, $R^{99'}$, $R^{99''}$ and $R^{99*}$ are independently of each other $C_3$-$C_{25}$alkyl, or $C_3$-$C_{25}$alkyl interrupted by one or more oxygen atoms.

$R^{121}$, $R^{122}$, $R^{123}$, $R^{124}$ and $R^{125}$ are independently of each other hydrogen, halogen, $C_1$-$C_{18}$alkoxy or $C_1$-$C_{25}$alkyl; most preferably hydrogen.

$R^{130}$ is $C_1$-$C_{25}$alkyl. Compounds of formula (IIIo) are most preferred.

Examples of compounds according to the invention are shown below:

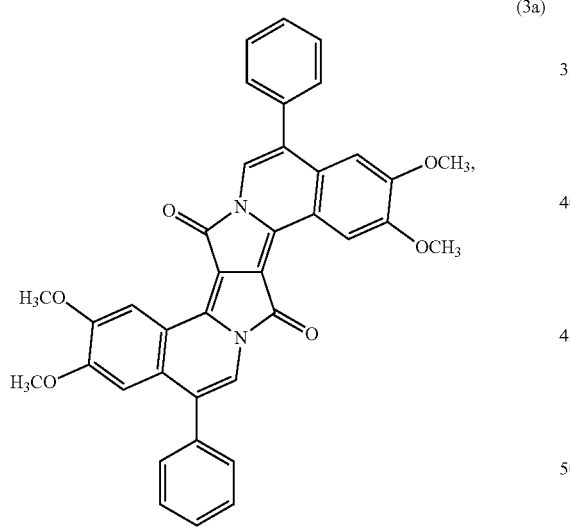

(3a)

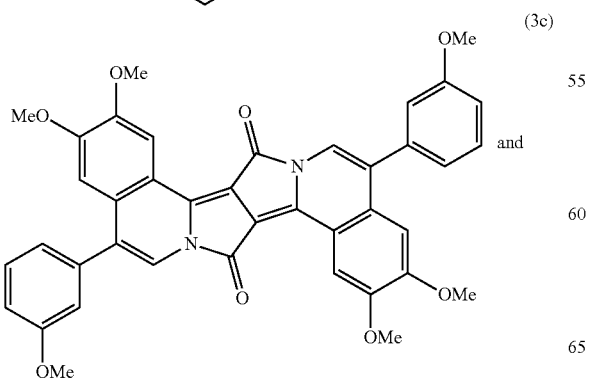

(3c)

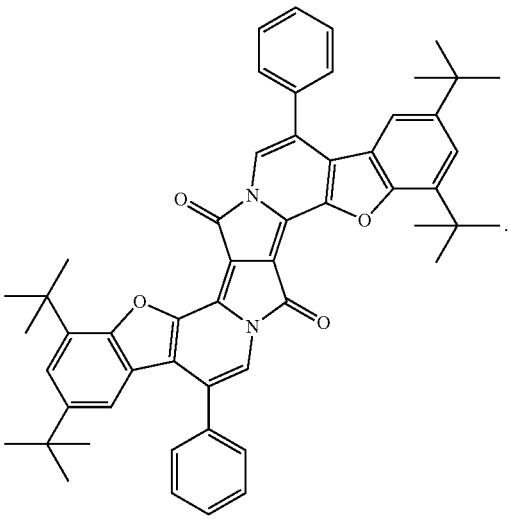

(3d)

Preferably the compound according to the invention is selected from the group consisting of the following compounds of formulae:

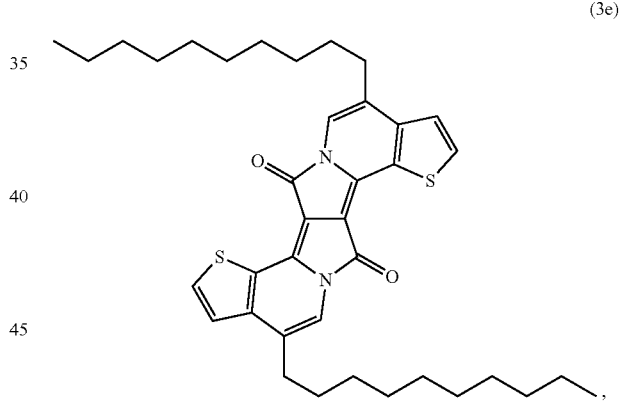

(3e)

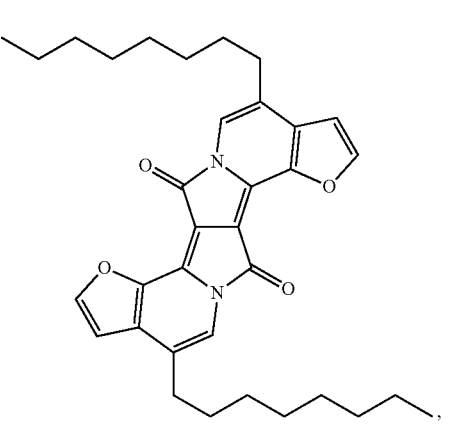

(3f)

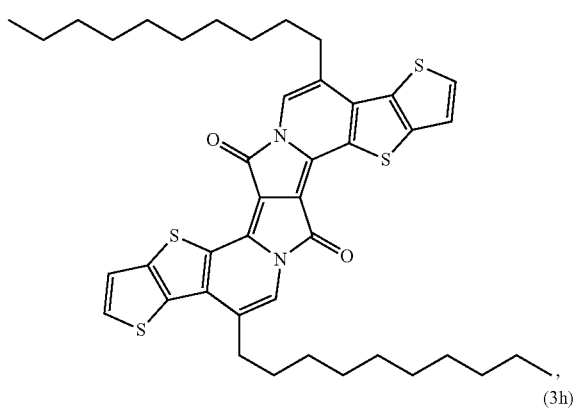
(3g)

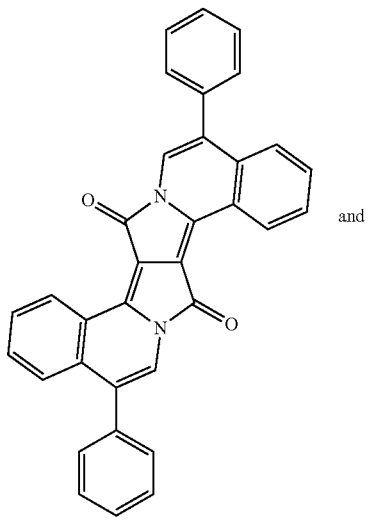
(3h)

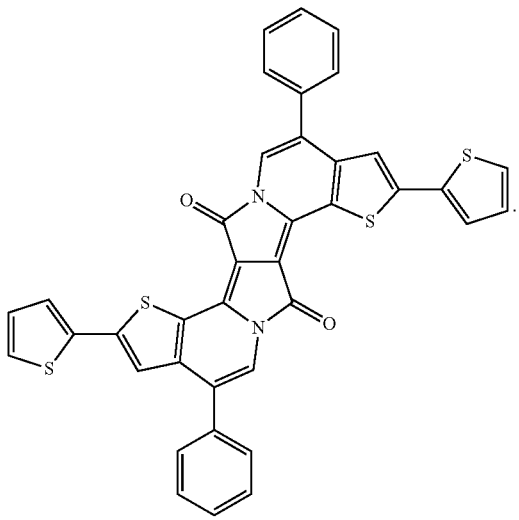
(3i)

In another preferred embodiment the present invention is directed to compounds of formula (IIIa), (IIIb), (IIIc), (IIId), (IIIe), (IIIf), (IIIg), (IIIh), (IIIi), (IIIj), (IIIk), (IIIl), (IIIm) and (IIIn), especially (IIIa), (IIIb), (IIId), (IIIf), (IIIh), (IIIi), (IIIj) and (IIIm), very especially (IIIb), (IIId) and (IIIj); wherein $R^1$, $R^{1'}$ and $R^{1''}$ are independently of each other H, $C_1$-$C_{25}$alkoxy, or $C_1$-$C_{25}$alkyl, $R^2$ is H, $C_1$-$C_{25}$alkoxy, or $C_1$-$C_{25}$alkyl, $R^3$ is a group of formula —$NA^1A^{1'}$, or a group

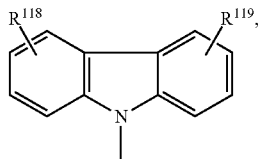

wherein $A^1$ and $A^{1'}$ are independently of each other,

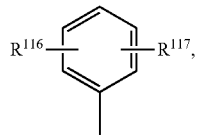

$R^{116}$ and $R^{119}$ are independently of each other hydrogen, or $C_1$-$C_{18}$alkyl. $R^{118}$ and $R^{117}$ are independently of each other $C_1$-$C_{18}$alkoxy, especially hydrogen, or $C_1$-$C_{18}$alkyl. $R^4$ is hydrogen, or $C_1$-$C_{25}$alkyl, which may optionally be interrupted by one or more oxygen or sulphur atoms, and X is O, S, or Se. $R^{24}$ to $R^{26}$ are preferably H, or $C_1$-$C_{25}$alkyl. $R^{14}$ and $R^{14'}$ are H. $R^{13}$ is $C_1$-$C_{25}$alkyl, $C_2$-$C_{25}$alkenyl, $C_2$-$C_{25}$alkenyl, which may optionally be interrupted by one or more oxygen atoms and/or is optionally substituted by a group $E^{Si}$ or one or more halogen atoms, especially F; $C_3$-$C_{10}$heteroaryl; $C_3$-$C_{10}$heteroaryl, which is substituted by halogen, $C_1$-$C_{18}$alkyl, or $C_1$-$C_{18}$alkoxy; or $C_1$-$C_{25}$alkyl, which may optionally be interrupted by one or more oxygen atoms and/or is optionally substituted by a group $E^{Si}$ or one or more halogen atoms, especially F. More preferred, $R^{13}$ is $C_1$-$C_{25}$alkyl, or $C_1$-$C_{25}$alkyl, which may optionally be interrupted by one or more oxygen atoms and/or is optionally substituted by a group $E^{Si}$ or one or more fluorine atoms. Most preferred $R^{13}$ is $C_1$-$C_{25}$alkyl.

$D^{Si}$ is preferably —$SiR^{161}R^{162}$—, wherein $R^{161}$ and $R^{162}$ are independently of each other $C_1$-$C_{25}$alkyl, especially $C_1$-$C_8$alkyl; $C_1$-$C_{25}$haloalkyl, especially $C_1$-$C_8$haloalkyl, such as, for example, —$CF_3$, —$(CH_2)_2CF_3$, —$(CH_2)_2(CF_2)_5CF_3$ and —$(CH_2)_2(CF_2)_6CF_3$; $C_2$-$C_{25}$alkenyl, especially $C_2$-$C_8$alkenyl; or phenyl; or —$SiR^{161}R^{162}$—(O—$SiR^{161}R^{162})_d$—, wherein d is 2 to 5 and $R^{161}$ and $R^{162}$ are $C_1$-$C_{25}$alkyl, especially $C_1$-$C_8$alkyl.

$E^{Si}$ is preferably —$SiR^{161}R^{162}R^{163}$. $R^{161}$, $R^{162}$ and $R^{163}$ are independently of each other $C_1$-$C_{25}$alkyl, especially $C_1$-$C_8$alkyl; $C_1$-$C_{25}$haloalkyl, especially $C_1$-$C_8$haloalkyl, such as, for example, —$CF_3$, —$(CH_2)_2CF_3$, —$(CH_2)_2(CF_2)_5CF_3$ and —$(CH_2)_2(CF_2)_6CF_3$; $C_2$-$C_{25}$alkenyl, especially $C_2$-$C_8$alkenyl; $C_3$-$C_{12}$cycloalkyl, especially $C_5$-$C_6$cycloalkyl, which might optionally be substituted with $C_1$-$C_4$alkyl; phenyl, —O—$SiR^{164}R^{165}R^{166}$, or —(O—$SiR^{164}R^{165})_d$—$R^{166}$. In case of a group —O—$SiR^{164}R^{165}R^{166}R^{164}$, $R^{165}$ and $R^{166}$ are independently of each other $C_1$-$C_8$alkyl, $C_1$-$C_8$haloalkyl, $C_2$-$C_8$alkenyl, or phenyl. In case of a group —(O—$SiR^{164}R^{165})_d$—$R^{166}R^{164}$ and $R^{165}$ are independently of each other $C_1$-$C_8$alkyl, $R^{166}$ is $C_1$-$C_8$alkyl, or phenyl and d is an integer of 2 to 5.

In another preferred embodiment the present invention is directed to compounds of formula (IIIo), (IIIp), (IIIq), (IIIr), (IIIs), (IIIt), (IIIu), (IIIv), (IIIw), (IIIx), (IIIy), (IIIz), (IIIaa), (IIIab), (IIIac), (IIIad), (IIIae), (IIIaf), (IIIag), (IIIah), (IIIai), (IIIaj), (IIIak), (IIIal), (IIIam), or (IIIan), especially (IIIo), (IIIw), (IIIx), (IIIy), (IIIz), (IIIac), (IIIad), (IIIaf), (IIIag), (IIIah), (IIIai), (IIIak), (IIIal), (IIIam), or (IIIan), very especially (IIIo), (IIIw), (IIIac), (IIIaf), (IIIag), (IIIah), (IIIak), or (IIIam); wherein $R^3$ is a group of formula —$NA^1A^{1'}$, or a group or a group

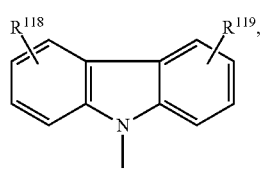

wherein
A¹ and A¹' are independently of each other

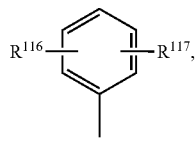

$R^{116}$ and $R^{119}$ are independently of each other hydrogen, $C_1$-$C_{18}$alkoxy, or $C_1$-$C_{18}$alkyl. $R^{118}$ and $R^{117}$ are independently of each other hydrogen, or $C_1$-$C_{18}$alkyl. $R^{24}$ to $R^{26}$ are preferably H, or $C_1$-$C_{25}$alkyl.

$R^{99}$, $R^{99'}$, $R^{99''}$ and $R^{99*}$ are independently of each other $C_3$-$C_{25}$alkyl, or $C_3$-$C_{25}$alkyl interrupted by one or more oxygen atoms.

$R^{121}$, $R^{122}$, $R^{123}$, $R^{124}$ and $R^{125}$ are independently of each other hydrogen, halogen, $C_1$-$C_{18}$alkoxy or $C_1$-$C_{25}$alkyl; most preferably hydrogen.

$R^{130}$ is $C_1$-$C_{18}$alkyl.

Examples of preferred compounds are shown below:

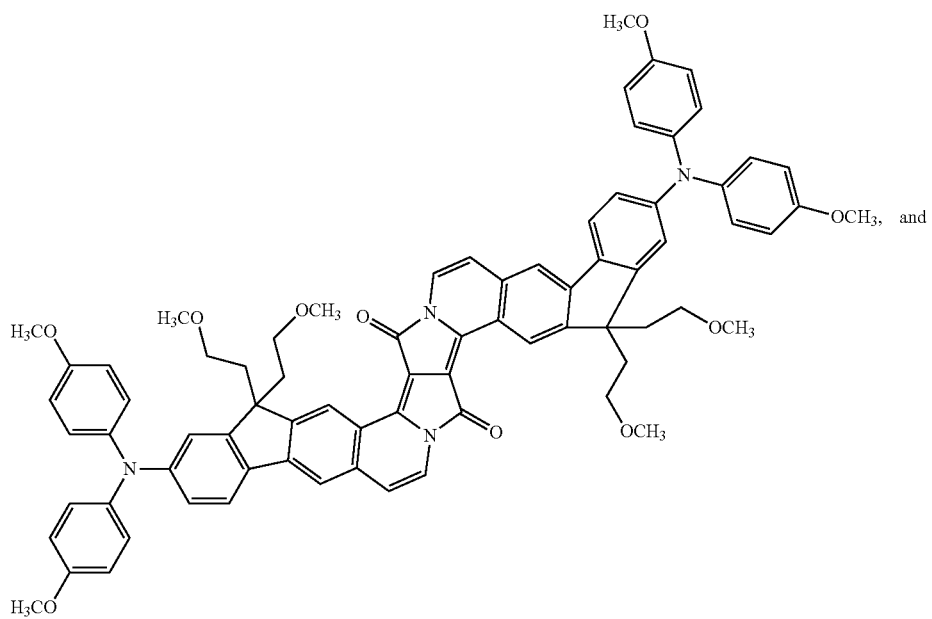

(4f)

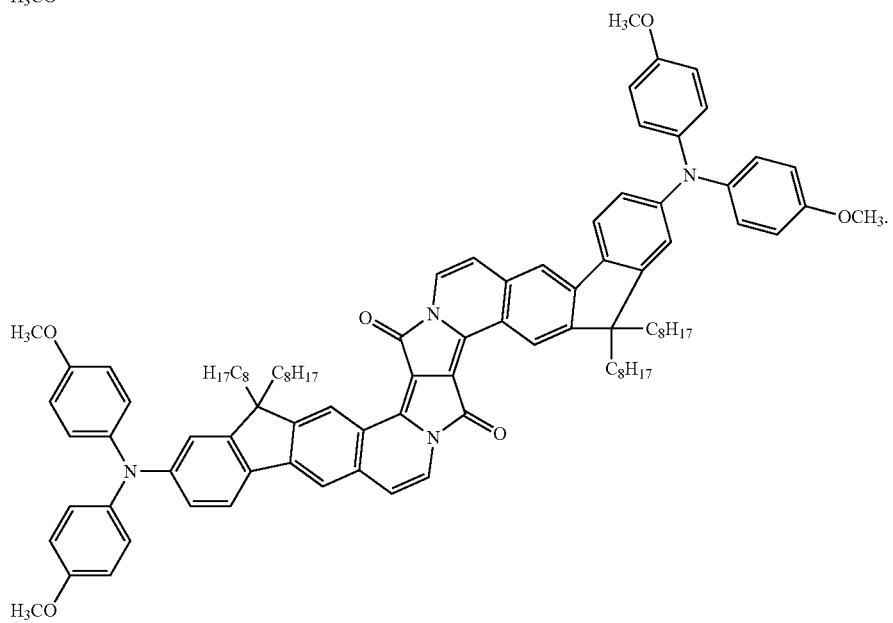

(4g)

The compounds wherein $R^3$ is a group of formula $-NA^1A^{1'}$, or a group

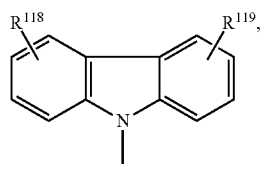

may be used in organic field effect transistors, organic light emitting devices, organic photovoltaic devices and organic photodiodes and as IR absorbers. In addition, these compounds show two-photon absorption (2PA) and can be used in the fields of two-photon excited fluorescence microscopy, two-photon induced polymerization and 3D-storage.

In addition, the present invention is directed to a method for the production of a compound of formula (III):

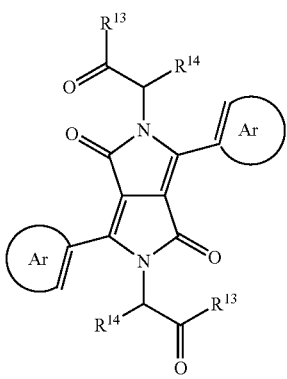
(III)

especially

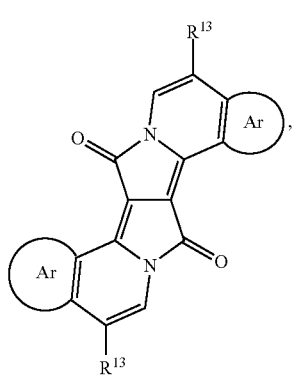

where $R^{13}$, $R^{14}$ and Ar are as defined in claim 1, characterized in that a) a diketopyrrolopyrrole of formula (I):

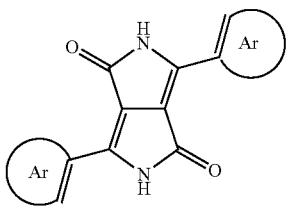
(I)

is reacted with a compound of formula

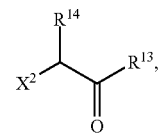

wherein $X^2$ is Cl, Br, or I; and then b) the N-alkylated derivative of formula (II) obtained in step a)

(II)

is submitted in the presence of acid to intramolecular condensation, obtaining the compound of formula (III).

The alkylation reaction in step a) is preferably carried out in the presence of tetrabutylammonium hydrogen sulfate, or $K_2C_3$ in dimethylformamide (DMF).

The cyclization reaction in step b) is preferably carried out in methylene chloride in the presence of trifluoromethanesulphonic acid.

Compound (4) can, for example, be prepared starting from the DPP derivative (2) optionally via the intermediate (5) as shown in the reaction scheme below:

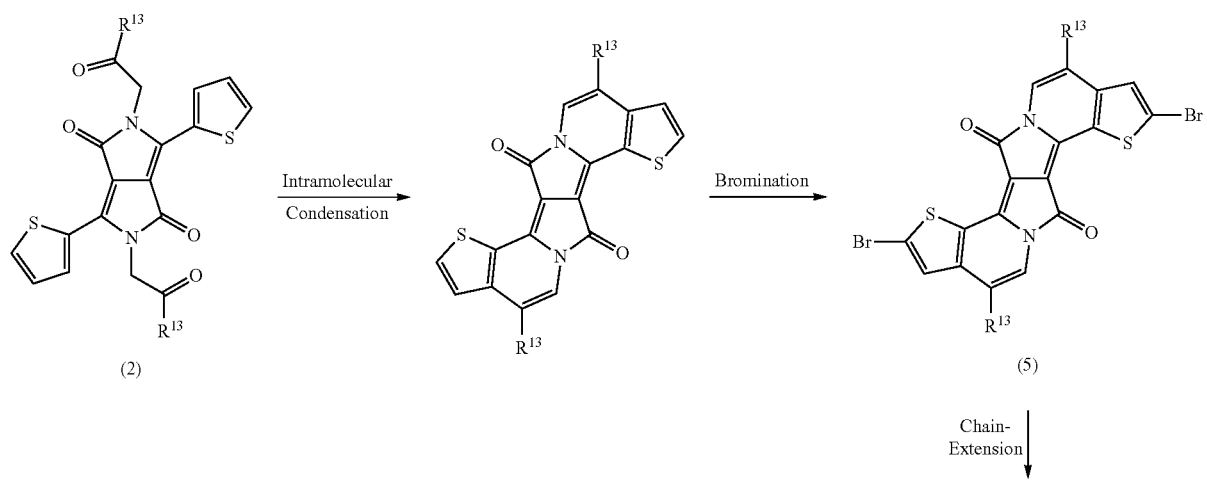

(2)

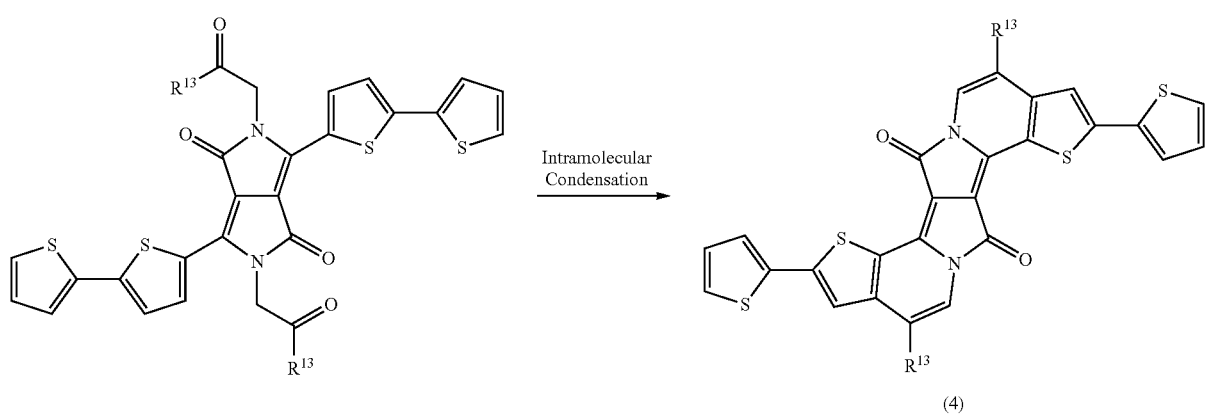

(4)

2a, 4a, 5a: $R^{13}$ = phenyl
2b, 4b, 5b: $R^{13}$ = tert-butyl

The bromination is carried out in a suitable solvent, like chloroform, using two equivalents of N-bromo-succinimide at a temperature between −30° C. and +50° C., preferably between −10° C. and room temperature, e.g. at 0° C.

The "chain-extension" of compound (5) with an additional thienyl residue can be effected, for example, by reaction with a mixture of 2-thienylboronic acid pinacol ester, $Pd_2(dba)_3$ [tris(dibenzylideneacetone)-di-palladium)] and tri-tert-butyl-phosphonium-tetrafluoroborate in tetrahydrofurane including a suitable base, such as, for example, $K_2CO_3$, $K_3PO_4$ and Li—OH. The bromination and chain-extension of DPP derivatives is described in more detail on pages 17 to 19 of WO2009/047104. WO2009/047104 discloses also possible starting DPP compounds for the synthesis of the compounds of formula (II).

Alternatively compounds of formula

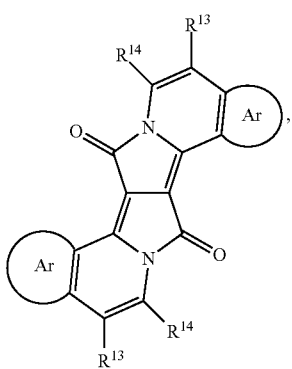

where $R^{13}$, $R^{14}$ and Ar are as defined above, can be obtained by reacting a diketopyrrolopyrrole of formula

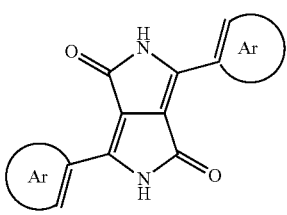

with a compound of formula

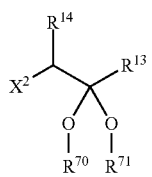

in the presence of a base, wherein $X^2$ is Cl, Br, or I; and then submitting the obtained N-alkylated derivative of formula

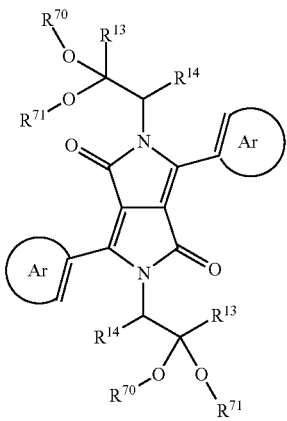

in the presence of acid to intramolecular condensation. In the acetals and ketals, oxygen can be replaced optionally by sulphur atoms.

$R^{70}$ and $R^{71}$ are independently of each other a $C_1$-$C_{25}$alkyl group which can optionally be substituted one or more times with $C_1$-$C_8$alkyl, $C_1$-$C_8$alkoxy and/or can optionally be interrupted by —O—, —S—, —$NR^{39}$—. Preferably, $R^{70}$ and $R^{71}$ are independently of each other a $C_1$-$C_{25}$alkyl group, especially a $C_1$-$C_4$alkyl group. Optionally $R^{70}$ and $R^{71}$ can form a five, or six membered ring.

The alkylation reaction is preferably carried out in the presence of tetrabutylammonium hydrogen sulfate, or $K_2C_3$ in dimethylformamide (DMF). The cyclization reaction is preferably carried out in methylene chloride in the presence of trifluoromethanesulphonic acid, or sulphuric acid.

Compounds of formula

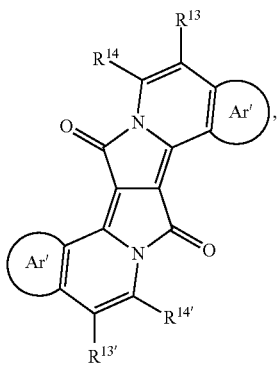

wherein Ar is a homo- or heteroaromatic system, which is substituted by Cl, Br, or I, are intermediates in the production of other small molecules, or polymers, especially polymers which can be used as functional dyes in dye sensitized and bulk heterojunction solar cells, organic light emitting diodes, photodiodes, organic field effect transistors, fluorescence imaging, sensors and solid-state dye lasers.

Accordingly, the present invention is directed to compounds of formula

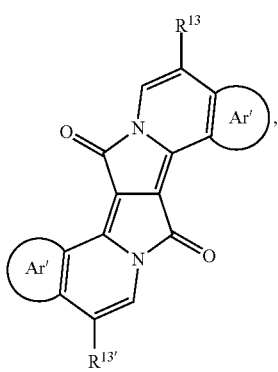

wherein Ar is selected from

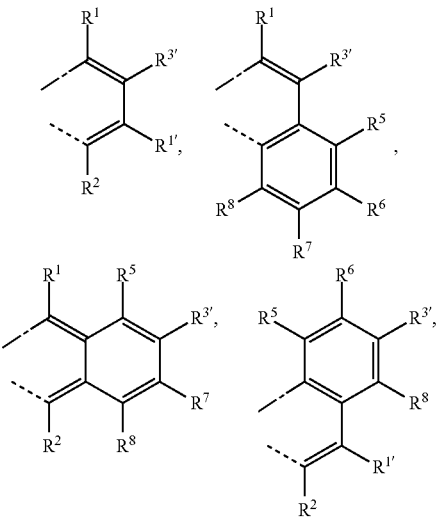

-continued

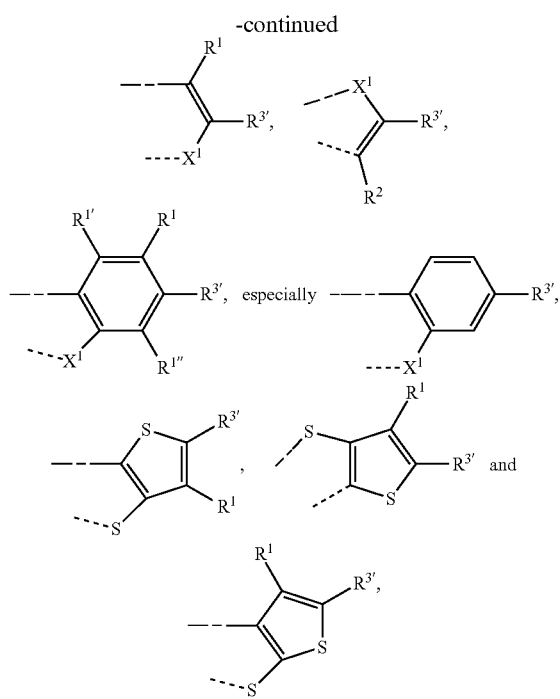

wherein the dotted lines denotes the bonds to the 6-membered ring (the dotted line -- indicates the bond to the carbon atom in para-position to the nitrogen atom, the dotted line ----- indicates the bond to the carbon atom in meta-position to the nitrogen atom),
$R^1$, $R^{1'}$, $R^{1''}$, $R^2$, $R^5$, $R^6$, $R^7$, $R^8$, $R^{13}$, $R^{13'}$, $R^{14}$, $R^{14'}$ and $X^1$ are as defined above,
$R^{3'}$ is Cl, Br, I,

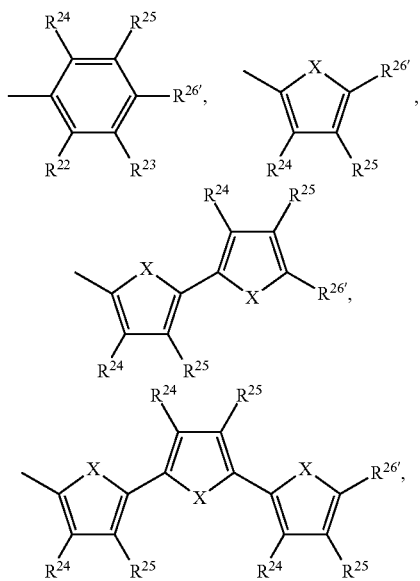

wherein X, $R^{24}$ and $R^{25}$ are as defined in claim 2 and $R^{26'}$ is Cl, Br, or I.

Preferably, X is O, S, or Se, more preferably X is O, or S, most preferred, X is S.

Preferably, $X^1$ is O, S, or Se, more preferably X is O, or S, most preferred, X is S.

Preferably, $R^4$ is hydrogen, or $C_1$-$C_{25}$alkyl, which may optionally be interrupted by one or more oxygen or sulphur atoms. More preferably, $R^4$ is $C_1$-$C_{25}$alkyl.

$R^5$, $R^6$, $R^7$, and $R^8$ are preferably hydrogen, halogen, especially F; $C_1$-$C_{25}$alkyl, or $C_1$-$C_{25}$alkyl substituted with one or more halogen atoms, especially F; more preferred hydrogen or $C_1$-$C_{25}$alkyl, most preferred H.

In another embodiment Ar' denotes a homo- or heteroaromatic system, which is selected from

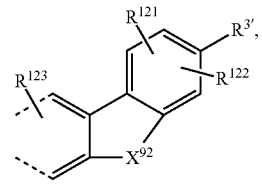

such as, for example,

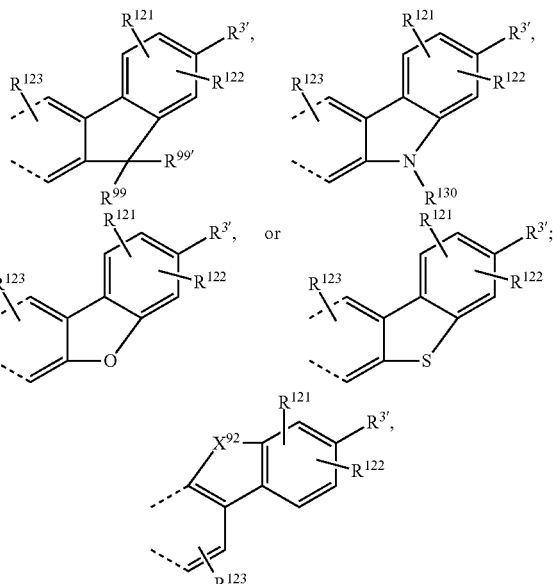

such as, for example,

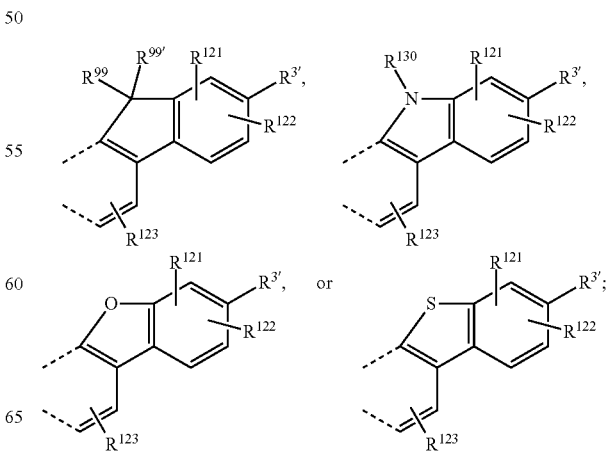

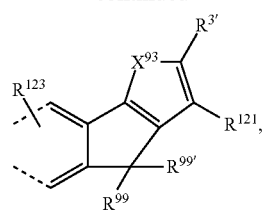
such as, for example,
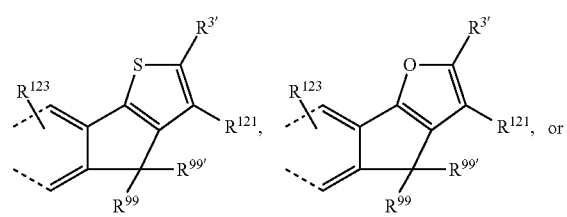
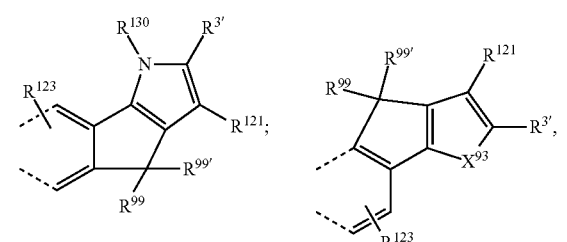
such as, for example,
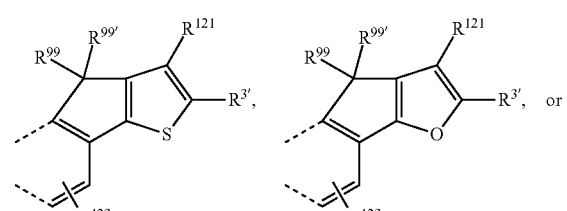
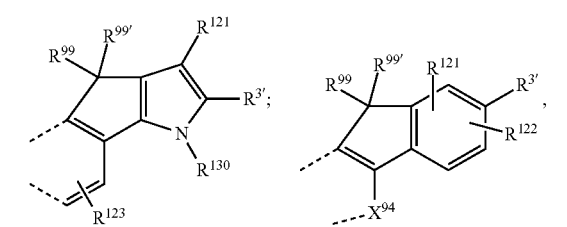
as, for example,
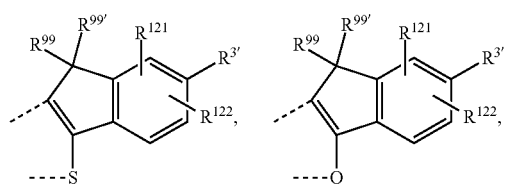
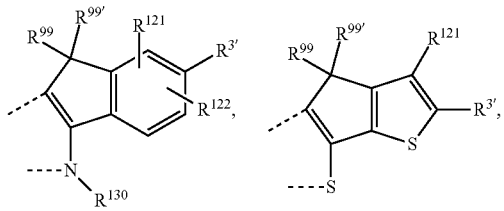
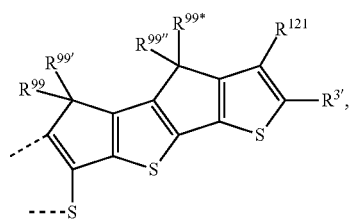
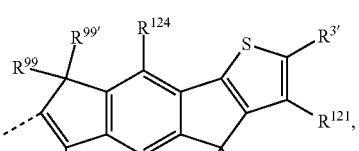
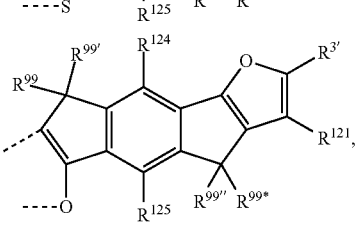
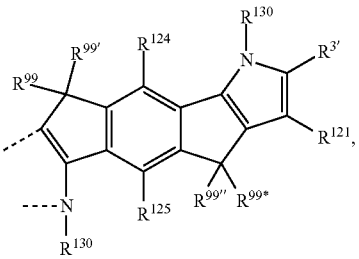
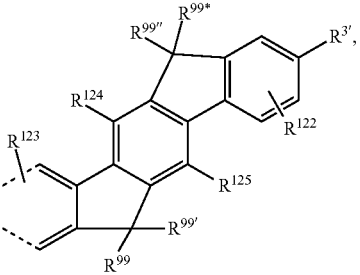
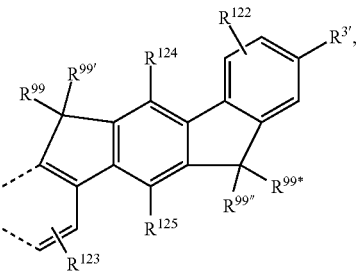

-continued

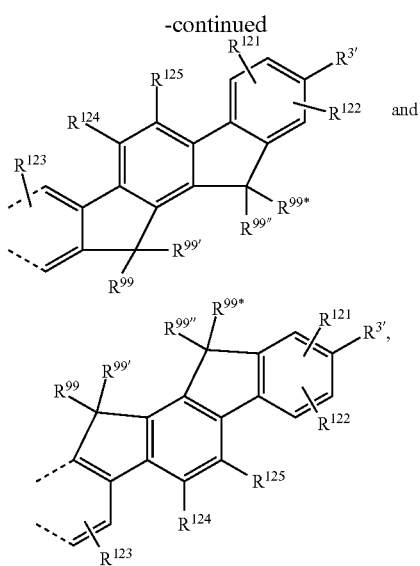

wherein $X^{92}$ is O, S, $CR^{99}R^{99'}$, or $NR^{130}$, $X^{93}$ is O, S, or $NR^{130}$, $X^{94}$ is O, S, or $NR^{130}$, $R^{99}$, $R^{99'}$, $R^{99''}$ and $R^{99*}$ are independently of each other hydrogen, $C_1$-$C_{25}$alkyl, or $C_1$-$C_{25}$alkyl substituted with one or more halogen atoms and/or interrupted by one or more oxygen atoms, or two moieties $R^{99}$ and $R^{99'}$ or $R^{99''}$ and $R^{99*}$ can form a 5 or 6 membered alkyl ring, which optionally can be substituted with one or more halogen atoms and/or interrupted by one or more oxygen atoms;

$R^{121}$, $R^{122}$, $R^{123}$, $R^{124}$ and $R^{125}$ are independently of each other hydrogen, halogen, $C_6$-$C_{18}$aryl; $C_6$-$C_{18}$aryl which is substituted by $C_1$-$C_{18}$alkyl, halogen; or $C_1$-$C_{18}$alkoxy; $C_1$-$C_{25}$alkyl, which may optionally be interrupted by one or more oxygen or sulphur atoms and/or is optionally substituted by one or more halogen atoms, especially F; or $C_7$-$C_{25}$arylalkyl;

$R^{130}$ is hydrogen, $C_6$-$C_{18}$aryl; $C_6$-$C_{18}$aryl which is substituted by $C_1$-$C_{18}$alkyl, halogen, especially F; or $C_1$-$C_{18}$alkoxy; $C_1$-$C_{25}$alkyl, which may optionally be interrupted by one or more oxygen or sulphur atoms and/or is optionally substituted by one or more halogen atoms, especially F; or $C_7$-$C_{25}$arylalkyl; and $R^{3'}$ is as defined above.

In said embodiment compounds of formula

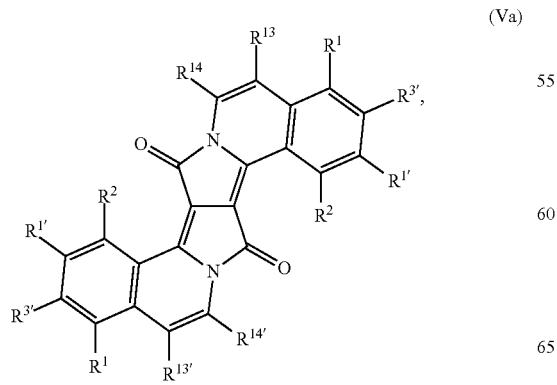

(Va)

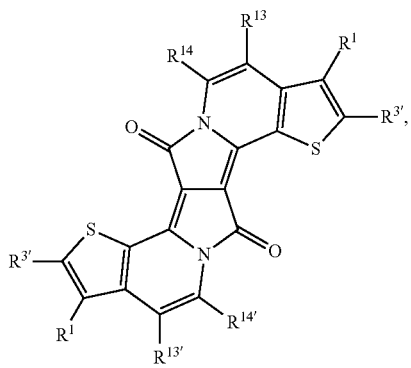

(Vb)

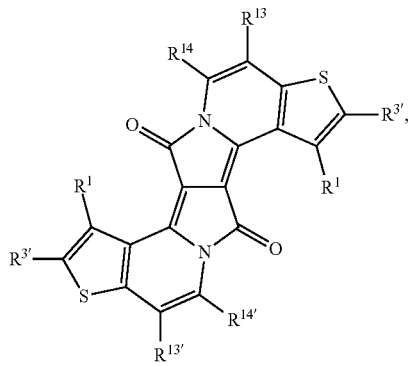

(Vc)

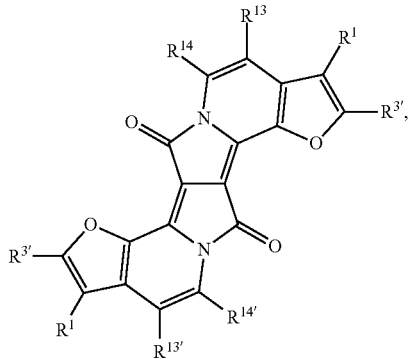

(Vd)

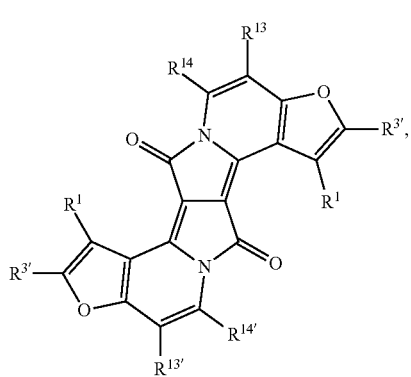

(Ve)

-continued
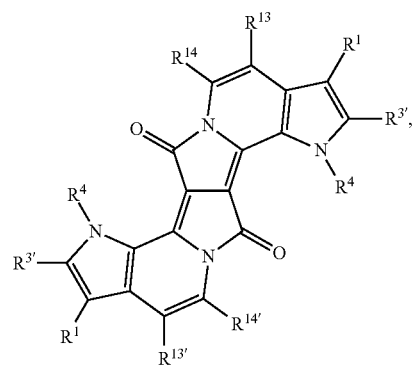
(Vf)
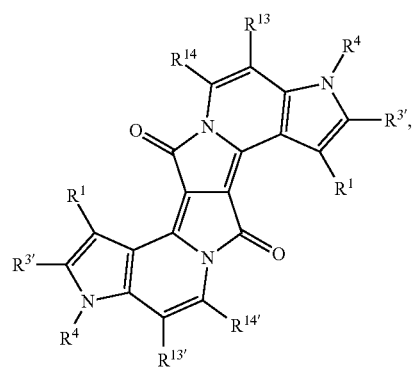
(Vg)
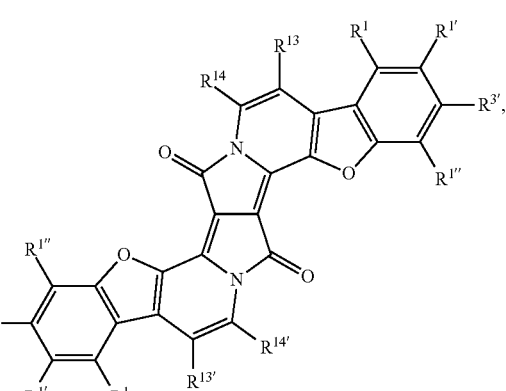
(Vh)
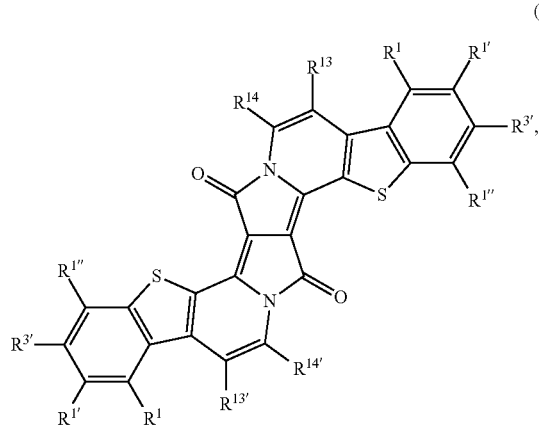
(Vi)
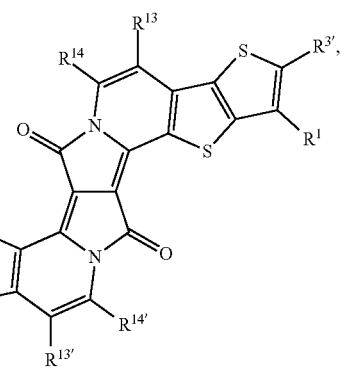
(Vj)
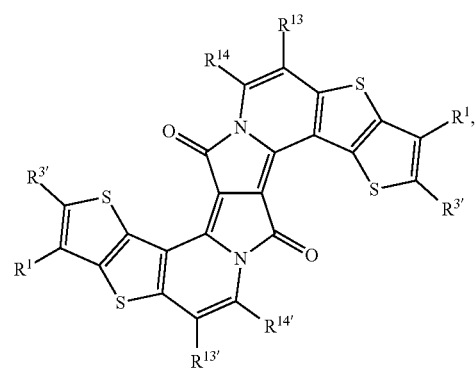
(Vk)
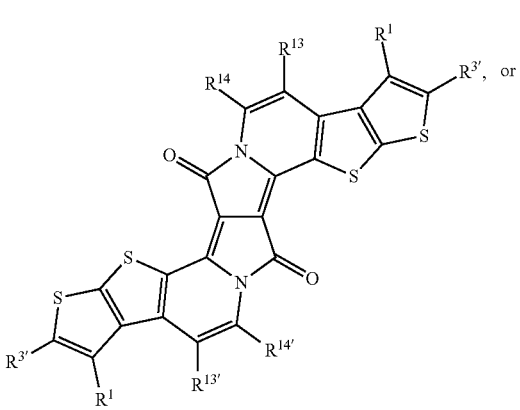
(Vl)
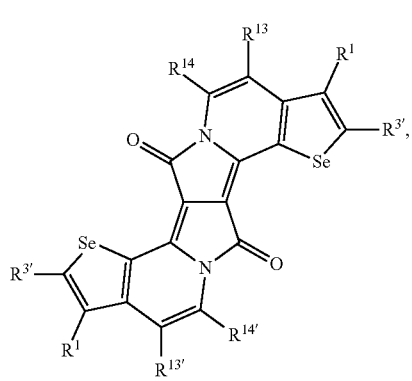
(Vm)

(Vn)
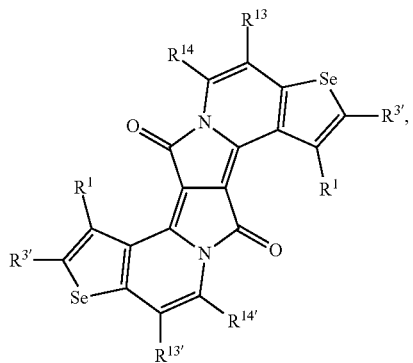
(Vb')
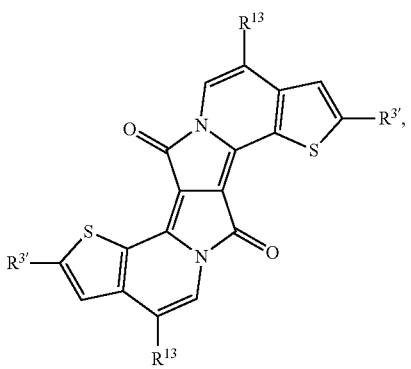
wherein
R¹, R¹', R¹", R² and R⁴ are as defined above,
R³' is Cl, Br, I,
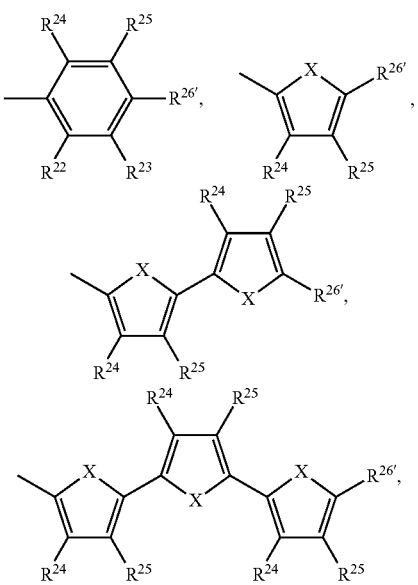
(Vc')
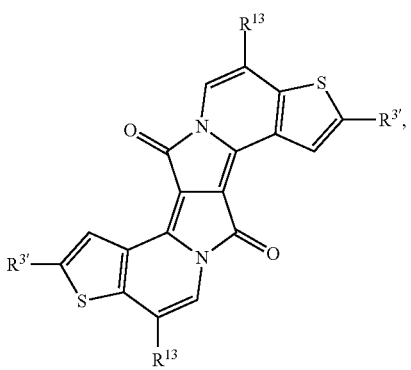
wherein X, $R^{24}$ and $R^{25}$ are as defined in claim 2 and $R^{26'}$ is Cl, Br, or I. Compounds of formula (Va), (Vb), (Vd), (Vf), (Vh), (Vi), (Vj) and (Vm) are preferred. Compounds of formula (Vb), (Vd) and (Vj) are most preferred.
In said embodiment compounds of formula
(Vd')
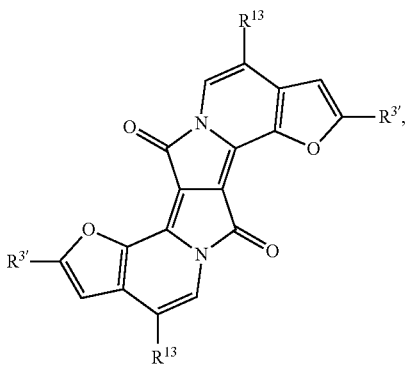
(Va')
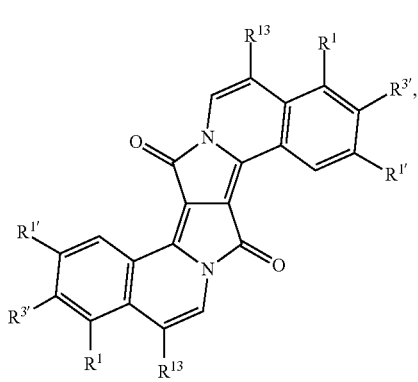
(Ve')
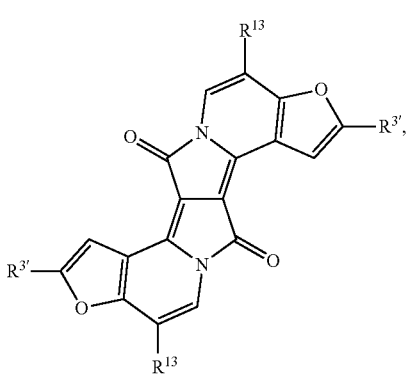

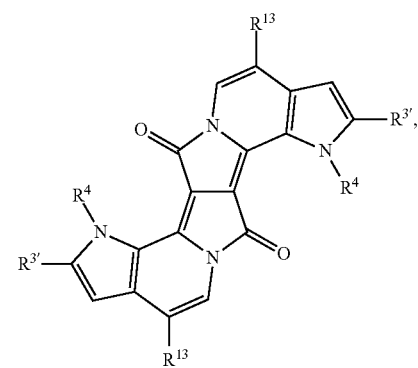 (Vf')
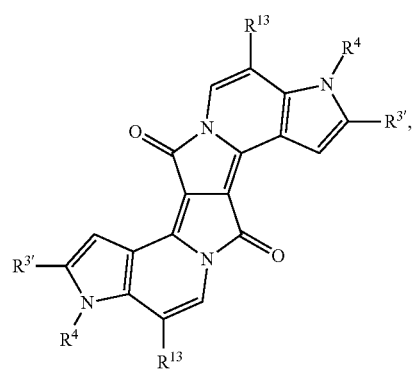 (Vg')
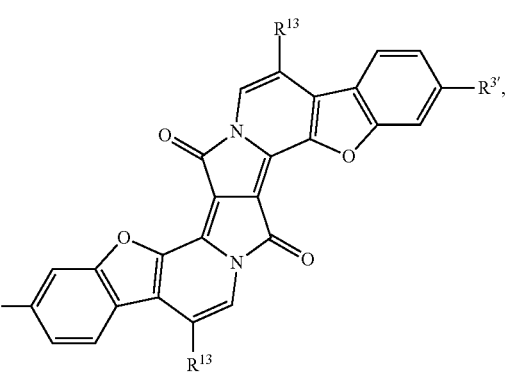 (Vh')
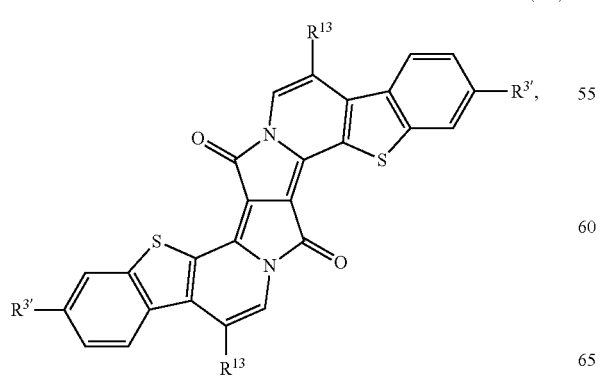 (Vi')
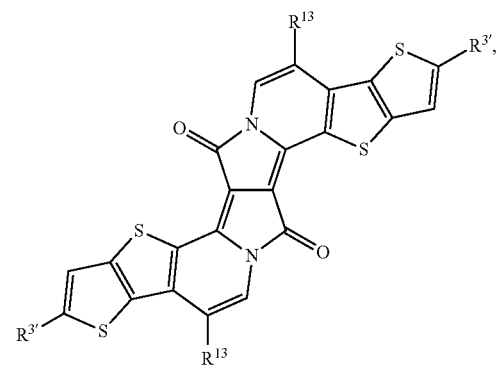 (Vj')
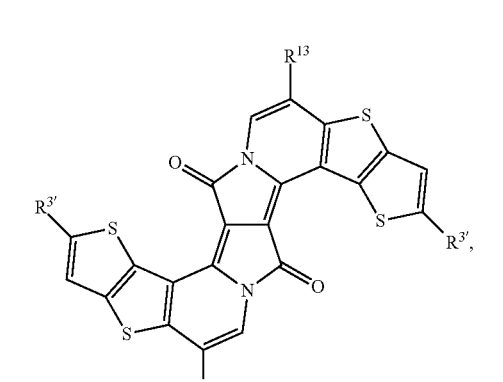 (Vk')
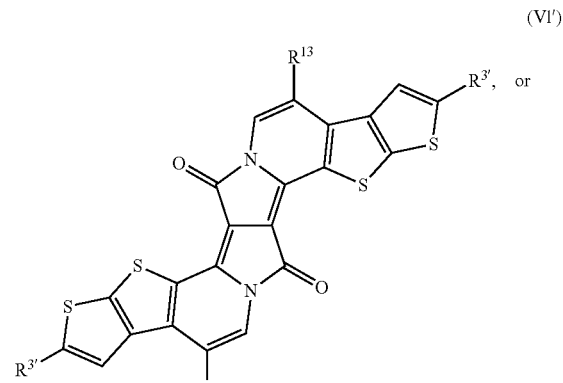 (Vl'), or
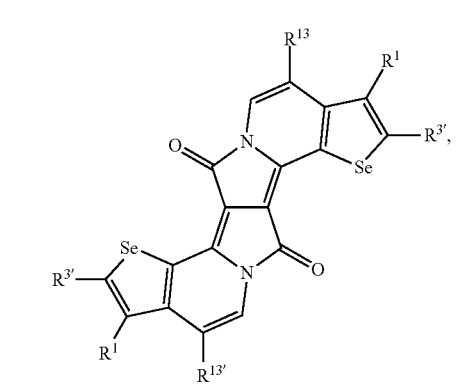 (Vm')

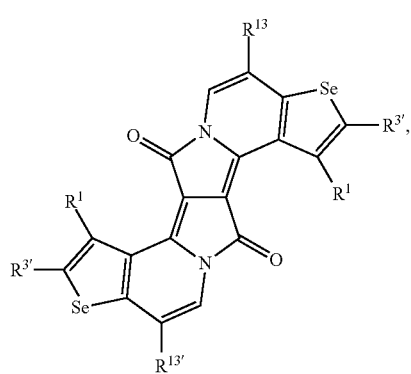
(Vn')
are more preferred, wherein $R^1$, $R^{1'}$, $R^4$ and $R^{13}$ are as defined above and $R^{3'}$ is Cl, Br, or I. Compounds of formula (Va'), (Vb'), (Vd'), (Vf'), (Vh'), (Vi'), (Vj'), or (Vm') are preferred. Compounds of formula (Vb'), (Vd') and (Vj') are most preferred.
In another embodiment compounds of formula
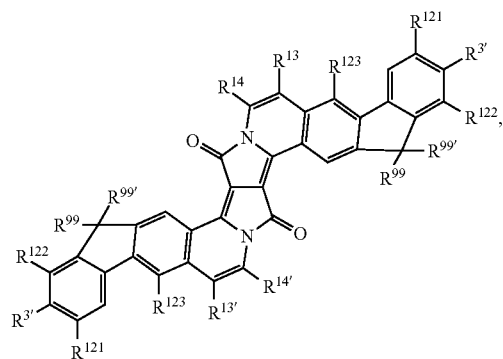
(Vo)
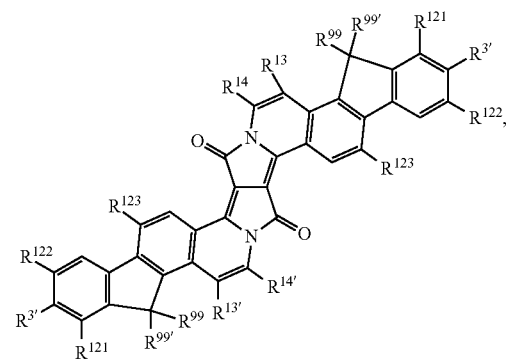
(Vp)
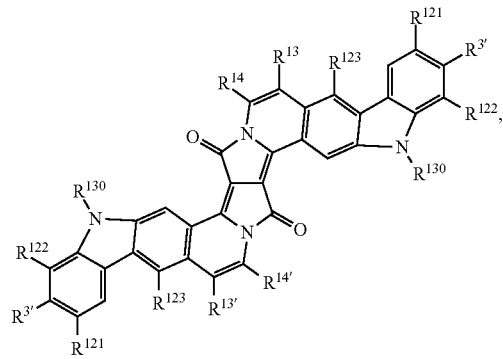
(Vq)
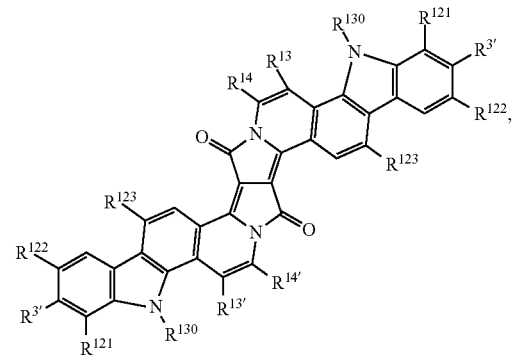
(Vr)
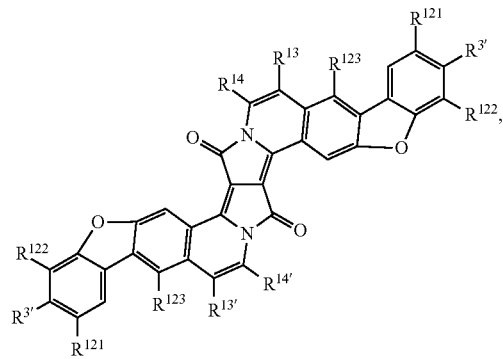
(Vs)
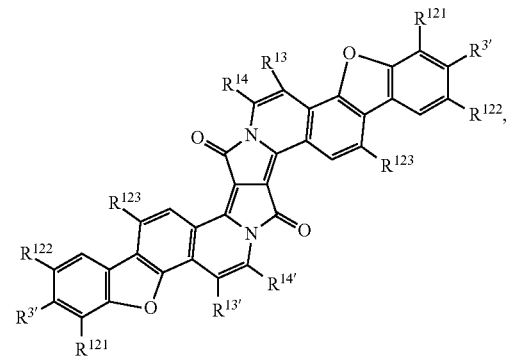
(Vt)

-continued
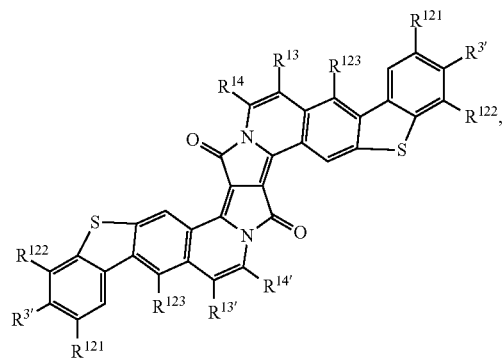 (Vu)
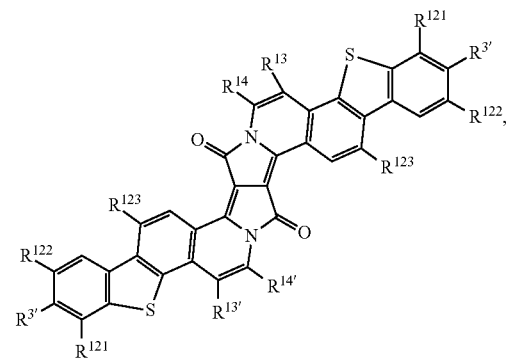 (Vv)
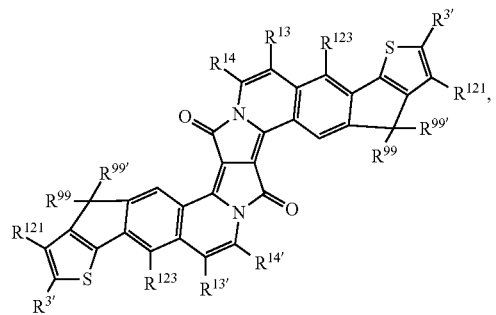 (Vw)
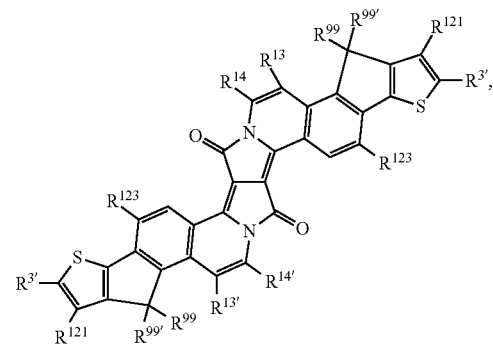 (Vx)
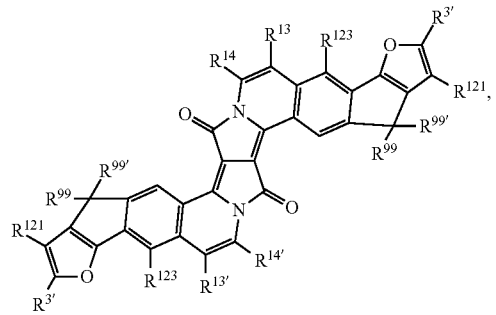 (Vy)
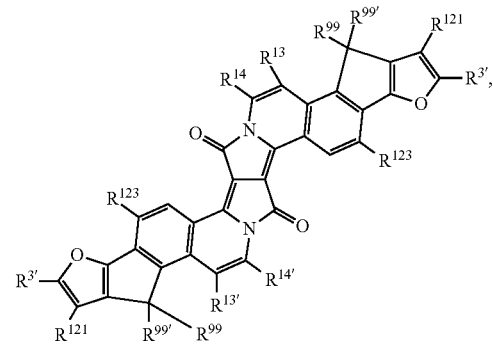 (Vz)
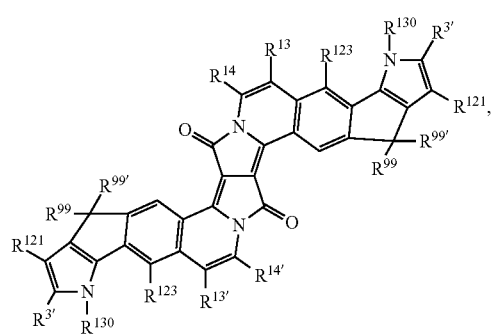 (Vaa)
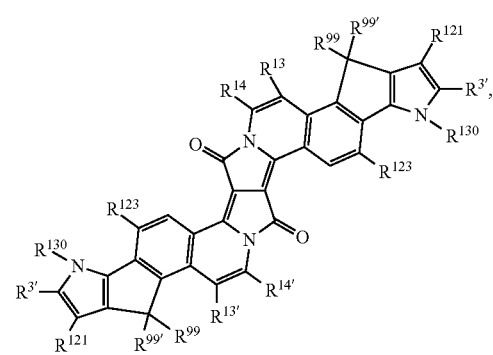 (Vab)

-continued
(Vac)
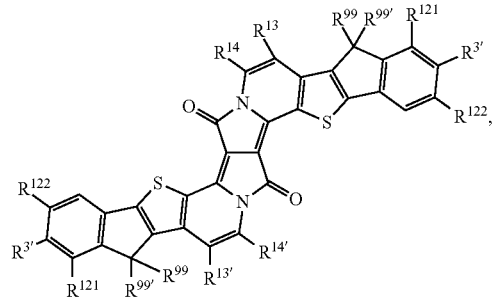
(Vad)
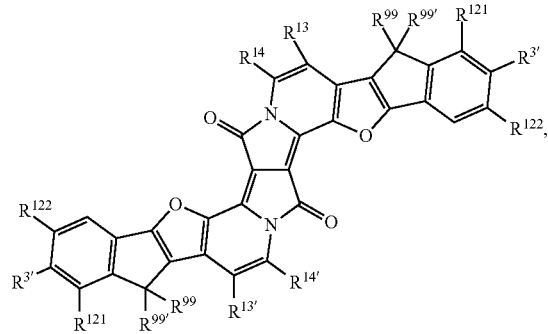
(Vac)
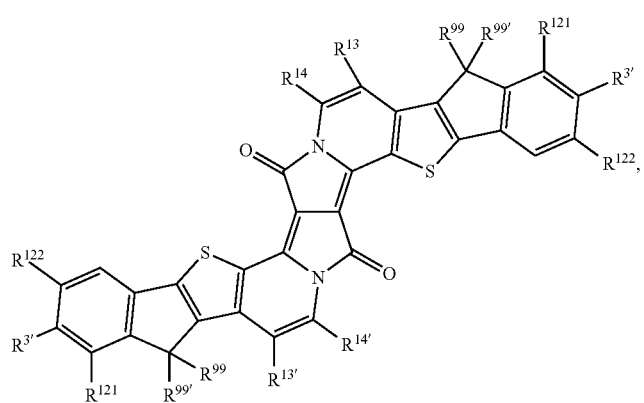
(Vae)
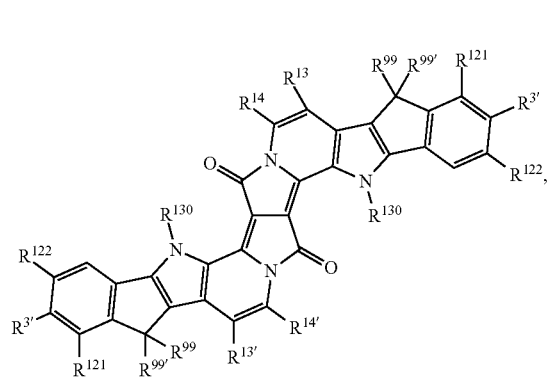
(Vaf)
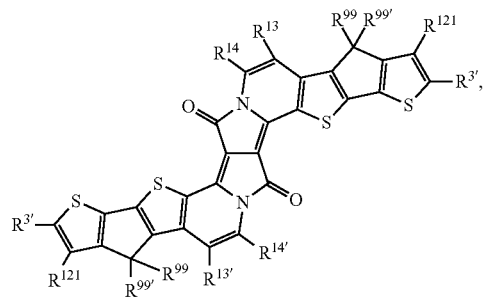
(Vag)
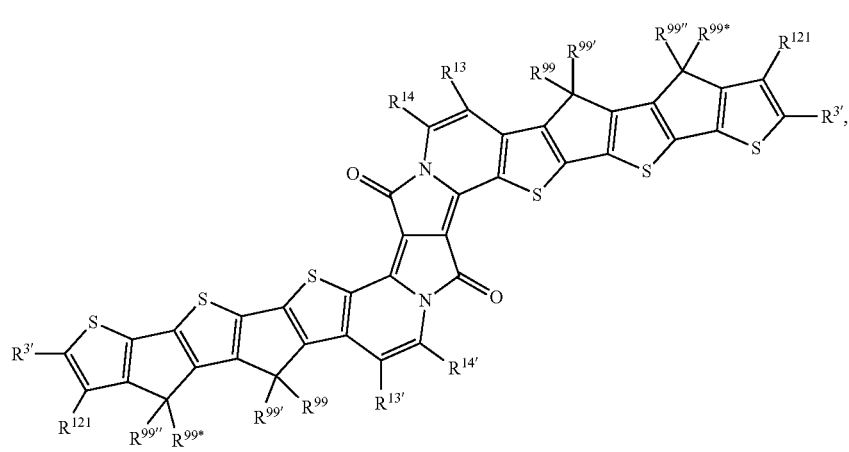

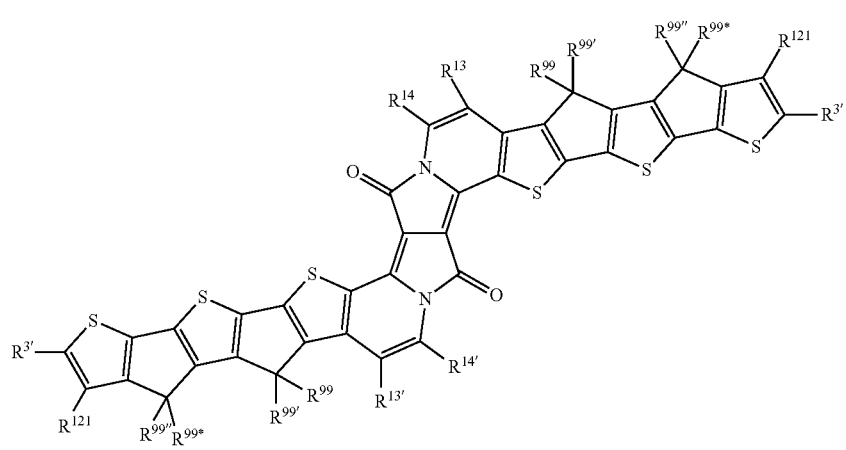
(Vag)
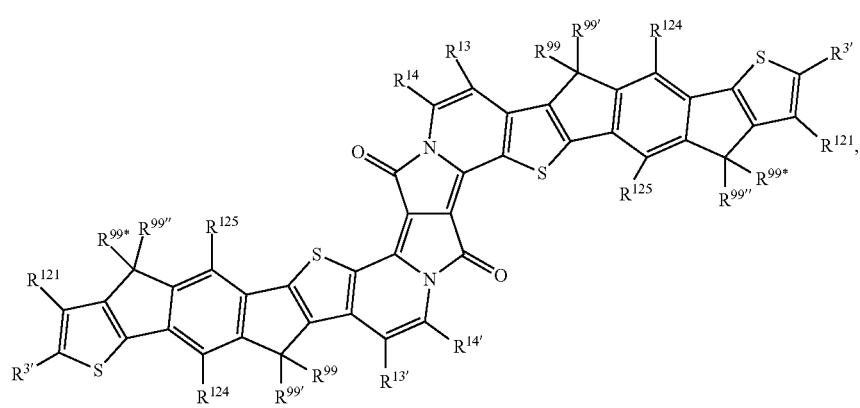
(Vah)
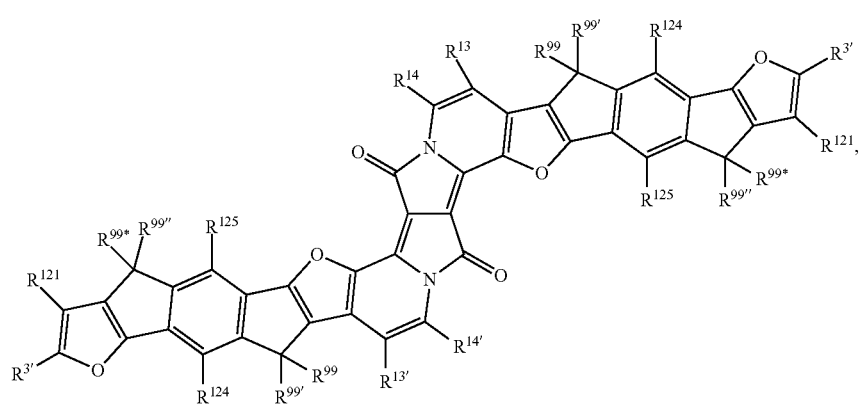
(Vai)
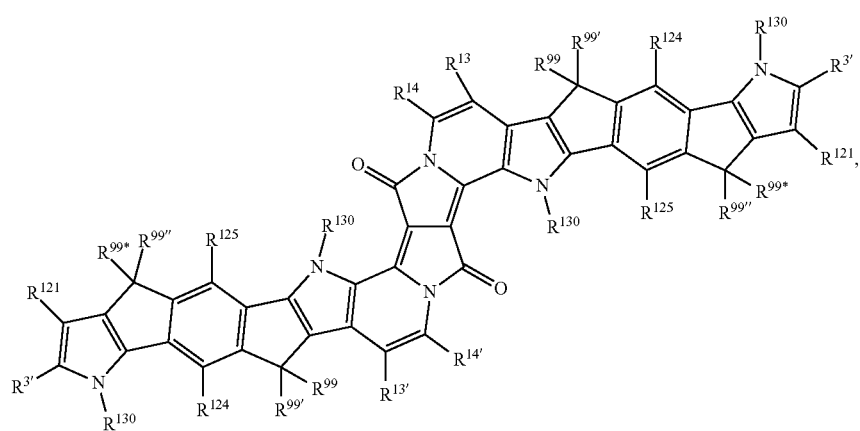
(Vaj)

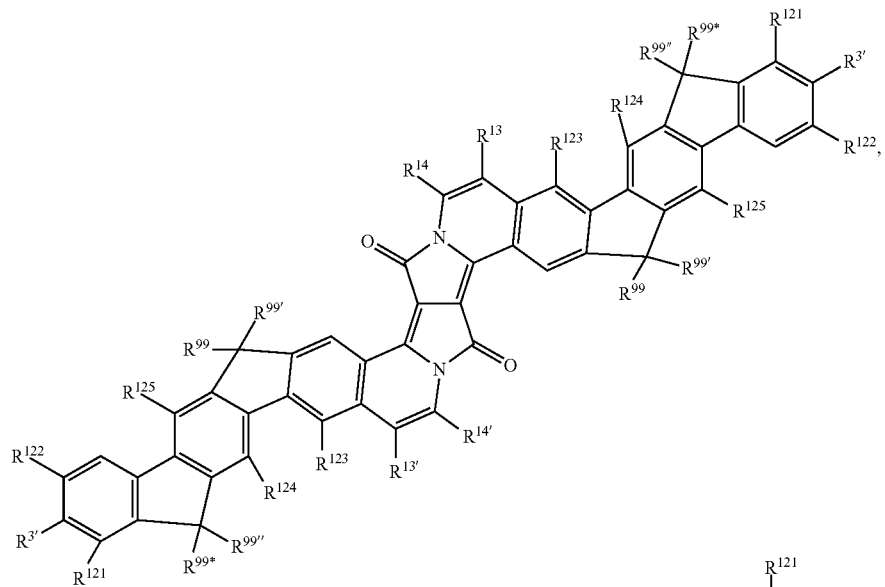
(Vak)
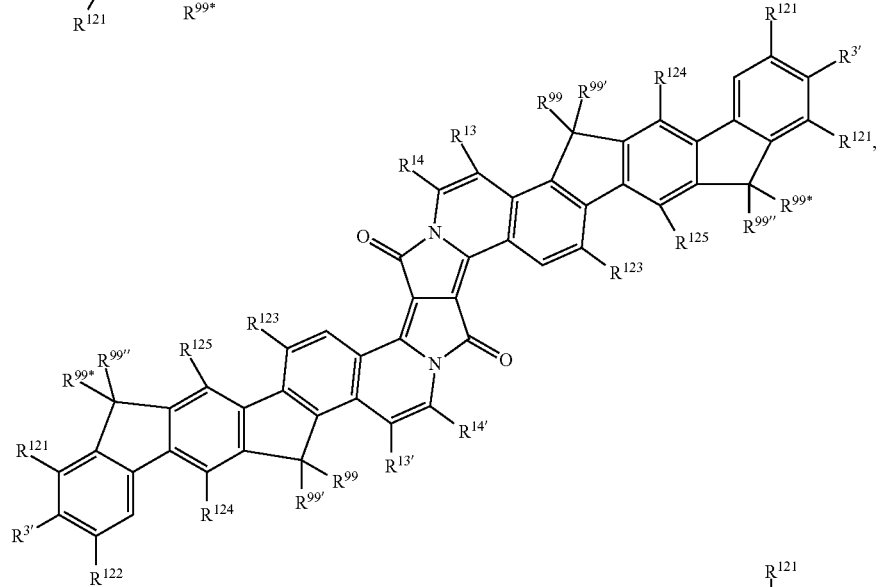
(Val)
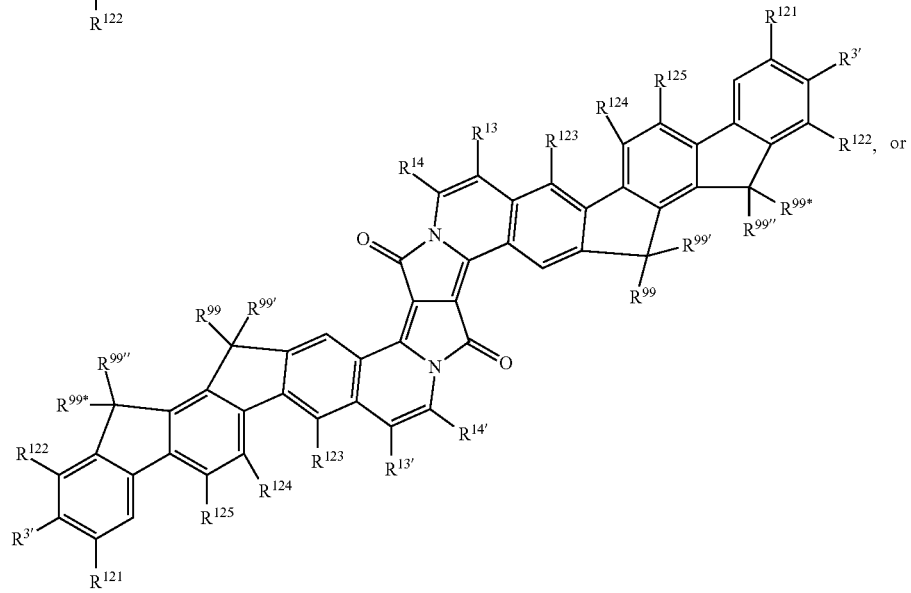
(Vam)

(Van)

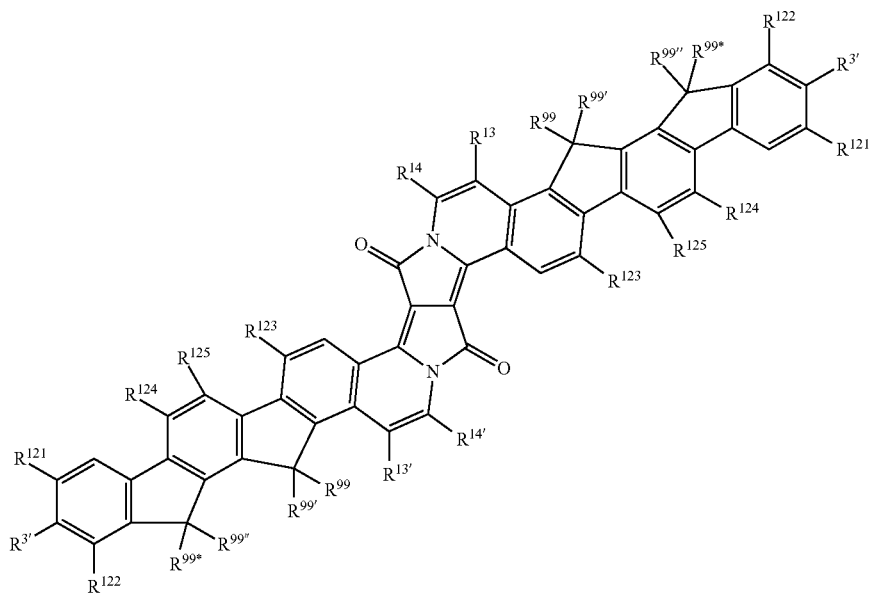

are preferred, wherein $R^{13}$, $R^{13'}$, $R^{14}$ and $R^{14'}$ may be the same or different and are selected from hydrogen or a $C_1$-$C_{38}$alkyl group;

$R^{99}$, $R^{99'}$, $R^{99''}$ and $R^{99*}$ are independently of each other hydrogen, $C_1$-$C_{25}$alkyl, or $C_1$-$C_{25}$alkyl interrupted by one or more oxygen atoms; preferably $C_3$-$C_{25}$alkyl, or $C_3$-$C_{25}$alkyl which is interrupted by one or more oxygen atoms;

$R^{121}$, $R^{122}$, $R^{123}$, $R^{124}$ and $R^{125}$ are independently of each other hydrogen, halogen, $C_1$-$C_{18}$alkoxy or $C_1$-$C_{25}$alkyl; preferably hydrogen;

$R^{130}$ is hydrogen, $C_6$-$C_{18}$aryl; $C_6$-$C_{18}$aryl which is substituted by $C_1$-$C_{18}$alkyl, halogen, especially F; or $C_1$-$C_{18}$alkoxy; $C_1$-$C_{25}$alkyl, which may optionally be interrupted by one or more oxygen or sulphur atoms and/or is optionally substituted by one or more halogen atoms, especially F; or $C_7$-$C_{25}$arylalkyl; and $R^3$ is as defined above.

Except for $R^{3'}$ the same preferences apply for the compounds of formula (Vo) to (Van) than for the compounds of formula (IIIo) to (IIIan).

Preferably, $R^1$, $R^{1'}$ and $R^{1'''}$ are independently of each other H, $C_1$-$C_{25}$alkoxy, or $C_1$-$C_{25}$alkyl. More preferred, $R^1$, $R^{1'}$ and $R^{1'''}$ are independently of each other hydrogen, or $C_1$-$C_{25}$alkyl, most preferred hydrogen.

Preferably, $R^2$ is H, $C_1$-$C_{25}$alkoxy, or $C_1$-$C_{25}$alkyl. More preferred, $R^2$ is hydrogen, or $C_1$-$C_{25}$alkyl. Most preferred $R^2$ is hydrogen.

Preferably, $R^{3'}$ is Cl, Br, I, or a group of formula

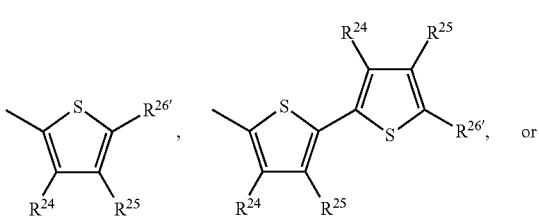

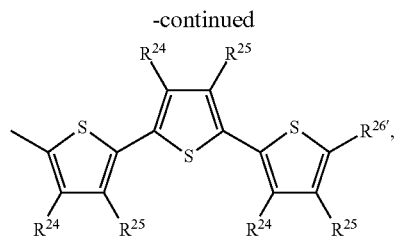

wherein $R^{24}$ and $R^{25}$ are as defined above and are preferably H, or $C_1$-$C_{25}$alkyl, more preferably H. More preferred, $R^{3'}$ is Cl, Br, I, or a group of formula

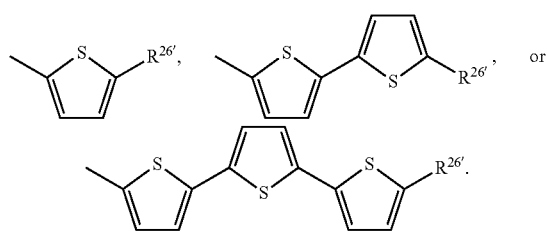

$R^{26'}$ is Cl, Br, or I, especially Br, or I, very especially Br. Most preferred, $R^{3'}$ is Cl, Br, I, or a group of formula

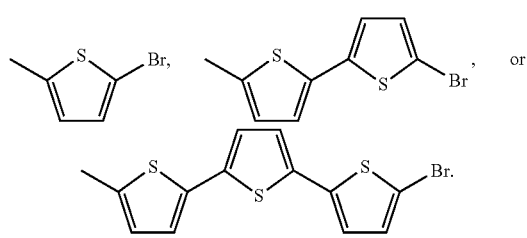

Preferably, R⁴ is hydrogen, or $C_1$-$C_{25}$alkyl, which may optionally be interrupted by one or more oxygen or sulphur atoms. More preferably, R⁴ is $C_1$-$C_{25}$alkyl.

In a preferred embodiment the present invention is directed to compounds of formula (IIIa), (IIIb), (Vc), (Vd), (Ve), (Vf), (Vg), (Vh), (Vi), (Vj), (Vk), and (Vl), especially (Va), (Vb), (Vd), (Vf), (Vh), (Vi) and (Vj), very especially (Vb), (Vd) and (Vj); wherein R¹, R¹' and R¹'' are independently of each other H, $C_1$-$C_{25}$alkoxy, or $C_1$-$C_{25}$alkyl, R² is H, $C_1$-$C_{25}$alkoxy, or $C_1$-$C_{25}$alkyl, R³' is Cl, Br, I, or a group of formula

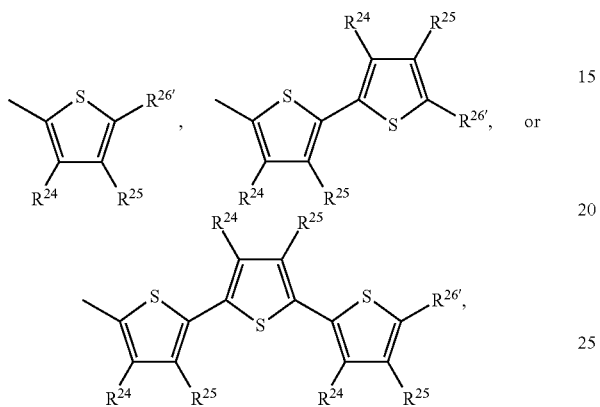

R⁴ is hydrogen, or $C_1$-$C_{25}$alkyl, which may optionally be interrupted by one or more oxygen or sulphur atoms. R²⁴ and R²⁵ are preferably H, or $C_1$-$C_{25}$alkyl. R²⁶' is Cl, Br, or I. R¹⁴ and R¹⁴' are H. R¹³ and R¹³' are $C_1$-$C_{25}$alkyl, $C_2$-$C_{25}$alkenyl, $C_2$-$C_{25}$alkenyl, which may optionally be interrupted by one or more oxygen atoms and/or is optionally substituted by a group $E^{Si}$ or one or more halogen atoms, especially F; $C_3$-$C_{10}$heteroaryl; $C_3$-$C_{10}$heteroaryl, which is substituted by halogen, $C_1$-$C_{18}$alkyl, or $C_1$-$C_{18}$alkoxy; or $C_1$-$C_{25}$alkyl, which may optionally be interrupted by one or more oxygen atoms and/or is optionally substituted by a group $E^{Si}$ or one or more halogen atoms, especially F. More preferred, R¹³ is $C_1$-$C_{25}$alkyl, or $C_1$-$C_{25}$alkyl, which may optionally be interrupted by one or more oxygen atoms and/or is optionally substituted by a group $E^{Si}$ or one or more fluorine atoms. Most preferred R¹³ is $C_1$-$C_{25}$alkyl.

$D^{Si}$ is preferably —$SiR^{161}R^{162}$—, wherein $R^{161}$ and $R^{162}$ are independently of each other $C_1$-$C_{25}$alkyl, especially $C_1$-$C_8$alkyl; $C_1$-$C_{25}$haloalkyl, especially $C_1$-$C_8$haloalkyl, such as, for example, —$CF_3$, —$(CH_2)_2CF_3$, —$(CH_2)_2(CF_2)_5$$CF_3$ and —$(CH_2)_2(CF_2)_6CF_3$; $C_2$-$C_{25}$alkenyl, especially $C_2$-$C_8$alkenyl; or phenyl; or —$SiR^{161}R^{162}$—(O—$SiR^{161}R^{162})_d$—, wherein d is 2 to 5 and $R^{161}$ and $R^{162}$ are $C_1$-$C_{25}$alkyl, especially $C_1$-$C_8$alkyl.

$E^{Si}$ is preferably —$SiR^{161}R^{162}R^{163}$. $R^{161}$, $R^{162}$ and $R^{163}$ are independently of each other $C_1$-$C_{25}$alkyl, especially $C_1$-$C_8$alkyl; $C_1$-$C_{25}$haloalkyl, especially $C_1$-$C_8$haloalkyl, such as, for example, —$CF_3$, —$(CH_2)_2CF_3$, —$(CH_2)_2(CF_2)_5$$CF_3$ and —$(CH_2)_2(CF_2)_6CF_3$; $C_2$-$C_{25}$alkenyl, especially $C_2$-$C_8$alkenyl; $C_3$-$C_{12}$cycloalkyl, especially $C_5$-$C_6$cycloalkyl, which might optionally be substituted with $C_1$-$C_4$alkyl; phenyl, —O—$SiR^{164}R^{165}R^{166}$, or —(O—$SiR^{164}R^{165})_d$—$R^{166}$. In case of a group —O—$SiR^{164}R^{165}R^{166}R^{164}$, $R^{165}$ and $R^{166}$ are independently of each other $C_1$-$C_8$alkyl, $C_1$-$C_8$haloalkyl, $C_2$-$C_8$alkenyl, or phenyl. In case of a group —(O—$SiR^{164}R^{165})_d$—$R^{166}R^{164}$ and $R^{165}$ are independently of each other $C_1$-$C_8$alkyl, $R^{166}$ is $C_1$-$C_8$alkyl, or phenyl and d is an integer of 2 to 5.

In a more preferred embodiment the present invention is directed to compounds of formula (Va), (Vb), (Vc), (Vd), (Ve), (Vf), (Vg), (Vh), (Vi), (Vj), (Vk), and (Vl), especially (Va), (Vb), (Vd), (Vf), (Vh), (Vi) and (Vj), very especially (Vb), (Vd) and (Vj); R¹, R¹' and R¹'' are independently of each other hydrogen, or $C_1$-$C_{25}$alkyl, especially hydrogen; R² is hydrogen, or $C_1$-$C_{25}$alkyl, especially hydrogen, R³' is Cl, Br, I, or a group of formula

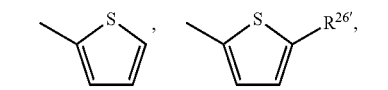

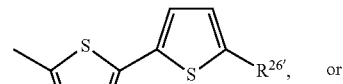

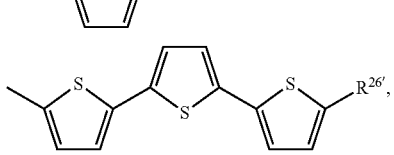

R²⁶' is Cl, Br, or I; especially Br, or I,

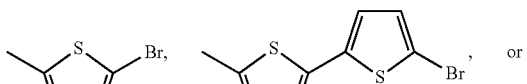

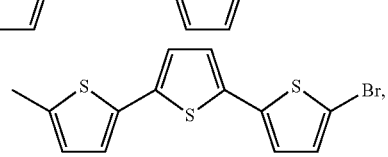

R⁴ is $C_1$-$C_{25}$alkyl. R¹⁴ and R¹⁴' are H. R¹³ and R¹³' are $C_1$-$C_{25}$alkyl, or $C_1$-$C_{25}$alkyl, which may optionally be interrupted by one or more oxygen atoms and/or is optionally substituted by a group $E^{Si}$ or one or more fluorine atoms. More preferred R¹³ and R¹³' are $C_1$-$C_{25}$alkyl.

$D^{Si}$ is preferably —$SiR^{161}R^{162}$—, wherein $R^{161}$ and $R^{162}$ are independently of each other $C_1$-$C_{25}$alkyl, especially $C_1$-$C_8$alkyl; $C_1$-$C_{25}$haloalkyl, especially $C_1$-$C_8$haloalkyl, such as, for example, —$CF_3$, —$(CH_2)_2CF_3$, —$(CH_2)_2(CF_2)_5$$CF_3$ and —$(CH_2)_2(CF_2)_6CF_3$; $C_2$-$C_{25}$alkenyl, especially $C_2$-$C_8$alkenyl; or phenyl; or —$SiR^{161}R^{162}$—(O—$SiR^{161}R^{162})_d$—, wherein d is 2 to 5 and $R^{161}$ and $R^{162}$ are $C_1$-$C_{25}$alkyl, especially $C_1$-$C_8$alkyl.

Examples of such intermediates are shown below:

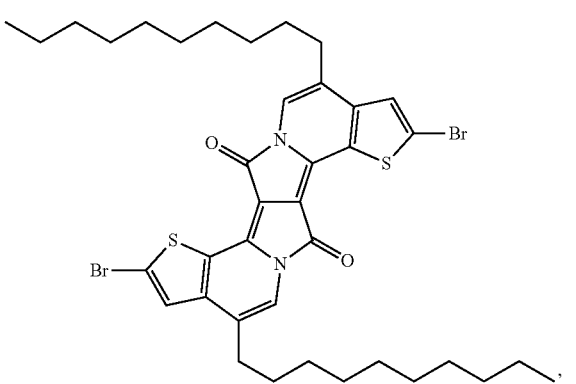

(IM5a)

(IM5b)
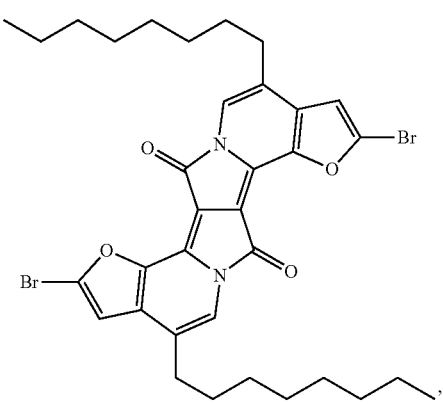
(IM5c)
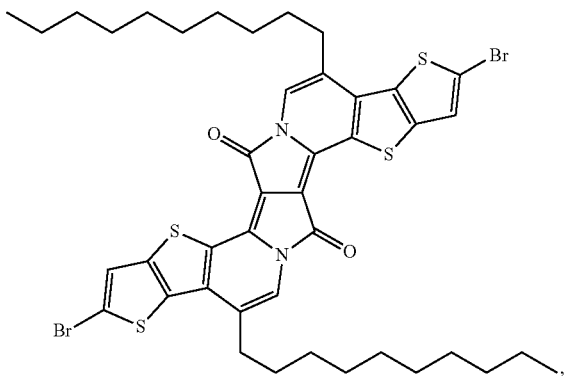
(IM5d)
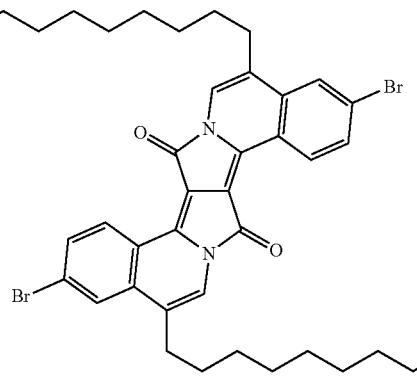
and
(IM5e)
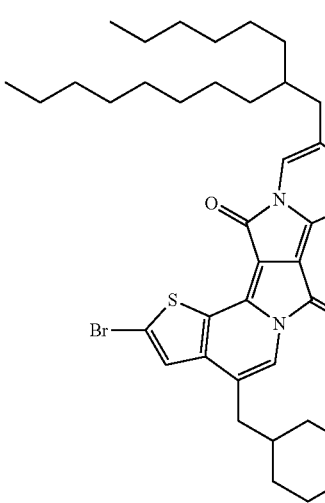
Additional examples of compounds of formula (V) are shown below:
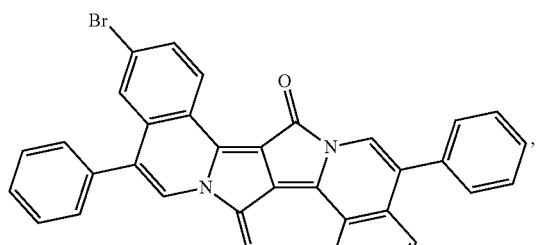
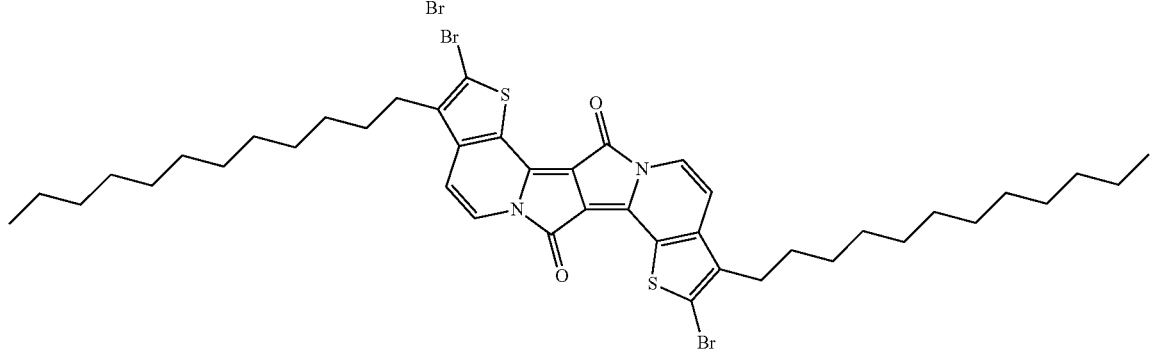

-continued
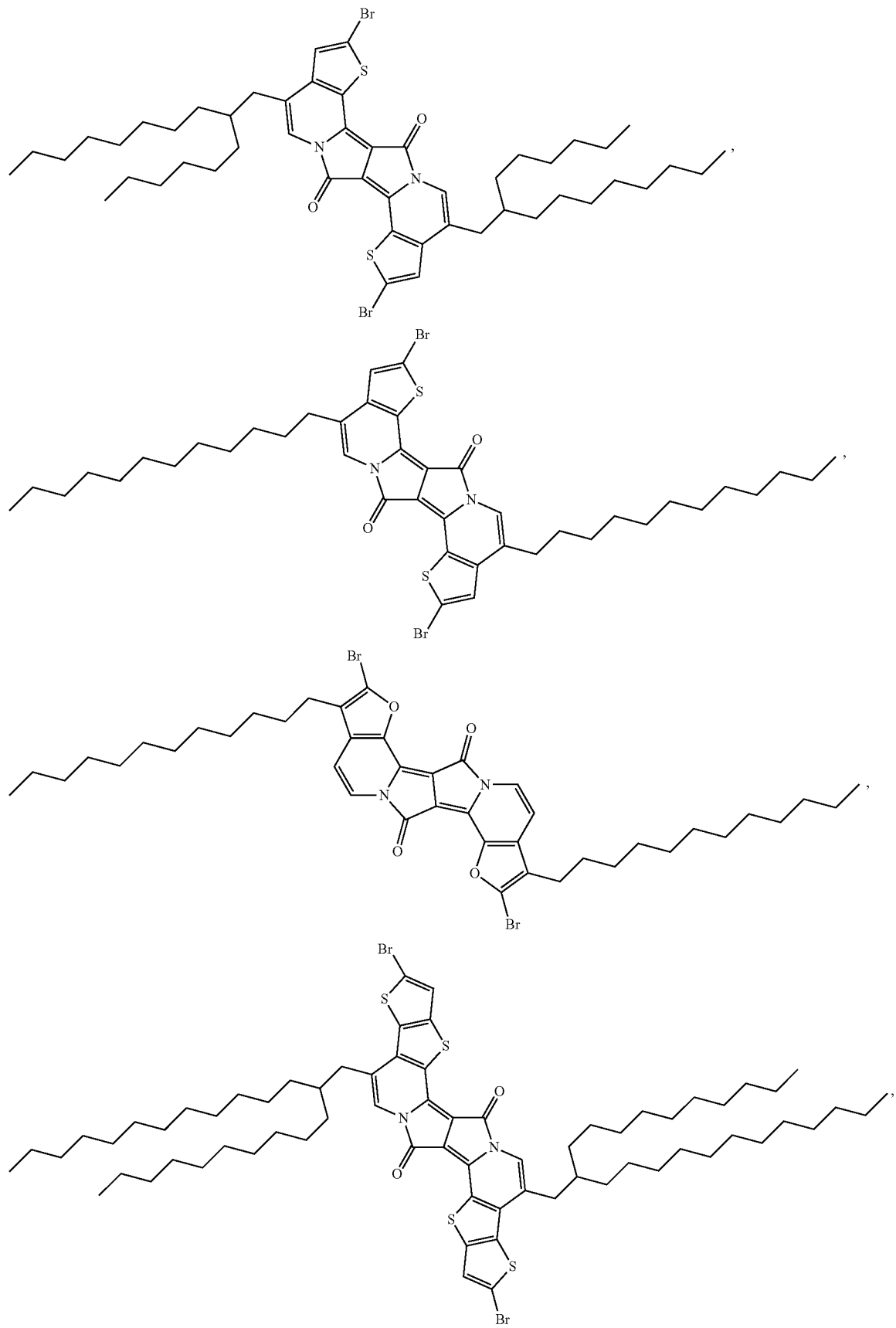

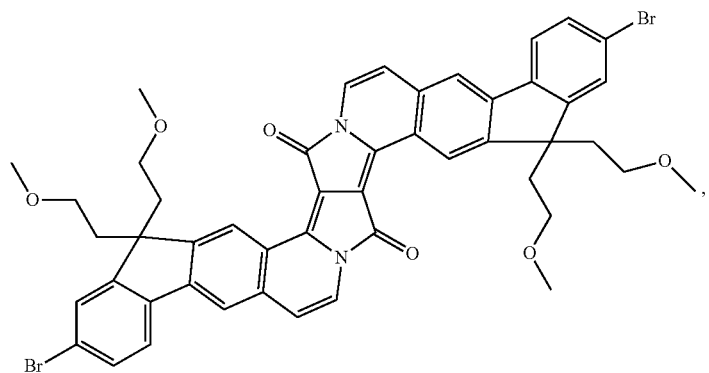
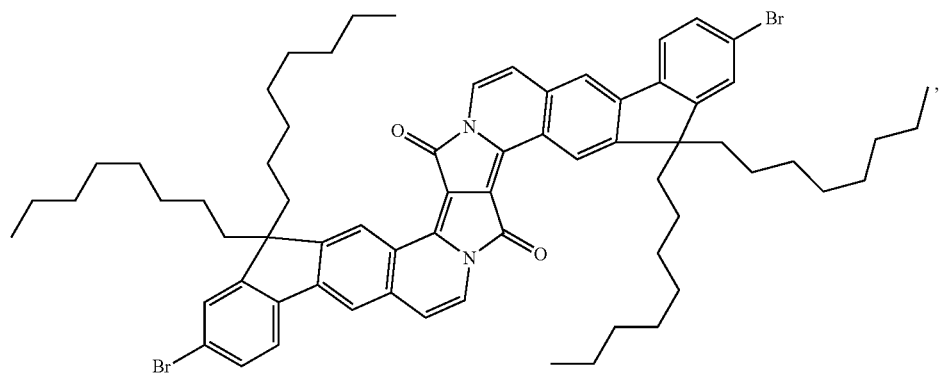
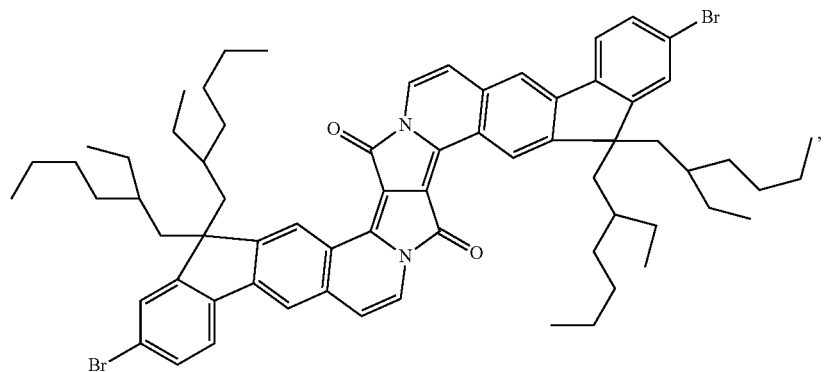
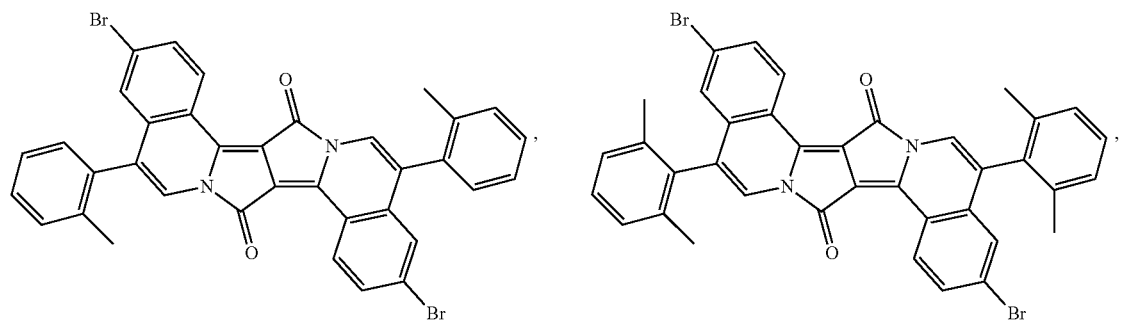

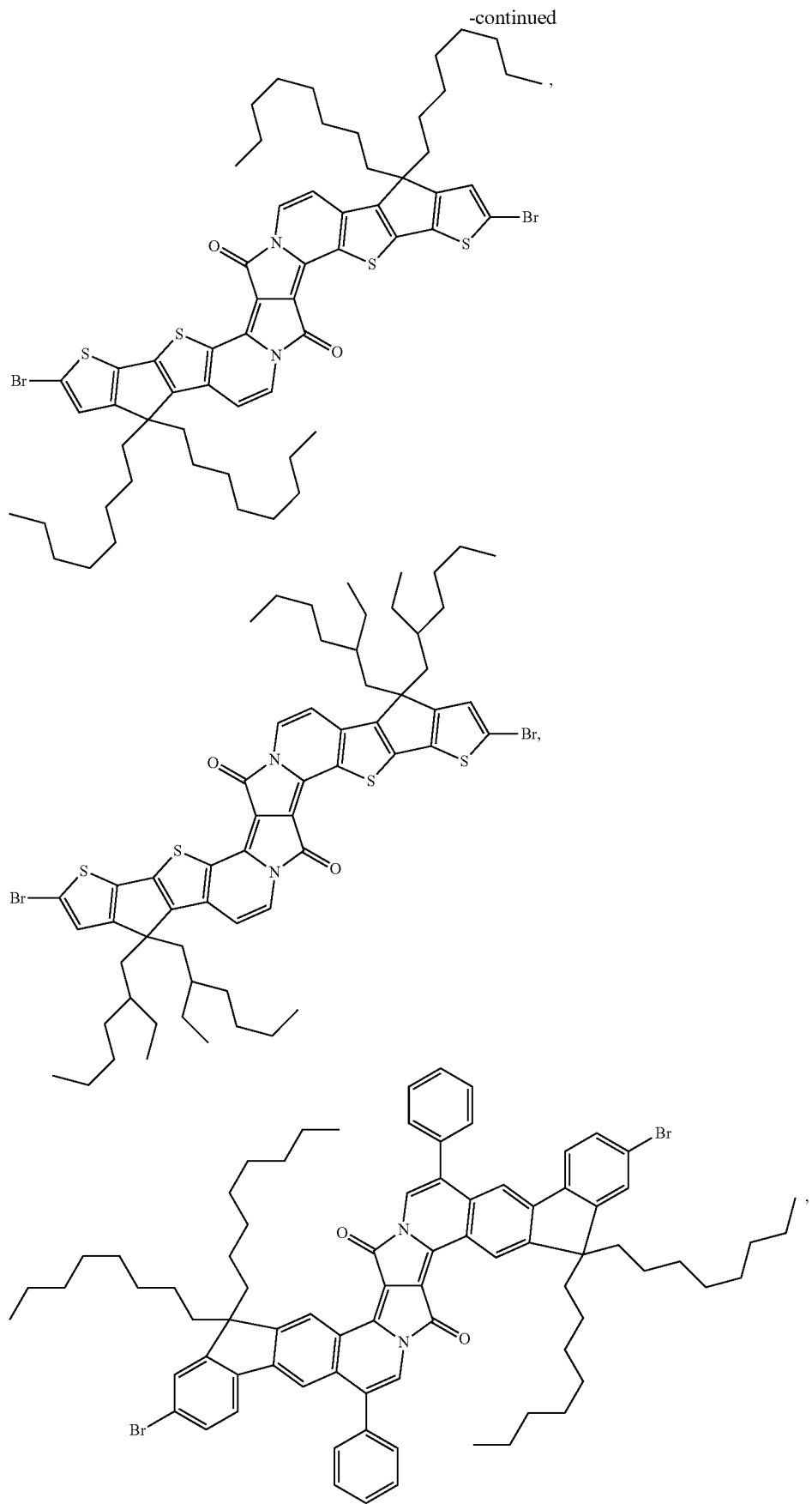

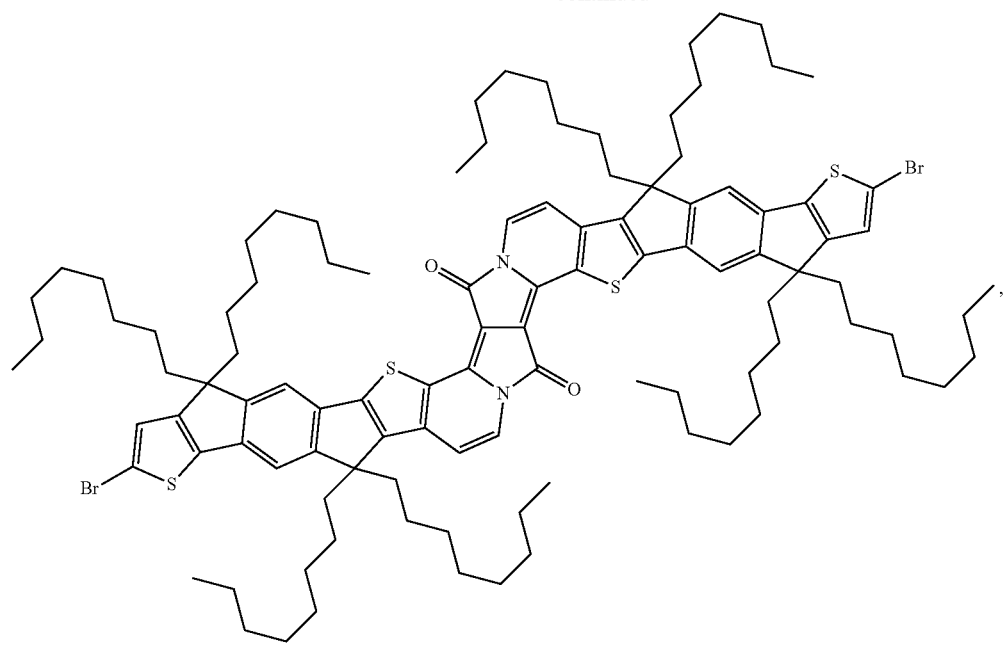
,
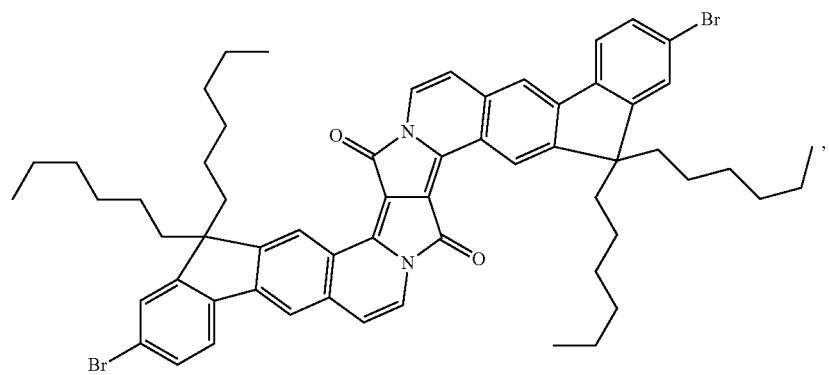
,
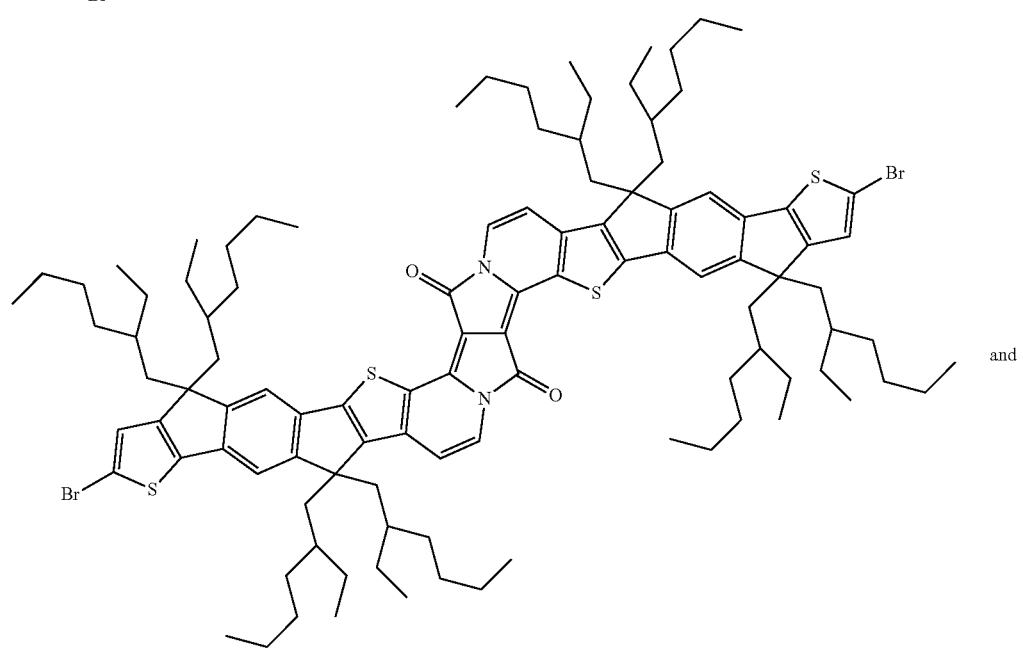
and

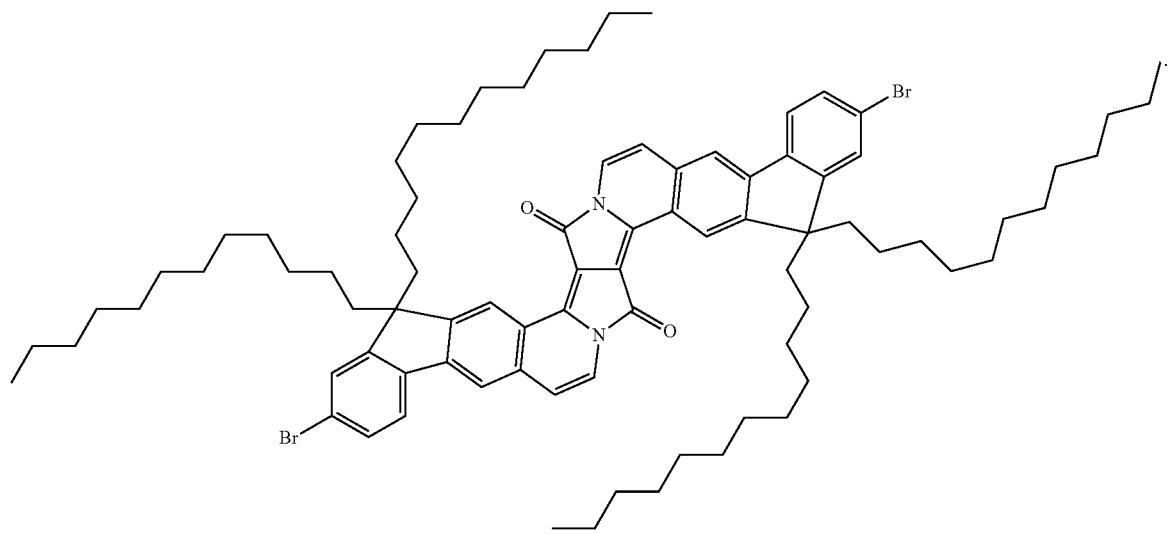

The compounds of formula (I) are known, or can be prepared according to known procedures. Reference is made, for example, to WO2009047104, wherein in addition methods for halogenations as well as chain-extensions are described.

Preferably, in step a) the alkylation reaction is carried out in the presence of tetrabutylammonium hydrogen sulfate (TBAHS), $K_2C_3$ and DMF, preferably at a temperature of 20-140° C., especially 90-130° C., very especially about 90° C., and the product obtained is isolated from the reaction mixture after precipitation with water by extraction, preferably with methylene chloride. Preferably, in step b) the cyclization reaction is carried out in methylene chloride in the presence of trifluoromethanesulphonic acid, or sulphuric acid. Instead of methylene chloride toluene, chlorobenzene, dichlorobenzene and sulfolane may be used.

Method of Production of the Compounds According to the Invention

All the compounds of formula (III) can be obtained in a three-step synthesis according to one general scheme. In the first step, aromatic nitriles 0 are submitted, by a known method, to transformation to the diketopyrrolopyrroles (I) (DPP). The previously known diketopyrrolopyrroles (which are used as red pigments) were alkylated on the nitrogen atoms with e.g. a 2-bromo-aldehyde or a 2-bromo-ketone (or preferably their acetals, respectively ketals), obtaining the so-called N-alkyl derivatives (II). These substances are then submitted in the presence of an acid to intramolecular condensation of the Friedel-Crafts type, which leads to formation of the condensed dyes and pigments (III) of previously unknown structure (Scheme 1).

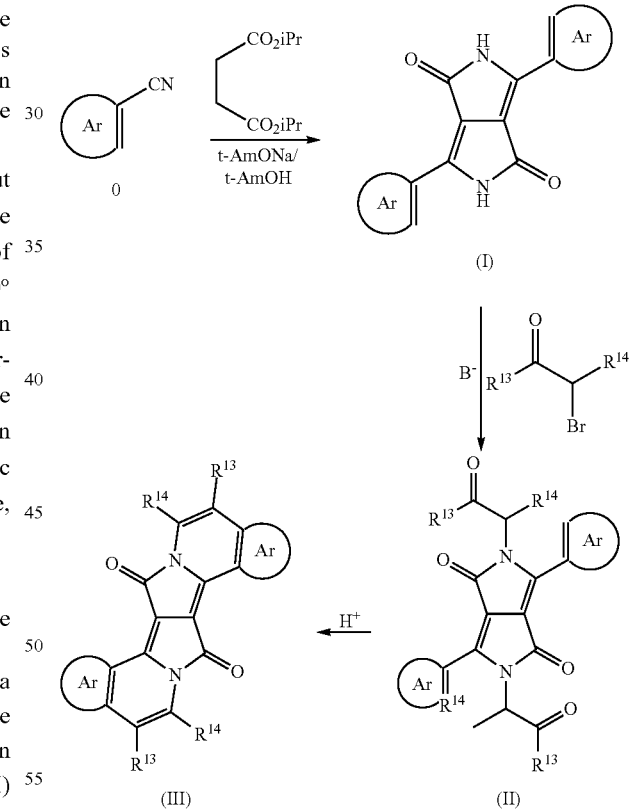

The method of production of the new compounds is simple in execution. The yield of the individual steps is good or very good. In many cases the final compounds can be isolated from the reaction mixture without using chromatography.

A detailed description of the production of the compounds of formula (III) is given in the Examples that follow.

The following compounds of formula (IN-1) to (IN-17) are intermediates in the production of the compounds of formula (III), are new and form a further subject of the present application:

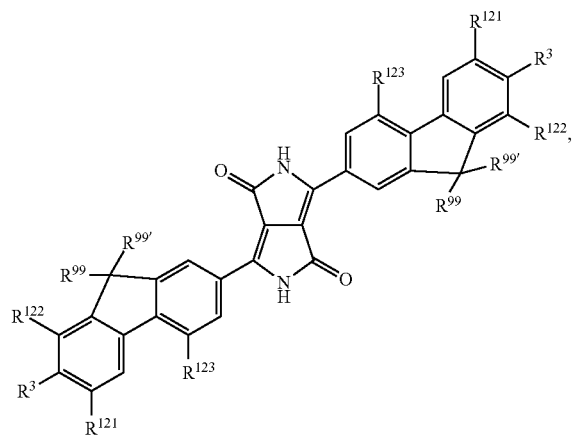
(IN-1)
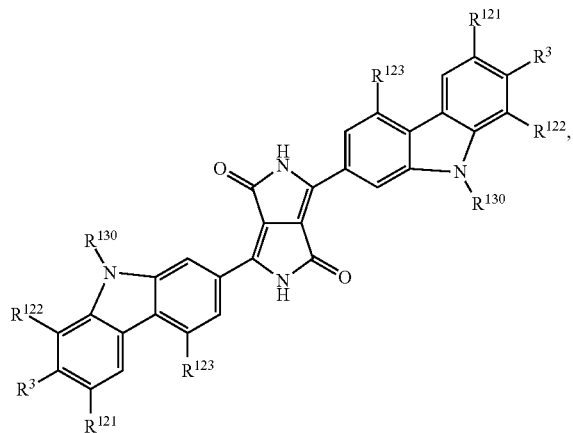
(IN-2)
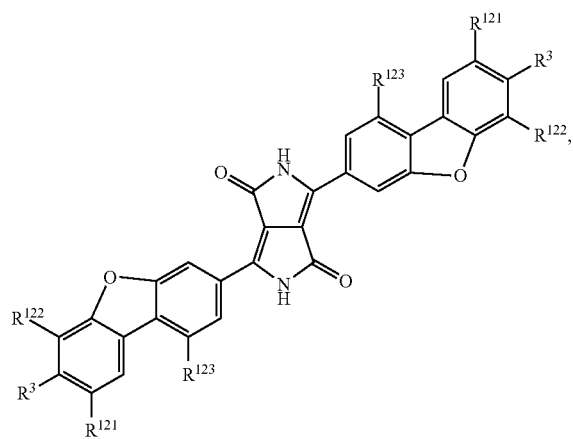
(IN-3)
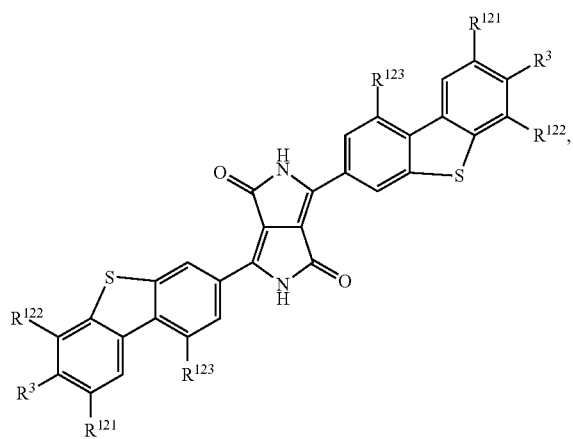
(IN-4)
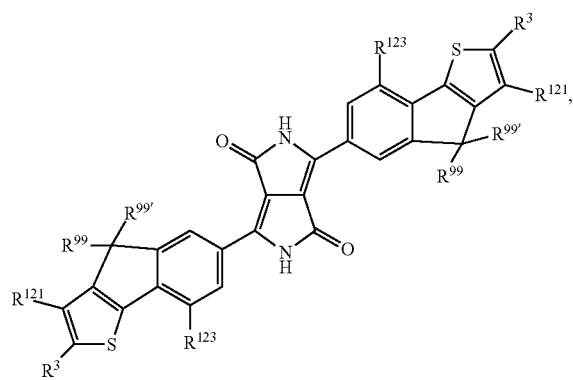
(IN-5)
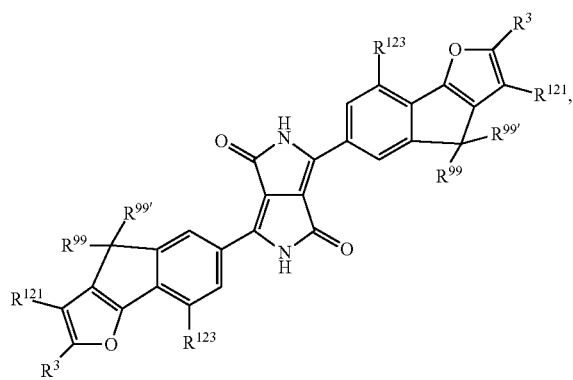
(IN-6)

-continued
(IN-7)
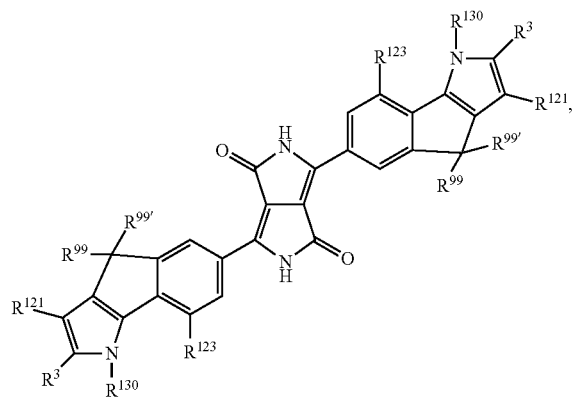
(IN-8)
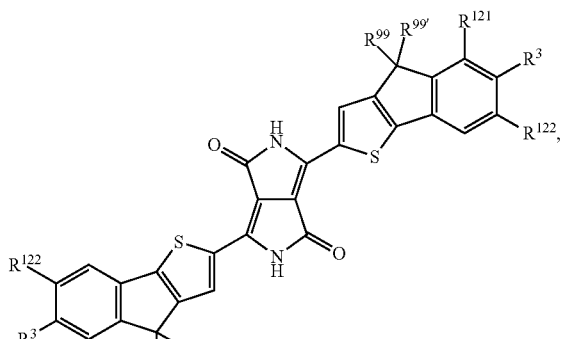
(IN-9)
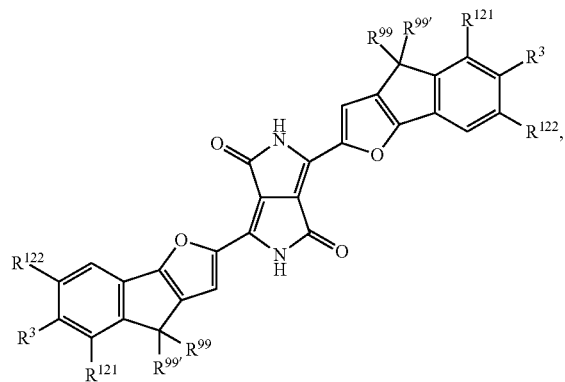
(IN-10)
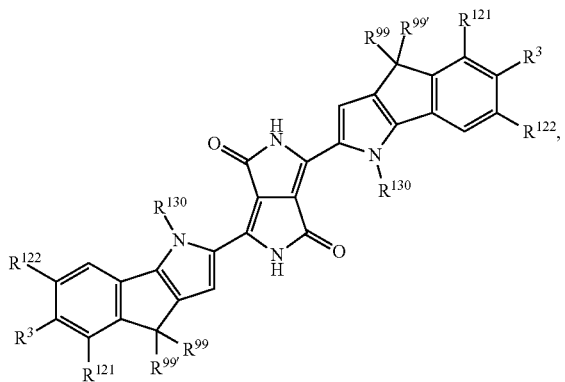
(IN-11)
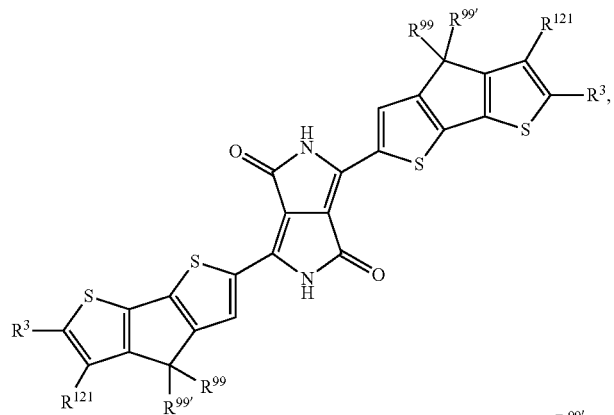
(IN-12)
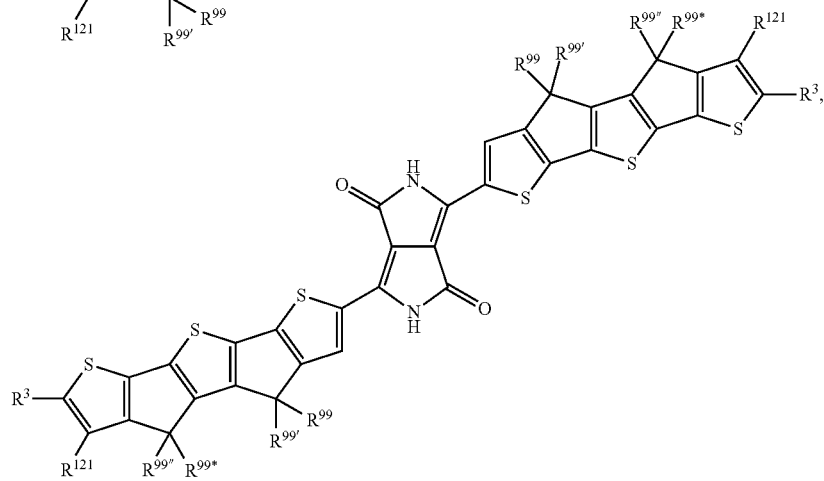

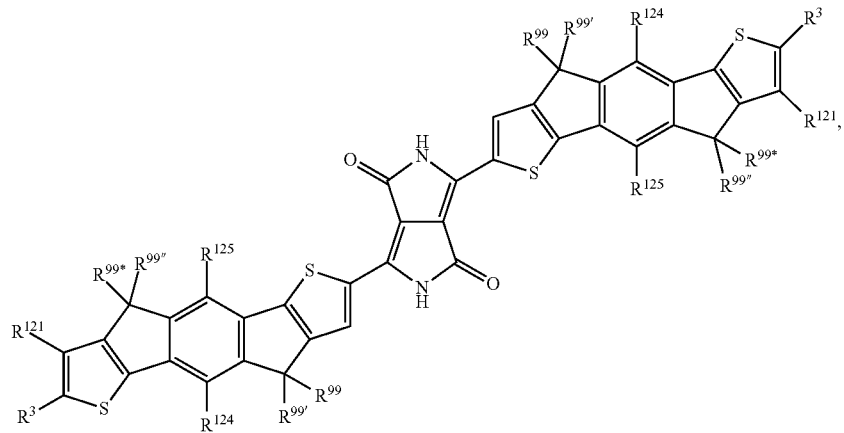
(IN-13)
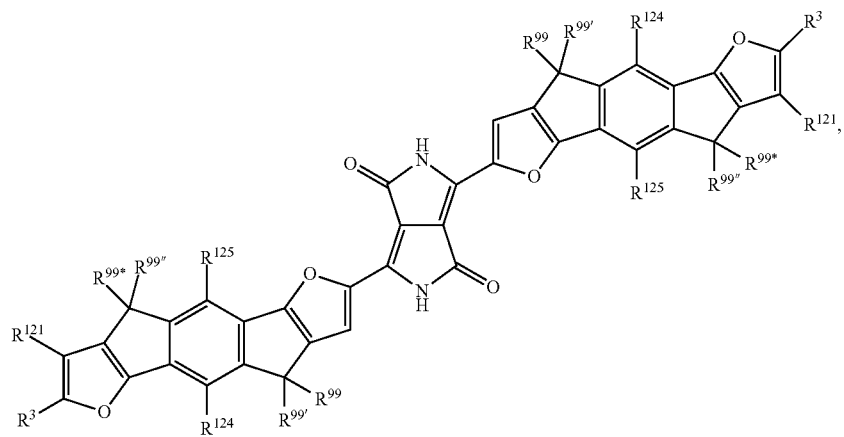
(IN-14)
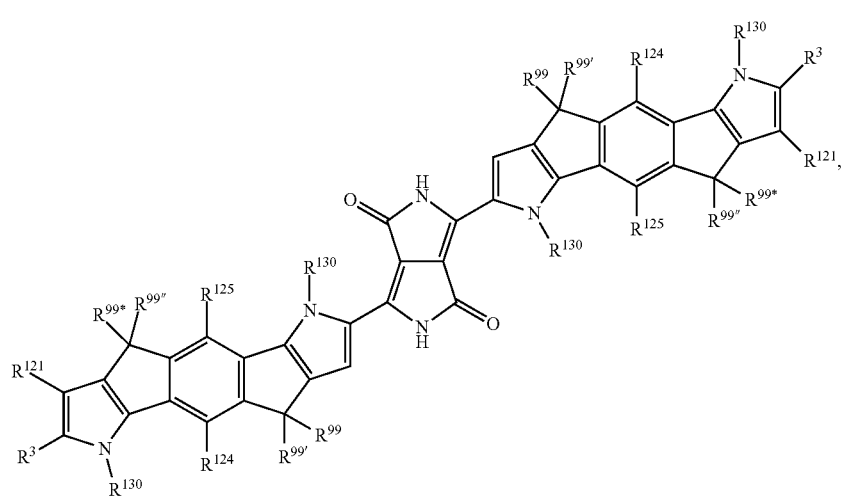
(IN-15)

(IN-16)
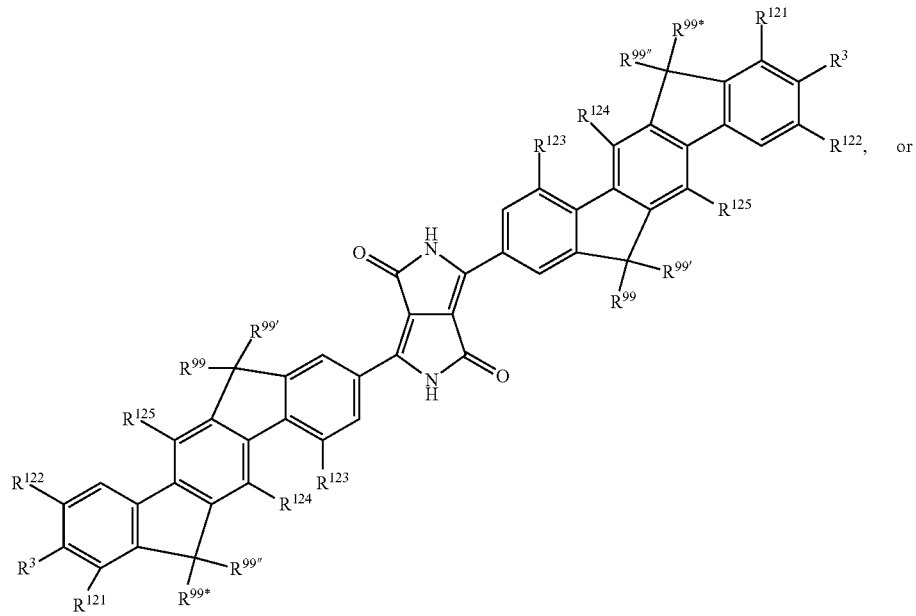
or
(IN-17)
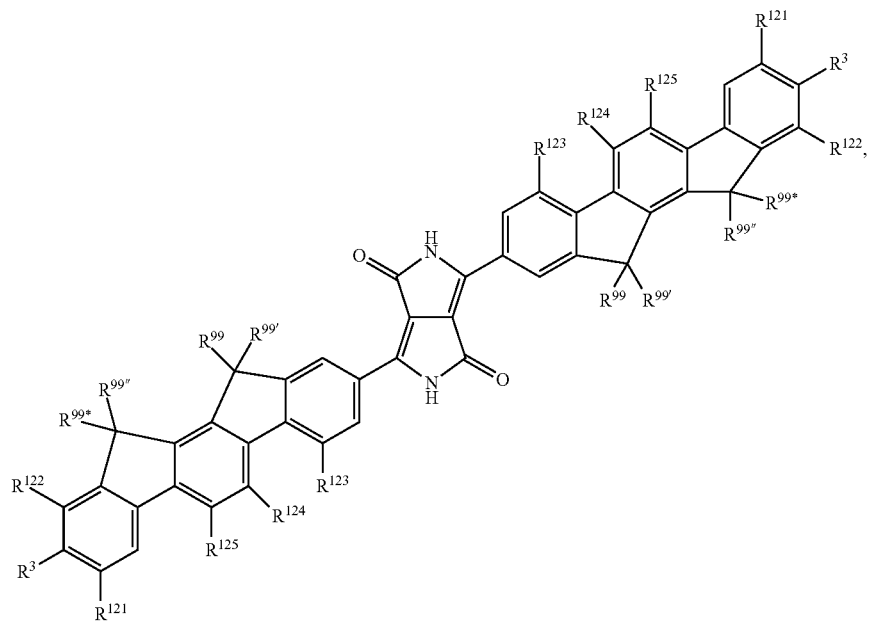
wherein
R³ is hydrogen, halogen, especially F; cyano, $C_1$-$C_{25}$alkoxy, $C_1$-$C_{25}$alkyl substituted with one or more halogen atoms, especially F; $C_1$-$C_{25}$alkyl,
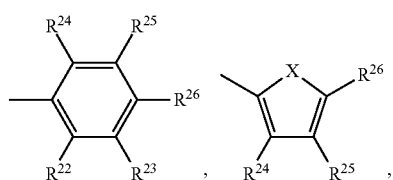
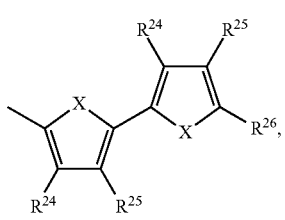

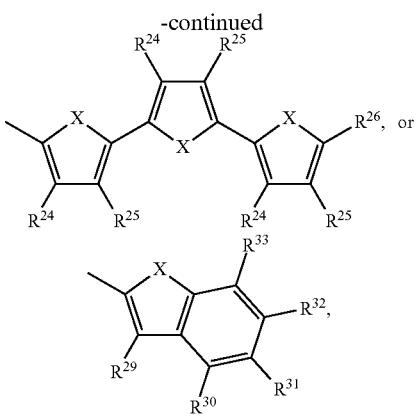

wherein
R$^{22}$ to R$^{25}$ and R$^{29}$ to R$^{33}$ represent independently of each other H, F, cyano, C$_1$-C$_{25}$alkoxy, C$_1$-C$_{25}$alkyl substituted with one or more halogen atoms, especially F; or C$_1$-C$_{25}$alkyl, and
R$^{26}$ is H, F, cyano, phenyl, C$_1$-C$_{25}$alkoxy, C$_1$-C$_{25}$alkyl substituted with one or more halogen atoms, or C$_1$-C$_{25}$alkyl;
R$^{99}$, R$^{99'}$, R$^{99''}$ and R$^{99}$* are independently of each other hydrogen, C$_1$-C$_{25}$alkyl, or C$_1$-C$_{25}$alkyl interrupted by one or more oxygen atoms; preferably C$_3$-C$_{25}$alkyl, or C$_3$-C$_{25}$alkyl which is interrupted by one or more oxygen atoms;
R$^{121}$, R$^{122}$, R$^{123}$, R$^{124}$ and R$^{125}$ are independently of each other hydrogen, halogen, C$_1$-C$_{18}$alkoxy or C$_1$-C$_{25}$alkyl; preferably hydrogen; and
R$^{130}$ is hydrogen, C$_6$-C$_{18}$aryl; C$_6$-C$_{18}$aryl which is substituted by C$_1$-C$_{18}$alkyl, halogen, especially F; or C$_1$-C$_{18}$alkoxy; C$_1$-C$_{25}$alkyl, which may optionally be interrupted by one or more oxygen or sulphur atoms and/or is optionally substituted by one or more halogen atoms, especially F; or C$_7$-C$_{25}$arylalkyl. Preferably, X is O, S, or Se, more preferably X is O, or S, most preferred, X is S.

Compounds (IN-1), (IN-11), (IN-12), (IN-13), (IN-16) and (IN-17) are preferred, compounds (IN-1), (IN-11), (IN-13) and (IN-16) are more preferred; and compounds (IN-1), (IN-11) and (IN-13) are particularly preferred. Compound (IN-1) is most preferred.

Halogen is fluorine, chlorine, bromine and iodine, especially fluorine.

C$_1$-C$_{25}$alkyl (C$_1$-C$_{18}$alkyl) is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl or pentacosyl. C$_1$-C$_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. C$_1$-C$_4$alkyl is typically methyl, ethyl, n-propyl, isopropyl, n-butyl, sec.-butyl, isobutyl, tert.-butyl.

C$_1$-C$_{25}$haloalkyl means a C$_1$-C$_{25}$alkyl group which is substituted with one or more halogen atoms, especially fluorine atoms.

A C$_1$-C$_{25}$alkyl group, which is substituted by one, or more halogen atoms, is a C$_1$-C$_{25}$alkyl group, wherein all, or part of the hydrogen atoms of the corresponding alkyl group have been replaced by halogen atoms, especially fluorine atoms, such as for example —CF$_3$, —CF$_2$CF$_3$, —CF$_2$CF$_2$CF$_3$, —CF(CF$_3$)$_2$, —(CF$_2$)$_3$CF$_3$, and —C(CF$_3$)$_3$.

C$_2$-C$_{25}$alkenyl (C$_2$-C$_{18}$alkenyl) groups are straight-chain or branched alkenyl groups, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

C$_{2-25}$alkinyl (C$_{2-18}$alkinyl) is straight-chain or branched and preferably C$_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

C$_3$-C$_{12}$cycloalkyl is, for example, cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted.

C$_1$-C$_{25}$alkoxy (C$_1$-C$_{18}$alkoxy) groups are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy.

Examples of C$_1$-C$_8$alkoxy are methoxy, ethoxy, n-propoxy, isopropoxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy and 2-ethylhexoxy, preferably C$_1$-C$_4$alkoxy such as typically methoxy, ethoxy, n-propoxy, isopropoxy, n-butoxy, sec.-butoxy, isobutoxy, tert.-butoxy. The term "alkylthio group" means the same groups as the alkoxy groups, except that the oxygen atom of the ether linkage is replaced by a sulfur atom.

Examples of an acyl group include a formyl group, an acetyl group, a propionyl group, an isobutyryl group, a valeryl group, an isovaleryl group, a pivaloyl group, a hexanoyl group, a cyclohexanoyl group, a benzoyl group, and an ethoxycarbonyl group. An acyloxy group is a group containing an acyl group in their structure.

The C$_7$-C$_{25}$arylalkyl groups can be substituted one to five times with C$_1$-C$_8$alkyl, C$_1$-C$_8$alkoxy, CF$_3$ and/or F. Examples are benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably C$_7$-C$_{18}$aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred C$_7$-C$_{12}$aralkyl such as benzyl, 2-benzyl-2-propyl, 3-phenyl-ethyl, α,α-dimethylbenzyl, ω-phenyl-butyl, or ω,ω-dimethyl-ω-phenyl-butyl, in which both the aliphatic hydrocarbon group and aromatic hydrocarbon group may be unsubstituted or substituted. Preferred examples are benzyl, 2-phenylethyl, 3-phenylpropyl, naphthylethyl, naphthylmethyl, and cumyl.

C$_6$-C$_{24}$aryl (C$_6$-C$_{18}$aryl) is typically phenyl, indenyl, azulenyl, naphthyl, biphenyl, as-indacenyl, s-indacenyl, acenaphthylenyl, fluorenyl, phenanthryl, fluoranthenyl, triphenylenyl, chrysenyl, naphthacen, picenyl, perylenyl, pentaphenyl, hexacenyl, pyrenyl, or anthracenyl, preferably phenyl, 1-naphthyl, 2-naphthyl, 4-biphenyl, 9-phenanthryl, 2- or 9-fluorenyl, 3- or 4-biphenyl, which may be unsubstituted or substituted. Examples of $C_6$-$C_{12}$aryl are phenyl, 1-naphthyl, 2-naphthyl, 3- or 4-biphenyl, 2- or 9-fluorenyl or 9-phenanthryl, which may be unsubstituted or substituted.

Heteroaryl is typically $C_2$-$C_{20}$heteroaryl, i.e. a ring with five to seven ring atoms or a condensed ring system, wherein nitrogen, oxygen or sulfur are the possible hetero atoms, and is typically an unsaturated heterocyclic group with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl or phenoxazinyl, which can be unsubstituted or substituted.

Possible substituents of the above-mentioned aryl, or heteroaryl groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, a nitro group, or a silyl group, especially $C_1$-$C_8$alkyl, $C_1$-$C_8$alkoxy, $C_1$-$C_8$alkylthio, halogen, halo-$C_1$-$C_8$alkyl, or a cyano group.

$C_1$-$C_{25}$alkyl interrupted by one or more O is, for example, $(CH_2CH_2O)_{1-9}$—$R^x$, where $R^x$ is H or $C_1$-$C_{10}$alkyl, $CH_2$—$CH(OR^{y'})$—$CH_2$—O—$R^y$, where $R^y$ is $C_1$-$C_{18}$alkyl, and $R^{y'}$ embraces the same definitions as $R^y$ or is H. $C_1$-$C_{25}$alkyl interrupted by one or more S is, for example, $(CH_2CH_2S)_{1-9}$—$R^x$, where $R^x$ is H or $C_1$-$C_{10}$alkyl, $CH_2$—$CH(SR^{y'})$—$CH_2$—S—$R^y$, where $R^y$ is $C_1$-$C_{18}$alkyl, and $R^{y'}$ embraces the same definitions as $R^y$ or is H.

A cycloalkyl-alkyl group is an alkyl group substituted by a cycloalkyl group, e.g. cyclohex-yl-methyl. $C_3$-$C_{12}$cycloalkyl-alkyl group, which may optionally be interrupted by one or more oxygen atoms is, for example,

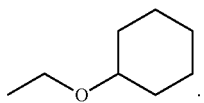

If a substituent, such as, for example, $R^{24}$ and $R^{25}$, occurs more than one time in a group, it can be different in each occurrence.

The homo- or heteroaromatic system (Ar) is selected from the group consisting of benzene, furan, thiopene, pyrrole, selenophene, benzofuran, benzothiophene, indole, benzoselenophene, thieno[2,3-b]thiophene and thieno[3,2-b]thiophene. The homo- or heteroaromatic system may be unsubstituted, or substituted. Examples of substituents are halogen, especially F; cyano, $C_1$-$C_{25}$alkoxy, $C_1$-$C_{25}$alkyl, $C_1$-$C_{25}$alkyl substituted with one or more halogen atoms, especially F;

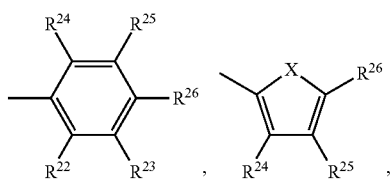

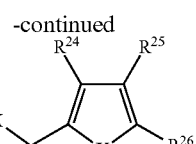

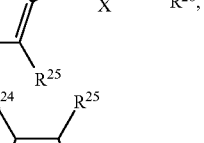

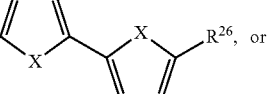

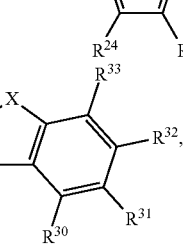

wherein X, $R^{22}$ to $R^{26}$ and $R^{29}$ to $R^{33}$ are as defined above.

The compounds of formula (III) may be used as functional dyes in dye sensitized and bulk heterojunction solar cells, organic light-emitting diodes, photodiodes, organic field-effect transistors, fluorescence imaging, sensors and solid-state dye lasers.

Advantageously, the compound of formula (III), or an organic semiconductor material, layer or component, comprising the compound of formula (III) can be used in organic photovoltaics (solar cells) and photodiodes, or in an organic field effect transistor (OFET).

A mixture containing the compound of formula (III) results in a semi-conducting layer comprising the compound of formula (III) (typically 0.1% to 99.9999% by weight, more specifically 1% to 99.9999% by weight, even more specifically 5% to 99.9999% by weight, especially 20 to 85% by weight) and at least another material. The other material can be, but is not restricted to another compound of formula (III), a semi-conducting polymer, a non-conductive polymer, organic small molecules, carbon nanotubes, a fullerene derivative, inorganic particles (quantum dots, quantum rods, quantum tripods, $TiO_2$, ZnO etc.), conductive particles (Au, Ag etc.), insulator materials like the ones described for the gate dielectric (PET, PS etc.).

Accordingly, the present invention also relates to an organic semiconductor material, layer or component, comprising a compound of formula (III) and to a semiconductor device, comprising a compound of formula (III) and/or an organic semiconductor material, layer or component. The semiconductor device is especially a sensor, a diode, a photodiode, an organic field effect transistor, a transistor for flexible displays, and/or a solar cell (photovoltaic cell).

The semiconductor is preferably an organic photovoltaic (PV) device (solar cell), a photodiode, or an organic field effect transistor. The structure and the components of the OPV and OFET device will be described in more detail below.

Accordingly, the invention provides organic photovoltaic (PV) devices (solar cells) comprising a compound of the formula (III).

The compound of formula (III) for use in an electronic device is preferably a compound of formula (IIIa), (IIIb), (IIId), (IIIf), (IIIg), (IIIh), (IIIi), (IIIj) and (IIIm), especially (IIIb), (IIId) and (IIIj); more preferably a compound of formula (IIIa'), (IIIb'), (IIId'), (IIIf'), (IIIg'), (IIIh'), (IIIi'), (IIIj') and (IIIm'), very especially (IIIb'), (IIId') and (IIIj').

In another preferred embodiment the compound of formula (III) for use in an electronic device is preferably a compound of formula (IIIo), (IIIw), (IIIx), (IIIy), (IIIz), (IIIac), (IIIad), (IIIaf), (IIIag), (IIIah), (IIIai), (IIIak), (IIIal), (IIIam), or (IIIan), especially (IIIo), (IIIw), (IIIac), (IIIaf), (IIIag), (IIIah), (IIIak), or (IIIam); very especially (IIIo), (IIIaf), or (IIIah). A compound of formula (IIIo) is most preferred.

The structure of organic photovoltaic devices (solar cells) is, for example, described in C. Deibel et al. Rep. Prog. Phys. 73 (2010) 096401 and Christoph Brabec, Energy Environ. Sci 2. (2009) 347-303.

The PV device comprise in this order:
(a) a cathode (electrode),
(b) optionally a transition layer, such as an alkali halogenide, especially lithium fluoride,
(c) a photoactive layer,
(d) optionally a smoothing layer,
(e) an anode (electrode),
(f) a substrate.

The photoactive layer comprises the compounds of the formula (III). Preferably, the photoactive layer is made of a compound of the formula (III), as an electron donor and an acceptor material, like a fullerene, particularly a functionalized fullerene PCBM, as an electron acceptor. As stated above, the photoactive layer may also contain a polymeric binder. The ratio of the small molecules of formula (III) to the polymeric binder can vary from 5 to 95 percent. Preferably, the polymeric binder is a semicristalline polymer such as polystyrene (PS), high-density polyethylene (HDPE), polypropylene (PP) and polymethylmethacrylate (PMMA).

The fullerenes useful in this invention may have a broad range of sizes (number of carbon atoms per molecule). The term fullerene as used herein includes various cage-like molecules of pure carbon, including Buckminsterfullerene ($C_{60}$) and the related "spherical" fullerenes as well as carbon nanotubes. Fullerenes may be selected from those known in the art ranging from, for example, $C_{20}$-$C_{1000}$. Preferably, the fullerene is selected from the range of $C_{60}$ to $C_{96}$. Most preferably the fullerene is $C_{60}$ or $C_{70}$, such as [60]PCBM, or [70]PCBM. It is also permissible to utilize chemically modified fullerenes, provided that the modified fullerene retains acceptor-type and electron mobility characteristics. The acceptor material can also be a material selected from the group consisting of another compound of formula III, or any semi-conducting polymer, provided that the polymers retain acceptor-type and electron mobility characteristics, organic small molecules, carbon nanotubes, inorganic particles (quantum dots, quantum rods, quantum tripods, $TiO_2$, ZnO etc.).

The photoactive layer is made of a compound of the formula (III) as an electron donor and a fullerene, particularly functionalized fullerene PCBM, as an electron acceptor. These two components are mixed with a solvent and applied as a solution onto the smoothing layer by, for example, the spin-coating method, the drop casting method, the Langmuir-Blodgett ("LB") method, the ink jet printing method and the dripping method. A squeegee or printing method could also be used to coat larger surfaces with such a photoactive layer. Instead of toluene, which is typical, a dispersion agent such as chlorobenzene is preferably used as a solvent. Among these methods, the vacuum deposition method, the spin-coating method, the ink jet printing method and the casting method are particularly preferred in view of ease of operation and cost.

In the case of forming the layer by using the spin-coating method, the casting method and ink jet printing method, the coating can be carried out using a solution and/or dispersion prepared by dissolving, or dispersing the composition in a concentration of from 0.01 to 90% by weight in an appropriate organic solvent such as benzene, toluene, xylene, tetrahydrofurane, methyltetrahydrofurane, N,N-dimethylformamide, acetone, acetonitrile, anisole, dichloromethane, dimethylsulfoxide, chlorobenzene, 1,2-dichlorobenzene and mixtures thereof.

The photovoltaic (PV) device can also consist of multiple junction solar cells that are processed on top of each other in order to absorb more of the solar spectrum. Such structures are, for example, described in App. Phys. Let. 90, 143512 (2007), Adv. Funct. Mater. 16, 1897-1903 (2006) and WO2004/112161.

A so called tandem solar cell comprise in this order:
(a) a cathode (electrode),
(b) optionally a transition layer, such as an alkali halogenide, especially lithium fluoride,
(c) a photoactive layer,
(d) optionally a smoothing layer,
(e) a middle electrode (such as Au, Al, ZnO, $TiO_2$ etc.)
(f) optionally an extra electrode to match the energy level,
(g) optionally a transition layer, such as an alkali halogenide, especially lithium fluoride,
(h) a photoactive layer,
(i) optionally a smoothing layer,
(j) an anode (electrode),
(k) a substrate. The compound of formula (III) is comprised by at least one of the photoactive layers.

The PV device can also be processed on a fiber as described, for example, in US20070079867 and US 20060013549.

Due to their excellent self-organising properties the materials or films comprising the compounds of the formula (III) can also be used alone or together with other materials in or as alignment layers in LCD or OLED devices, as described for example in US2003/0021913.

An OFET device according to the present invention preferably comprises:
a source electrode,
a drain electrode,
a gate electrode,
a semiconducting layer,
one or more gate insulator layers, and
optionally a substrate, wherein the semiconductor layer comprises a compound of formula (III).

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

Preferably the OFET comprises an insulator having a first side and a second side, a gate electrode located on the first side of the insulator, a layer comprising a compound of formula III located on the second side of the insulator, and a drain electrode and a source electrode located on the polymer layer.

The OFET device can be a top gate device or a bottom gate device.

Suitable structures and manufacturing methods of an OFET device are known to those skilled in the art and are described in the literature, for example in WO03/052841.

Typically the semiconducting layer of the present invention is at most 1 micron (=1 µm) thick, although it may be thicker if required. For various electronic device applications, the thickness may also be less than about 1 micron. For example, for use in an OFET the layer thickness may typically be 100 nm or less. The exact thickness of the layer will depend, for example, upon the requirements of the electronic device in which the layer is used.

The insulator layer (dielectric layer) generally can be an inorganic material film or an organic polymer film. Illustrative examples of inorganic materials suitable as the gate dielectric layer include silicon oxide, silicon nitride, aluminum oxide, barium titanate, barium zirconium titanate and the like. Illustrative examples of organic polymers for the gate dielectric layer include polyesters, polycarbonates, poly (vinyl phenol), polyimides, polystyrene, poly(methacrylate)s, poly(acrylate)s, epoxy resin, photosensitive resists as described in WO07/113107 and the like. In the exemplary embodiment, a thermally grown silicon oxide ($SiO_2$) may be used as the dielectric layer.

The thickness of the dielectric layer is, for example from about 10 nanometers to about 2000 nanometers depending on the dielectric constant of the dielectric material used. A representative thickness of the dielectric layer is from about 100 nanometers to about 500 nanometers. The dielectric layer may have a conductivity that is for example less than about $10^{-12}$ S/cm.

The gate insulator layer may comprise for example a fluoropolymer, like e.g. the commercially available Cytop 809M®, or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont), or Fluoro-pel® (from Cytonix) or the perfluorosolvent FC 43® (Acros, No. 12377).

In the gate electrode and the source/drain electrodes included in the OFET of the present invention, a typical metal may be used, specific examples thereof include, but are not limited to, platinum (Pt), palladium (Pd), gold (Au), silver (Ag), copper (Cu), aluminum (Al), nickel (Ni). Alloys and oxides, such as molybdenum trioxide and indium tin oxide (ITO), may also be used. Preferably, the material of at least one of the gate, source and drain electrodes is selected from the group Cu, Ag, Au or alloys thereof. The source and drain electrodes may be deposited by thermal evaporation and patterned using standard photolithography and lift off techniques as are known in the art.

The substrate may be rigid or flexible. Rigid substrates may be selected from glass or silicon and flexible substrates may comprise thin glass or plastics such as poly(ethylene terephthalate) (PET), polyethylenenaphthalate (PEN), polycarbonate, polycarbonate, polyvinylalcohol, polyacrylate, polyimide, polynorbornene, and polyethersulfone (PES).

Alternatively, conductive polymers may be deposited as the source and drain electrodes. An example of such a conductive polymer is poly(ethylene dioxythiophene) (PEDOT) although other conductive polymers are known in the art. Such conductive polymers may be deposited from solution using, for example, spin coating or ink jet printing techniques and other solution deposition techniques.

The source and drain electrodes are preferably formed from the same material for ease of manufacture. However, it will be appreciated that the source and drain electrodes may be formed of different materials for optimisation of charge injection and extraction respectively.

Typical thicknesses of source and drain electrodes are about, for example, from about 40 nanometers to about 1 micrometer with the more specific thickness being about 100 to about 400 nanometers.

The length of the channel defined between the source and drain electrodes may be up to 500 microns, but preferably the length is less than 200 microns, more preferably less than 100 microns, most preferably less than 20 microns.

Other layers may be included in the device architecture. For example, a self assembled monolayer (SAM) may be deposited on the gate, source or drain electrodes, substrate, insulating layer and organic semiconductor material to promote crystallity, reduce contact resistance, repair surface characteristics and promote adhesion where required. Exemplary materials for such a monolayer include chloro- or alkoxy-silanes with long alkyl chains, such as, for example, octadecyltrichlorosilane.

In a preferred embodiment, the deposition of at least one compound of the general formula (III) (and if appropriate further semiconductor materials) is carried out by a gas phase deposition process (physical vapor deposition, PVD). PVD processes are performed under high-vacuum conditions and comprise the following steps: evaporation, transport, deposition. It has been found that, surprisingly, the compounds of the general formula (III) are suitable particularly advantageously for use in a PVD process, since they essentially do not decompose and/or form undesired by-products. The material deposited is obtained in high purity. In a specific embodiment, the deposited material is obtained in the form of crystals or comprises a high crystalline content. In general, for the PVD, at least one compound of the general formula III is heated to a temperature above its evaporation temperature and deposited on a substrate by cooling below the crystallization temperature. The temperature of the substrate in the deposition is preferably within a range from about 20 to 250° C., more preferably from 50 to 200° C.

The resulting semiconductor layers generally have a thickness which is sufficient for ohmic contact between source and drain electrodes. The deposition can be effected under an inert atmosphere, for example under nitrogen, argon or helium. The deposition is effected typically at ambient pressure or under reduced pressure. A suitable pressure range is from about $10^{-7}$ to 1.5 bar.

The compound of the formula (III) is preferably deposited on the substrate in a thickness of from 10 to 1000 nm, more preferably from 15 to 250 nm. In a specific embodiment, the compound of the formula (III) is deposited at least partly in crystalline form. For this purpose, especially the above-described PVD process is suitable. Moreover, it is possible to use previously prepared organic semiconductor crystals. Suitable processes for obtaining such crystals are described by R. A. Laudise et al. in "Physical Vapor Growth of Organic Semi-Conductors", Journal of Crystal Growth 187 (1998), pages 449-454, and in "Physical Vapor Growth of Centimeter-sized Crystals of α-Hexathiophene", Journal of Crystal Growth 1982 (1997), pages 416-427, which are incorporated here by reference.

OFETs have a wide range of possible applications. One such application is to drive pixels in an optical device (apparatus), preferably an organic optical device. Examples of such optical devices include photoresponsive devices, in particular photodetectors, and light-emissive devices, in particular organic light emitting devices. High mobility OTFTs are particularly suited as backplanes for use with active matrix organic light emitting devices, e.g. for use in display applications.

High efficiency of energy conversion, excellent field-effect mobility, high open-circuit voltages ($V_{oc}$), good on/off current ratios and/or excellent stability can be observed, when the according to the invention are used in organic field effect transistors, organic photovoltaics (solar cells) and photodiodes.

The following examples are included for illustrative purposes only and do not limit the scope of the claims. Unless otherwise stated, all parts and percentages are by weight.

EXAMPLES

Example 1

1. Synthesis of 1,4-Diketo-3,6-di(3,4-dimethoxyphenyl)pyrrolo[3,4-c]pyrrole (1a)

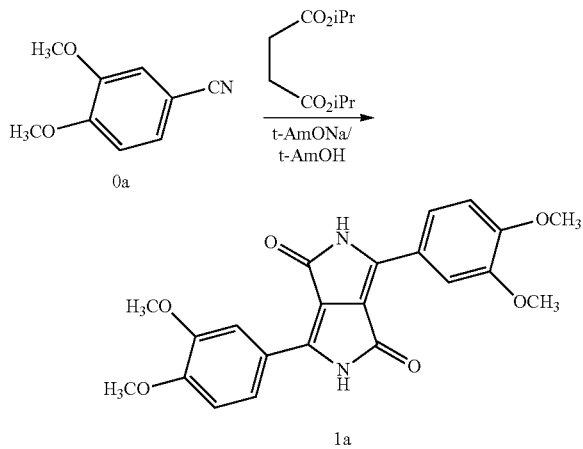

A three-necked flask equipped with a reflux condenser and magnetic stirrer is charged with 40 ml of tert-amyl alcohol, 1.15 g of sodium (50 mmol) and a catalytic amount of iron(III) chloride. The mixture is heated at the boiling point until the sodium has reacted completely. Then the reaction mixture is cooled to 90° C. and 23 mmol of nitrile is added with a syringe (solid nitriles should be dissolved beforehand in a small amount of tert-amyl alcohol). The mixture is heated to 110° C. and 2.1 ml (10 mmol) of diisopropyl succinate is added dropwise in the space of 30 min. After reaction at 110° C. for 16 h, the flask contents are cooled and 100 ml of a mixture of water, methanol and acetic acid in volumetric proportions 1:1:1 is added. The suspension obtained is heated for some minutes at the boiling point and then cooled to 30° C. The precipitate is filtered off, washed several times with hot water and methanol and dried under reduced pressure.

Yield: 736 mg (18%). Red powder. M.p.: Decomposition >370° C. $^1$H-NMR (500 MHz, DMSO-$d_6$, 80° C.): δ 10.84 (s, 2H), 8.18 (d, J=2.0 Hz, 2H), 8.10 (dd, $J_1$=2.0 Hz, $J_2$=8.4 Hz, 2H), 7.11 (d, J=8.4 Hz, 2H), 3.88 (s, 6H), 3.86 (s, 6H). $^{13}$C-NMR (125 MHz, DMSO-$d_6$): δ 163.0, 152.5, 149.7, 143.7, 122.4, 121.5, 112.8, 112.4, 109.9, 56.5, 56.4. HRMS (EI 70 eV) calc. for $C_{22}H_{20}N_2O_6$ ($M^+$): 408.1321. found: 408.1316. Calc. elem. anal. (%) for the formula $C_{22}H_{20}N_2O_6$: C, 64.70; H, 4.94; N, 6.86. found: C, 64.64; H, 4.99; N, 6.62.

2. General Method of Synthesis of Diketones 2a, 2b and 2c

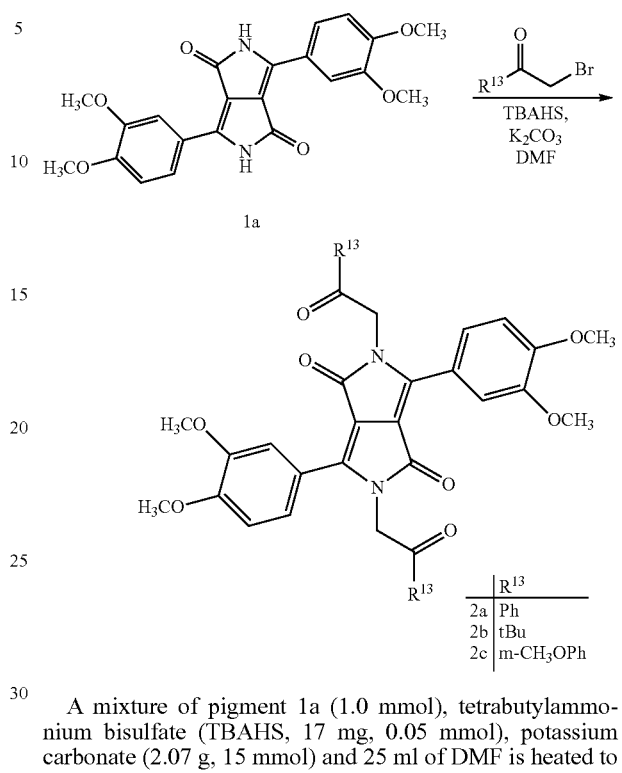

| | $R^{13}$ |
|---|---|
| 2a | Ph |
| 2b | tBu |
| 2c | m-CH$_3$OPh |

A mixture of pigment 1a (1.0 mmol), tetrabutylammonium bisulfate (TBAHS, 17 mg, 0.05 mmol), potassium carbonate (2.07 g, 15 mmol) and 25 ml of DMF is heated to 120° C. under an argon atmosphere. Then a given amount of α-bromoketone is added dropwise by a syringe (30 min). The reaction mixture is stirred for 2 h, cooled and diluted with water and methylene chloride. The aqueous layer is extracted with methylene chloride, combined organic layers are washed with water and brine and dried over sodium sulfate. Solvents are evaporated, the product is separated by the column chromatography in the given eluting system.

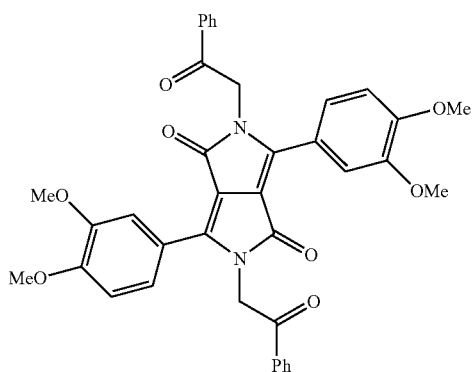 [SMILES: COc1ccc(C2=C3C(=O)N(CC(=O)c4ccccc4)C(c4ccc(OC)c(OC)c4)=C3C(=O)N2CC(=O)c2ccccc2)cc1OC]

2,5-Bis(2-oxo-2-phenylethyl)-1,4-diketo-3,6-bis(3,4-dimethoxyphenyl)pyrrolo[3,4-c]pyrrole (2a)

Prepared from 1a (408 mg, 1.0 mmol). α-Bromoketone used: phenacyl bromide (1.99 g, 10.0 mmol) which is dissolved in 4 ml of DMF prior to use. Purified by the column chromatography (methylene chloride:acetone 49:1→19:1) and recrystallized from CHCl$_3$/EtOH. Yield: 191 mg (30%). Orange solid. Mp: Decomposition >250° C.

¹H NMR (500 MHz, CDCl₃) δ 8.03-7.96 (m, 4H), 7.66-7.59 (m, 2H), 7.54-7.45 (m, 6H), 7.28 (dd, J=8.5, 2.1 Hz, 2H), 6.87 (d, J=8.5 Hz, 2H), 5.28 (s, 4H), 3.88 (s, 6H), 3.81 (s, 6H). ¹³C NMR (126 MHz, CDCl₃) δ 193.6, 162.6, 151.6, 149.1, 148.0, 134.7, 134.0, 128.9, 128.1, 121.7, 120.6, 112.1, 111.1, 109.2, 56.0 (2 signals), 48.9. HRMS (ESI) calcd for $C_{38}H_{32}N_2O_8Na$ (M+Na⁺): 667.2051. found: 667.2062.

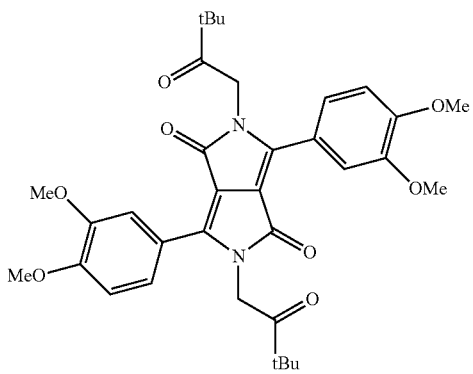 [SMILES: COc1ccc(C2=C3C(=O)N(CC(=O)C(C)(C)C)C(c4ccc(OC)c(OC)c4)=C3C(=O)N2CC(=O)C(C)(C)C)cc1OC]

2,5-Bis(3,3-dimethyl-2-oxobutyl)-1,4-diketo-3,6-bis(3,4-dimethoxyphenyl)pyrrolo[3,4-c]pyrrole (2b)

Prepared from 1a (408 mg, 1.0 mmol). α-Bromoketone used: 1-bromo-3,3-dimethylbutan-2-one (0.67 ml, 5.0 mmol). Purified by the column chromatography (methylene chloride:acetone 49:1→19:1) and recrystallized from CHCl₃/pentane. Yield: 210 mg (35%). Red powder. Mp: 203-204° C. ¹H NMR (500 MHz, CDCl₃) δ 7.38 (d, J=2.0 Hz, 2H), 7.19 (dd, J=8.4, 2.1 Hz, 2H), 6.91 (d, J=8.5 Hz, 2H), 4.75 (s, 4H), 3.92 (s, 6H), 3.91 (s, 6H), 1.19 (s, 18H). ¹³C NMR (126 MHz, CDCl₃) δ 209.3, 162.5, 151.5, 149.2, 148.1, 121.8, 120.7, 112.0, 111.0, 109.2, 56.2, 56.0, 47.1, 43.4, 26.4. HRMS (ESI) calcd for $C_{34}H_{40}N_2O_8Na$ (M+Na⁺): 627.2682. found: 627.2678.

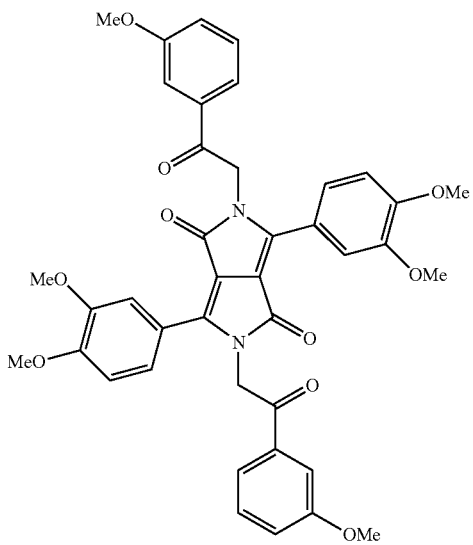 [SMILES: COc1cccc(C(=O)CN2C(=O)C3=C(c4ccc(OC)c(OC)c4)N(CC(=O)c4cccc(OC)c4)C(=O)C3=C2c2ccc(OC)c(OC)c2)c1]

2,5-Bis(2-oxo-2-(3-methoxyphenyl)ethyl)-1,4-diketo-3,6-bis(3,4-dimethoxyphenyl)-pyrrolo[3,4-c]pyrrole (2c)

Prepared from 1a (408 mg, 1.0 mmol). α-Bromoketone used: 3'-methoxyphenacyl bromide (2.29 g, 10.0 mmol) which is dissolved in 4 ml of DMF prior to use. Purified by the column chromatography (methylene chloride:acetone 19:1) and recrystallized from CHCl₃/MeOH. Yield: 417 mg (59%). Orange solid. Mp: 232-224° C. ¹H NMR (500 MHz, CDCl₃) δ 7.56 (d, J=8.1 Hz, 2H), 7.51 (d, J=2.0 Hz, 2H), 7.50 (dd, J=2.4, 1.6 Hz, 2H), 7.40 (t, J=8.0 Hz, 2H), 7.30-7.25 (m, 2H), 7.16 (ddd, J=8.3, 2.6, 0.8 Hz, 2H), 6.87 (d, J=8.5 Hz, 2H), 5.27 (s, 4H), 3.89 (s, 6H), 3.85 (s, 6H), 3.83 (s, 6H). ¹³C NMR (126 MHz, CDCl₃) δ 193.4, 162.6, 160.0, 151.6, 149.1, 148.0, 135.9, 130.0, 121.6, 120.6 (2 signals), 120.5, 112.3, 112.1, 111.1, 109.2, 56.1, 56.0, 55.5, 49.0. HRMS (EI) calcd for $C_{40}H_{36}N_2O_{10}$ (M⁺): 704.2370. found: 704.2376.

3. Cyclization of Diketones 2a and 2c

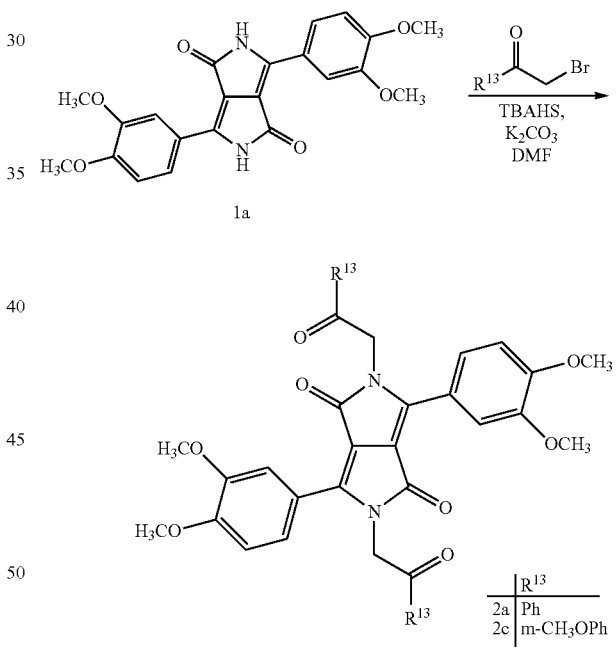

| | R¹³ |
|---|---|
| 2a | Ph |
| 2c | m-CH₃OPh |

General Specification

Diketone 2 (0.25 mmol) is dissolved in 5 ml of dry dichloromethane under argon. Subsequently trifluoromethanesulfonic acid (0.49 ml, 5.5 mmol) is slowly added and the reaction mixture is stirred at room temperature for 1 h. Then triethylamine (0.92 ml, 6.6 mmol) is added dropwise in order to neutralize acid. The reaction mixture is then poured into a beaker containing 100 ml of methanol and cooled. Resulting suspension is then filtered, precipitate is ultrasonificated in boiling methanol for several minutes, filtered off and dried under vacuum.

3.1

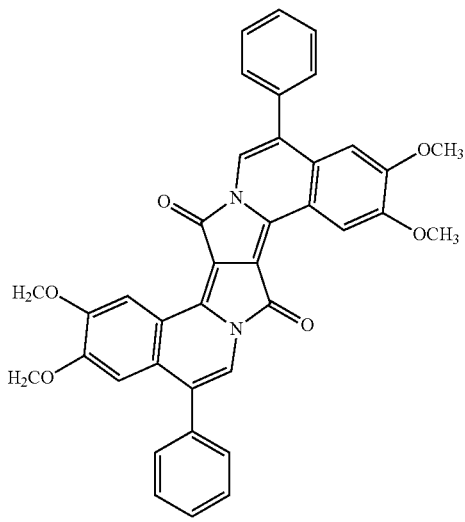
(3a)

150 mg (99%) of 3a is obtained from 2a as a dark violet solid. Mp: Decomposition >340° C. $^1$H NMR (500 MHz, CDCl$_3$:TFA-d 4:1) δ 8.49 (s, 2H), 8.41 (s, 2H), 7.67-7.60 (m, 6H), 7.49 (s, 2H), 7.49-7.44 (m, 4H), 4.32 (s, 6), 4.09 (s, 6H). $^{13}$C NMR (126 MHz, CDCl$_3$: TFA-d 4:1) δ 167.0, 155.2, 148.1, 141.4, 139.3, 132.5, 131.3, 130.3, 130.0, 129.7, 129.1, 122.7, 122.3, 108.0, 107.0, 57.9, 57.5. HRMS (FD) calcd for C$_{38}$H$_{28}$N$_2$O$_6$ (M$^+$): 608.1947, found: 608.1971.

3.2

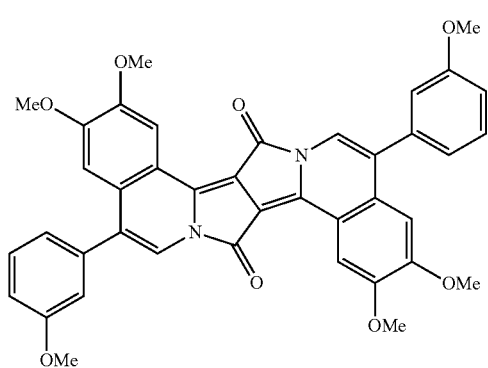
(3c)

Prepared from 2c (176 mg, 0.25 mmol). 155 mg (93%) of 3c is obtained as violet powder. Mp: Decomposition >400° C. $^1$H NMR (600 MHz, CDCl$_3$:TFA-d 4:1) δ 8.50 (s, 2H), 8.41 (s, 2H), 7.58 (t, J=8.0 Hz, 2H), 7.52 (s, 2H), 7.23 (d, J=7.4 Hz, 2H), 7.12 (d, J=7.5 Hz, 2H), 7.07 (s, 2H), 4.32 (s, 6H), 4.11 (s, 6H), 3.95 (s, 6H). HRMS (FD) calcd for C$_{38}$H$_{28}$N$_2$O$_6$ (M$^+$): 608.1947. found: 608.1971. HRMS (FD) calcd for C$_{40}$H$_{32}$N$_2$O$_8$ (M$^+$): 668.2159. found: 668.2147.

Example 2

1. Method of the Synthesis of Diketone 2d

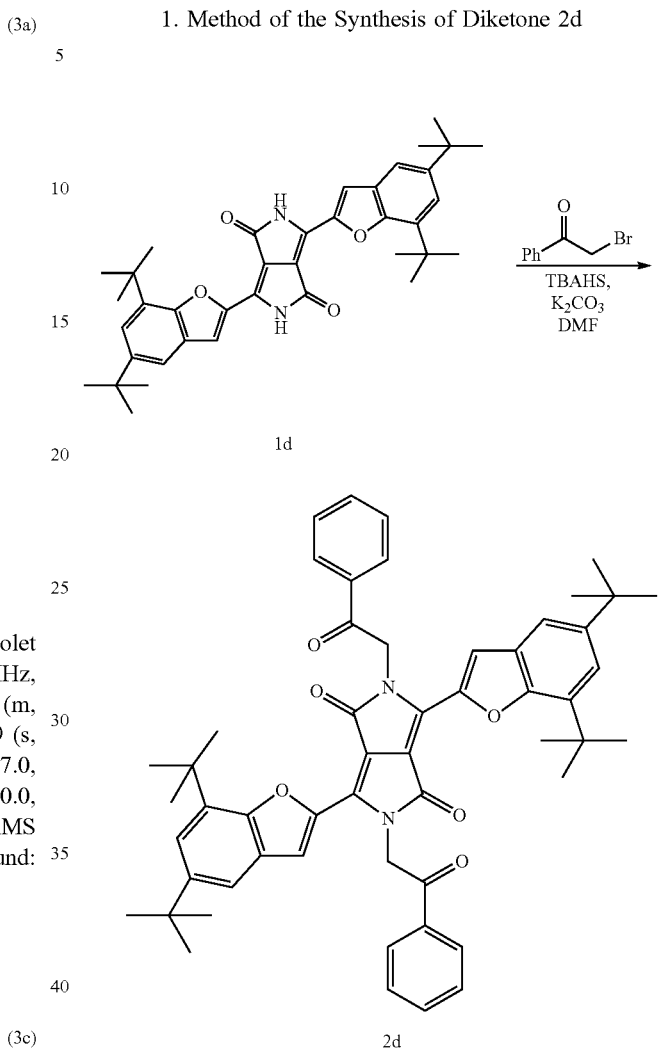

A mixture of pigment 1d (1.0 mmol), tetrabutylammonium bisulfate (TBAHS, 17 mg, 0.05 mmol), potassium carbonate (2.07 g, 15 mmol) and 25 ml of DMF is heated to 120° C. under an argon atmosphere. Then the solution of phenacyl bromide (1.99, 10 mmol) in 4 ml of DMF is slowly added (30 min). The reaction mixture is stirred for 2 h, cooled and diluted with water and methylene chloride. The aqueous layer is extracted with methylene chloride, combined organic layers are washed with water and brine and dried over sodium sulfate. Solvents are evaporated, the product is purified by the column chromatography (toluene:methylene chloride 1:1) and recrystallized from CHCl$_3$/MeOH. Yield: 230 mg (28%). Dark brown solid. Mp: Decomposition >320° C. $^1$H NMR (500 MHz, CDCl$_3$) δ 8.75 (s, 2H), 8.11 (s, 2H), 8.09 (d, J=1.3 Hz, 2H), 7.70-7.63 (m, 2H), 7.58-7.52 (m, 4H), 7.51 (d, J=1.5 Hz, 2H), 7.28 (s, 2H), 5.89 (s, 4H), 1.34 (s, 18H), 1.15 (s, 18H). $^{13}$C NMR (126 MHz, CDCl$_3$) δ 192.3, 160.7, 152.4, 147.0, 144.9, 134.9, 134.7, 133.9, 133.8, 128.8, 128.5, 128.4, 122.7, 117.5, 116.6, 108.6, 49.2, 34.9, 34.0, 31.6, 29.6. HRMS (ESI) calcd for C$_{54}$H$_{57}$N$_2$O$_6$ (M+H$^+$): 829.4217. found: 829.4194.

2. Synthesis of Compound 3d

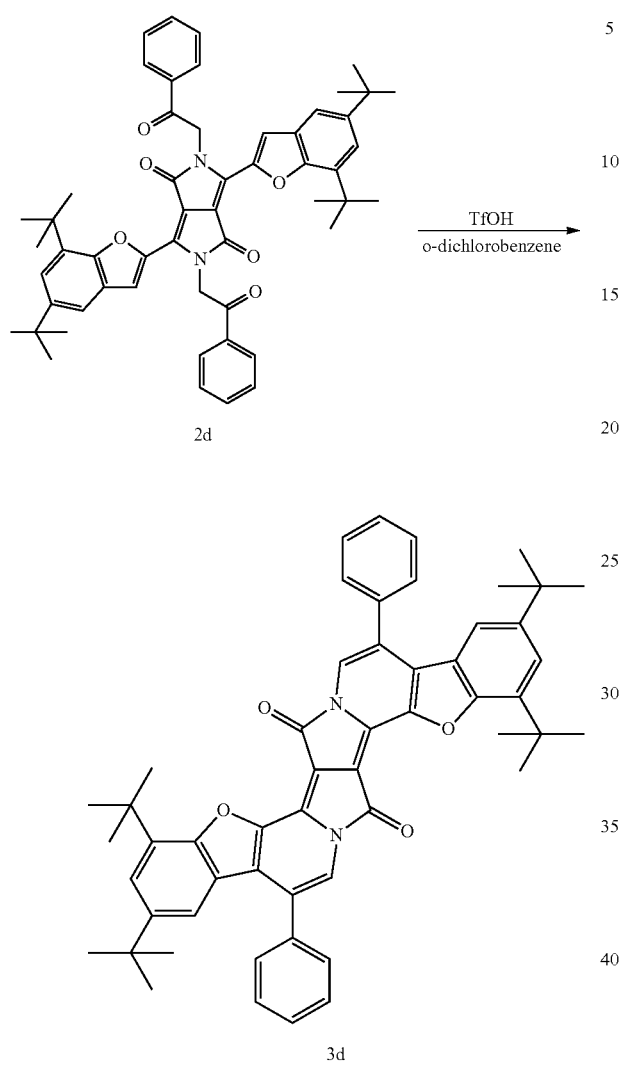

2d

3d

Diketone 2d (207 mg, 0.25 mmol) is dissolved in 5 ml of o-dichlorobenzene. Subsequently trifluoromethanesulfonic acid (0.49 ml, 5.5 mmol) is slowly added and the reaction mixture is stirred at 140° C. for 20 min. Then the reaction mixture is cooled down and triethylamine (0.92 ml, 6.6 mmol) is added dropwise in order to neutralize acid. Obtained mixture is then poured into a beaker containing 100 ml of methanol and cooled. Resulting suspension is then filtered, precipitate is recrystallized from CHCl$_3$/MeOH to give 116 mg (59%) of 3d as violet powder. Mp: >400° C. (decomposition >360° C.). $^1$H NMR (500 MHz, CDCl$_3$) δ 8.14 (s, 2H), 7.65-7.62 (m, 4H), 7.58-7.52 (m, 8H), 7.31 (d, J=1.9 Hz, 2H), 1.68 (s, 18H), 1.25 (s, 18H). $^{13}$C NMR (126 MHz, CDCl$_3$) δ 155.1, 154.4, 146.9, 145.5, 135.5, 135.0, 129.1, 128.8, 128.7, 128.3, 127.1, 124.4, 123.6, 122.5, 122.4, 117.1, 110.0, 96.0, 35.0, 34.9, 31.6, 29.9. HRMS (ESI) calcd for C$_{54}$H$_{53}$N$_2$O$_4$ (M+H$^+$): 793.4005. found: 793.4009.

Spectroscopic data of compounds 3a, 3b and 3d as well as comparative compounds

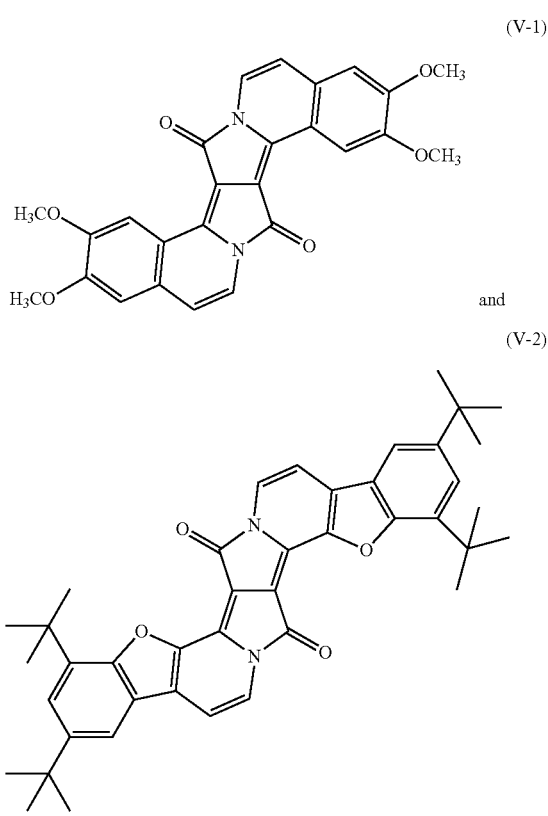

(=compounds (3a) and (3e), respectively disclosed in WO2013/092474) are shown in the table below. Rhodamine B in EtOH or Rhodamine 6G in EtOH are used as standards for quantum yield measurements.

| Comp. | solvent | $^{max}λ_{abs}$ [nm] | $^{max}λ_{em}$ [nm] | Stokes shift [cm$^{-1}$] | ε$_{max}$ [M$^{-1}$ cm$^{-1}$] | φ$_{fl}$ |
|---|---|---|---|---|---|---|
| V-1 | CHCl$_3$ | 593 | 600 | 200 | 110000 | 0.19 |
| V-1 | DMF | 593 | 601 | 220 | 91000 | 0.22 |
| V-2 | CHCl$_3$ | 643 | 652 | 210 | 120000 | 0.05 |
| V-2 | DMF | 645 | 655 | 240 | 107000 | 0.02 |
| 3a | CHCl$_3$ | 600 | 605 | 140 | 100000 | 0.89 |
| 3b | CHCl$_3$ | 601 | 609 | 220 | 85000 | 0.85 |
| 3d | CHCl$_3$ | 654 | 661 | 160 | 150000 | 0.81 |

The absorption and emission maxima of new compounds 3a, 3b and 3d are similar to those reported for compounds V-1 and V-2. Whereas the fluorescence quantum yield of new compounds 3a, 3b and 3d is typically around 80%, whereas the fluorescence quantum yield of compounds V-1 and V-2 is in the range of 5-40%. High fluorescence quantum yield is critical parameter for application in organic electronics.

In addition, solubility of new compounds 3a, 3b and 3d (in typical organic solvents) is order of magnitude higher than that of compound V-1. Reference is made to the below table.

| Comp. | Solubility [mol/l] in CHCl₃ | Solubility [mol/l] in Toluene | Solubility [mg/l] in CHCl₃ | Solubility [mg/l] in Toluene |
|---|---|---|---|---|
| V-1 | $2.72 \cdot 10^{-4}$ | $6.13 \cdot 10^{-6}$ | 126 | 2.85 |
| 3a | $3.46 \cdot 10^{-3}$ | $4.70 \cdot 10^{-5}$ | 2110 | 28.6 |
| 3b | $9.55 \cdot 10^{-4}$ | $5.34 \cdot 10^{-5}$ | 639 | 35.7 |

Accordingly, the new π-expanded diketopyrroles of the present invention have two clear advantages over the previously π-expanded diketopyrroles described in WO2013/092474 and Daniel T. Gryko et al., Organic Letters 14 (2012) 2670: fluorescence quantum yield and solubility.

Example 3

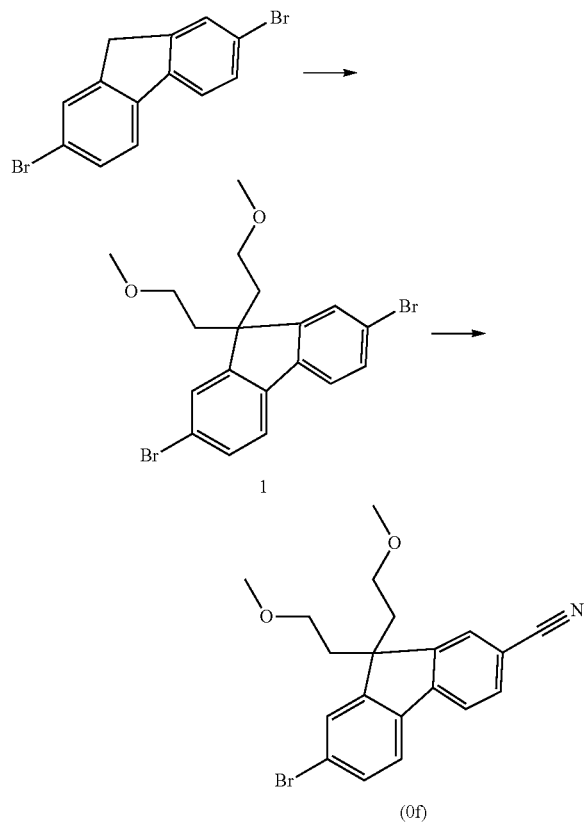

7-bromo-9,9-di(2-methoxyethyl)-9H-fluorene-2-carbonitrile 2: A mixture of 2,7-dibromo-9H-fluorene (11.34 g, 35 mmol), potassium iodide (100 mg, 0.60 mmol) and 150 ml of THF is stirred under argon at room temperature. Sodium hydride (7.00 g, 175 mmol, 60% in mineral oil) is carefully added in portions and the mixture is stirred for additional 15 min. Subsequently 1-chloro-2-methoxyethane (9.6 ml, 105 mmol) is added dropwise and the reaction mixture is stirred for 3 days at room temperature. The reaction is quenched by dropwise addition of 200 ml of water. The resulting black mixture is acidified with 6M HCl (color disappeared) and extracted three times with methylene chloride. Combined organic layers are washed twice with water and dried over sodium sulfate. Solvents are removed under reduced pressure and obtained solid residue is recrystallized from ethanol to give 13.40 g (87%) of 2,7-dibromo-9,9-di(2-methoxyethyl)-9H-fluorene as a white powder. Mp: 138-140° C. ¹H NMR (500 MHz, CDCl₃) δ7.55 (d, J=1.4 Hz, 2H), 7.53 (d, J=8.1 Hz, 2H), 7.49 (dd, J=8.1, 1.7 Hz, 2H), 3.02 (s, 6H), 2.68 (dd, J=8.4, 6.7 Hz, 4H), 2.49-2.15 (m, 4H). ¹³C NMR (126 MHz, CDCl₃) δ 150.8, 138.4, 130.8, 126.5, 121.8, 121.3, 68.1, 58.4, 51.7, 39.4. HRMS (EI) calcd for $C_{19}H_{20}Br_2O_2$ (M⁺): 437.9830. found: 437.9831.

2,7-Dibromo-9,9-di(2-methoxyethyl)-9H-fluorene (13.21 g, 30 mmol), copper(I) cyanide (2.78 g, 31 mmol) and 100 ml of DMF are stirred under argon at 160° C. in a tightly closed pressure vessel. After 40 h the reaction mixture is cooled down and a solution of 26 g of $FeCl_3 \cdot 6H_2O$ in 40 ml of concentrated hydrochloric acid and 10 ml of water is added. Resulting mixture is stirred for 20 min at 90° C., cooled down, diluted with water and extracted with 5 portions of methylene chloride. Organic layers are combined, washed twice with water and dried over MgSO₄. The product is purified by silica-gel chromatography (chloroform→chloroform:ethyl acetate 9:1) and recrystallized from ethanol. 5.20 g (45%) of 0f is obtained as off-white powder. Mp: 193-196° C. ¹H NMR (500 MHz, CDCl₃) δ 7.75 (dd, J=7.9, 0.6 Hz, 1H), 7.70 (dd, J=1.4, 0.6 Hz, 1H), 7.66 (dd, J=7.9, 1.4 Hz, 1H), 7.64-7.59 (m, 2H), 7.55 (dd, J=8.1, 1.8 Hz, 1H), 2.99 (s, 6H), 2.78-2.70 (m, 2H), 2.70-2.62 (m, 2H), 2.41-2.27 (m, 4H). ¹³C NMR (126 MHz, CDCl₃) δ 151.9, 149.6, 143.8, 137.5, 131.9, 131.1, 127.0, 126.8, 123.4, 122.2, 120.5, 119.30, 110.7, 68.0, 58.4, 52.0, 39.2. HRMS (ESI) calcd for $C_{20}H_{20}BrNO_2Na$ (M+Na⁺): 408.0570. found: 408.0575.

1. Synthesis of Diketopyrrolopyrroles 1f and 1g

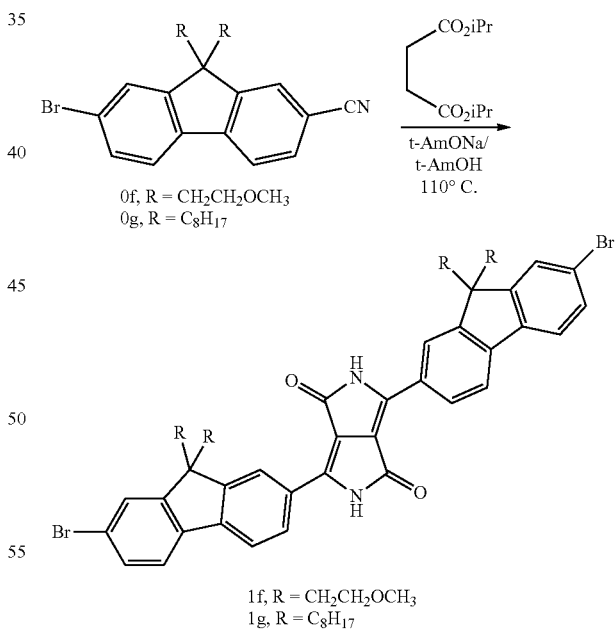

3,6-Bis(7-bromo-9,9-di(2-methoxyethyl)-9H-fluoren-2-yl)-1,4-diketopyrrolo[3,4-c]pyrrole (0f)

Prepared from 7-bromo-9,9-di(2-methoxyethyl)-9H-fluorene-2-carbonitrile (N-3, 4.87 g, 12.6 mmol). After the reaction mixture is acidified and cooled down, obtained precipitate is filtered off, washed several times with hot water and methanol and dried under vacuum. 0f (1.66 g, 32%) was obtained as dark brown powder. Mp >400° C. $^1$H NMR (500 MHz, CDCl$_3$:TFA-d 4:1) δ 8.48 (br s, 2H, 1-H at fluorenyl), 8.22 (br s, 2H, 3-H at fluorenyl), 7.96 (br s, 2H, 4-H at fluorenyl), 7.72 (d, J=8.0 Hz, 2H, 5-H at fluorenyl), 7.69-7.62 (m, 4H, 6-H and 8-H at fluorenyl), 3.17 (s, 12H, OCH$_3$), 3.11-2.95 (m, 8H, CH$_2$CH$_2$OCH$_3$), 2.59 (br s, 4H, CH$_2$CH$_2$OCH$_3$), 2.50 (br s, 4H, CH$_2$CH$_2$OCH$_3$). HRMS (ESI) calcd for C$_{44}$H$_{42}$Br$_2$N$_2$O$_6$Na (M+Na$^+$): 875.1301. found: 875.1307.

3,6-Bis(7-bromo-9,9-dioctyl-9H-fluoren-2-yl)-1,4-diketopyrrolo[3,4-c]pyrrole (0g)

Under an argon atmosphere, in a three-necked flask equipped with a reflux condenser and magnetic stirrer are placed 20 ml of tert-amyl alcohol, catalytic amount of iron(III) chloride and sodium (0.690 g, 30 mmol). The mixture is heated under reflux until sodium is completely reacted (about 1 h). Then the reaction mixture is cooled to 90° C. and 7-bromo-9,9-dioctyl-9H-fluorene-2-carbonitrile (6.23 g, 12.6 mmol) is added. The mixture is then heated to 110° C. and 1.23 ml (6.0 mmol) of diisopropyl succinate is added dropwise (30 min). After 16 h of reaction at 110° C., the mixture is cooled and 30 ml of water/acetic acid 1:1 is added. Resulting mixture is refluxed for a few minutes and cooled to 30° C. Water and dichloromethane are added and layers are separated. Aqueous layer is extracted three times with dichloromethane, combined organic layers are washed twice with water and dried over Na$_2$SO$_4$. Solvents are evaporated and obtained residue is dissolved in hot toluene. Product is precipitated by an excess addition of EtOH and the resulting mixture is cooled down. Precipitate is filtered off and dried under vacuum. 0g (1.53 g, 24%) is obtained as brown powder. Mp 383-389° C. $^1$H NMR (500 MHz, CDCl$_3$:TFA-d 4:1) δ 8.34 (br s, 2H, 1-H at fluorenyl), 8.18 (br s, 2H, 3-H at fluorenyl), 7.91 (d, J=7.2 Hz, 2H, 4-H at fluorenyl), 7.68 (d, J=7.8 Hz, 2H, 5-H at fluorenyl), 7.62-7.52 (m, 4H, 6-H and 8-H at fluorenyl), 2.13 (td, J=12.1, 3.8 Hz, 4H, CH$_2$CH$_2$(CH$_2$)$_5$CH$_3$), 2.03 (td, J=12.1, 3.8 Hz, 4H, CH$_2$CH$_2$(CH$_2$)$_5$CH$_3$), 1.29-1.02 (m, 40H, CH$_2$CH$_2$(CH$_2$)$_5$CH$_3$), 0.82 (t, J=7.1 Hz, 12H, CH$_3$), 0.77-0.60 (m, 8H, CH$_2$CH$_2$(CH$_2$)$_5$CH$_3$). $^{13}$C NMR (126 MHz, CDCl$_3$:TFA-d 4:1) δ 165.2, 155.2, 152.6, 147.8, 146.8, 139.0, 131.2, 128.4, 127.2, 125.6, 125.4, 124.2, 123.8, 122.9, 121.4, 56.4, 40.5, 32.3, 30.3, 29.7, 29.6, 24.3, 23.1, 14.2. HRMS (ESI) calcd for C$_{64}$H$_{82}$Br$_2$N$_2$O$_2$ (M$^+$): 1068.4743. found: 1068.4716.

2. Synthesis of Diketones 2f and 2g

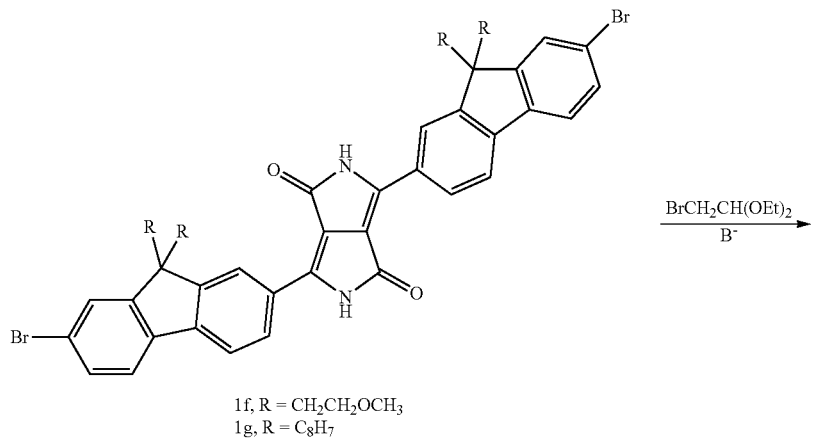

1f, R = CH$_2$CH$_2$OCH$_3$
1g, R = C$_8$H$_7$

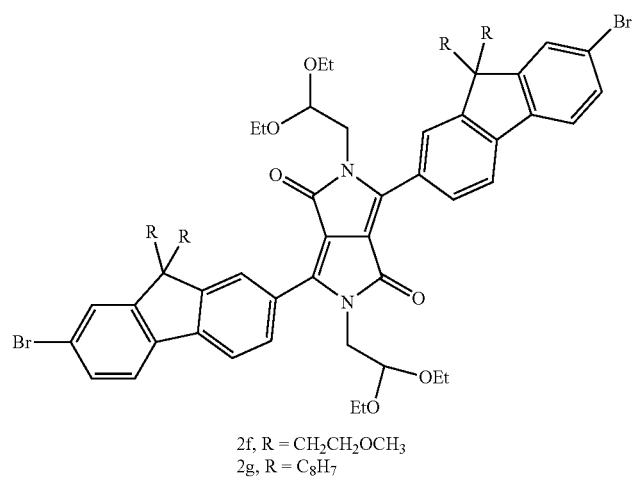

2f, R = CH$_2$CH$_2$OCH$_3$
2g, R = C$_8$H$_7$ 3,6-Bis(7-bromo-9,9-di(2-methoxyethyl)-9H-fluoren-2-yl)2,5-bis(2,2-diethoxyethyl)-1,4-diketopyrrolo[3,4-c]pyrrole (2f): A mixture of 3,6-bis(7-bromo-9,9-di(2-methoxyethyl)-9H-fluoren-2-yl)-1,4-diketopyrrolo[3,4-c]pyrrole (1f, 684 mg, 0.80 mmol), tetrabutylammonium bisulfate (TBAHS, 14 mg, 0.04 mmol), potassium carbonate (1.66 g, 12 mmol) and 20 ml of DMF is heated to 130° C. under an argon atmosphere. Then bromoacetaldehyde diethyl acetal (1.20 ml, 8.0 mmol) is added dropwise by a syringe (30 min). The reaction mixture is stirred for 16 h at 130° C., cooled and diluted with water and dichloromethane. The aqueous layer is extracted with five portions of dichloromethane, combined organic layers are washed with water and brine and dried over sodium sulfate. Solvents are evaporated, the product is separated by the column chromatography (dichloromethane:acetone 19:1→9:1) and recrystallized by slow addition of MeOH to the solution of product in small amount of CHCl$_3$. 2f (440 mg, 51%) is obtained as orange-yellow fluorescent powder. Mp 197-199° C. (CHCl$_3$/MeOH). $^1$H NMR (500 MHz, CDCl$_3$) δ 8.23 (d, J=1.1 Hz, 2H, 1-H at fluorenyl), 8.16 (dd, J=8.0, 1.5 Hz, 2H, 3-H at fluorenyl), 7.82 (d, J=8.0 Hz, 2H, 4-H at fluorenyl), 7.65-7.60 (m, 4H, 5-H and 8-H at fluorenyl), 7.53 (dd, J=8.2, 1.7 Hz, 2H, 6-H at fluorenyl), 4.97 (t, J=5.6 Hz, 2H, NCH$_2$CH (OEt)$_2$), 3.90 (d, J=5.6 Hz, 4H, NCH$_2$CH(OEt)$_2$), 3.73 (dq, J=9.3, 7.0 Hz, 4H, OCH$_2$CH$_3$), 3.55 (dq, J=9.4, 7.0 Hz, 4H, OCH$_2$CH$_3$), 3.05 (s, 12H, OCH$_3$), 2.85-2.73 (m, 8H, CH$_2$CH$_2$OCH$_3$), 2.45 (ddd, J=14.0, 9.5, 5.6 Hz, 4H, CH$_2$CH$_2$OCH$_3$), 2.34 (ddd, J=14.0, 9.5, 5.6 Hz, 4H, CH$_2$CH$_2$OCH$_3$), 1.19 (t, J=7.0 Hz, 12H, OCH$_2$CH$_3$). $^{13}$C NMR (126 MHz, CDCl$_3$) δ 163.4, 152.1, 149.1 (2 signals), 142.3, 138.5, 130.9, 129.7, 127.1, 126.8, 124.3, 122.5, 121.8, 120.3, 109.6, 100.4, 68.3, 63.8, 58.4, 51.8, 45.8, 39.3, 15.5. HRMS (ESI) calcd for C$_{56}$H$_{66}$Br$_2$N$_2$O$_{10}$Na (M+Na$^+$): 1107.2982. found: 1107.3010.

3,6-Bis(7-bromo-9,9-dioctyl-9H-fluoren-2-yl)-2,5-bis(2,2-diethoxyethyl)-1,4-diketopyrrolo[3,4-c]pyrrole (2g)

A mixture of 3,6-bis(7-bromo-9,9-dioctyl-9H-fluoren-2-yl)-1,4-diketopyrrolo[3,4-c]pyrrole (1g, 1.24 g, 1.16 mmol), potassium carbonate (2.40 g, 17.4 mmol) and 25 ml of NMP is heated to 120° C. under an argon atmosphere. Then bromoacetaldehyde diethyl acetal (1.75 ml, 11.6 mmol) is added dropwise by a syringe (30 min). The reaction mixture is stirred for 1 h at 120° C., then the second portion of bromoacetaldehyde diethyl acetal (1.75 ml, 11.6 mmol) is added and the reaction is stirred overnight at 130° C., cooled and diluted with water. The product is extracted with three portions of hexane, combined organic layers are washed twice with water and brine and dried over sodium sulfate. Solvents are evaporated, the product is separated by the column chromatography (hexanes:ethyl acetate 29:1→19:1). After evaporation and drying under vacuum, 2g (0.696 g, 46%) is obtained as red-orange fluorescent oil, which solidifies after standing overnight at ambient temperature. The product can be used in next steps without further purification. If higher purity is necessary, it can be recrystallized by slow addition of MeOH to the solution of product in small amount of CHCl$_3$. Mp 100-102° C. (CHCl$_3$/MeOH). $^1$H NMR (500 MHz, CDCl$_3$) δ 8.18 (s, 2H, 1-H at fluorenyl), 8.15 (dd, J=8.0, 1.4 Hz, 2H, 3-H at fluorenyl), 7.80 (d, J=7.9 Hz, 2H, 4-H at fluorenyl), 7.61 (d, J=8.2 Hz, 2H, 5-H at fluorenyl), 7.54-7.46 (m, 4H, Ar—H, 6-H and 8-H at fluorenyl), 4.99 (t, J=5.6 Hz, 2H, NCH$_2$CH(OEt)$_2$), 3.90 (d, J=5.6 Hz, 4H, NCH$_2$CH(OEt)$_2$), 3.73 (dq, J=9.3, 7.0 Hz, 4H, OCH$_2$CH$_3$), 3.55 (dq, J=9.3, 7.0 Hz, 4H, OCH$_2$CH$_3$), 2.06 (ddd, J=13.3, 10.5, 6.3 Hz, 4H, CH$_2$CH$_2$(CH$_2$)$_5$CH$_3$), 1.96 (ddd, J=13.3, 10.5, 6.3 Hz, 4H, CH$_2$CH$_2$(CH$_2$)$_5$CH$_3$), 1.31-1.00 (m, 52H, CH$_2$CH$_2$(CH$_2$)$_5$CH$_3$ and OCH$_2$CH$_3$), 0.82 (t, J=7.2 Hz, 12H, CH$_2$CH$_2$(CH$_2$)$_5$CH$_3$), 0.73-0.61 (m, 8H, CH$_2$CH$_2$(CH$_2$)$_5$CH$_3$). $^{13}$C NMR (126 MHz, CDCl$_3$) δ 163.5, 153.9, 150.7, 149.3, 143.0, 139.3, 130.2, 129.4, 126.8, 126.4, 124.1, 122.2, 121.7, 120.1, 109.5, 100.5, 63.7, 55.8, 45.9, 40.1, 31.8, 30.0, 29.3, 29.2, 23.9, 22.6, 15.5, 14.1. HRMS (ESI) calcd for C$_{76}$H$_{106}$Br$_2$N$_2$O$_6$Na (M+Na$^+$): 1323.6315. found: 1323.6322.

3. Synthesis of Compounds 5f and 5g

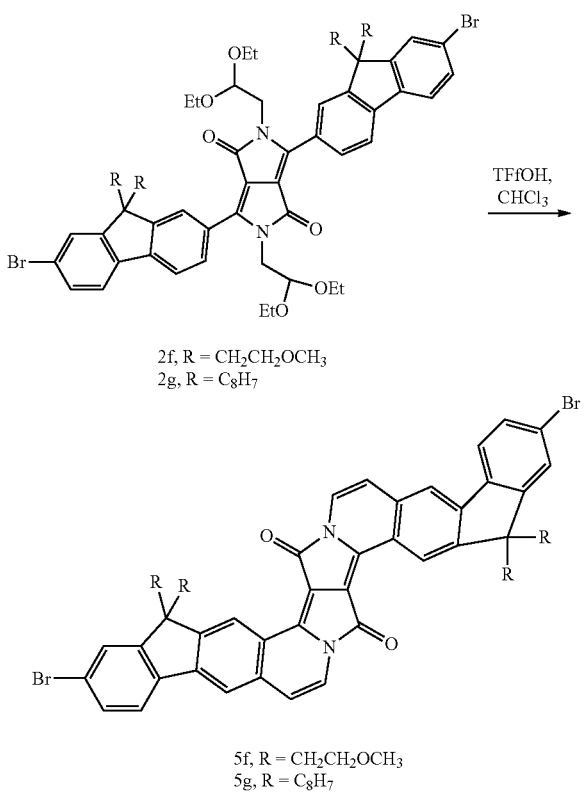

2f, R = CH$_2$CH$_2$OCH$_3$
2g, R = C$_8$H$_7$

5f, R = CH$_2$CH$_2$OCH$_3$
5g, R = C$_8$H$_7$

General Specification:

Dye 2f (109 mg, 0.100 mmol) or 2g (130 mg, 0.100 mmol) is dissolved in 2 ml of chloroform under an argon atmosphere. Subsequently trifluoromethanesulfonic acid (0.44 ml, 5.0 mmol) is slowly added and the reaction mixture is stirred at 60° C. for 1 h. Then the reaction mixture is cooled down and triethyl amine (0.84 ml, 6.0 mmol) is slowly added in order to neutralize acid. To obtained dark blue mixture 100 ml of MeOH is slowly added and the resulting suspension is cooled down and the precipitate is filtered off, washed with hot methanol and dried under vacuum.

6,17-Dibromo-8,8,19,19-tetra(2-methoxyethyl)-8H, 19H-fluoreno[3″,2″:7′,8′]indolizino-[2′1′:3,4]pyrrolo[2,1-a]indeno[1,2-g]isoquinoline-10,21-dione (5f)

Prepared from 2f (109 mg, 0.10 mmol). Yield: 82 mg (91%). Dark violet crystals. Mp 354-356° C. (CHCl$_3$/

MeOH). ¹H NMR (500 MHz, CDCl₃) δ 9.26 (s, 2H, 9-H and 20-H), 7.91 (d, J=7.3 Hz, 2H, 1-H and 12-H), 7.84 (s, 2H, 3-H and 14-H), 7.70 (d, J=8.1 Hz, 2H, 4-H and 15-H), 7.67 (d, J=1.4 Hz, 2H, 7-H and 18-H), 7.57 (dd, J=8.1, 1.8 Hz, 2H, 5-H and 16-H), 6.88 (d, J=7.3 Hz, 2H, 2-H and 13-H), 3.01 (s, 12H, OCH₃), 2.92-2.78 (m, 8H, CH₂CH₂OCH₃), 2.61 (ddd, J=14.5, 8.9, 5.7 Hz, 4H, CH₂CH₂OCH₃), 2.40 (ddd, J=14.1, 9.0, 5.5 Hz, 4H, CH₂CH₂OCH₃). ¹³C NMR (126 MHz, CDCl₃) δ 155.8, 152.7, 150.0, 144.4, 141.4, 137.8, 134.6, 131.1, 127.2, 124.1, 123.6, 123.2, 122.7, 122.3, 117.4, 112.3, 101.5, 68.4, 58.3, 51.9, 39.5. HRMS (ESI) calcd for C₄₈H₄₂Br₂N₂O₆ (M⁺): 900.1410. found: 900.1396.

6,17-Dibromo-8,8,19,19-tetraoctyl-8H,19H-fluoreno [3″,2″:7′,8′]indolizino-[2′1′:3,4]pyrrolo[2,1-a]indeno[1,2-g]isoquinoline-10,21-dione (5g)

Prepared from 2g (130 mg, 0.10 mmol). Yield: 104 mg (93%). Dark blue powder. Mp 194-197° C. ¹H NMR (500 MHz, CDCl₃) δ 9.19 (s, 2H, 9-H and 20-H), 7.91 (d, J=7.3 Hz, 2H, 1-H and 12-H), 7.83 (s, 2H, 3-H and 14-H), 7.70 (d, J=7.9 Hz, 2H, 4-H and 15-H), 7.59-7.50 (m, 4H, 7-H and 18-H+, 5-H and 16-H), 6.88 (d, J=7.4 Hz, 2H, 2-H and 13-H), 2.29-2.15 (m, 4H, CH₂CH₂(CH₂)₅CH₃), 2.12-1.98 (m, 4H, CH₂CH₂(CH₂)₅CH₃), 1.32-0.94 (m, 40H, CH₂CH₂(CH₂)₅CH₃), 0.78 (t, J=7.1 Hz, 12H, CH₂CH₂(CH₂)₅CH₃), 0.72-0.62 (m, 8H, CH₂CH₂(CH₂)₅CH₃). ¹³C NMR (126 MHz, CDCl₃) δ 156.0, 154.4, 151.6, 145.2, 141.5, 138.4, 134.3, 130.5, 126.7, 124.1, 123.5, 123.0, 122.3, 122.2, 117.1, 112.4, 101.4, 55.8, 40.4, 31.8, 29.8, 29.2 (2 signals), 23.4, 22.6, 14.0. HRMS (ESI) calcd for C₆₈H₈₃Br₂N₂O₂ (M⁺): 1117.4821. found: 1117.4784.

4. Synthesis of Compounds 4f and 4g

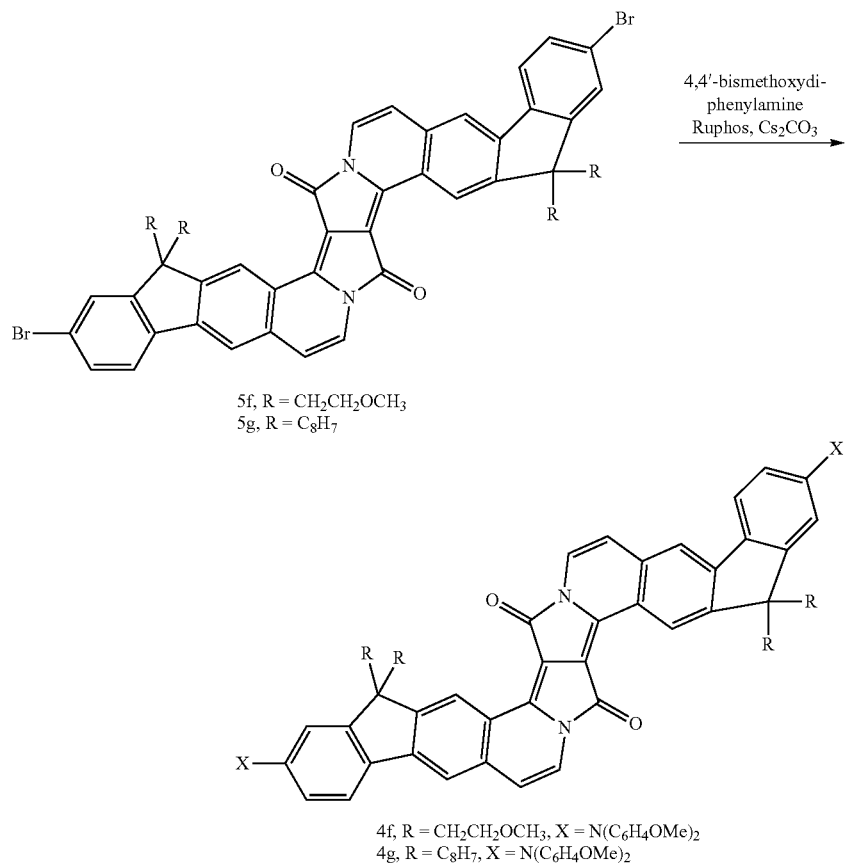

5f, R = CH₂CH₂OCH₃
5g, R = C₈H₇

4f, R = CH₂CH₂OCH₃, X = N(C₆H₄OMe)₂
4g, R = C₈H₇, X = N(C₆H₄OMe)₂

In a 20 ml Schlenk flask containing a magnetic stirring bar are placed: dye 5f (45 mg, 0.050 mmol) or 5g (56 mg, 0.050 mmol), 4,4'-bismethoxydiphenylamine (34 mg, 0.148 mmol), (2-dicyclohexylphosphino-2',6'-diisopropoxy-1,1'-biphenyl)[2-(2'-amino-1,1'-biphenyl)]-palladium(II) methanesulfonate ((RuPhos)precatalyst (Buchwald et al., Chem. Sci. 4 (2013) 916, 2.5 mg, 0.003 mmol), 2-dicyclohexylphosphino-2',6'-diisopropoxybiphenyl (RuPhos, 1.4 mg, 0.003 mmol) and caesium carbonate (98 mg, 0.300 mmol). The vessel is evacuated and backfilled with argon (3 times). Then 3 ml of anhydrous toluene is added under a positive pressure of argon. The flask was again carefully evacuated and backfilled with argon three-times, the vessel is tightly closed and the reaction mixture is stirred for given time at 120° C. (above boiling point). After the mixture is cooled, water and dichloromethane are added, layers are separated. The aqueous layer is extracted with dichloromethane 3 times. Combined organic layers are washed with water twice and dried over Na₂SO₄. Solvents are evaporated and the product is purified by column chromatography in the given eluting system.

6,17-Bis(di(4-methoxyphenyl)amino)-8,8,19,19-tetra (2-methoxyethyl)-8H,19H-fluoreno-[3",2":7',8']indolizino[2'1:3,4]pyrrolo[2,1-a]indeno[1,2-g]isoquinoline-10,21-dione (4f)

Prepared from 5f (45 mg, 0.050 mmol). Reaction time: 40 h. Purified by column chromatography (dichloromethane:acetone 9:1→17:3) and recrystallized by slow addition of MeOH to the solution of product in hot toluene. Yield: 23 mg (38%). Black powder. Mp 376-380° C. (CHCl$_3$/MeOH). $^1$H NMR (500 MHz, CDCl$_3$, 50° C.) δ 9.20 (s, 2H, 9-H and 20-H), 7.87 (br s, 2H, Ar—H), 7.65 (s, 2H, 3-H and 14-H), 7.57 (d, J=8.4 Hz, 2H, Ar—H), 7.13-7.05 (m, 8H, 2-H and 6-H at 4-methoxyphenyl), 7.02 (s, 2H, Ar—H), 6.92 (br s, 2H, Ar—H), 6.89-683 (m, 8H, 3-H and 5-H at 4-methoxyphenyl), 6.80 (d, J=7.4 Hz, 2H, 2-H and 13-H), 3.82 (s, 12H, C$_6$H$_4$OCH$_3$), 3.05 (s, 12H, CH$_2$CH$_2$OCH$_3$), 2.98-2.87 (m, 8H, CH$_2$CH$_2$OCH$_3$), 2.54-2.44 (m, 4H, CH$_2$CH$_2$OCH$_3$), 2.29-2.18 (m, 4H, CH$_2$CH$_2$OCH$_3$). HRMS (ESI) calcd for C$_{76}$H$_{70}$N$_4$O$_{10}$ (M$^+$): 1198.5092. found: 1198.5092.

6,17-Bis(di(4-methoxyphenyl)amino)-8,8,19,19-tetraoctyl-8H,19H-fluoreno[3",2":7',8']-indolizino[2'1':3,4]pyrrolo[2,1-a]indeno[1,2-g]isoquinoline-10,21-dione (4g)

Prepared from 5g (56 mg, 0.050 mmol). Reaction time: 20 h. Yield: 46 mg (65%). Purified by the column chromatography (toluene:acetone 1000:1→100:1) and recrystallized by slow addition of MeOH to the solution of product in CHCl$_3$. Dark green solid. Mp 223-226° C. $^1$H NMR (500 MHz, C$_6$D$_6$) δ 9.70 (s, 2H, 9-H and 20-H), 7.81 (d, J=7.3 Hz, 2H, 1-H and 12-H), 7.56 (d, J=8.3 Hz, 2H, 4-H and 15-H), 7.39 (d, J=1.8 Hz, 2H, 7-H and 18-H), 7.36 (s, 2H, 3-H and 14-H), 7.24-7.19 (m, 8H, 2-H and 6-H at 4-methoxyphenyl), 7.19 (d, J=1.8 Hz, 2H, 5-H and 16-H partially covered by benzene residual peak), 6.86-6.76 (m, 8H, 3-H and 5-H at 4-methoxyphenyl), 6.23 (d, J=7.4 Hz, 2H, 2-H and 13-H), 3.32 (s, 12H, C$_6$H$_4$OCH$_3$), 2.46-2.33 (m, 4H, CH$_2$(CH$_2$)$_6$CH$_3$), 2.06-1.92 (m, 4H, CH$_2$(CH$_2$)$_6$CH$_3$), 1.46-1.00 (m, 48H, CH$_2$(CH$_2$)$_6$CH$_3$), 0.82 (t, J=7.0 Hz, 12H, CH$_2$(CH$_2$)$_6$CH$_3$). $^{13}$C NMR (126 MHz, C$_6$D$_6$) δ 156.9, 156.2, 154.6, 152.2, 150.7, 146.5, 141.4, 141.3, 134.7, 133.0, 127.2, 123.8, 123.2, 122.4, 122.1, 120.3, 116.0, 115.5, 115.3, 111.9, 101.6, 55.7, 55.1, 40.9, 32.3, 30.5, 29.8, 29.7, 24.7, 23.1, 14.4. HRMS (ESI) calcd for C$_{96}$H$_{111}$N$_4$O$_6$ (M+H$^+$): 1415.8504. found: 1415.8467.

Example 4

Synthesis of Compound 6a

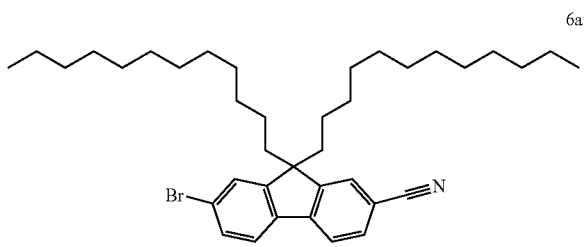 [SMILES: CCCCCCCCCCCCC1(CCCCCCCCCCCC)c2cc(Br)ccc2-c2ccc(C#N)cc21]

6a 50g of [286438-45-7] are dissolved in 300 ml of dry dimethylformamide, followed by the addition of 7.16 g CuCN. The reaction mixture is then stirred for 24 hours at reflux. The reaction mixture is cooled to RT, poured on water and the product is then extracted with ethylacetate. After drying the organic phase with MgSO$_4$, the ethylacetate solution is filtered over HYFLO and then the solvent is evaporated. The product is purified by chromatography over silicagel to obtain a compound of formula 6a. $^1$H-NMR data (ppm, CDCl$_3$): 7.77 1H d, 7.74-7.61 3H m, 7.55-7.51 2H m, 1.97 4H t, 1.33-1.07 36H m, 0.89 6H t, 0.65-0.49 4H m.

Synthesis of Compound 6b

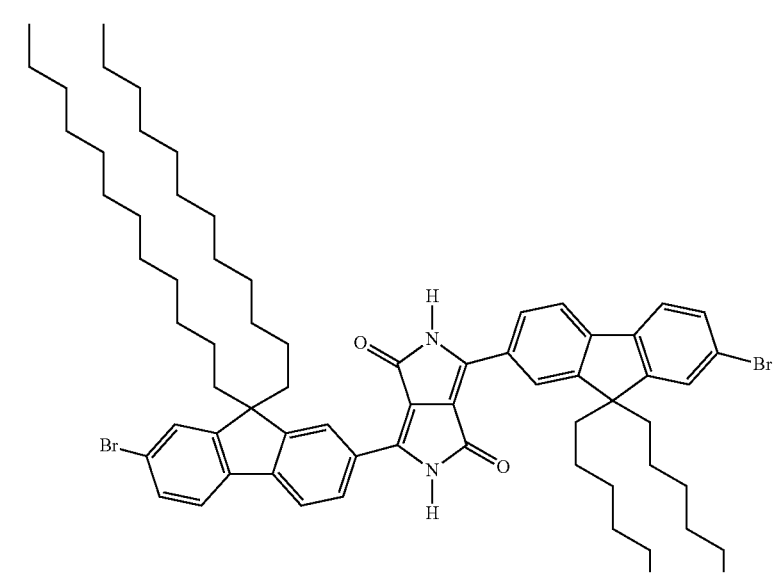

6b

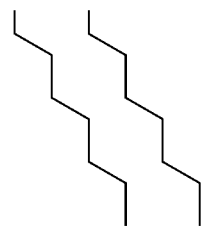

200 ml of tert-amylalcohol are placed in a reactor under nitrogen, and then 50 mg of Fe(III)Cl$_3$ are added. The mixture is heated to 90° C. and then 1.88 g of sodium metal is added and the mixture is heated to reflux. As soon as the sodium is dissolved and reacted completely, a solution of 200 ml of tert-amylalcohol containing 19.35 g of compound 6a and 4.15 g of di-tert-amylsuccinate is added dropwise to the first solution. The reaction mixture is then stirred over night at reflux. The violet reaction mixture is then cooled to 40° C. and poured on methanol/ice mixture. The mixture is filtered and the violet precipitate is washed with water, methanol and acetone and then dried to give a compound of formula 6b. The product is directly used in the next step.

Synthesis of Compound 6c

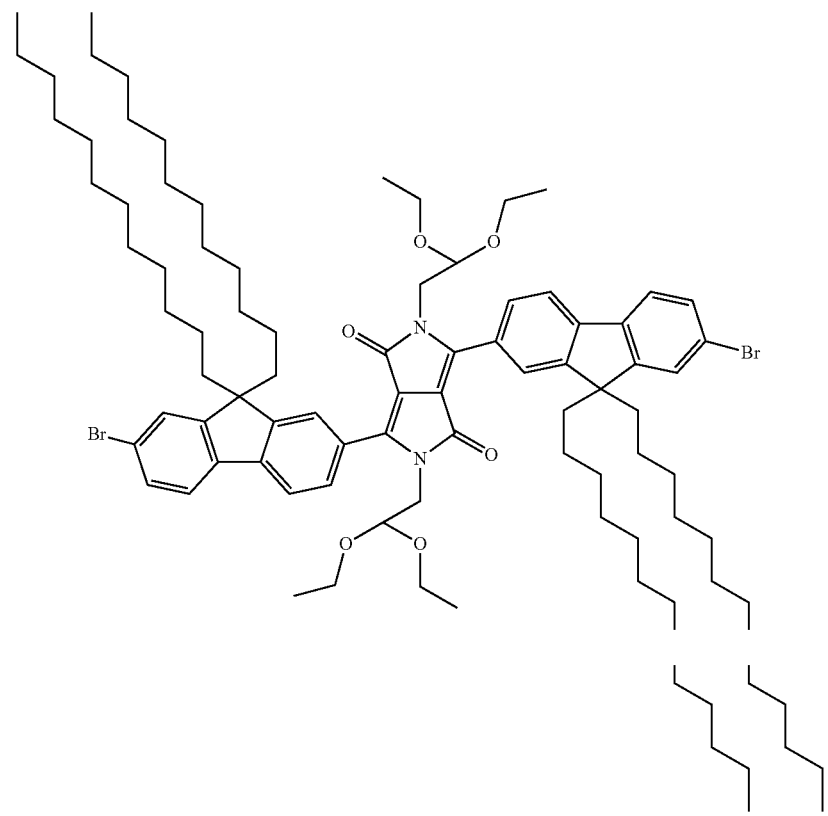

6c 2 g of compound 6b, 2.43 g of 1-bromo-2,2-diethoxy-ethane, 0.13 g of KI and 1.71 g of K$_2$CO$_3$ are added to 40 ml of dry dimethylformamide. The mixture is then stirred over night at 90° C. The reaction mixture is cooled and poured on water/ice. The product is extracted with ethylacetate. The organic phase is dried over MgSO$_4$ and evaporated. The crude product is used directly in the next step.

Synthesis of Compound 6d

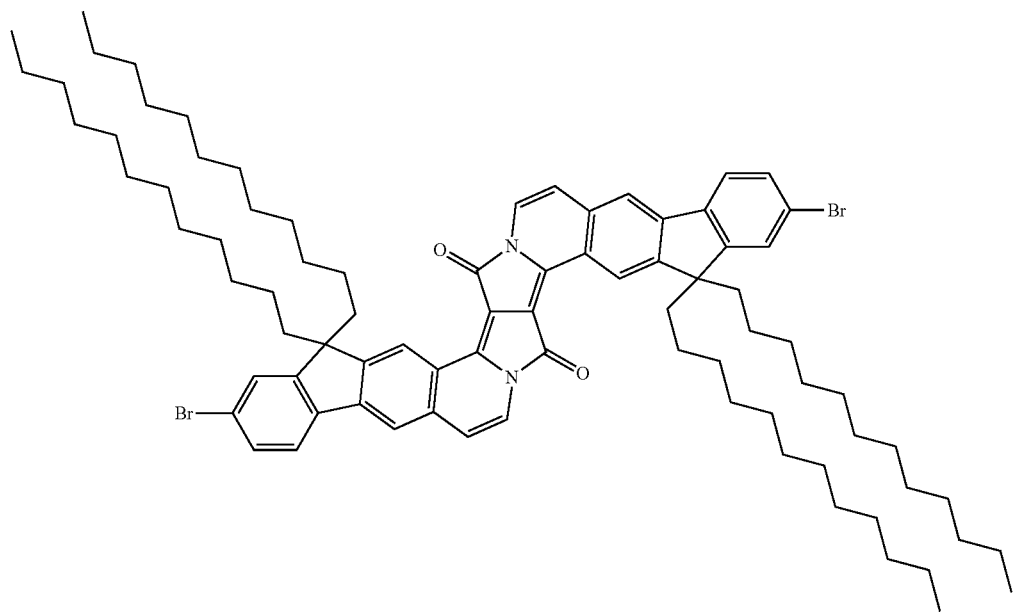

2.6 g of compound 6c is dissolved in 10 ml of methylenechloride. Then 10 ml of concentrated sulfuric acid are added and the mixture is stirred at reflux overnight. The reaction mixture is then poured on ice/water, and the product is extracted with chloroform. The organic phase is dried over $MgSO_4$ and evaporated. The product is purified by chromatography over silica gel to give a compound of formula 6d. $^1$H-NMR data (ppm, $CDCl_3$): 9.21 2H s, 7.93 2H d, 7.85 2H s, 7.72 2H d, 7.58 2H s, 7.55 2H d, 6.90 2H d, 2.30-2.20 4H m, 2.12-2.01 4H m, 1.30-1.02 72H m, 0.66 12H t, 0.73-0.65 8H m.

Example 5

Synthesis of Compound 7a [403699-44-5]

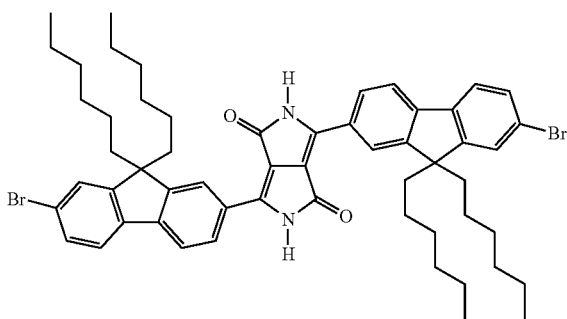

Compound 7a is obtained from compound [189367-54-2] according to compound 6a. $^1$H-NMR data (ppm, $CDCl_3$): 7.77 1H d, 7.74-7.61 3H m, 7.55-7.51 2H m, 1.97 4H t, 1.25-1.02 12H m, 0.80 6H t, 0.65-0.50 4H m.

Synthesis of Compound 7b

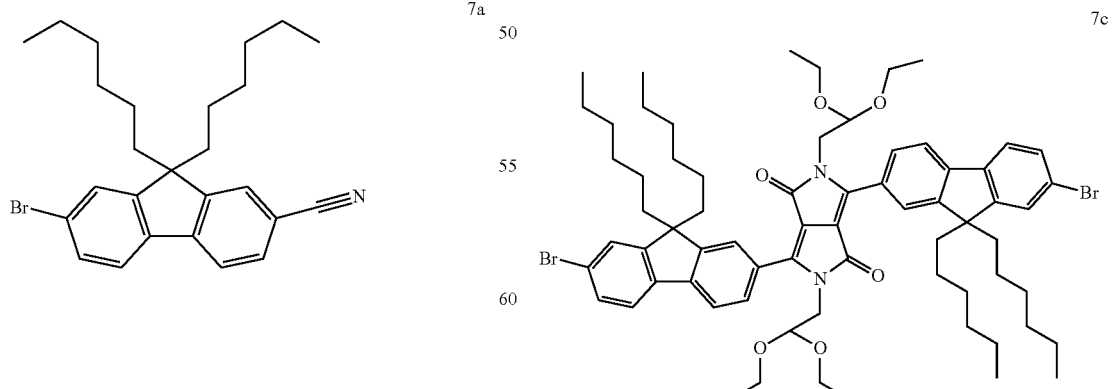

Compound 7b is obtained from compound 7a according to compound 6b. $^1$H-NMR data (ppm, DMSO-$d_6$): 8.67 2H d, 8.51 2H s, 8.00 2H d, 7.87 2H d, 7.74 2H s, 7.57 2H d, 2.12-1.95 8H bs, 1.12-0.95 24H bm, 0.80-0.65 12H bt, 0.62-0.48 8H bs.

Synthesis of Compound 7c

Compound 7c is obtained from compound 7b according to compound 6c. $^1$H-NMR data (ppm, $CDCl_3$): 8.18 2H s, 8.16

2H d, 7.82 2H d, 7.63 2H d, 7.52 2H s, 7.50 2H d, 5.00 2H t, 3.91 4H d, 3.80-3.70 4H m, 3.62-3.51 4H m, 2.11-1.93 8H m, 1.23 12H t, 1.21-1.05 24H m, 0.79 12H t, 0.75-0.65 8H bm.

Synthesis of Compound 7d

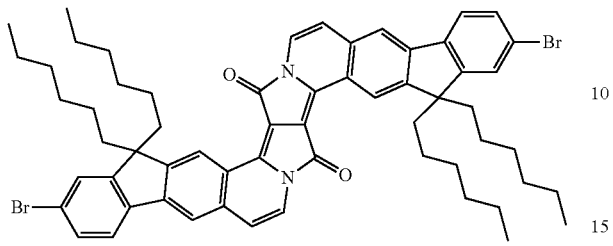

7d

Compound 7d is obtained from compound 7c according to compound 6d. $^1$H-NMR data (ppm, CDCl$_3$): 9.21 2H s, 7.93 2H d, 7.85 2H s, 7.72 2H d, 7.58 2H s, 7.55 2H d, 6.91 2H d, 2.29-2.19 4H m, 2.11-2.01 4H m, 1.20-1.00 24H m, 0.76 12H t, 0.73-0.65 8H m.

Example 6

Synthesis of Compound 8a

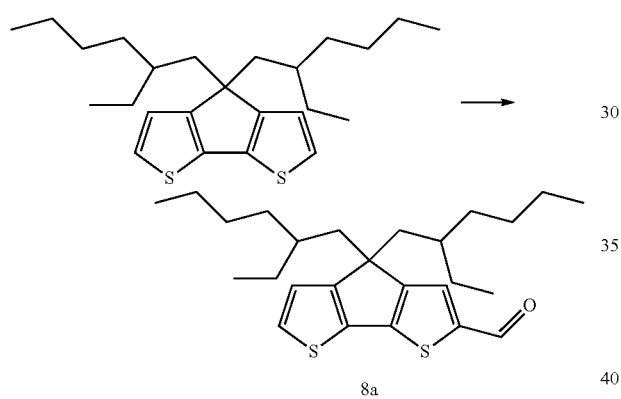

8a 18 g of [365547-20-2] are dissolved in 150 ml of dry tetrahydrofuran under nitrogen. This solution is then cooled to −60° C. Then 18.2 ml of 2.7M butyllithium in heptane are added slowly. The reaction mixture is stirred for 30 minutes at −60° C. Then it is allowed to warm to 0° C. for 5 minutes, and cooled again to −60° C. Then 4.2 ml of anhydrous dimethylformamide are added and the reaction mixture is allowed to warm up to room temperature. The reaction is quenched with water and the aqueous layer is extracted with ethylacetate. The organic phase is dried with MgSO$_4$ and evaporated to give a compound of formula 8a. $^1$H-NMR data (ppm, CDCl$_3$): 9.85 1H s, 7.58 1H s, 7.39 1H d, 7.01 1H d, 2.05-1.85 4H m, 1.12-0.81 16H m, 0.81-0.70 6H m, 0.70-0.55 8H m.

Synthesis of Compound 8b

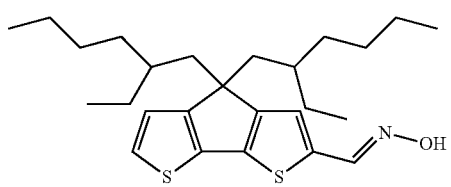

8b 18.57 g of compound 8a are dissolved in 190 ml of absolute ethanol. Then 4.2 ml of pyridine are added, followed by 3.63 g of hydroxylamine-hydrochloride. The reaction mixture is refluxed for 6 hours under nitrogen. Then the mixture is still stirred over night at room temperature. The ethanol is evaporated under reduced pressure and the residue is dissolved in ethylacetate, then washed with 4M HCl. The organic phase is separated and dried over MgSO$_4$. The product of formula 8b is obtained and is used directly in the next step.

Synthesis of Compound 8c

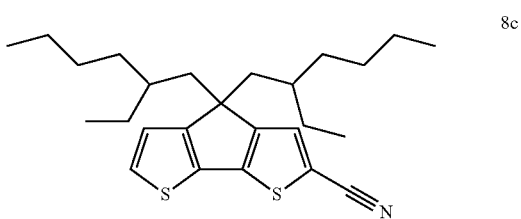 [SMILES: CCCCC(CC)CC1(CC(CC)CCCC)c2ccsc2-c2sc(C#N)cc21]

8c

To 20.12 g of compound 8b are added 190 ml of acetic anhydride and the solution is stirred at reflux overnight. The solution is cooled to room temperature and is poured slowly on ice/water. The product is extracted with ethylacetate. The organic phase is separated, dried over MgSO4 and the solvent is evaporated. The product is purified by chromatography over silica gel to get a compound of formula 8c. $^1$H-NMR data (ppm, CDCl$_3$): 7.44 1H s, 7.34 1H d, 6.99 1H d, 1.98-1.85 4H m, 1.12-0.81 16H m, 0.81-0.70 6H m, 0.70-0.50 8H m.

Synthesis of Compound 8d

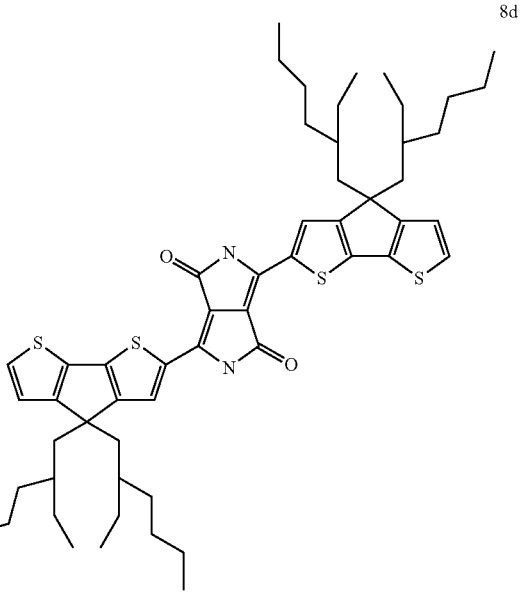

8d

Compound 8d is obtained from compound 8c according to compound 6b. $^1$H-NMR data (ppm, CDCl$_3$): 9.55 2H very broad s, 8.11-8.05 2H m, 7.35 2H d, 7.03 2H d, 2.20-1.93 8H m, 1.10-0.82 32H m, 0.82-0.68 12H m, 0.68-0.55 16H m.

Synthesis of Compound 8e

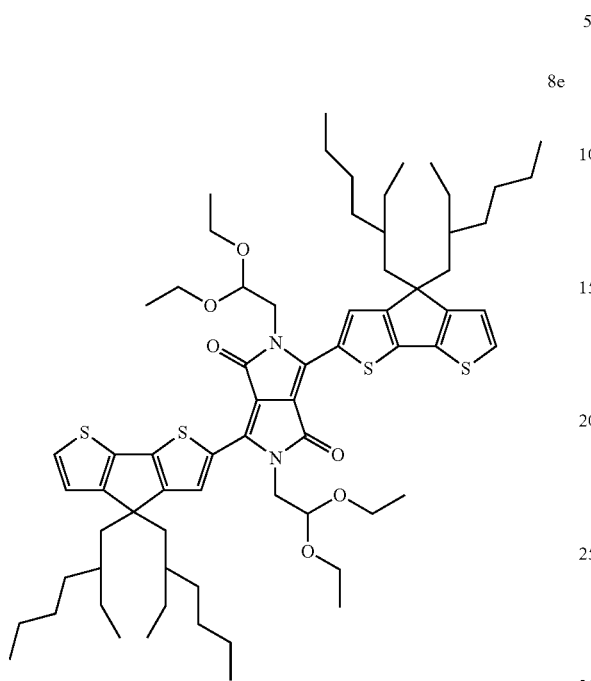

Compound 8e is obtained from compound 8d according to compound 6c.

Synthesis of Compound 8f

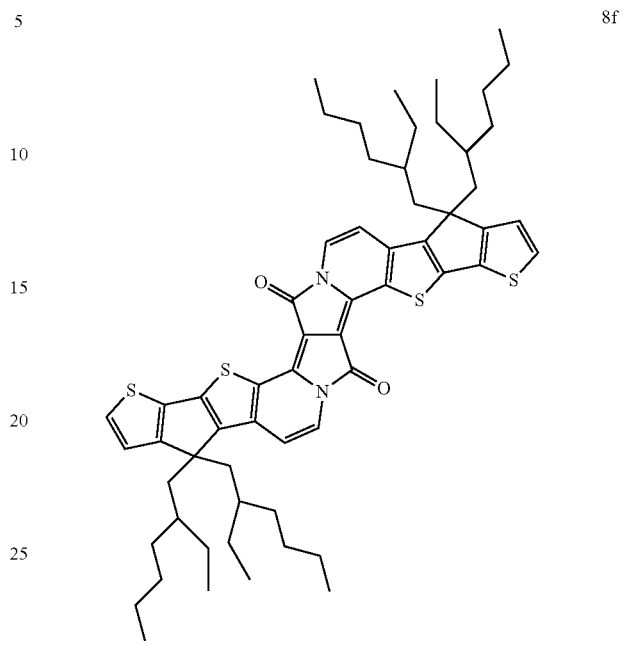

Compound 8f is obtained from compound 8e according to compound 6d.

Example 7

Synthesis of Compound 9a

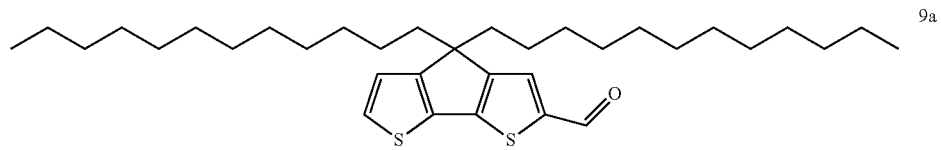 [SMILES: CCCCCCCCCCCCC1(CCCCCCCCCCCC)c2ccsc2-c2sc(C=O)cc21]

Compound 9a is obtained from compound [1201921-87-0] according to compound 8a. $^1$H-NMR data (ppm, CDCl$_3$): 9.86 1H s, 7.59 1H s, 7.41 1H d, 7.00 1H d, 2.00-1.83 4H m, 1.42-1.08 36H m, 1.06-0.95 4H m, 0.90 6H t.

Synthesis of Compound 9b

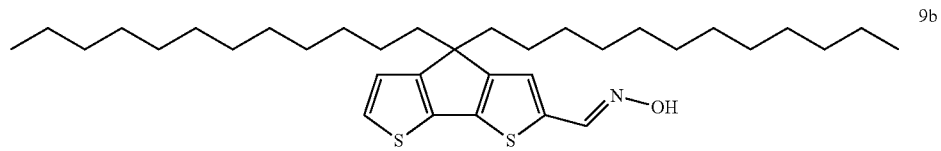 [SMILES: CCCCCCCCCCCCC1(CCCCCCCCCCCC)c2ccsc2-c2sc(/C=N/O)cc21]

Compound 9b is obtained from compound 9a according to compound 8b. The product has been used directly in the next step.

Synthesis of Compound 9c
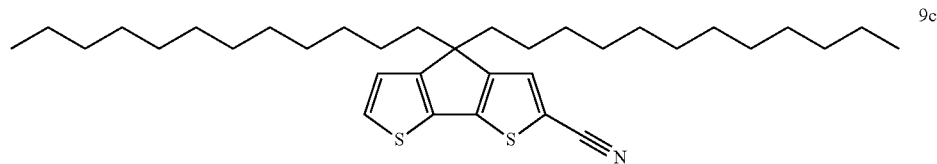 [SMILES: CCCCCCCCCCCCC1(CCCCCCCCCCCC)c2ccsc2-c2sc(C#N)cc21]
Compound 9c is obtained from compound 9b according to compound 8c. ¹H-NMR data (ppm, CDCl₃): 7.43 1H s, 7.35 1H d, 6.98 1H d, 1.90-1.82 4H m, 1.38-1.10 36H m, 0.98-0.85 10H m.
Synthesis of Compound 9d
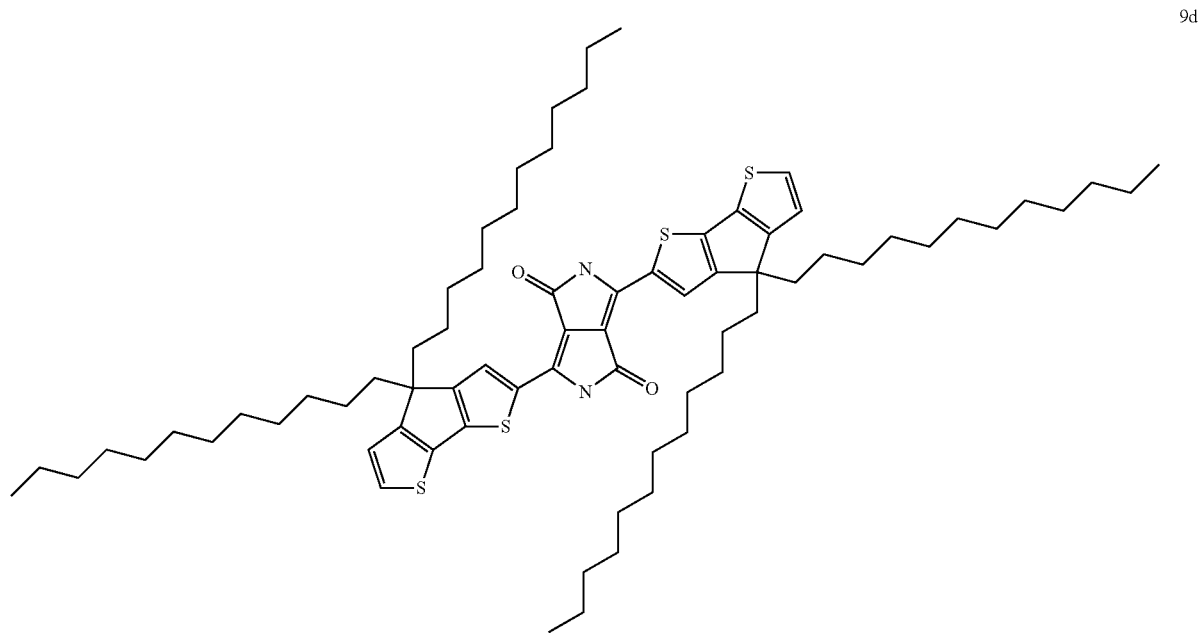 [SMILES: CCCCCCCCCCCCC1(CCCCCCCCCCCC)c2ccsc2-c2sc(C3=C4C(=O)NC(c5cc6c(s5)-c5sccc5C6(CCCCCCCCCCCC)CCCCCCCCCCCC)=C4C(=O)N3)cc21]
Compound 9d is obtained from compound 9c according to compound 8d. ¹H-NMR data (ppm, CDCl₃): 8.36 2H broad s, 8.06 2H broad s, 7.36 2H d, 7.00 2H d, 2.00-1.88 8H m, 1.32-1.10 72H m, 1.06-0.90 8H m, 0.87 12H t.

Synthesis of Compound 9e

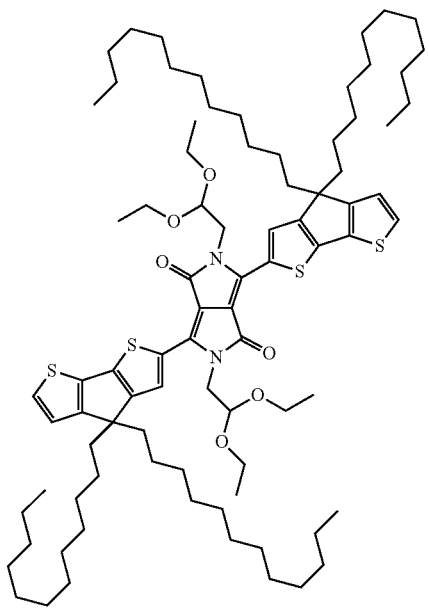

Compound 9e is obtained from compound 9d according to compound 8e. $^1$H-NMR data (ppm, CDCl$_3$): 8.66 2H s, 7.34 2H d, 7.01 2H d, 4.94 2H t, 4.26 4H d, 3.87-3.80 4H m, 3.63-3.57 4H m, 2.01-1.85 8H m, 1.38-1.10 72H m, 1.10-0.92 8H m, 0.89 12H t.

Synthesis of Compound 9f

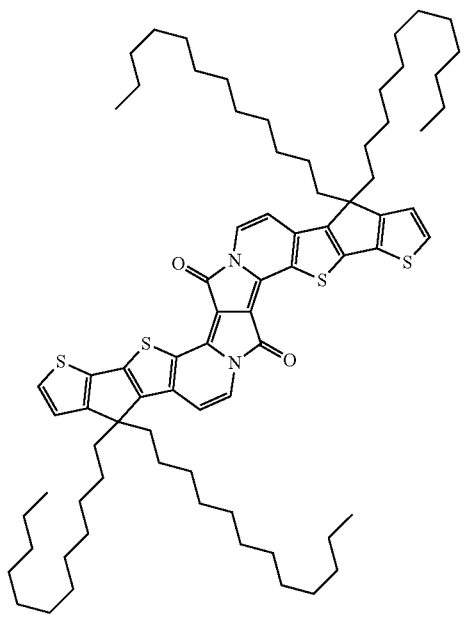

Compound 9f is obtained from compound 9e according to compound 8f.

The invention claimed is:

1. A compound of formula (III):

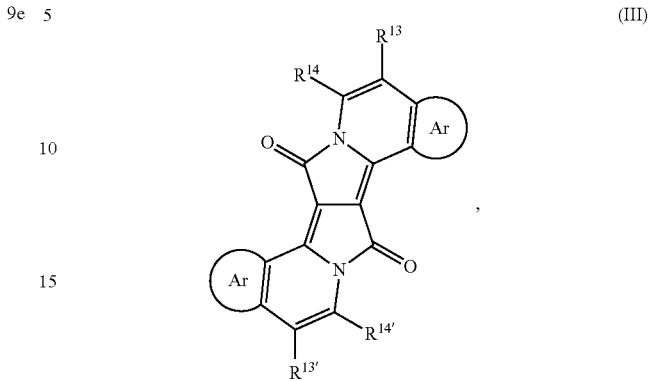

wherein

Ar denotes a homo- or heteroaromatic system, which may be substituted, or unsubstituted; and $R^{13}$, $R^{13'}$, $R^{14}$ and $R^{14'}$ are independently of each other hydrogen, $C_1$-$C_{25}$alkyl, $C_2$-$C_{25}$alkenyl, $C_2$-$C_{25}$alkenyl, which may optionally be interrupted by one or more oxygen or sulphur atoms and/or is optionally substituted by a group $E^{Si}$ or one or more halogen atoms; $C_2$-$C_{25}$alkinyl, $C_3$-$C_{12}$cycloalkyl, $C_3$-$C_{12}$cycloalkyl-alkyl, which may optionally be interrupted by one or more oxygen or sulphur atoms and/or is optionally substituted by a group $E^{Si}$ or one or more halogen atoms; $C_7$-$C_{25}$arylalkyl, $C_7$-$C_{25}$arylalkyl which may optionally be interrupted by one or more oxygen or sulphur atoms and/or is optionally substituted by a group $E^{Si}$ or one or more halogen atoms; $C_6$-$C_{18}$aryl; $C_6$-$C_{18}$aryl which is substituted by halogen, $C_1$-$C_{18}$alkyl, or $C_1$-$C_{18}$alkoxy, or $C_1$-$C_{25}$alkyl, which may optionally be interrupted by one or more oxygen or sulphur atoms and/or is optionally substituted by one or more halogen atoms; $C_3$-$C_{10}$heteroaryl; $C_3$-$C_{10}$heteroaryl, which is substituted by halogen, $C_1$-$C_{18}$alkyl, or $C_1$-$C_{18}$alkoxy; or $C_1$-$C_{25}$alkyl, which may optionally be interrupted by a group $D^{Si}$, or one or more oxygen or sulphur atoms and/or is optionally substituted by one or more halogen atoms;

$E^{Si}$ is —SiR$^{161}$R$^{162}$R$^{163}$ or —O—SiR$^{161}$R$^{162}$R$^{163}$;

$D^{Si}$ is —SiR$^{161}$R$^{162}$—, —SiR$^{161}$R$^{162}$—(O—SiR$^{161}$R$^{162})_d$— or —O—SiR$^{161}$R$^{162}$—;

$R^{161}$, $R^{162}$ and $R^{163}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—SiR$^{164}$R$^{165}$R$^{166}$, —(O—SiR$^{164}$R$^{165})_d$—R$^{166}$, $C_1$-$C_{25}$alkoxy, $C_3$-$C_{24}$(hetero)aryloxy, NR$^{167}$R$^{168}$, halogen, $C_1$-$C_{25}$acyloxy, phenyl, phenyl, which is substituted 1 to 3 times by $C_1$-$C_{25}$alkyl, halogen, cyano or $C_1$-$C_{25}$alkoxy;

$R^{164}$, $R^{165}$ and $R^{166}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—SiR$^{169}$R$^{170}$R$^{171}$, —(O—SiR$^{169}$R$^{170})_d$—R$^{171}$, $C_1$-$C_{25}$alkoxy, $C_3$-$C_{24}$(hetero)aryloxy, NR$^{167}$R$^{168}$, halogen, $C_1$-$C_{25}$acyloxy, phenyl, phenyl which is substituted 1 to 3 times by $C_1$-$C_{25}$alkyl, halogen, cyano or $C_1$-$C_{25}$alkoxy;

$R^{169}$, $R^{170}$ and $R^{171}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—Si(CH$_3$)$_3$, $C_1$-$C_{25}$alkoxy, $C_3$-$C_{24}$(hetero)aryloxy, NR$^{167}$R$^{168}$, halogen, $C_1$-$C_{25}$acyloxy, phenyl, phenyl, which is substituted 1 to 3 times by $C_1$-$C_{25}$alkyl, halogen, cyano or $C_1$-$C_{25}$alkoxy;

$R^{167}$ and $R^{168}$ are independently of each other hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms; or $C_7$-$C_{25}$arylalkyl;

d is an integer from 1 to 50; with the proviso that at least one of $R^{13}$, $R^{13'}$, $R^{14}$ and $R^{14'}$ is different from hydrogen.

2. The compound of formula (III) according to claim 1, wherein Ar denotes a homo- or heteroaromatic system, which is selected from

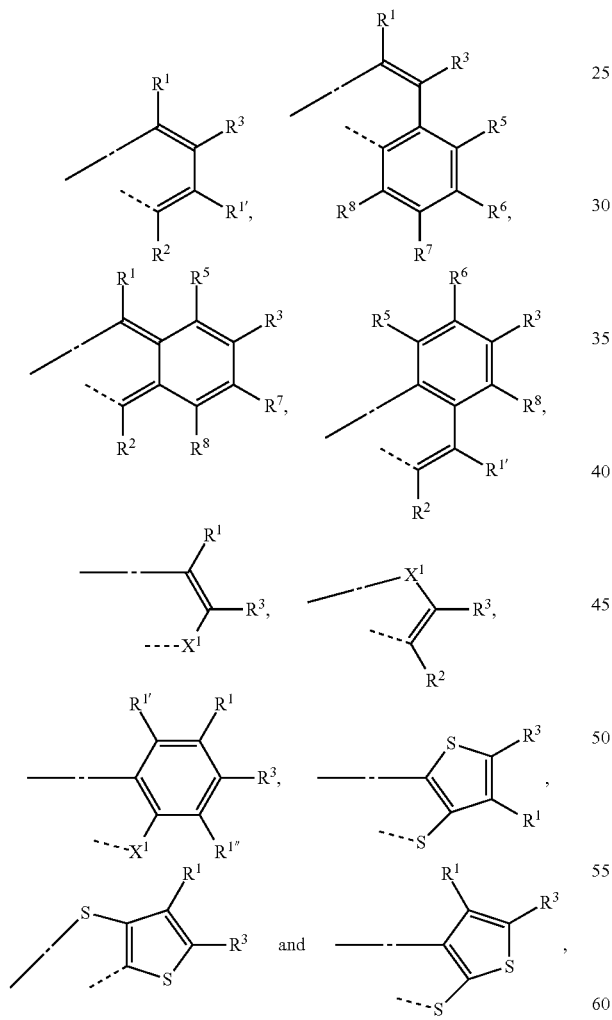

wherein the dotted lines denotes the bonds to the 6-membered ring; the dotted line – – indicates the bond to the carbon atom in para-position to the nitrogen atom, the dotted line ····· indicates the bond to the carbon atom in meta-position to the nitrogen atom, $R^1$, $R^{1'}$ and $R^{1''}$ are independently of each other H, halogen; cyano, $C_1$-$C_{25}$alkoxy, $C_1$-$C_{25}$alkyl substituted with one or more halogen atoms; or $C_1$-$C_{25}$alkyl, $R^2$ is H, halogen; cyano, $C_1$-$C_{25}$alkoxy, or $C_1$-$C_{25}$alkyl, $R^3$ is hydrogen, halogen; cyano, $C_1$-$C_{25}$alkoxy, $C_1$-$C_{25}$alkyl substituted with one or more halogen atoms; $C_1$-$C_{25}$alkyl,

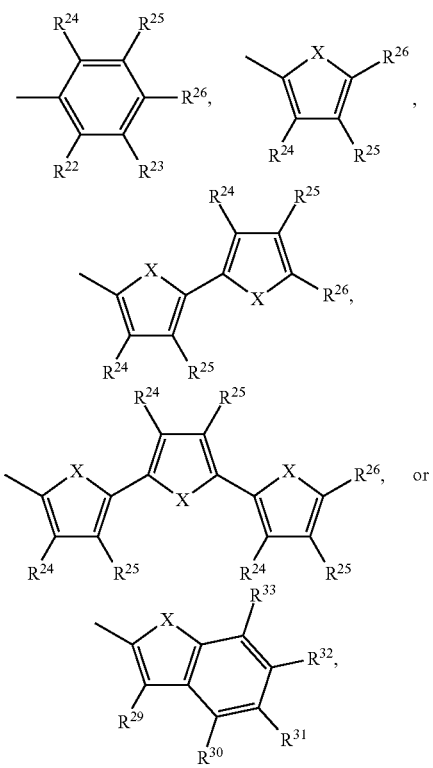

wherein $R^{22}$ to $R^{25}$ and $R^{29}$ to $R^{33}$ represent independently of each other H, F, cyano, $C_1$-$C_{25}$alkoxy, $C_1$-$C_{25}$alkyl substituted with one or more halogen atoms; or $C_1$-$C_{25}$alkyl, and $R^{26}$ is H, F, cyano, phenyl, $C_1$-$C_{25}$alkoxy, $C_1$-$C_{25}$alkyl substituted with one or more halogen atoms, or $C_1$-$C_{25}$alkyl; or $R^3$ is a group of formula —NA$^1$A$^{1'}$, or a group,

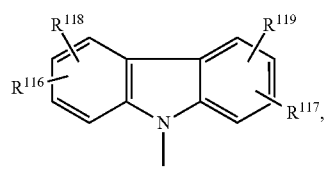

wherein
A$^1$ and A$^{1'}$ are independently of each other $C_1$-$C_{18}$alkyl,

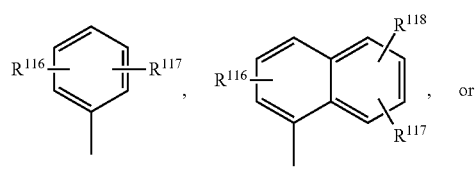

133

-continued

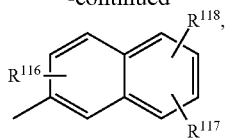

R$^{116}$, R$^{117}$, R$^{118}$ and R$^{119}$ are independently of each other hydrogen, C$_1$-C$_{18}$alkyl, which may optionally be interrupted by —O—, or C$_1$-C$_{18}$alkoxy;

R$^5$, R$^6$, R$^7$ and R$^8$ are independently of each other hydrogen, halogen; cyano, C$_1$-C$_{25}$alkyl, C$_1$-C$_{25}$alkoxy, or C$_1$-C$_{25}$alkyl substituted with one or more halogen atoms;

X and X$^1$ are independently of each other O, S, Se, or NR$^4$,

R$^4$ is hydrogen, C$_6$-C$_{18}$aryl; C$_6$-C$_{18}$aryl which is substituted by C$_1$-C$_{18}$alkyl, halogen; or C$_1$-C$_{18}$alkoxy; C$_1$-C$_{25}$alkyl, which may optionally be interrupted by one or more oxygen or sulphur atoms and/or is optionally substituted by one or more halogen atoms; or C$_7$-C$_{25}$arylalkyl; or Ar denotes a homo- or heteroaromatic system, which is selected from

134

-continued

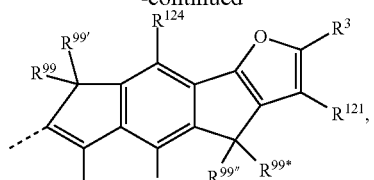

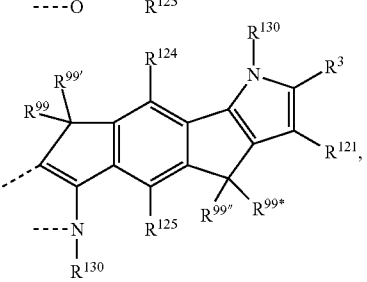

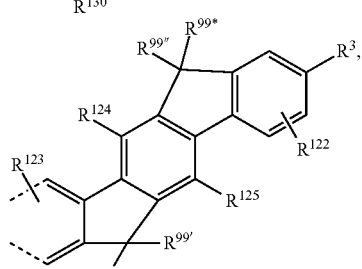

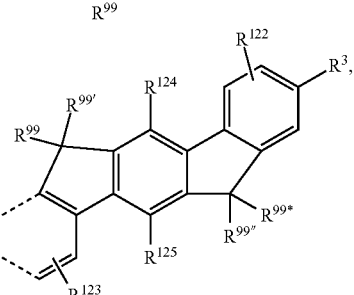

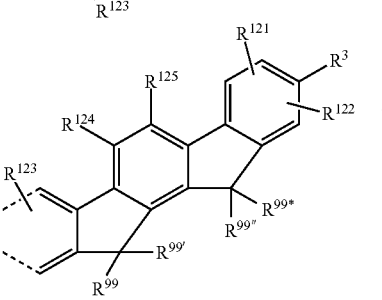

and

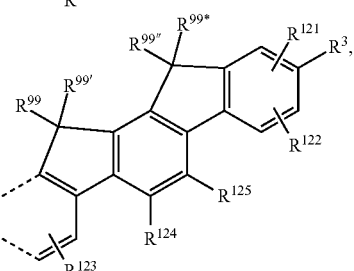

wherein
X$^{92}$ is O, S, CR$^{99}$R$^{99'}$, or NR$^{130}$, X$^{93}$ is O, S, or NR$^{130}$, X$^{94}$ is O, S, or NR$^{130}$, R$^{99}$, R$^{99'}$, R$^{99''}$ and R$^{99*}$ are independently of each other hydrogen, C$_1$-C$_{25}$alkyl, or C$_1$-C$_{25}$alkyl substituted with one or more halogen atoms and/or interrupted by one or more oxygen atoms, or two moieties $R^{99}$ and $R^{99'}$ or $R^{99''}$ and $R^{99*}$ can form a 5 or 6 membered alkyl ring, which optionally can be substituted with one or more halogen atoms and/or interrupted by one or more oxygen atoms;

$R^{121}$, $R^{122}$, $R^{123}$, $R^{124}$ and $R^{125}$ are independently of each other hydrogen, halogen, $C_6$-$C_{18}$aryl; $C_6$-$C_{18}$aryl which is substituted by $C_1$-$C_{18}$alkyl, halogen; or $C_1$-$C_{18}$alkoxy; $C_1$-$C_{25}$alkyl, which may optionally be interrupted by one or more oxygen or sulphur atoms and/or is optionally substituted by one or more halogen atoms; or $C_7$-$C_{25}$arylalkyl;

$R^{130}$ is hydrogen, $C_6$-$C_{18}$aryl; $C_6$-$C_{18}$aryl which is substituted by $C_1$-$C_{18}$alkyl, halogen; or $C_1$-$C_{18}$alkoxy; $C_1$-$C_{25}$alkyl, which may optionally be interrupted by one or more oxygen or sulphur atoms and/or is optionally substituted by one or more halogen atoms; or $C_7$-$C_{25}$arylalkyl; and $R^3$ is as defined above.

3. The compound according to claim 2, which is a compound of formula

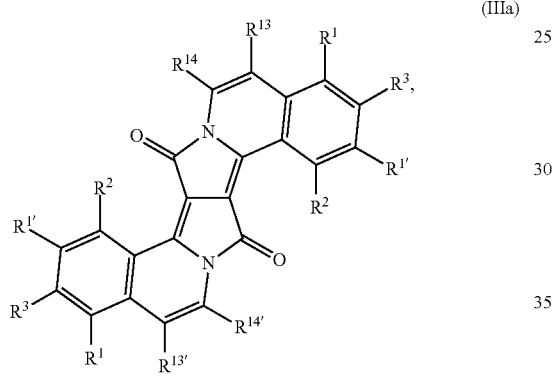
(IIIa)

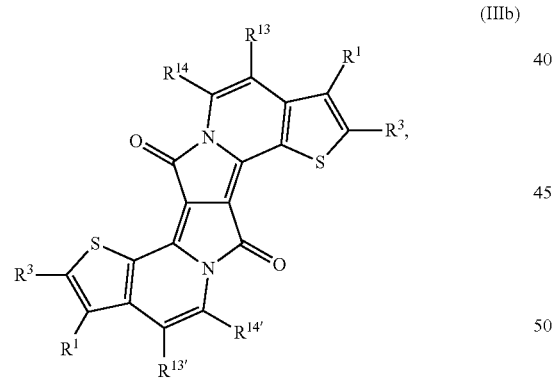
(IIIb)

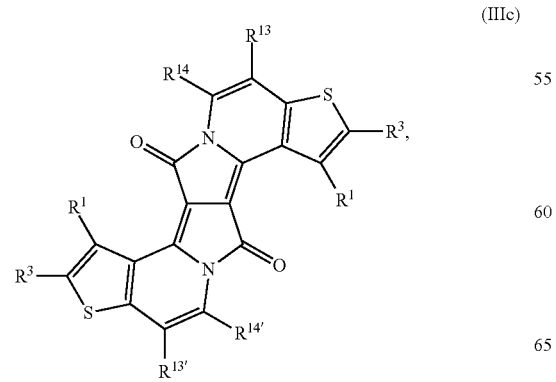
(IIIc)

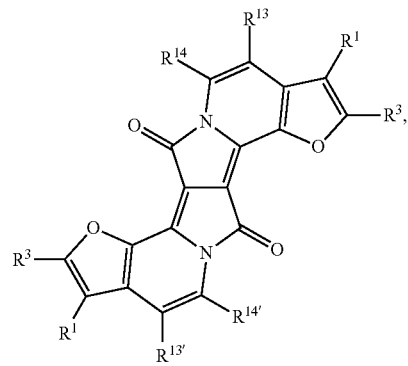
(IIId)

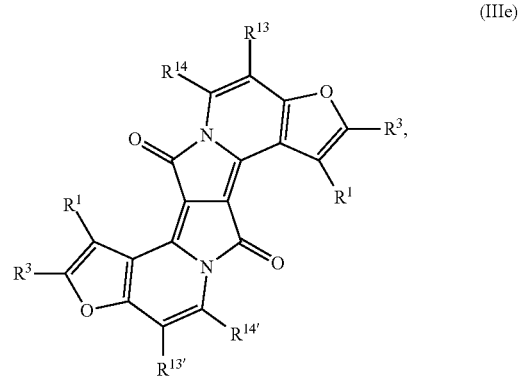
(IIIe)

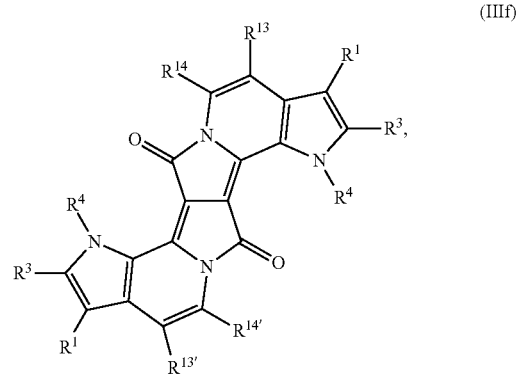
(IIIf)

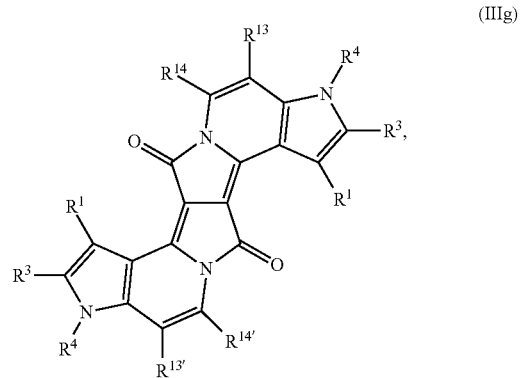
(IIIg)

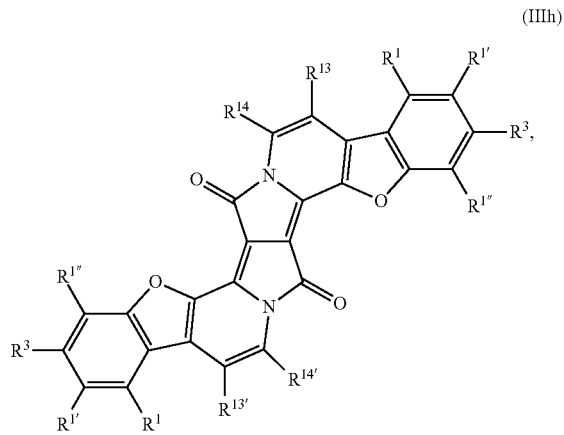
(IIIh)
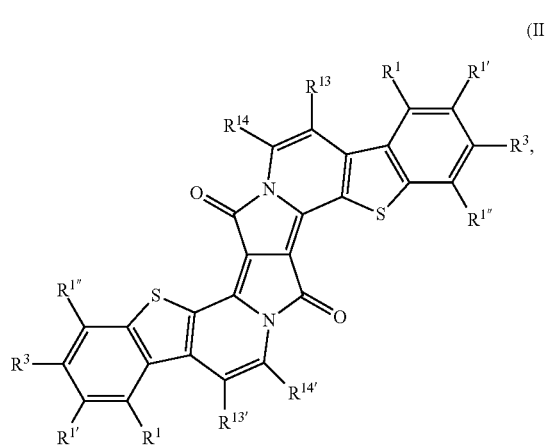
(IIIi)
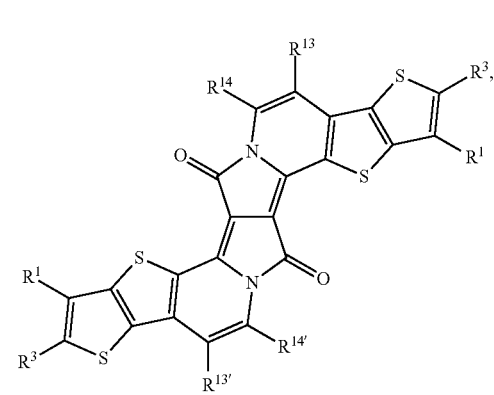
(IIIj)
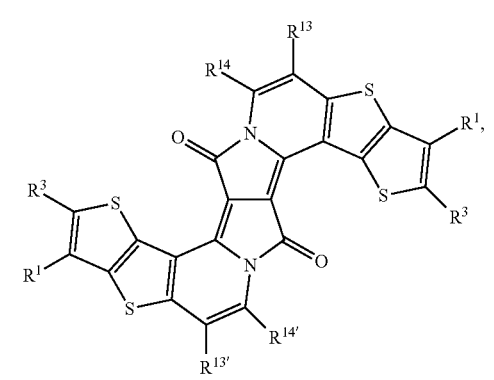
(IIIk)
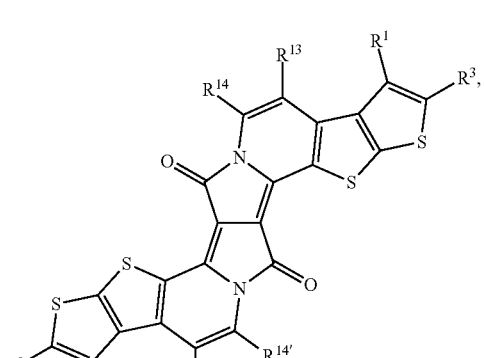
(IIIl)
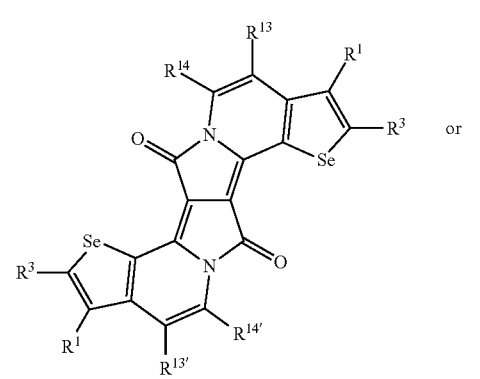
(IIIm)
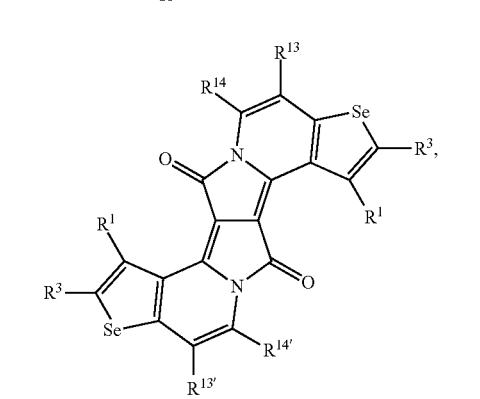
(IIIn)
wherein
R¹, R¹', and R¹'' are independently of each other H, halogen; cyano, $C_1$-$C_{25}$alkoxy, $C_1$-$C_{25}$alkyl substituted with one or more halogen atoms; or $C_1$-$C_{25}$alkyl,
R² is H, halogen; cyano, $C_1$-$C_{25}$alkoxy, or $C_1$-$C_{25}$alkyl,
R³ is hydrogen, halogen; cyano, $C_1$-$C_{25}$alkoxy, $C_1$-$C_{25}$alkyl substituted with one or more halogen atoms; $C_1$-$C_{25}$alkyl,
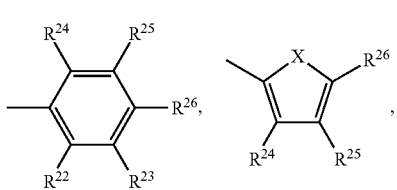

-continued

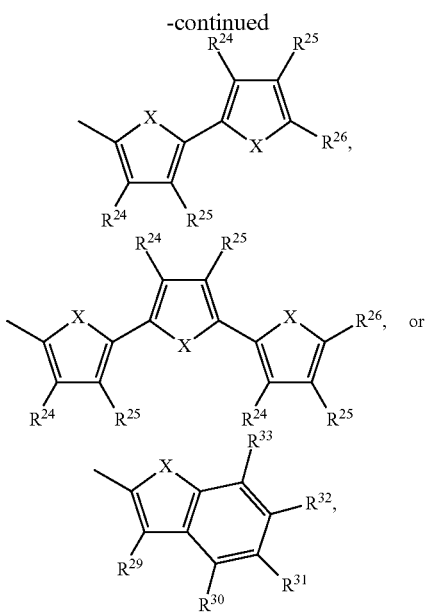

wherein $R^{22}$ to $R^{25}$ and $R^{29}$ to $R^{33}$ represent independently of each other H, F, cyano, $C_1$-$C_{25}$alkoxy, $C_1$-$C_{25}$alkyl substituted with one or more halogen atoms; or $C_1$-$C_{25}$alkyl, and $R^{26}$ is H, F, cyano, phenyl, $C_1$-$C_{25}$alkoxy, $C_1$-$C_{25}$alkyl substituted with one or more halogen atoms, or $C_1$-$C_{25}$alkyl; or $R^3$ is a group of formula —$NA^1A^{1'}$, or a group

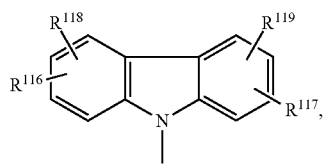

wherein $A^1$ and $A^{1'}$ are independently of each other $C_1$-$C_{18}$alkyl,

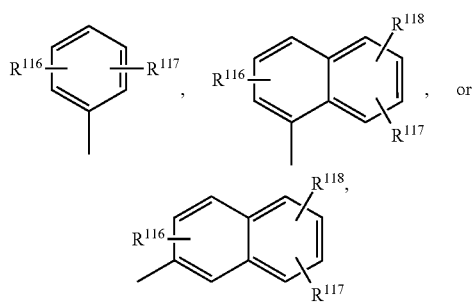

$R^{116}$, $R^{117}$, $R^{118}$ and $R^{119}$ are independently of each other hydrogen, $C_1$-$C_{18}$alkyl, which may optionally be interrupted by —O—, or $C_1$-$C_{18}$alkoxy;

X is O, S, Se, or $NR^4$, and $R^4$ is hydrogen, $C_6$-$C_{18}$aryl; $C_6$-$C_{18}$aryl which is substituted by $C_1$-$C_{18}$alkyl, halogen; or $C_1$-$C_{18}$alkoxy; $C_1$-$C_{25}$alkyl, which may optionally be interrupted by one or more oxygen or sulphur atoms and/or is optionally substituted by one or more halogen atoms; or $C_7$-$C_{25}$arylalkyl, and $R^{13}$, $R^{13'}$, $R^{14}$ and $R^{14'}$ are independently of each other hydrogen, $C_1$-$C_{25}$alkyl, $C_2$-$C_{25}$alkenyl, $C_2$-$C_{25}$alkenyl, which may optionally be interrupted by one or more oxygen or sulphur atoms and/or is optionally substituted by a group $E^{Si}$ or one or more halogen atoms; $C_2$-$C_{25}$alkinyl, $C_3$-$C_{12}$cycloalkyl, $C_3$-$C_{12}$cycloalkylalkyl, which may optionally be interrupted by one or more oxygen or sulphur atoms and/or is optionally substituted by a group $E^{Si}$ or one or more halogen atoms; $C_7$-$C_{25}$arylalkyl, $C_7$-$C_{25}$arylalkyl which may optionally be interrupted by one or more oxygen or sulphur atoms and/or is optionally substituted by a group $E^{Si}$ or one or more halogen atoms; $C_6$-$C_{18}$aryl; $C_6$-$C_{18}$aryl which is substituted by halogen, $C_1$-$C_{18}$alkyl, or $C_1$-$C_{18}$alkoxy, or $C_1$-$C_{25}$alkyl, which may optionally be interrupted by one or more oxygen or sulphur atoms and/or is optionally substituted by one or more halogen atoms; $C_3$-$C_{10}$heteroaryl; $C_3$-$C_{10}$heteroaryl, which is substituted by halogen, $C_1$-$C_{18}$alkyl, or $C_1$-$C_{18}$alkoxy; or $C_1$-$C_{25}$alkyl, which may optionally be interrupted by a group $D^{Si}$, or one or more oxygen or sulphur atoms and/or is optionally substituted by one or more halogen atoms;

$E^{Si}$ is —$SiR^{161}R^{162}R^{163}$ or —O—$SiR^{161}R^{162}R^{163}$;

$D^{Si}$ is —$SiR^{161}R^{162}$—, —$SiR^{161}R^{162}$—(O—$SiR^{161}R^{162})_d$— or —O—$SiR^{161}R^{162}$—;

$R^{161}$, $R^{162}$ and $R^{163}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—$SiR^{164}R^{165}R^{166}$, —(O—$SiR^{164}R^{165})_d$—$R^{166}$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl, which is substituted 1 to 3 times by $C_1$-$C_{25}$alkyl, halogen, cyano or $C_1$-$C_{25}$alkoxy;

$R^{164}$, $R^{165}$ and $R^{166}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—$SiR^{169}R^{170}R^{171}$, —(O—$SiR^{169}R^{170})_d$—$R^{171}$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl which is substituted 1 to 3 times by $C_1$-$C_{25}$alkyl, halogen, cyano or $C_1$-$C_{25}$alkoxy;

$R^{169}$, $R^{170}$ and $R^{171}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—$Si(CH_3)_3$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl, which is substituted 1 to 3 times by $C_1$-$C_{25}$alkyl, halogen, cyano or $C_1$-$C_{25}$alkoxy;

$R^{167}$ and $R^{168}$ are independently of each other hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms; or $C_7$-$C_{25}$arylalkyl;

d is an integer from 1 to 50; with the proviso that at least one of $R^{13}$, $R^{13'}$, $R^{14}$ and $R^{14'}$ is different from hydrogen; or which is a compound of formula
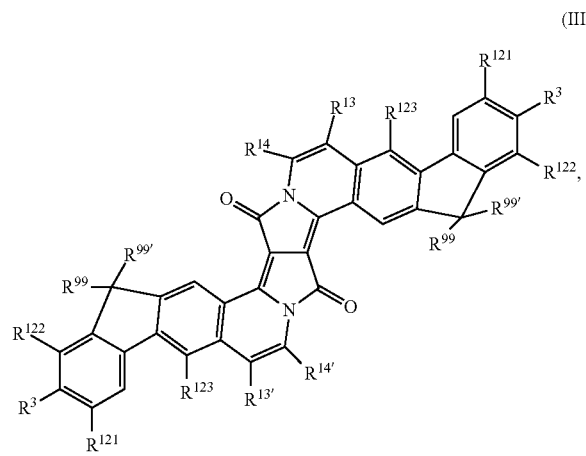
(IIIo)
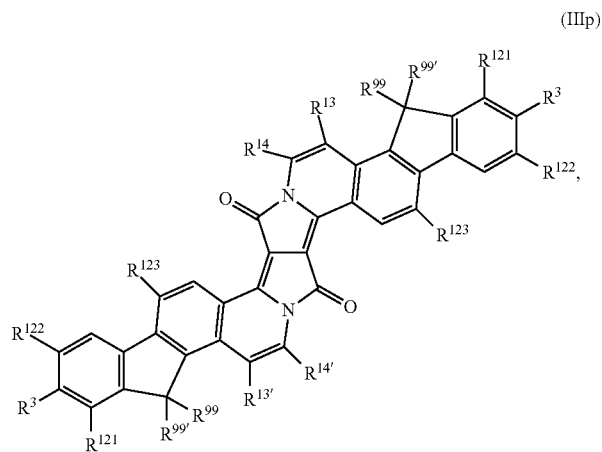
(IIIp)
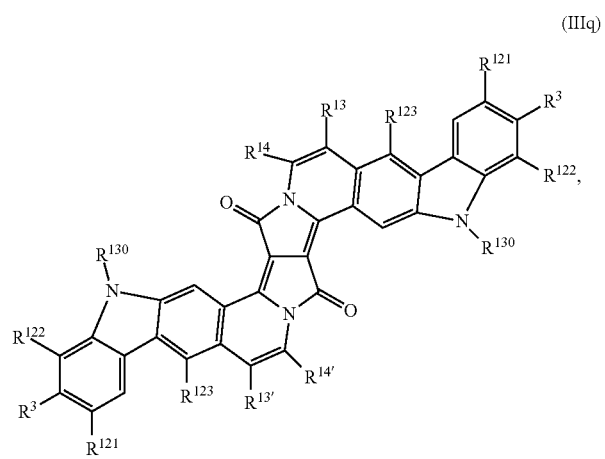
(IIIq)
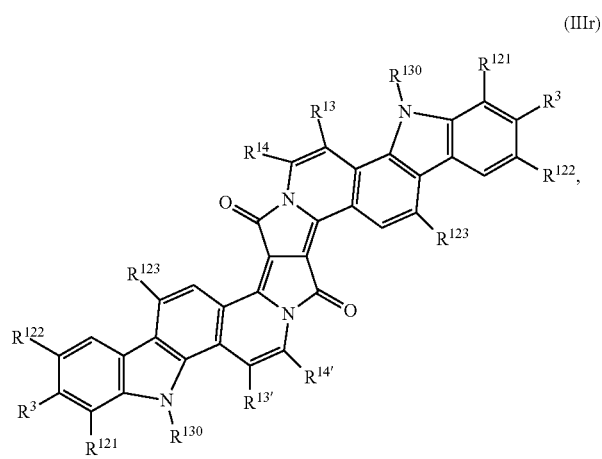
(IIIr)
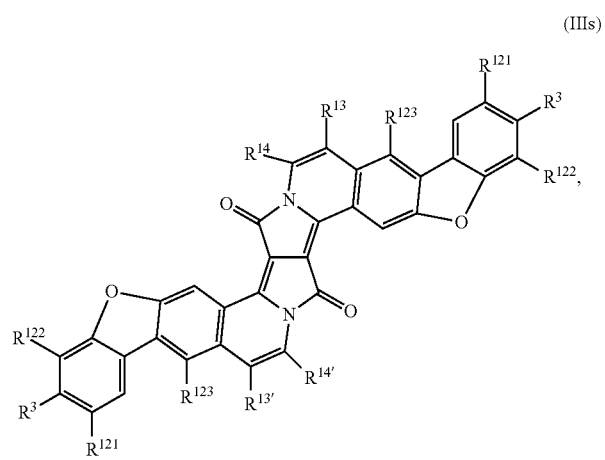
(IIIs)
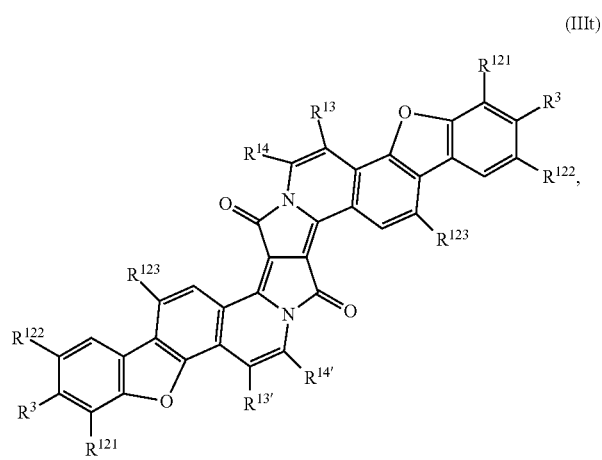
(IIIt)

-continued
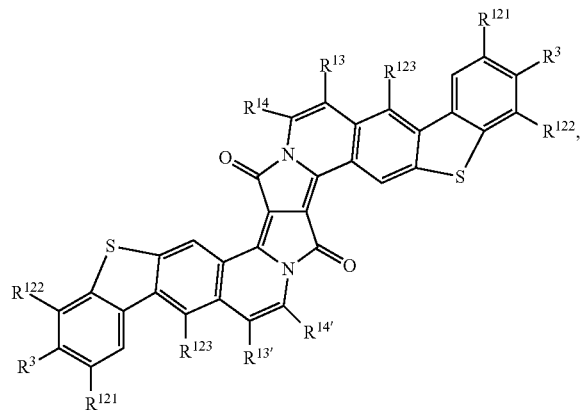
(IIIu)
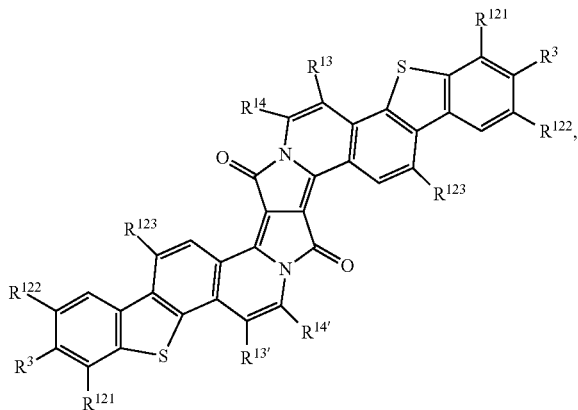
(IIIv)
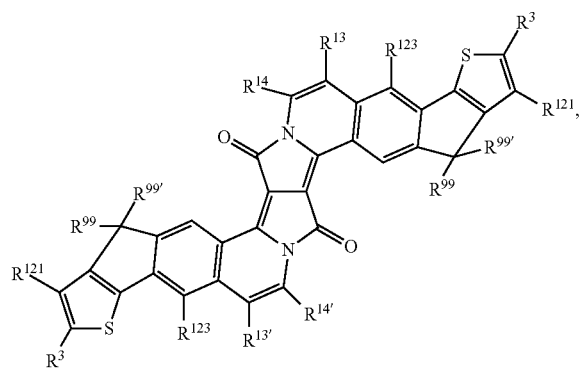
(IIIw)
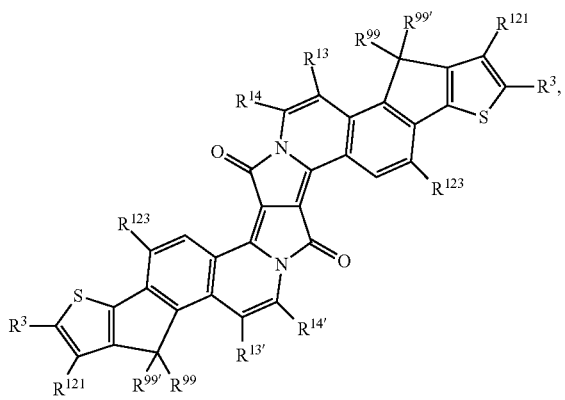
(IIIx)
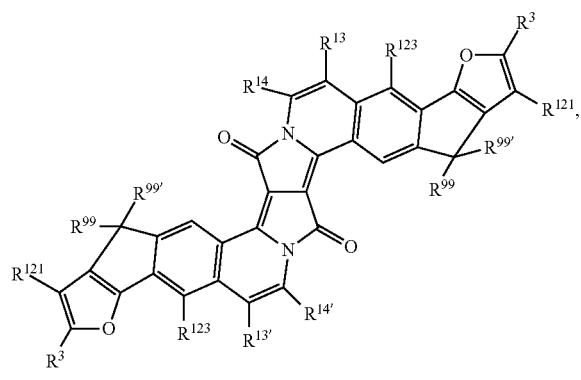
(IIIy)
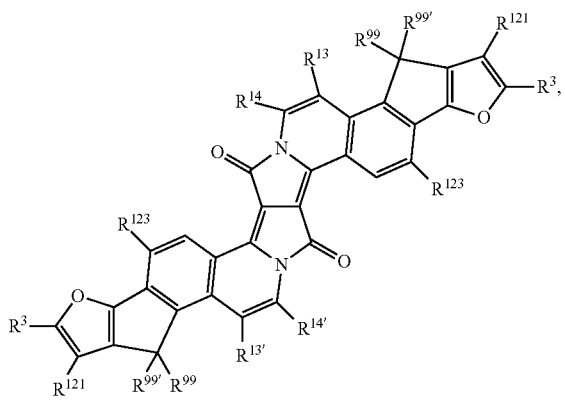
(IIIz)

-continued
(IIIaa)
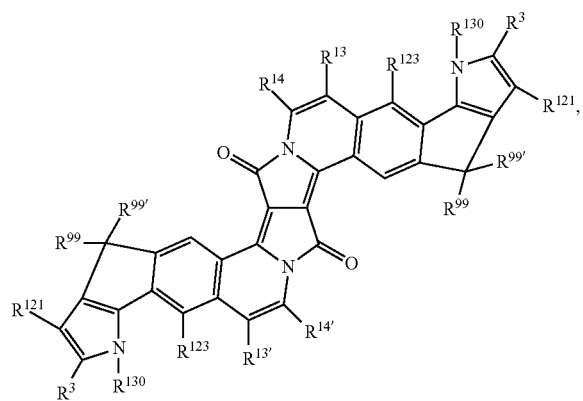
(IIIab)
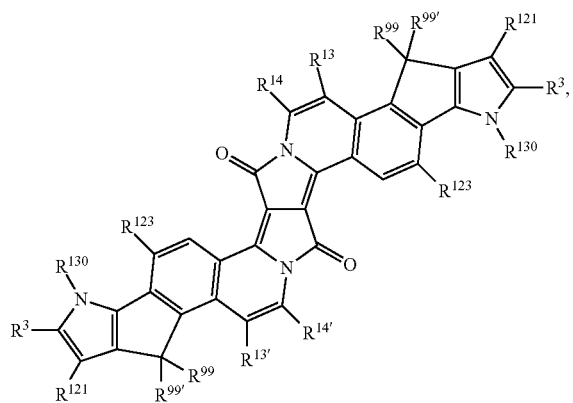
(IIIac)
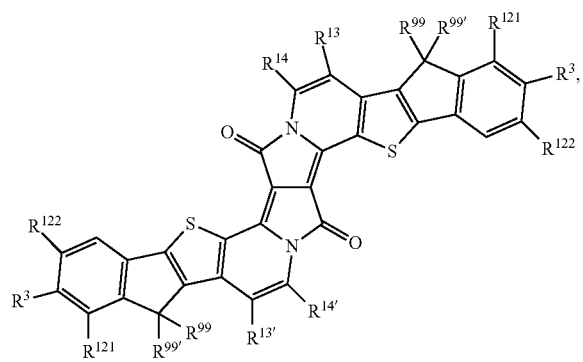
(IIIad)
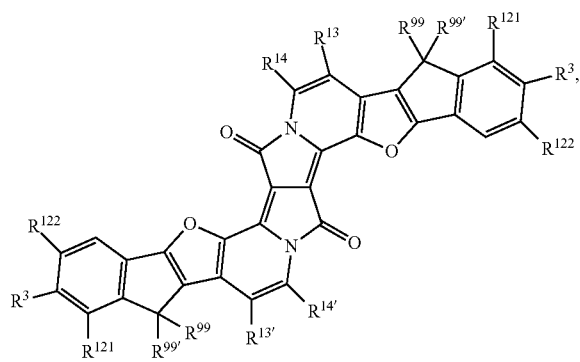
(IIIae)
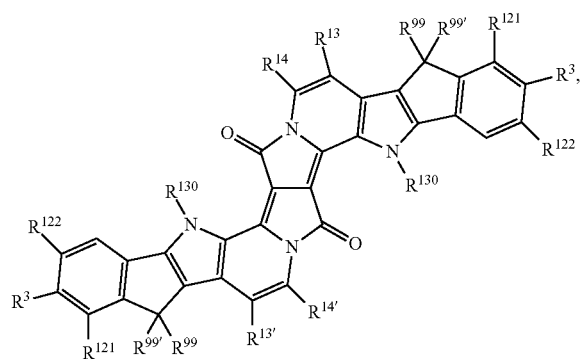
(IIIaf)
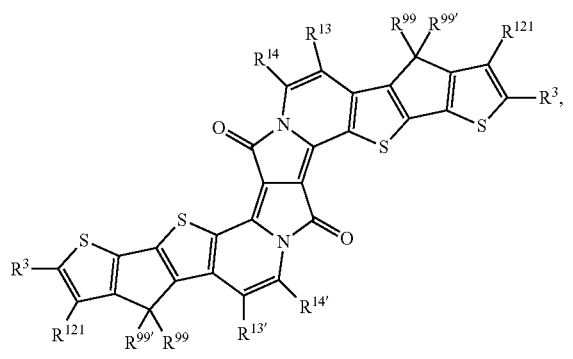
(IIIag)
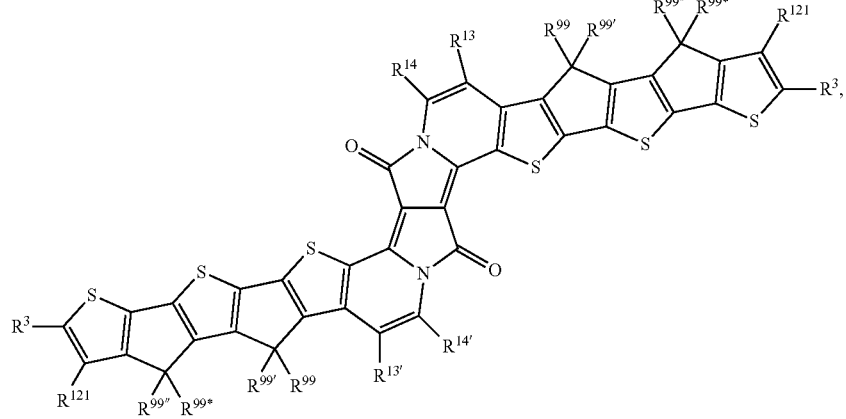

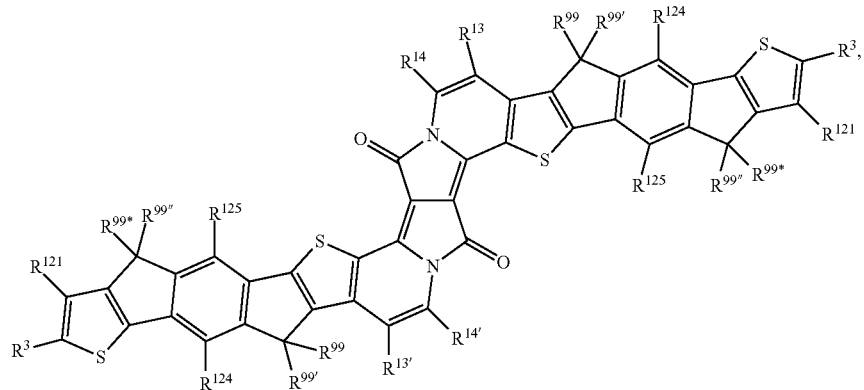
(IIIah)
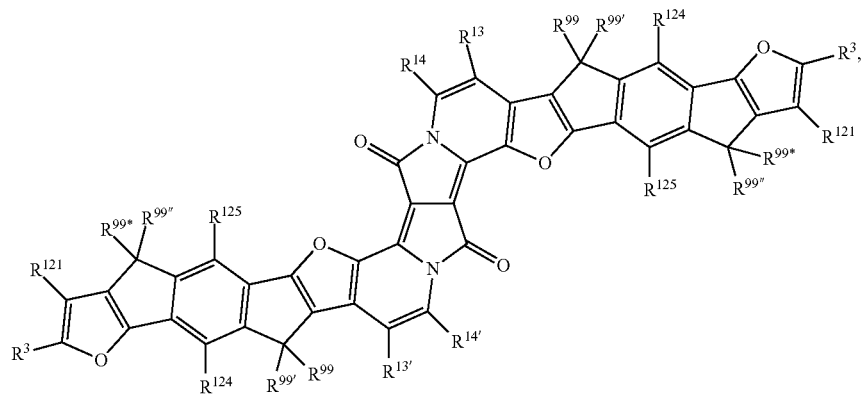
(IIIai)
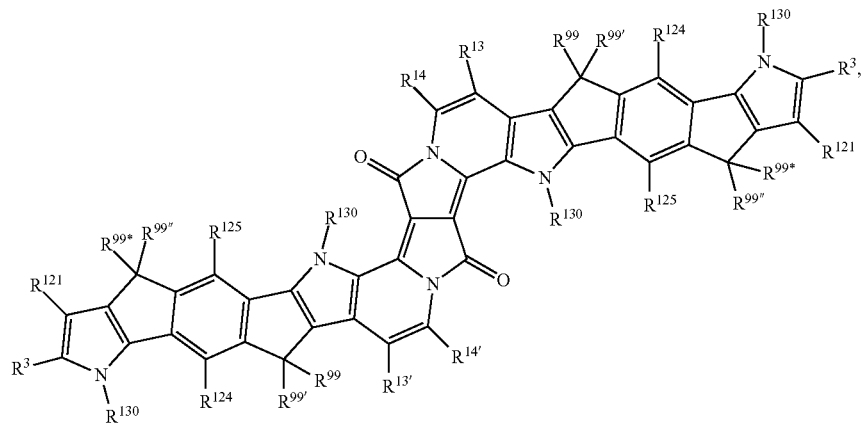
(IIIaj)

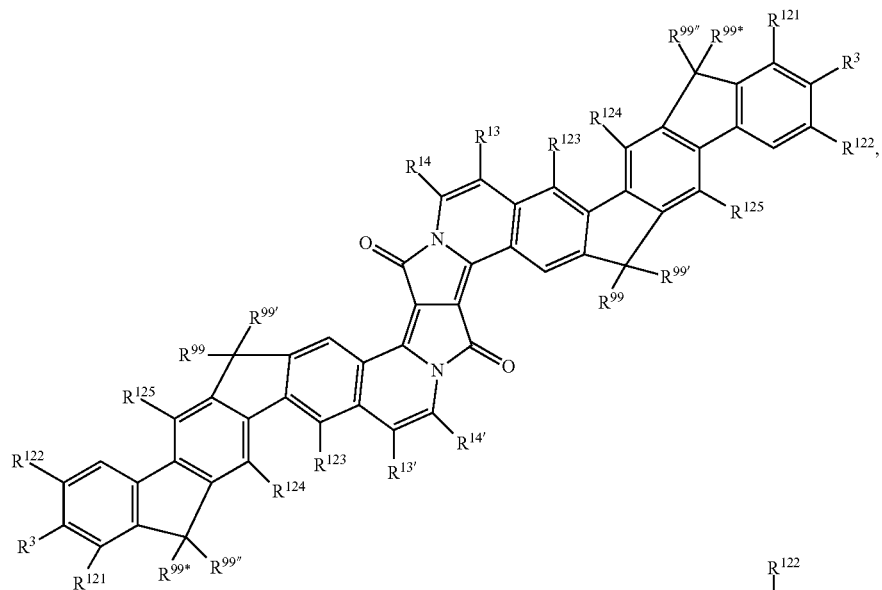
(IIIak)
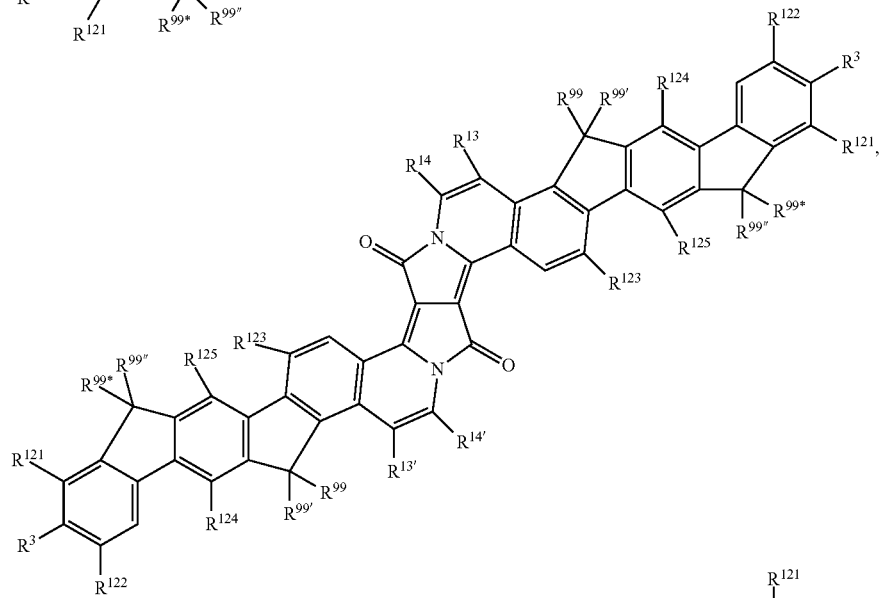
(IIIal)
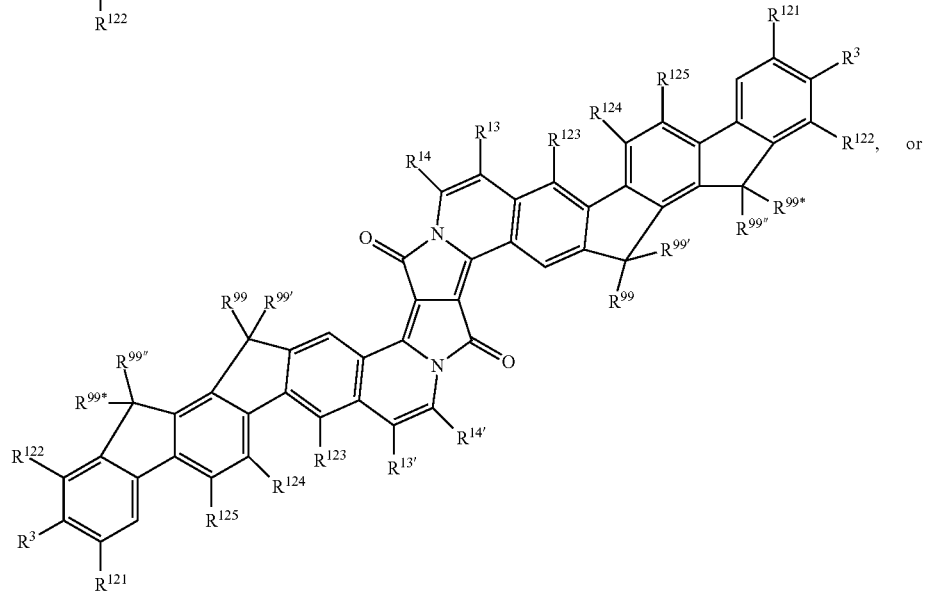
(IIIam)
or

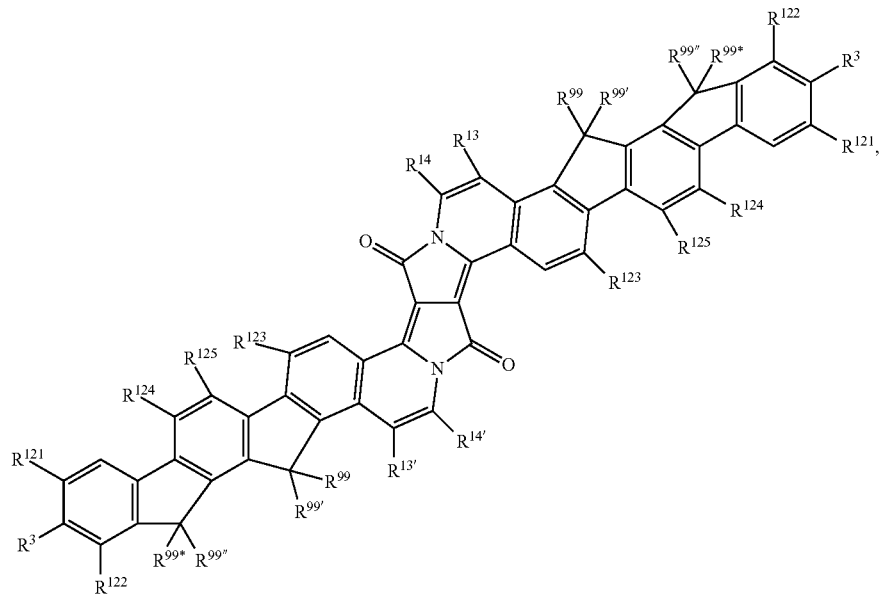
(IIIan)

R¹³, R¹³', R¹⁴ and R¹⁴' may be the same or different and are selected from hydrogen or a $C_1$-$C_{38}$alkyl group;

R⁹⁹, R⁹⁹', R⁹⁹'' and R⁹⁹* are independently of each other hydrogen, $C_1$-$C_{25}$alkyl, or $C_1$-$C_{25}$alkyl interrupted by one or more oxygen atoms; preferably $C_3$-$C_{25}$alkyl, or $C_3$-$C_{25}$alkyl which is interrupted by one or more oxygen atoms;

R¹²¹, R¹²², R¹²³, R¹²⁴ and R¹²⁵ are independently of each other hydrogen, halogen, $C_1$-$C_{18}$alkoxy or $C_1$-$C_{25}$alkyl; preferably hydrogen;

R¹³⁰ is hydrogen, $C_6$-$C_{18}$aryl; $C_6$-$C_{18}$aryl which is substituted by $C_1$-$C_{18}$alkyl, halogen; or $C_1$-$C_{18}$alkoxy; $C_1$-$C_{25}$alkyl, which may optionally be interrupted by one or more oxygen or sulphur atoms and/or is optionally substituted by one or more halogen atoms; or $C_7$-$C_{25}$arylalkyl; and R³ is as defined above.

4. The compound according to claim 3, wherein R¹, R¹', and R¹* are independently of each other H, $C_1$-$C_{25}$alkoxy, or $C_1$-$C_{25}$alkyl.

5. The compound according to claim 3, wherein R² is H, $C_1$-$C_{25}$alkoxy, or $C_1$-$C_{25}$alkyl.

6. The compound according to claim 3, wherein R³ is hydrogen, F, cyano, $C_1$-$C_{25}$alkyl,

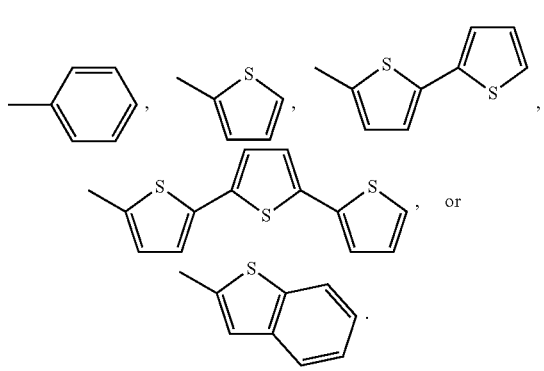

7. The compound according to claim 3, which is selected from (3a)

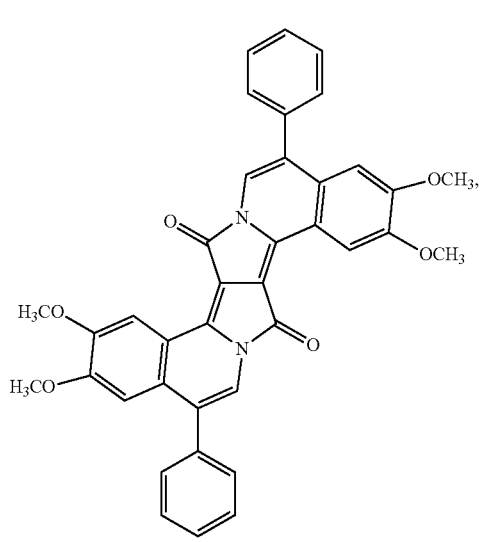

(3e)

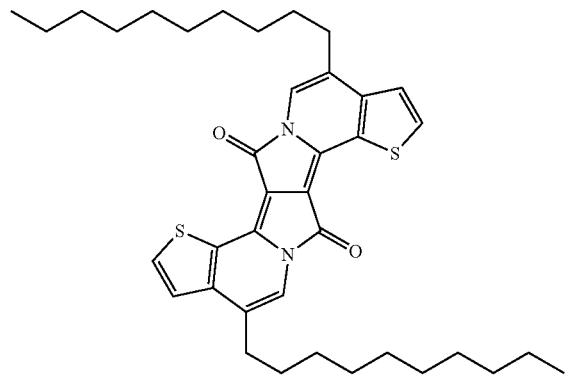

(3f)
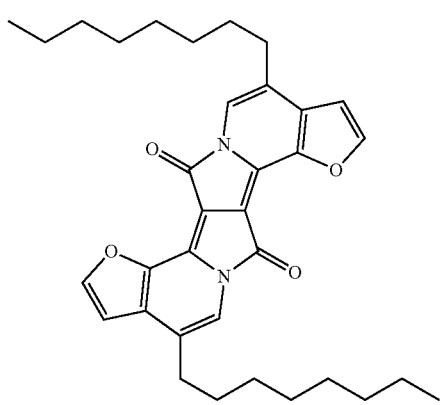
,
(3g)
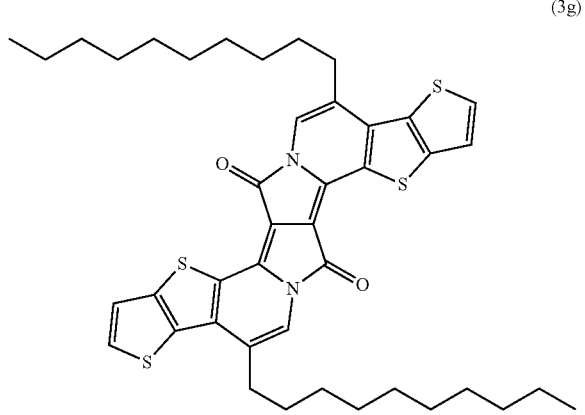
,
(3h)
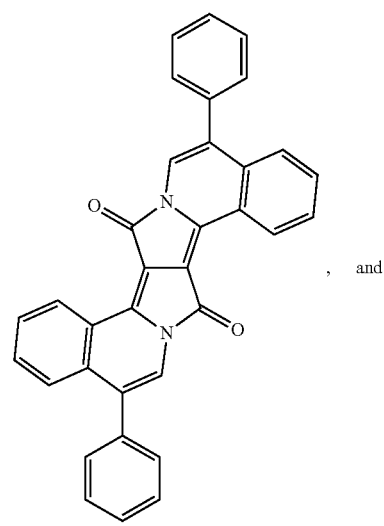
, and
(3i)
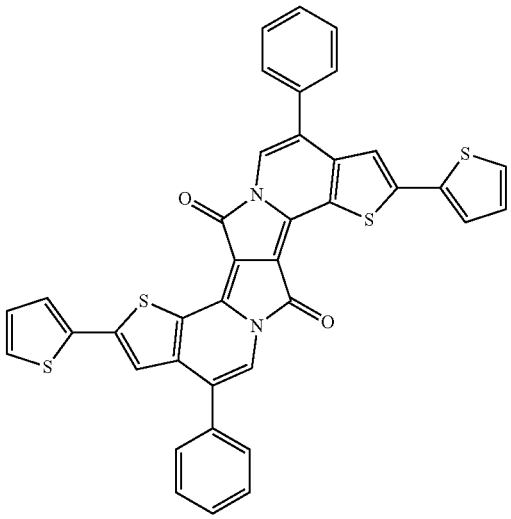
.
8. A method for the production of the compound of formula (III) according to claim 1:
(III)
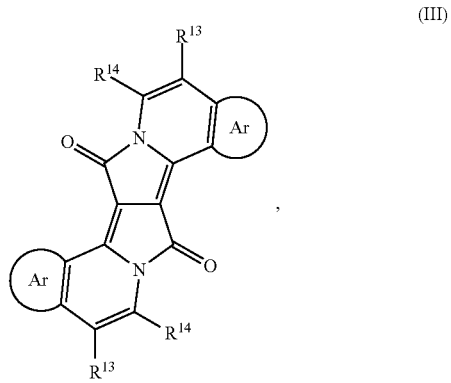
,
$R^{13}$, $R^{14}$ and Ar are as defined in claim 1,
the method comprising the steps of
a) reacting a diketopyrrolopyrrole of formula (I):
(I)
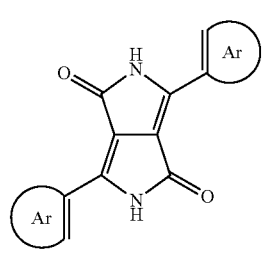

with a compound of formula

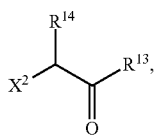

wherein $X^2$ is C, Br, or I; and then b) submitting the N-alkylated derivative of formula (II) obtained in step a)

(II)

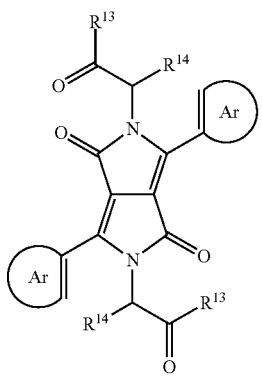

in the presence of acid to intramolecular condensation, to obtain the compound of formula (III).

9. The method according to claim 8, wherein step a) is an alkylation reaction carried out in the presence of tetrabutylammonium hydrogen sulfate, $K_2CO_3$ and dimethylformamide (DMF).

10. The method according to claim 8, wherein step b) is a cyclization reaction carried out in methylene chloride in the presence of trifluoromethanesulphonic acid.

11. A method of using the compounds of formula (III) according to claim 1, comprising:

adding the compounds of formula (III) as organic pigments in the development of fluorometric techniques, in modern biomedical techniques and diagnostics including fluorescence imaging and the detection of cations, and in semiconductor devices.

12. An organic semiconductor material, layer or component, comprising a compound according to claim 1.

13. A semiconductor device, comprising a compound according to claim 1, and/or an organic semiconductor material, layer or component comprising a compound according to claim 1.

14. The semiconductor device according to claim 13, which is an organic photovoltaic device, a photodiode, or an organic field effect transistor.

15. Process for the preparation of an organic semiconductor device, which process comprises applying a solution and/or dispersion of a compound according to claim 1 in an organic solvent to a suitable substrate and removing the solvent; or which process comprises evaporation of a compound according to claim 1.

16. A compound of formula (V)

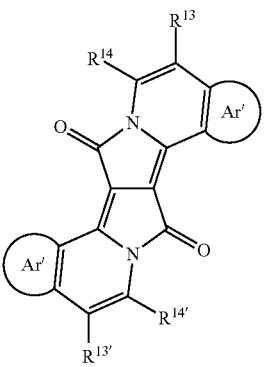

wherein Ar' is selected from

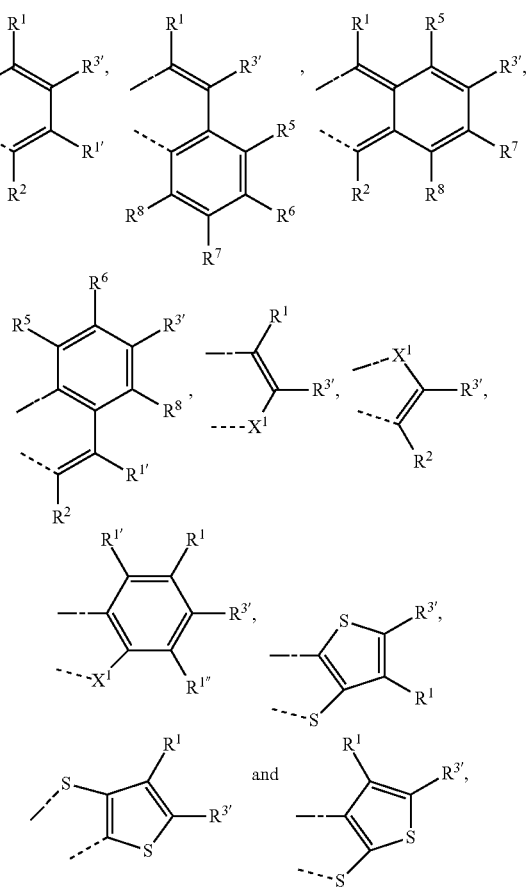

wherein the dotted lines denotes the bonds to the 6-membered ring; the dotted line --- indicates the bond to the carbon atom in para-position to the nitrogen atom, the dotted line ----- indicates the bond to the carbon atom in meta-position to the nitrogen atom, $R^{13}$, $R^{13'}$, $R^{14}$ and $R^{14'}$ are independently of each other hydrogen, $C_1$-$C_{25}$alkyl, $C_2$-$C_{25}$alkenyl, $C_2$-$C_{25}$alkenyl, which may optionally be interrupted by one or more oxygen or sulphur atoms and/or is optionally substituted by a group $E^{Si}$ or one or more halogen atoms; $C_2$-$C_{25}$alkinyl, $C_3$-$C_{12}$cycloalkyl, $C_3$-$C_{12}$cycloalkylalkyl, which may optionally be interrupted by one or more oxygen or sulphur atoms and/or is optionally substituted by a group $E^{Si}$ or one or more halogen atoms; $C_7$-$C_{25}$arylalkyl, $C_7$-$C_{25}$arylalkyl which may optionally be interrupted by one or more oxygen or sulphur atoms and/or is optionally substituted by a group $E^{Si}$ or one or more halogen atoms; $C_6$-$C_{18}$aryl; $C_6$-$C_{18}$aryl which is substituted by halogen, $C_1$-$C_{18}$alkyl, or $C_1$-$C_{18}$alkoxy, or $C_1$-$C_{25}$alkyl, which may optionally be interrupted by one or more oxygen or sulphur atoms and/or is optionally substituted by one or more halogen atoms; $C_3$-$C_{10}$heteroaryl; $C_3$-$C_{10}$heteroaryl, which is substituted by halogen, $C_1$-$C_{18}$alkyl, or $C_1$-$C_{18}$alkoxy; or $C_1$-$C_{25}$alkyl, which may optionally be interrupted by a group $D^{Si}$, or one or more oxygen or sulphur atoms and/or is optionally substituted by one or more halogen atoms;

$E^{Si}$ is —$SiR^{161}R^{162}R^{163}$ or —O—$SiR^{161}R^{162}R^{163}$;

$D^{Si}$ is —$SiR^{161}R^{162}$—, —$SiR^{161}R^{162}$—(O—$SiR^{161}R^{162})_d$— or —O—$SiR^{161}R^{162}$—;

$R^{161}$, $R^{162}$ and $R^{163}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—$SiR^{164}R^{165}R^{166}$, —(O—$SiR^{164}R^{165})_d$—$R^{166}$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl, which is substituted 1 to 3 times by $C_1$-$C_{25}$alkyl, halogen, cyano or $C_1$-$C_{25}$alkoxy;

$R^{164}$, $R^{165}$ and $R^{166}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—$SiR^{169}R^{170}R^{171}$, —(O—$SiR^{169}R^{170})_d$—$R^{171}$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl which is substituted 1 to 3 times by $C_1$-$C_{25}$alkyl, halogen, cyano or $C_1$-$C_{25}$alkoxy;

$R^{169}$, $R^{170}$ and $R^{171}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—$Si(CH_3)_3$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl, which is substituted 1 to 3 times by $C_1$-$C_{25}$alkyl, halogen, cyano or $C_1$-$C_{25}$alkoxy;

$R^{167}$ and $R^{168}$ are independently of each other hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms; or $C_7$-$C_{25}$arylalkyl;

d is an integer from 1 to 50; with the proviso that at least one of $R^{13}$, $R^{13'}$, $R^{14}$ and $R^{14'}$ is different from hydrogen, $R^1$, $R^{1'}$, and $R^{1''}$ are independently of each other H, halogen; cyano, $C_1$-$C_{25}$alkoxy, $C_1$-$C_{25}$alkyl substituted with one or more halogen atoms; or $C_1$-$C_{25}$alkyl, $R^2$ is H, halogen; cyano, $C_1$-$C_{25}$alkoxy, or $C_1$-$C_{25}$alkyl, $R^5$, $R^6$, $R^7$, and $R^8$ are independently of each other hydrogen, halogen; cyano, $C_1$-$C_{25}$alkyl, $C_1$-$C_{25}$alkoxy, or $C_1$-$C_{25}$alkyl substituted with one or more halogen atoms, $R^{3'}$ is Cl, Br, I,

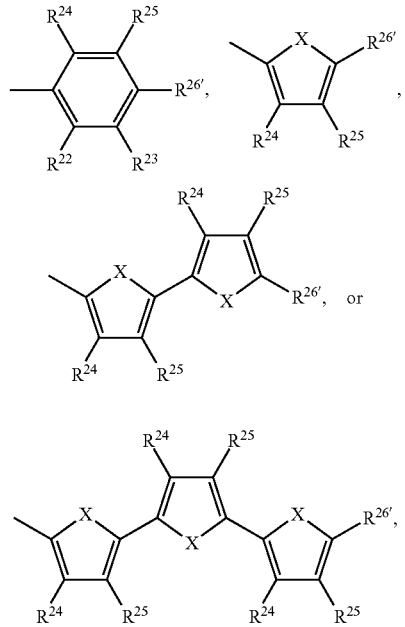

wherein

X and $X^1$ are independently of each other O, S, Se, or $NR^4$, $R^4$ is hydrogen, $C_6$-$C_{18}$aryl; $C_6$-$C_{18}$aryl which is substituted by $C_1$-$C_{18}$alkyl, halogen; or $C_1$-$C_{18}$alkoxy; $C_1$-$C_{25}$alkyl, which may optionally be interrupted by one or more oxygen or sulphur atoms and/or is optionally substituted by one or more halogen atoms; or $C_7$-$C_{25}$arylalkyl;

$R^{22}$ to $R^{25}$ are independently of each other H, F, cyano, $C_1$-$C_{25}$alkoxy, $C_1$-$C_{25}$alkyl substituted with one or more halogen atoms; or $C_1$-$C_{25}$alkyl and $R^{26'}$ is Cl, Br, or I.

17. The compound according to claim 16, which is selected from

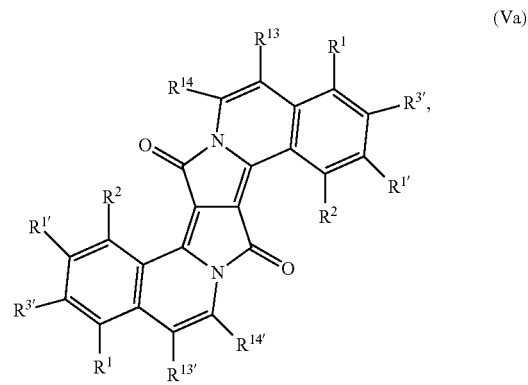

(Va)

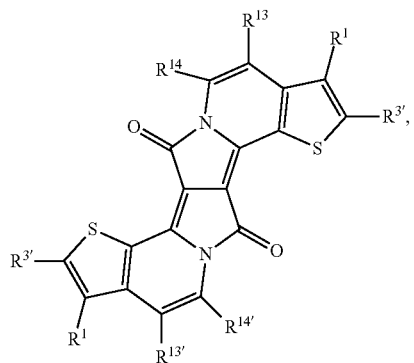
(Vb)
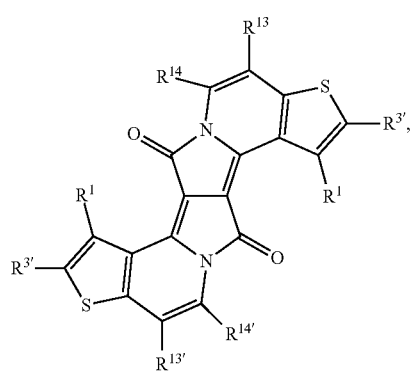
(Vc)
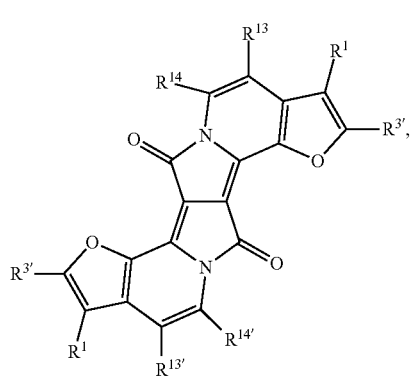
(Vd)
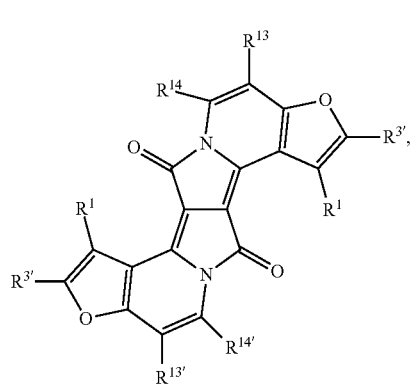
(Ve)
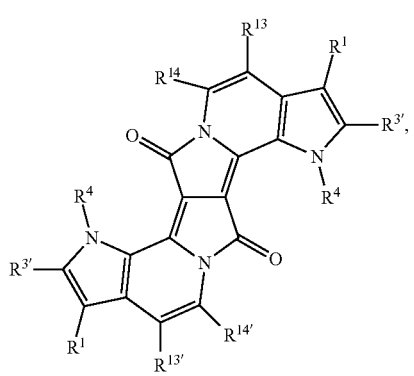
(Vf)
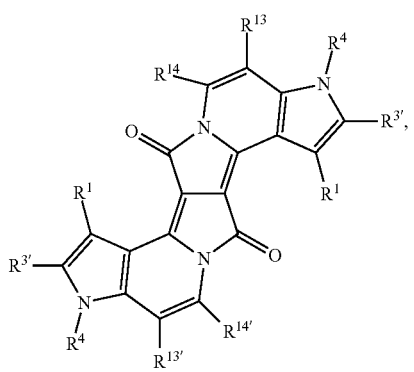
(Vg)
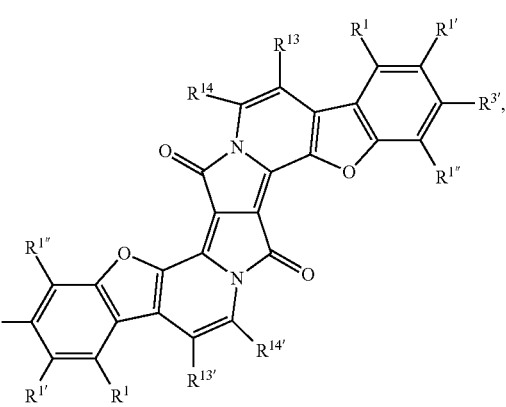
(Vh)
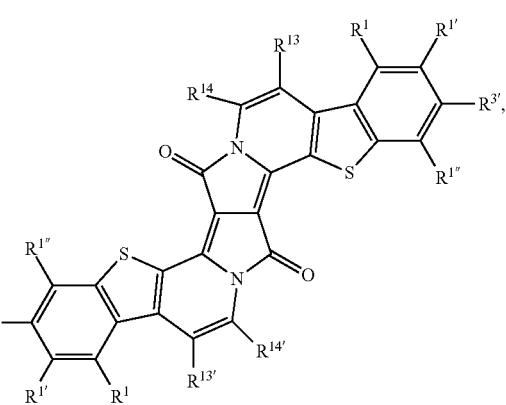
(Vi)

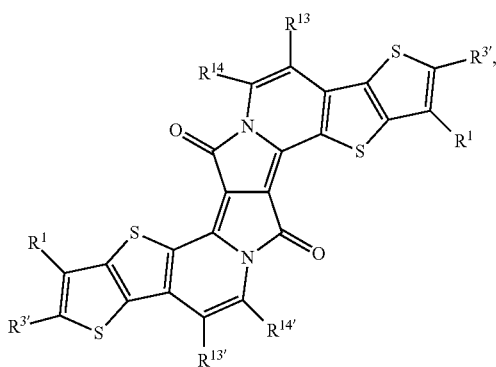
(Vj)

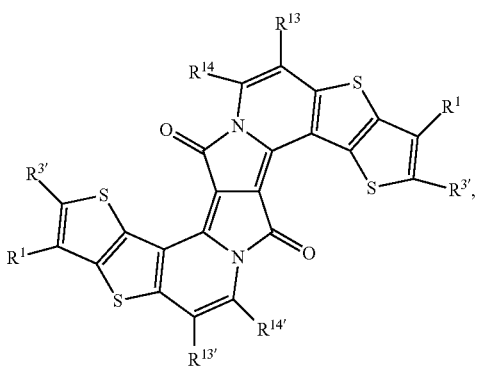
(Vk)

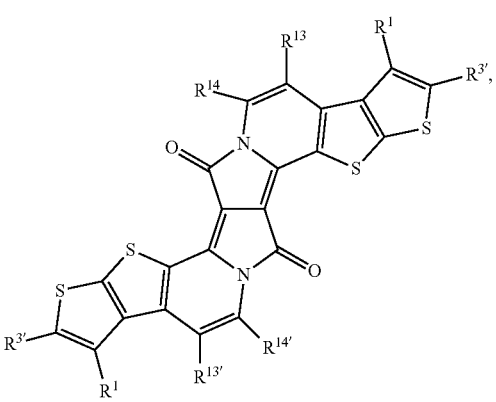
(Vl)

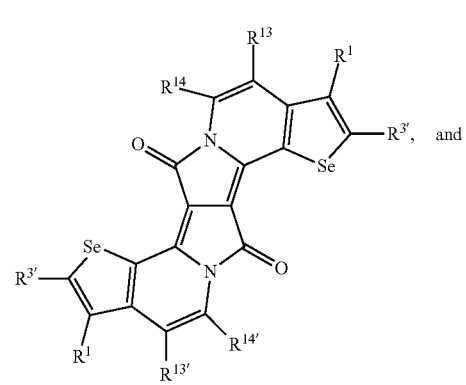
(Vm)

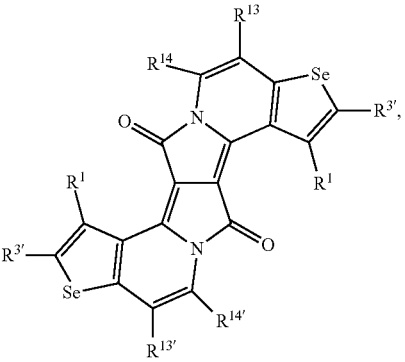
(Vn)

wherein $R^1$, $R^{1'}$, and $R^{1''}$ are independently of each other H, halogen; cyano, $C_1$-$C_{25}$alkoxy, $C_1$-$C_{25}$alkyl substituted with one or more halogen atoms; or $C_1$-$C_{25}$alkyl, $R^2$ is H, halogen; cyano, $C_1$-$C_{25}$alkoxy, or $C_1$-$C_{25}$alkyl, and $R^4$ is hydrogen, $C_6$-$C_{18}$aryl; $C_6$-$C_{18}$aryl which is substituted by $C_1$-$C_{18}$alkyl, halogen; or $C_1$-$C_{18}$alkoxy; $C_1$-$C_{25}$alkyl, which may optionally be interrupted by one or more oxygen or sulphur atoms and/or is optionally substituted by one or more halogen atoms; or $C_7$-$C_{25}$arylalkyl, $R^{13}$, $R^{13'}$, $R^{14}$ and $R^{14'}$ are independently of each other hydrogen, $C_1$-$C_{25}$alkyl, $C_2$-$C_{25}$alkenyl, $C_2$-$C_{25}$alkenyl, which may optionally be interrupted by one or more oxygen or sulphur atoms and/or is optionally substituted by a group $E^{Si}$ or one or more halogen atoms; $C_2$-$C_{25}$alkinyl, $C_3$-$C_{12}$cycloalkyl, $C_3$-$C_{12}$cycloalkylalkyl, which may optionally be interrupted by one or more oxygen or sulphur atoms and/or is optionally substituted by a group $E^{Si}$ or one or more halogen atoms; $C_7$-$C_{25}$arylalkyl, $C_7$-$C_{25}$arylalkyl which may optionally be interrupted by one or more oxygen or sulphur atoms and/or is optionally substituted by a group $E^{Si}$ or one or more halogen atoms; $C_6$-$C_{18}$aryl; $C_6$-$C_{18}$aryl which is substituted by halogen, $C_1$-$C_{15}$alkyl, or $C_1$-$C_{15}$alkoxy, or $C_1$-$C_{25}$alkyl, which may optionally be interrupted by one or more oxygen or sulphur atoms and/or is optionally substituted by one or more halogen atoms; $C_3$-$C_{10}$heteroaryl; $C_3$-$C_{10}$heteroaryl, which is substituted by halogen, $C_1$-$C_{18}$alkyl, or $C_1$-$C_{18}$alkoxy; or $C_1$-$C_{25}$alkyl, which may optionally be interrupted by a group $D^{Si}$, or one or more oxygen or sulphur atoms and/or is optionally substituted by one or more halogen atoms;

$E^{Si}$ is —$SiR^{161}R^{162}R^{163}$ or —O—$SiR^{161}R^{162}R^{163}$;

$D^{Si}$ is —$SiR^{161}R^{162}$—, —$SiR^{161}R^{162}$—(O—$SiR^{161}R^{162})_d$— or —O—$SiR^{161}R^{162}$—;

$R^{161}$, $R^{162}$ and $R^{163}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—$SiR^{164}R^{165}R^{166}$, —(O—$SiR^{164}R^{165})_d$—$R^{166}$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl, which is substituted 1 to 3 times by $C_1$-$C_{25}$alkyl, halogen, cyano or $C_1$-$C_{25}$alkoxy;

$R^{164}$, $R^{165}$ and $R^{166}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—SiR$^{169}$R$^{170}$R$^{171}$, —(O—SiR$^{169}$R$^{170}$)$_d$—R$^{171}$, C$_1$-C$_{25}$alkoxy, C$_3$-C$_{24}$(hetero)aryloxy, NR$^{167}$R$^{168}$, halogen, C$_1$-C$_{25}$acyloxy, phenyl, phenyl which is substituted 1 to 3 times by C$_1$-C$_{25}$alkyl, halogen, cyano or C$_1$-C$_{25}$alkoxy;

R$^{169}$, R$^{170}$ and R$^{171}$ are independently of each other hydrogen, C$_1$-C$_{25}$alkyl, C$_3$-C$_{12}$cycloalkyl, which might optionally be substituted with C$_1$-C$_4$alkyl; C$_1$-C$_{25}$haloalkyl, C$_2$-C$_{25}$alkenyl, —O—Si(CH$_3$)$_3$, C$_1$-C$_{25}$alkoxy, C$_3$-C$_{24}$(hetero)aryloxy, NR$^{167}$R$^{168}$, halogen, C$_1$-C$_{25}$acyloxy, phenyl, phenyl, which is substituted 1 to 3 times by C$_1$-C$_{25}$alkyl, halogen, cyano or C$_1$-C$_{25}$alkoxy;

R$^{167}$ and R$^{168}$ are independently of each other hydrogen, C$_6$-C$_{18}$aryl; C$_6$-C$_{18}$aryl which is substituted by C$_1$-C$_{18}$alkyl, or C$_1$-C$_{18}$alkoxy; or C$_1$-C$_{25}$alkyl, which may optionally be interrupted by one or more oxygen or sulphur atoms; or C$_7$-C$_{25}$arylalkyl;

d is an integer from 1 to 50; with the proviso that at least one of R$^{13}$, R$^{13'}$, R$^{14}$ and R$^{14'}$ is different from hydrogen, R$^{3'}$ is Cl, Br, I,

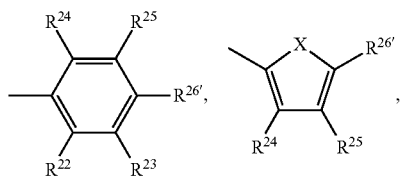

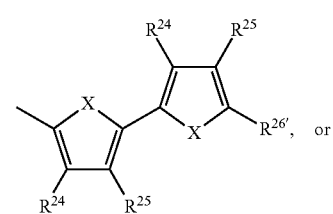

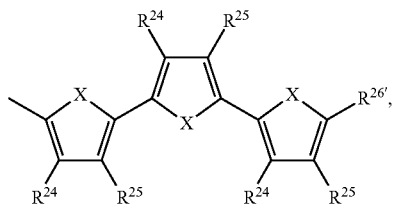

wherein

X is O, S, Se, or NR$^4$,

R$^{24}$ and R$^{25}$ are independently of each other H, F, cyano, C$_1$-C$_{25}$alkoxy, C$_1$-C$_{25}$alkyl substituted with one or more halogen atoms; or C$_1$-C$_{25}$alkyl and R$^{26'}$ is Cl, Br, or I.

18. The compound according to claim 17, which is selected from

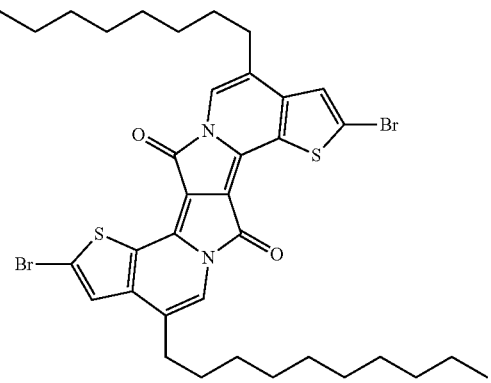
(IM5a)

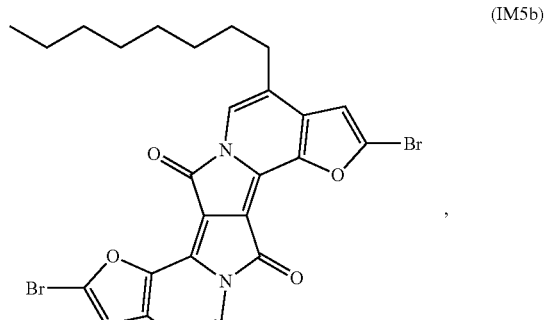
(IM5b)

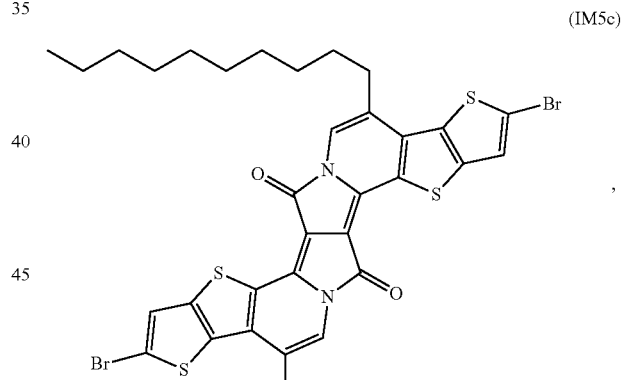
(IM5c)

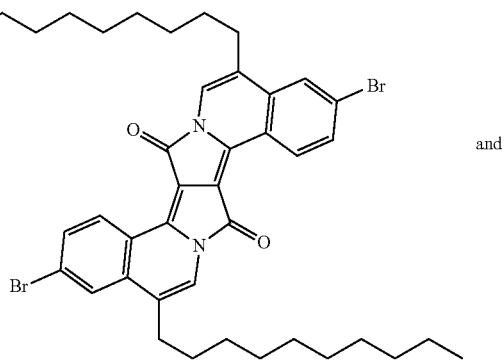
(IM5d)

and

-continued
(IM5e)
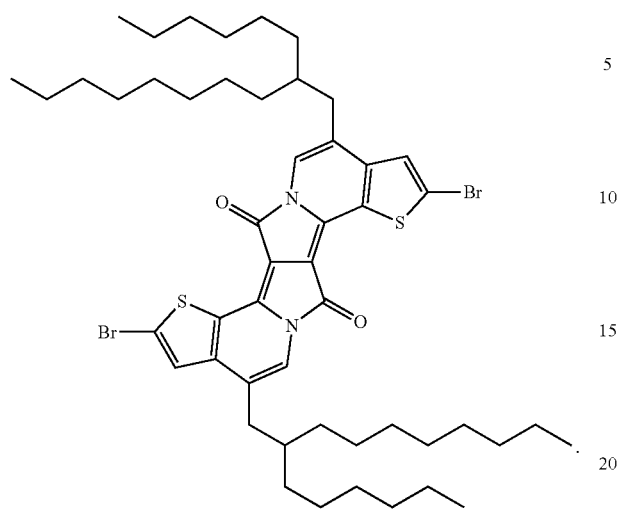
19. A method of using the compounds of claim 16 for the production of polymers, comprising:
    adding the compounds of claim 16 as intermediates in the production of polymers.
* * * * *